United States Patent
Lys et al.

(10) Patent No.: US 6,459,919 B1
(45) Date of Patent: Oct. 1, 2002

(54) PRECISION ILLUMINATION METHODS AND SYSTEMS

(75) Inventors: Ihor Lys; George G. Mueller, both of Boston; Frederick Marshall Morgan, Quincy, all of MA (US)

(73) Assignee: Color Kinetics, Incorporated, Boston, MA (US)

( * ) Notice: Subject to any disclaimer, the term of this patent is extended or adjusted under 35 U.S.C. 154(b) by 0 days.

(21) Appl. No.: 09/213,189

(22) Filed: Dec. 17, 1998

Related U.S. Application Data

(63) Continuation-in-part of application No. 08/920,156, filed on Aug. 26, 1997, now Pat. No. 6,016,038.
(60) Provisional application No. 60/079,285, filed on Mar. 25, 1998, provisional application No. 60/078,861, filed on Mar. 20, 1998, provisional application No. 60/090,920, filed on Jun. 26, 1998, provisional application No. 60/071,281, filed on Dec. 17, 1997, and provisional application No. 60/068,792, filed on Dec. 24, 1997.

(51) Int. Cl.⁷ .................................................. A61B 5/00
(52) U.S. Cl. ...................... 600/407; 600/476; 315/291; 315/302; 315/312; 362/234; 362/253
(58) Field of Search ................................. 600/407, 476; 315/291, 292, 302, 307, 312, 324, 300, 316, 362; 362/234, 253

(56) References Cited

U.S. PATENT DOCUMENTS

| | | | |
|---|---|---|---|
| 3,746,918 A | 7/1973 | Drucker et al. | 315/77 |
| 4,298,869 A | 11/1981 | Okuno | 340/782 |
| 4,329,625 A | 5/1982 | Nishizawa et al. | 315/158 |
| 4,367,464 A | 1/1983 | Kurahashi et al. | 340/701 |
| 4,388,567 A | 6/1983 | Yamazaki et al. | 315/291 |
| 4,420,711 A | 12/1983 | Takahashi et al. | 315/296 |
| 4,625,152 A | 11/1986 | Nakai | 315/317 |
| 4,727,289 A | 2/1988 | Uchida | 315/71 |

(List continued on next page.)

FOREIGN PATENT DOCUMENTS

| | | |
|---|---|---|
| AU | 6 267 9 | 12/1996 |
| CA | 2 178 432 | 12/1996 |
| EP | 0534 710 B1 | 1/1996 |
| EP | 0752 632 A2 | 1/1997 |
| FR | 2 640 791 | 6/1990 |
| GB | 2 176 042 A | 12/1986 |
| JP | 0604 3830 | 2/1994 |
| JP | 9 320 766 | 12/1997 |
| WO | WO 89 05086 | 6/1989 |
| WO | WO 94 18809 | 8/1994 |
| WO | WO 95 13498 | 5/1995 |
| WO | WO 96 41098 | 12/1996 |

OTHER PUBLICATIONS

"LM117/LM317A/LM317 3–Terminal Adjustable Regulator", National Semiconductor Corporation, May 1997, pp. 1–20.

"DS96177 RS–485/RS–422 Differential Bus Repeater", National Semiconductor Corporation, Feb. 1996, pp. 1–8.

"DS2003/DA9667/DS2004 High Current/Voltage Darlington Drivers", National Semiconductor Corporation, Dec. 1995, pp. 1–8.

"LM140A/LM140/LM340A/LM7800C Series 3–Terminal Positive Regulators", National Semiconductor Corporation, Jan. 1995, pp. 1–14.

*Primary Examiner*—Ruth S. Smith
(74) *Attorney, Agent, or Firm*—Wolf, Greenfield & Sacks, P.C.

(57) ABSTRACT

Methods and systems are provided for illuminating a material using an LED system, a processor for controlling the LED system and a positioning system for positioning the LED system in a spatial relationship with the material being illuminated. Furthermore, these methods and systems are available for producing certain color characteristics in an illuminated material or environment. These methods and systems can be applied to a plurality of materials, including biological entities. These methods and systems can be adapted for use in a medical applications, and are advantageously employed for diagnostic and therapeutic interventions.

47 Claims, 75 Drawing Sheets

U.S. PATENT DOCUMENTS

| | | | |
|---|---|---|---|
| 4,780,621 A | 10/1988 | Bartleucci et al. | 307/34 |
| 4,845,481 A | 7/1989 | Havel | 340/762 |
| 4,887,074 A | 12/1989 | Simon et al. | 340/782 |
| 5,008,595 A | 4/1991 | Kazar | 315/178 |
| 5,282,121 A | 1/1994 | Bornhorst et al. | 362/294 |
| 5,294,865 A | 3/1994 | Haraden | 315/58 |
| 5,350,977 A | 9/1994 | Hamamoto et al. | 315/291 |
| 5,357,170 A | 10/1994 | Luchaco et al. | 315/159 |
| 5,374,876 A | 12/1994 | Horibata et al. | 315/313 |
| 5,388,357 A | 2/1995 | Malita | 40/570 |
| 5,404,282 A | 4/1995 | Klinke et al. | 362/249 |
| 5,406,176 A | 4/1995 | Sugden | 315/292 |
| 5,410,328 A | 4/1995 | Yoksza et al. | 345/82 |
| 5,420,482 A | 5/1995 | Phares | 315/292 |
| 5,436,535 A | 7/1995 | Yang | 315/313 |
| 5,463,280 A | 10/1995 | Johnson | 315/187 |
| 5,504,395 A | 4/1996 | Johnson et al. | 315/71 |
| 5,545,950 A | 8/1996 | Cho | 315/56 |
| 5,561,346 A | 10/1996 | Byrne | 313/512 |
| 5,575,459 A | 11/1996 | Anderson | 362/240 |
| 5,592,051 A | 1/1997 | Korkala | 315/210 |
| 5,751,118 A | 5/1998 | Mortimer | 315/291 |
| 5,769,527 A | 6/1998 | Taylor et al. | 362/85 |
| 5,821,695 A | 10/1998 | Vilanilam et al. | 315/58 |
| 5,896,010 A | 4/1999 | Mikolajczak et al. | 315/77 |
| 5,924,784 A | 7/1999 | Chliwnyj et al. | 362/234 |
| 6,016,038 A | 1/2000 | Mueller et al. | 315/291 |
| 6,072,280 A | 6/2000 | Allen | 315/185 |

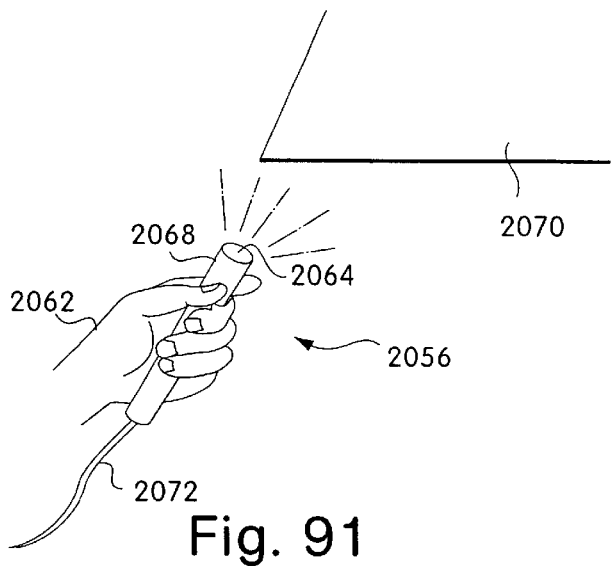
Fig. 91
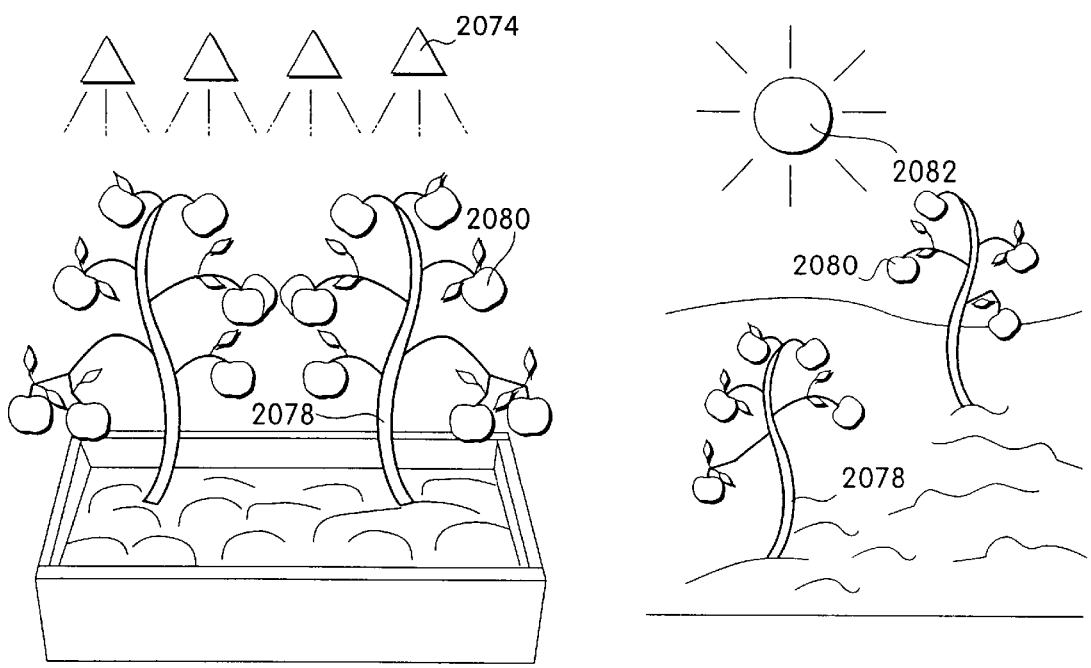
Fig. 92A
Fig. 92B

PRECISION ILLUMINATION METHODS AND SYSTEMS

CROSS REFERENCES TO RELATED APPLICATIONS

This application is a continuation-in-part (CIP) of U.S. non-provisional utility application entitled Multicolored LED Lighting Method and Apparatus, filed Aug. 26, 1997, application Ser. No. 08/920,156, naming George Mueller and Ihor Lys as inventors, now U.S. Pat. No. 6,016,038.

This application also claims the benefit under 35 U.S.C. § 119(e) of the following five U.S. provisional applications: Digitally Controlled Light Emitting Diode Systems and Methods, U.S. provisional patent application No. 60/071,281, filed Dec. 17, 1997, naming George Mueller and Ihor Lys as inventors; Multi-Color Intelligent Lighting, U.S. provisional patent application No. 60/068,792, filed Dec. 24, 1997, naming George Mueller and Ihor Lys as inventors; Digital Lighting Systems, U.S. provisional patent application No. 60/078,861, filed Mar. 20, 1998, naming Ihor Lys as inventor; System and Method for Controlled Illumination, U.S. provisional patent application No. 60/079,285, filed Mar. 25, 1998, naming George Mueller and Ihor Lys as inventors; Method for Software Driven Generation of Multiple Simultaneous High Speed Pulse Width Modulated Signals, U.S. provisional patent application No. 60/090,920, filed Jun. 26, 1998, naming Ihor Lys as inventor.

This application also is co-pending with the following applications: PCT/US98/26853 filed on Dec. 17, 1998; U.S. patent application Ser. No. 09/215,624 filed on Dec. 17, 1998; U.S. patent application Ser. No. 09/213,537 filed on Dec. 17, 1998; U.S. Pat. application Ser. No. 09/213,607 filed on Dec. 17, 1998; U.S. patent application Ser. No. 09/213,548 filed on Dec. 17, 1998; U.S. patent application Ser. No. 09/213,581 filed on Dec. 17, 1998; U.S. patent application Ser. No. 09/213,659 filed on Dec. 17, 1998; U.S. patent application Ser. No. 09/213,540 filed on Dec. 17, 1998.

The entire disclosure of each of the patents and patent applications referred to herein is hereby incorporated by reference.

DESCRIPTION OF THE RELATED ART

Light emitting diodes are known which, when disposed on a circuit, accept electrical impulses from the circuit and convert the impulses into light signals. LEDs are energy efficient, they give off virtually no heat, and they have a long lifetime.

A number of types of LED exist, including air gap LEDs, GaAs light-emitting diodes (which may be doubled and packaged as single unit offer greater reliability than conventional single-diode package), polymer LEDs, and semiconductor LEDs, among others. Most LEDs in current use are red. Conventional uses for LEDs include displays for low light environments, such as the flashing light on a modem or other computer component, or the digital display of a wristwatch. Improved LEDs have recently been used in arrays for longer-lasting traffic lights. LEDs have been used in scoreboards and other displays. Also, LEDs have been placed in arrays and used as television displays. Although most LEDs in use are red, yellow or white, LEDs may take any color; moreover, a single LED may be designed to change colors to any color in the color spectrum in response to changing electrical signals.

It is well known that combining the projected light of one color with the projected light of another color will result in the creation of a third color. It is also well known that three commonly used primary colors—red, blue and green—can be combined in different proportions to generate almost any color in the visible spectrum. The present invention takes advantage of these effects by combining the projected light from at least two light emitting diodes (LEDS) of different primary colors. It should be understood that for purposes of this invention the term "primary colors" encompasses any different colors that can be combined to create other colors.

Computer lighting networks that use LEDs are also known. U.S. Pat. No. 5,420,482, issued to Phares, describes one such network that uses different colored LEDs to generate a selectable color, primarily for use in a display apparatus. U.S. Pat. No. 4,845,481, issued to Havel, is directed to a multicolored display device. Havel uses a pulse width modulated signal to provide current to respective LEDs at a particular duty cycle. U.S. Pat. No. 5,184,114, issued to Brown, shows an LED display system. U.S. Pat. No. 5,134,387, issued to Smith et al., is directed to an LED matrix display.

Illumination systems exist in which a network of individual lights is controlled by a central driver, which may be a computer-controlled driver. Such illumination systems include theatrical lighting systems. The USITT DMX-512 protocol was developed to deliver a stream of data from a theatrical console to a series of theatrical lights.

The DMX-512 protocol was originally designed to standardize the control of light dimmers by lighting consoles. The DMX-512 protocol is a multiplexed digital lighting control protocol with a signal to control 512 devices, such device including dimmers, scrollers, non-dim relays, parameters of a moving light, or a graphical light in a computerized virtual reality set. DMX-512 is used for control for a network of devices. The DMX-512 protocol employs digital signal codes. When a transmitting device, such as a lighting console, sends digital codes, a receiving device, such as a dimmer, transforms these codes into a function command, such as dimming to a specified level. With digital systems, signal integrity is compromised less over long cable runs, relative to analog control. When a coded string of 0/1 digits are sent and received, the device will perform the desired task.

In hardware terms, DMX-512 protocol information is transferred between devices over metal wires using the RS-485 hardware protocol. This involves the use of two wires, known as a twisted pair. The first wire is referred to as a data+wire, and the second wire is referred to as a data−wire. The voltage used on the line is typically positive five volts. By way of example, to transmit a logical one, the data+wire is taken to positive five volts, and the data−wire to zero volts. To transmit a logical zero, the data+wire goes to zero volts, and the data−wire to positive five volts. This is quite different from the more common RS-232 interface, where one wire is always kept at zero volts. In RS-232, a logical one is transmitted by putting between positive six and positive twelve volts on the line, and a logical zero is transmitted by putting a voltage between negative six and negative twelve volts onto the line. RS-485 is generally understood to be better for data transmission than RS-232. With RS-232, the receiver has to measure if the incoming voltage is positive or negative. With RS-485, the receiver only needs to determine which line has the higher voltage on it.

The two wires over which RS-485 is transmitted are preferably twisted. Twisting means that disturbances on the line tend to affect both lines simultaneously, more or less by the same amount, so that the voltage on both lines will fluctuate, but the difference in voltage between the lines remains the same. The result is that noise is rejected from the line. Also, the drive capability of RS-485 drivers is higher than RS-232 drivers. As a result, the RS-485 protocol can connect devices over distances hundreds of times further than would be possible when using RS-232. RS-485 also increases the maximum data rate, i.e., the maximum amount of data which can be transmitted over the line every second. Communication between devices using RS-232 is normally about nine thousand six hundred baud (bits per second). Faster communication is possible, but the distances over which data can be transmitted are reduced significantly if communication is faster. By comparison, DMX-512 (using RS-485) permits data to be sent at two hundred fifty thousand baud (two hundred fifty thousand bits per second) over distances of hundreds of meters without problems. Every byte transmitted has one start bit, which is used to warn the receiver that the next character is starting, eight data bits (this conveys up to two hundred fifty six different levels) and two stop bits, which are used to tell the receiver that this is the end of the character. This means that every byte is transmitted as eleven bits, so that the length of each character is forty-four micro seconds.

The receiver looks at the two incoming signals on a pair of pins and compares the differences. A voltage rise on one wire and the inverse on the other will be seen as a differential and therefore deciphered as a digit. When both signals are identical, no difference is recognized and no digit deciphered. If interference was accidently transmitted along the line, it would impart no response as long as the interference was identical on both lines. The proximity of the two lines assist in assuring that distribution of interference is identical on both wires. The signal driver sends five hundred twelve device codes in a continual, repetitive stream of data. The receiving device is addressed with a number between one and five hundred twelve so it will respond only to data that corresponds to its assigned address.

A terminator resistor is typically installed at the end of a DMX line of devices, which reduces the possibility of signal reflection which can create errors in the DMX signal. The ohm value of the resistor is determined by the cable type used. Some devices allow for self termination at the end of the line. Multiple lines of DMX data can be distributed through an opto-repeater. This device creates a physical break in the line by transforming the electrical signals into light which spans a gap, then it is restored to electrical signals. This protects devices from damaging high voltage, accidentally travelling along the network. It will also repeat the original DMX data to several output lines. The input data is recreated at the outputs, eliminating distortion. The signal leaves the opto-repeater as strong as it left the console.

DMX messages are typically generated through computer software. Each DMX message is preceded with a "break," which is a signal for the receiver that the previous message has ended and the next message is about to start. The length of the break signal (equivalent to a logical zero on the line) has to be eighty-eight micro seconds according to the DMX specification. The signal can be more than eighty-eight micro seconds. After the break signal is removed from the line, there is a period during which the signal is at a logical one level. This is known as the "Mark" or 'Mark After Break' (MAB) time. This time is typically at least eight micro seconds. After the Mark comes the first character, or byte, which is knows as the "Start" character. This character is rather loosely specified, and is normally set to the value zero (it can vary between zero and two hundred fifty five).

This start character may be used to specify special messages. It is, for example, possible to have five hundred twelve dimmers which respond to messages with the start character set to zero, and another five hundred twelve dimmers which respond to messages with the start character set to one. If one transmits data for these one thousand twenty-four dimmers, and one sets the start character to zero for the first five hundred twelve dimmers, and to one for the second set of five hundred twelve dimmers, it is possible to control one thousand twenty four dimmers (or more if one wishes, using the same technique). The disadvantage is a reduction in the number of messages sent to each of the set of dimmers, in this example by a factor two. After the start character there are between one and five hundred twelve characters, which normally correspond to the up to five hundred twelve channels controlled by DMX. Each of these characters may have a value between zero (for 'off', zero percent) and two hundred fifty five (for full, one hundred percent). After the last character there may be another delay (at logic one level) before the next break starts. The number of messages which are transmitted every second are dependent on all the parameters listed above. In one case, where the break length is eighty-eight microseconds, the make after break length is eight micro seconds, and each character takes exactly forty-four micro seconds to transmit there will be forty-four messages per second, assuming that all five hundred twelve channels are being transmitted. Many lighting desks and other DMX sources transmit less than five hundred twelve channels, use a longer break and make after break time, and may have a refresh rate of seventy or eighty messages per second. Often, there is no benefit to be had from this, as the current value is not necessarily recalculated for each of the channels in each frame. The 'standard' DMX signal would allow for a lamp to be switched on and off twenty-two times per second, which is ample for many applications. Certain devices are capable of using sixteen-bit DMX. Normal eight bit messages allow two hundred fifty-six positions, which is inadequate for the positioning of mirrors and other mechanical devices. Having sixteen bits available per channel increases that quantity up to sixty-five thousand five hundred thirty-six steps, which removes the limitation of 'standard' DMX.

A significant problem with present lighting networks is that they require special wiring or cabling. In particular, one set of wires is needed for electrical power, while a second set of wires is needed for data, such as DMX-512 protocol data. Accordingly, the owner of an existing set of lights must undertake significant effort to rewire in order to have a digitally controlled lighting environment.

A second significant problem with present lighting networks is that particular lighting applications require particular lighting types. For example, LED based lights are appropriate for some applications, while incandescent lamps or halogen lamps may be more appropriate for other applications. A user who wishes to have a digitally controlled network of lights, in addition to rewiring, must currently add additional fixtures or replace old fixtures for each different type of light. Accordingly, a need has arisen for a lighting fixture that permits use of different types of digitally controlled lights.

Use of pulse width modulated signals to control electrical devices, such as motors, is also known. Traditional methods of providing pulse width modulated signals include hardware using software programmed timers, which in some instances is not cost effective if not enough timer modules are available, and one interrupt per count processes, in which a microprocessor receives periodic interrupts at a known rate. Each time through the interrupt loop the processor compares the current count with the target counts and updates one or more output pins, thus creating a pulse width modulated signal, or PWM. In this case, the speed equals the clock speed divided by cycles in the interrupt routine divided by desired resolution. In a third method, in a combination of the first two processes, software loops contain a variable number of instructions. The processor uses the hardware timer to generate a periodic interrupt, and then, depending on whether the pulse is to be very short or not, either schedules another interrupt to finish the PWM cycle, or creates the pulse by itself in the first interrupt routine by executing a series of instructions consuming a desired amount of time between two PWM signal updates. The difficulty with the third method is that for multiple PWM channels it is very difficult to arrange the timer based signal updates such that they do not overlap, and then to accurately change the update times for a new value of PWM signals. Accordingly, a new pulse width modulation method and system is needed to assisting in controlling electrical devices.

Many conventional illumination applications are subject to other drawbacks. Conventional light sources, such as halogen and incandescent sources may produce undesirable heat. Such sources may have very limited life spans. Conventional light sources may require substantial lens and filtering systems in order to produce color. It may be very difficult to reproduce precise color conditions with conventional light sources. Conventional light sources may not respond quickly to computer control. One or more of these drawbacks may have particular significance in particular existing lighting applications. Moreover, the combination of these drawbacks may have prevented the development of a number of other illumination applications. Accordingly, a need exists for illumination methods and systems that overcome the drawbacks of conventional illumination systems and that take advantage of the possibilities offered by overcoming such drawbacks.

SUMMARY OF THE INVENTION

Illumination methods and systems are provided herein that overcome many of the drawbacks of conventional illumination systems. In embodiments, methods and systems are provided for multicolored illumination. In an embodiment, the present invention is an apparatus for providing an efficient, computer-controlled, multicolored illumination network capable of high performance and rapid color selection and change.

In brief, disclosed herein is a current control for a lighting assembly, which may be an LED system or LED lighting assembly, which may be a pulse width modulated ("PWM") current control or other form of current control where each current-controlled unit is uniquely addressable and capable of receiving illumination color information on a computer lighting network. As used herein, "current control" means PWM current control, analog current control, digital current control, and any other method or system for controlling current.

As used herein, the term "LED system" means any system that is capable of receiving an electrical signal and producing a color of light in response to the signal. Thus, the term "LED system" should be understood to include light emitting diodes of all types, light emitting polymers, semiconductor dies that produce light in response to current, organic LEDs, electro-luminescent strips, and other such systems. In an embodiment, an "LED system" may refer to a single light emitting diode having multiple semiconductor dies that are individually controlled.

An LED system is one type of illumination source. As used herein "illumination source" should be understood to include all illumination sources, including LED systems, as well as incandescent sources, including filament lamps, pyro-luminescent sources, such as flames, candle-luminescent sources, such as gas mantles and carbon arch radiation sources, as well as photo-luminescent sources, including gaseous discharges, flourescent sources, phosphorescence sources, lasers, electro-luminescent sources, such as electro-luminescent lamps, light emitting diodes, and cathode luminescent sources using electronic satiation, as well as miscellaneous luminescent sources including galvano-luminescent sources, crystallo-luminescent sources, kine-luminescent sources, thermo-luminescent sources, triboluminescent sources, sonoluminescent sources, and radioluminescent sources. Illumination sources may also include luminescent polymers capable of producing primary colors.

The term "illuminate" should be understood to refer to the production of a frequency of radiation by an illumination source. The term "color" should be understood to refer to any frequency of radiation within a spectrum; that is, a "color," as used herein, should be understood to encompass frequencies not only of the visible spectrum, but also frequencies in the infrared and ultraviolet areas of the spectrum, and in other areas of the electromagnetic spectrum.

In a further embodiment, the invention includes a tree network configuration of lighting units (nodes). In another embodiment, the present invention comprises a heat dissipating housing, made out of a heat-conductive material, for housing the lighting assembly. The heat dissipating housing contains two stacked circuit boards holding respectively a power module and a light module. In another embodiment, the LED board is thermally connected to a separate heat spreader plate by means of a thermally conductive polymer and fasteners and should be considered substantially the same as an LED board with metal in center. The light module is adapted to be conveniently interchanged with other light modules having programmable current, and hence maximum light intensity, ratings. Such other light modules may include organic LEDs, electro-luminescent strips, and other modules, in addition to conventional LEDs. Other embodiments of the present invention involve novel applications for the general principles described herein.

Disclosed herein is a high performance computer controlled multicolored lighting network, which may be an LED lighting network. Disclosed herein is a LED lighting network structure capable of both a linear chain of nodes and a tree configuration. Disclosed herein is a heat-dissipating housing to contain the lighting units of the lighting network. Disclosed herein is a current-regulated LED lighting apparatus, wherein the apparatus contains lighting modules each having its own maximum current rating and each conveniently interchangeable with one another. Disclosed herein is a computer current-controlled LED lighting assembly for use as a general illumination device capable of emitting multiple colors in a continuously programmable twenty-four-bit spectrum. Disclosed herein are a flashlight, inclinometer, thermometer, general environmental indicator and lightbulb, all utilizing the general computer current-control principles of the present invention. Other aspects of the present disclosure will be apparent from the detailed description below.

The present invention provides applications for digitally controlled LED based lights. Systems and methods of the present invention include uses of such lights in a number of technical fields in which illumination technology is critical. Systems and methods of the present invention include systems whereby such lights may be made responsive to a variety of different signals. Systems and methods of the present invention include improved data and power distribution networks.

Systems and methods of the present invention include use of LEDs as part of or on a wide range of items to provide aesthetically appealing or function effects. The digitally controlled light emitting diodes (LEDs) of the present invention may be used in a number of technological fields in inventions more particularly described below.

The present disclosure further provides systems and methods for precision illumination. Precision illumination is understood to include those systems and methods that direct light at specified targets to achieve predetermined effects. The present invention provides a light source that does not generate excessive heat in the area being illuminated. The invention further provides facile alteration of light color being used for illumination. The invention further delivers illumination to a target material through a durable and manipulable apparatus.

The present invention provides a system for illuminating a material, including an LED system, a processor and a positioning system. The LED system is adapted for generating a range of frequencies within a spectrum, the processor is adapted for controlling the amount of electrical current supplied to the LED system, so that a particular amount of current supplied thereto generates a corresponding frequency within a spectrum, and the positioning system is capable of positioning the LED system in a spatial relationship with the material whereby the LED system illuminates the material. In one embodiment, the processor can be responsive to a signal relating to a feature of the material. In an embodiment, the positioning system can be capable of being directed by a part of an operator's body. In another embodiment, the positioning system can include a remote control system. In another embodiment, the illumination system described herein can include a robotic vision system.

The present invention provides a method for illuminating a material including the steps of providing an LED system, providing a processor, positioning the LED system in a spatial relationship with the material whereby the LED system illuminates the material, and producing light from the LED system. As described above, the LED system is adapted for generating a range of frequencies within a spectrum, and the processor is adapted for controlling the amount of electrical current supplied to the LED system, so that a particular amount of current supplied thereto generates a corresponding color within the spectrum. In one practice, the method can include providing an image capture system, wherein the image capture system is adapted for recording an image of the material. A practice of the method can include the steps of determining the range of frequencies within the spectrum for illuminating the material, and controlling the LED system to generate the corresponding color within the spectrum. The material being illuminated by these methods can include a biological entity. The biological entity can include a living organism. A method of the disclosed invention can include the steps of selecting an illumination condition to be produced in the material, illuminating the material with a range of frequencies produced by the LED system, and selecting from the range of frequencies produced by the LED system a set of colors, whereby the set of colors produces in the material said illumination condition. A practice of the methods of this invention can include a further step of illuminating the material with the selected set of colors.

The present invention provides a method for evaluating a material, including the steps of selecting an area of the material for evaluation, illuminating the area of the material with an LED system, determining at least one characteristic of a light reflected from the area, wherein the characteristic is selected from the group including color and intensity, and comparing the characteristic of the light reflected from the area with a set of known light parameters, whereby the set of known light parameters relates to a feature of said material. According to one practice of the method, the set of known light parameters relates to an abnormal feature of the material. In one embodiment, the material being evaluated comprises a biological entity.

The present invention provides a system for illuminating a body part, including a power source, an LED system connected to the power source, said LED system being adapted for illuminating the body organ, a medical instrument adapted for positioning the LED system in proximity to the body part to illuminate the body part, and a microprocessor for controlling the LED system. In one embodiment, the microprocessor is responsive to a signal relating to feature of the body part. The feature of the body part can be a structural condition. In one embodiment, the body part is illuminated in vivo. In one embodiment, the body part includes a lumen. In an embodiment, the medical instrument is adapted for insertion within a body cavity.

The present invention provides a method for diagnosing a condition of a body part, including the steps of selecting an area of the body part for evaluation, illuminating the area of the body part with an LED system, determining at least one characteristic of a light reflected from the area, wherein the characteristic is selected from the group including color and intensity, and comparing the characteristic of the light reflected from the area with a set of known light parameters, wherein the set of known light parameters relates to the condition of the body part. In one practice of the method, the set of known light parameters relates to a pathological condition of the body part. The method can include the additional step of administering an agent to a patient, wherein the agent is delivered to the body part, and whereby the agent alters the characteristic of the light reflected from the area of the body part.

The present invention provides a method for effecting a change in a material, including the steps of providing an LED system for generating a range of frequencies-within a spectrum, selecting from the range of colors a set of colors, whereby the set of colors produces in the material the change, illuminating the material with the LED system for a period of time predetermined to be effective in producing the change. In one embodiment, the material being illuminated can comprise a biological entity. The biological entity can comprise a living organism. The living organism can be a vertebrate. In one practice, the method can include the step of illuminating the an environment surrounding the living organism.

The present invention provides a method for treating a condition of a patient, including the steps of providing an LED system comprising a plurality of color-emitting semiconductor dies for generating a range of frequencies within a spectrum, selecting from the range of colors a set of colors, whereby the set of colors produces in the patient a therapeutic effect, and illuminating an area of the patient with the set of colors for a period of time predetermined to be effective in producing the therapeutic effect. In one embodiment, the area of the patient comprises an external surface of the patient. In one embodiment, the area of the patient comprises a body part. According to one practice of these methods, an agent can be administered to a patient, wherein the agent is delivered to the area of the patient, and whereby the agent alters the therapeutic effect achieved by illuminating the area of the patient with the set of colors.

The present invention provides an illumination system, including a power terminal, an LED system, a current sink coupled to the LED system, the current sink comprising an input responsive to an activation signal that enables flow of current through the current sink, an addressable controller having an alterable address, the controller coupled to the input and having a timer for generating the activation signal for a predefined portion of a timing cycle, the addressable controller further comprising a data receiver corresponding to the alterable address and indicative of the predefined portion of the timing cycle, and a positioning system capable of positioning the LED system in a spatial relationship with a material whereby the LED system illuminates the material.

Other practices and embodiments of the invention will, in part, be set forth below and will, in part, be obvious to one of ordinary skill in these arts given the following descriptions.

DESCRIPTION OF THE DRAWINGS

FIG. 91 depicts an embodiment comprising a precision illumination system held in an operator's hand.

FIG. 92A depicts fruit-bearing plants illuminated by an array of LED systems.

FIG. 92B depicts fruit-bearing plants illuminated by natural light.

DETAILED DESCRIPTION

The structure and operation of various methods and systems that are embodiments of the invention will now be described. It should be understood that many other ways of practicing the invention herein are available, and the embodiments described herein are exemplary and not limiting.

Figure 1:
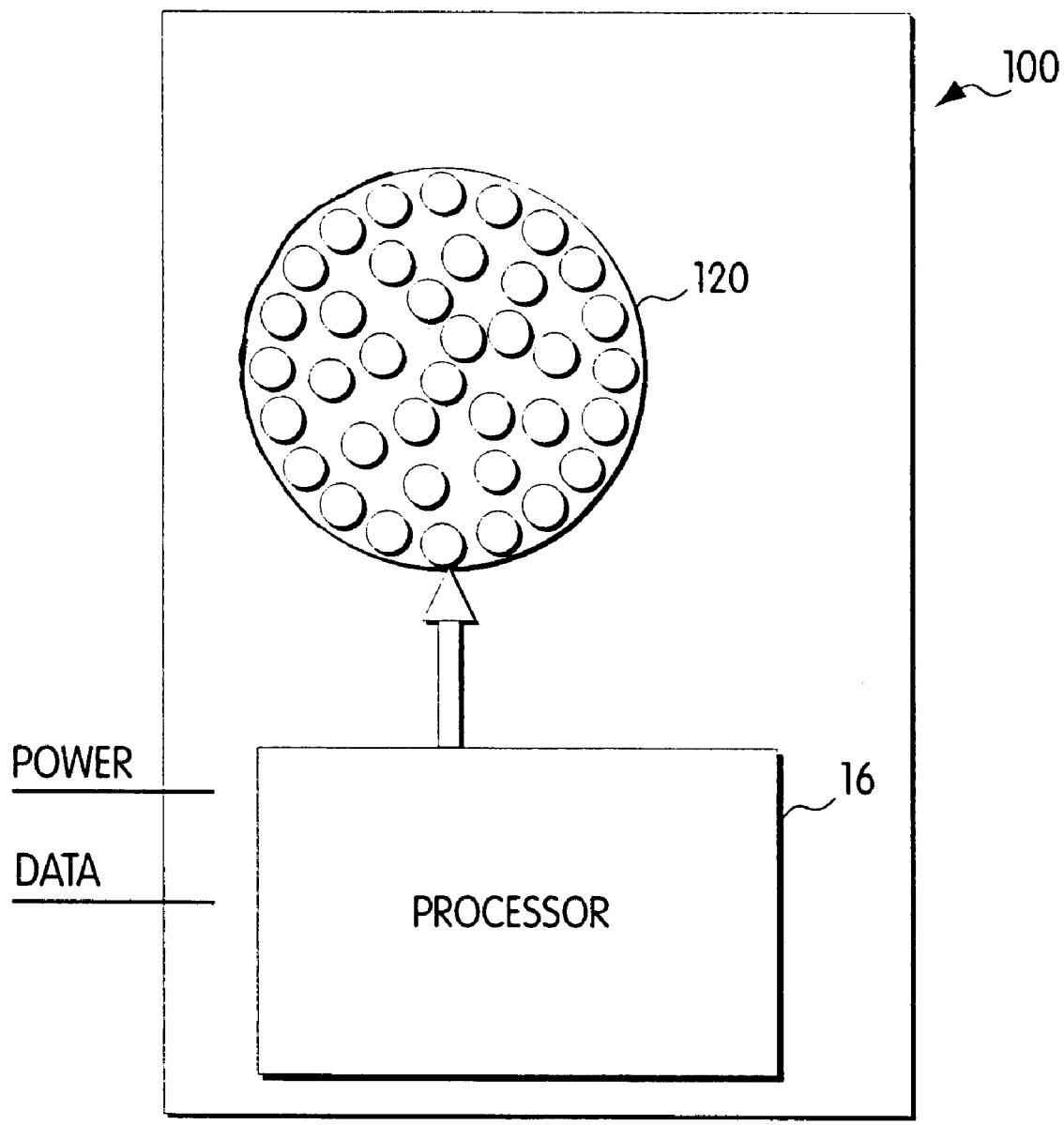
FIG. 1 depicts a light module of the present invention.

Referring to FIG. 1, a light module 100 is depicted in block diagram format. The light module 100 includes two components, a processor 16 and an LED system 120, which is depicted in FIG. 1 as an array of light emitting diodes. The term "processor" is used herein to refer to any method or system for processing in response to a signal or data and should be understood to encompass microprocessors, integrated circuits, computer software, computer hardware, electrical circuits, application specific integrated circuits, personal computers, chips, and other devices capable of providing processing functions. The LED system 120 is controlled by the processor 16 to produce controlled illumination. In particular, the processor 16 controls the intensity of different color individual LEDs, semiconductor dies, or the like of the LED system 120 to produce illumination in any color in the spectrum. Instantaneous changes in color, strobing and other effects, more particularly described below, can be produced with light modules such as the light module 100 depicted in FIG. 1. The light module 100 may be made capable of receiving power and data. The light module 100, through the processor 16, may be made to provide the various functions ascribed to the various embodiments of the invention disclosed herein.

Figure 2:
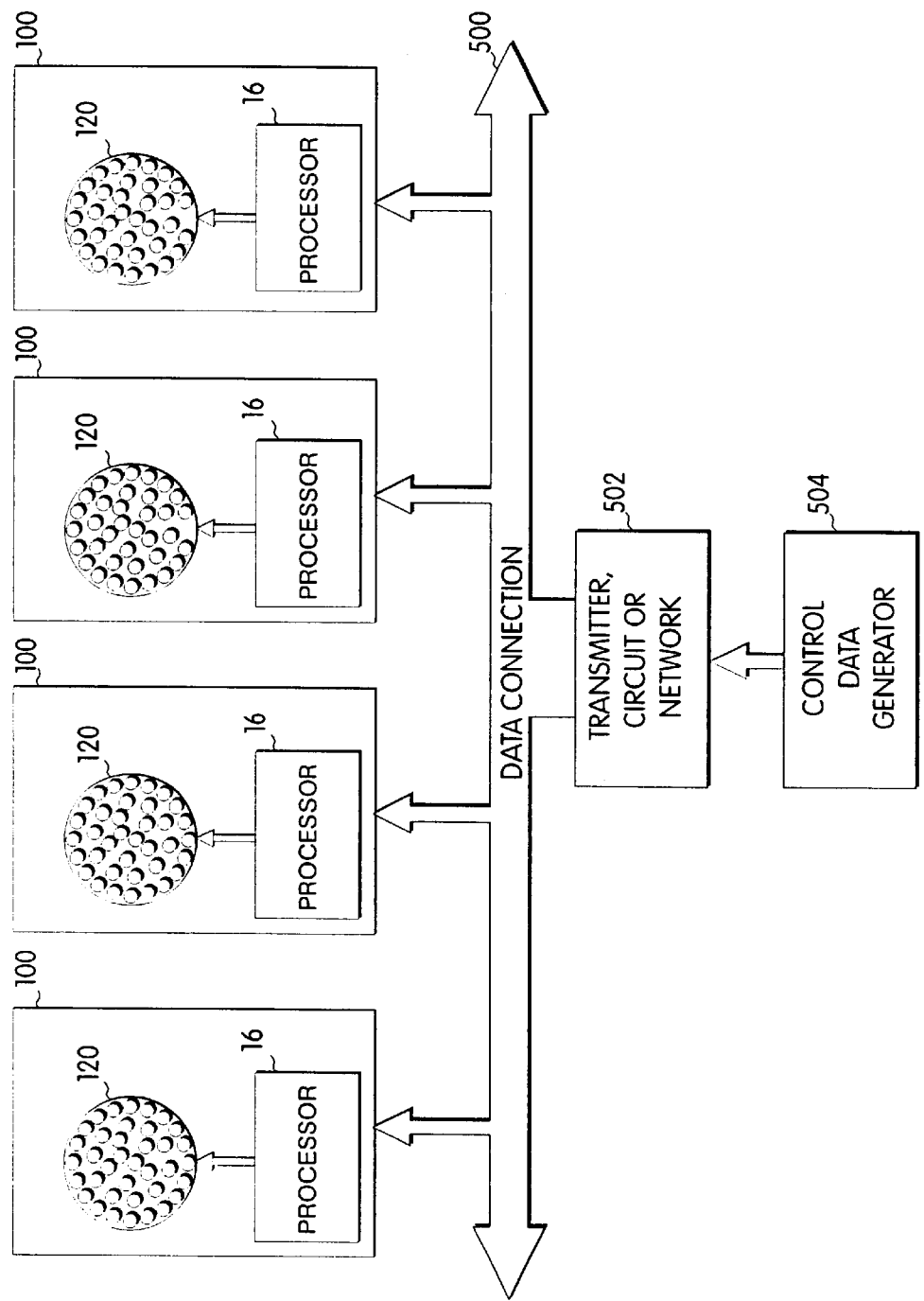
FIG. 2 depicts a light module of FIG. 1 in data connection with a generator of control data for the light module.

Referring to FIG. 2, the light module 100 may be constructed to be used either alone or as part of a set of such light modules 100. An individual light module 100 or a set of light modules 100 can be provided with a data connection 500 to one or more external devices, or, in certain embodiments of the invention, with other light modules 100. As used herein, the term "data connection" should be understood to encompass any system for delivering data, such as a network, a data bus, a wire, a transmitter and receiver, a circuit, a video tape, a compact disc, a DVD disc, a video tape, an audio tape, a computer tape, a card, or the like. A data connection may thus include any system of method to deliver data by radio frequency, ultrasonic, auditory, infrared, optical, microwave, laser, electromagnetic, or other transmission or connection method or system. That is, any use of the electromagnetic spectrum or other energy transmission mechanism could provide a data connection as disclosed herein. In embodiments of the invention, the light module 100 may be equipped with a transmitter, receiver, or both to facilitate communication, and the processor 16 may be programmed to control the communication capabilities in a conventional manner. The light modules 100 may receive data over the data connection 500 from a transmitter 502, which may be a conventional transmitter of a communications signal, or may be part of a circuit or network connected to the light module 100. That is, the transmitter 502 should be understood to encompass any device or method for transmitting data to the light module 100. The transmitter 502 may be linked to or be part of a control device 504 that generates control data for controlling the light modules 100. In an embodiment of the invention, the control device 504 is a computer, such as a laptop computer. The control data may be in any form suitable for controlling the processor 16 to control the LED system 120. In embodiment of the invention, the control data is formatted according to the DMX-512 protocol, and conventional software for generating DMX-512 instructions is used on a laptop or personal computer as the control device 504 to control the light modules 100. The light module 100 may also be provided with memory for storing instructions to control the processor 16, so that the light module 100 may act in stand alone mode according to pre-programmed instructions.

Figure 3:
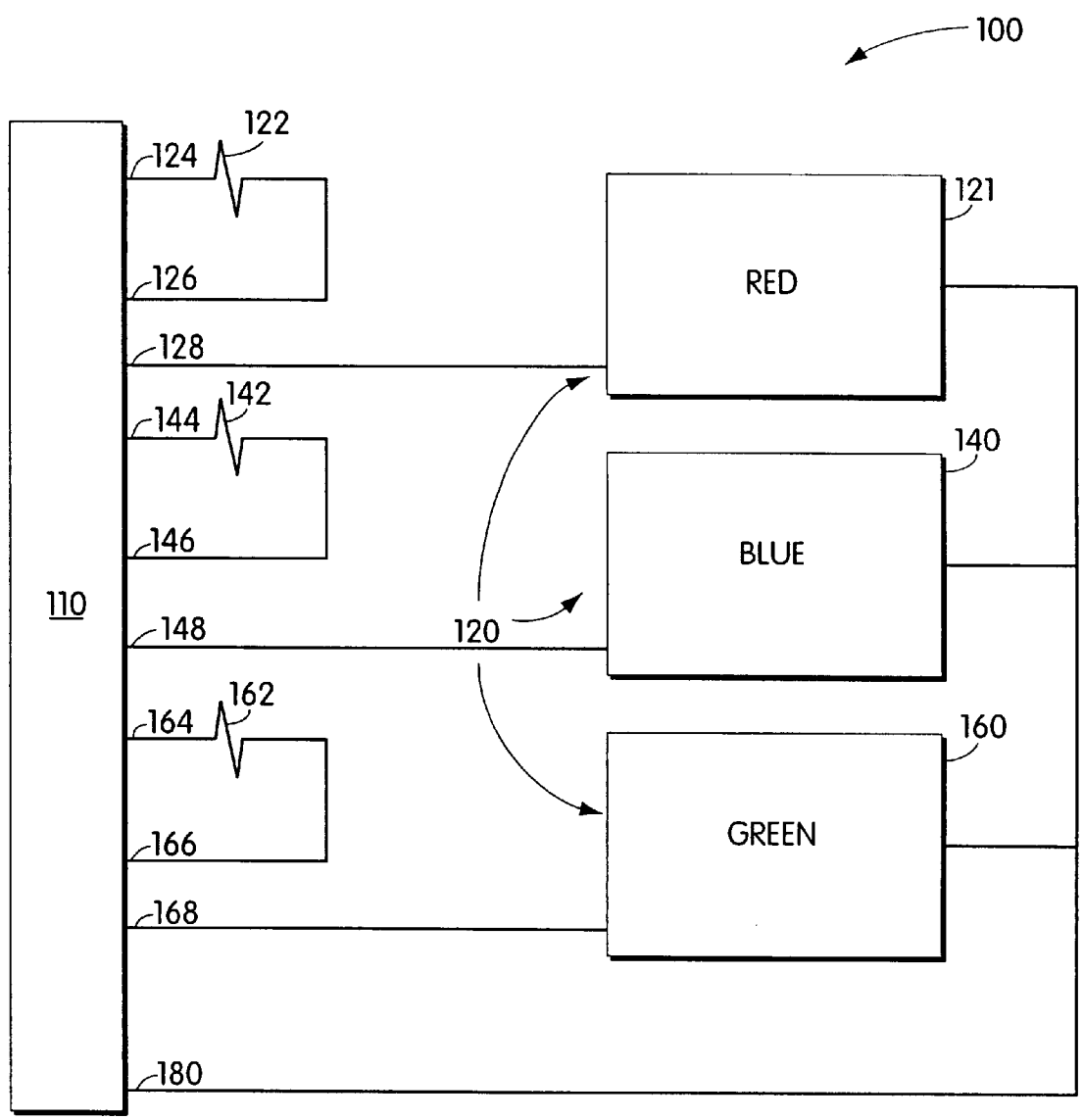
FIG. 3 depicts a schematic of an embodiment of light module.
Figure 4:
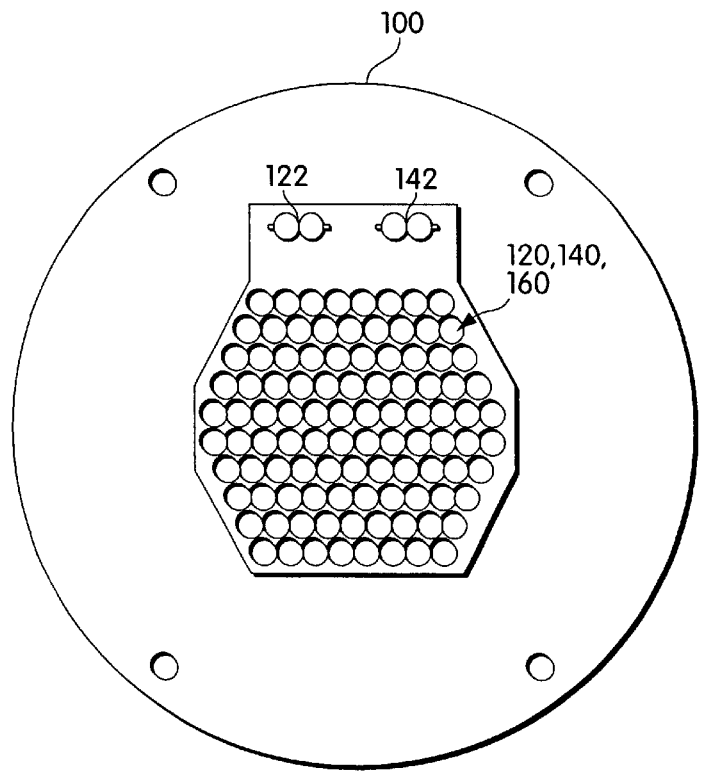
FIG. 4 depicts an array of LEDs in an embodiment of a light module.
Figure 5:
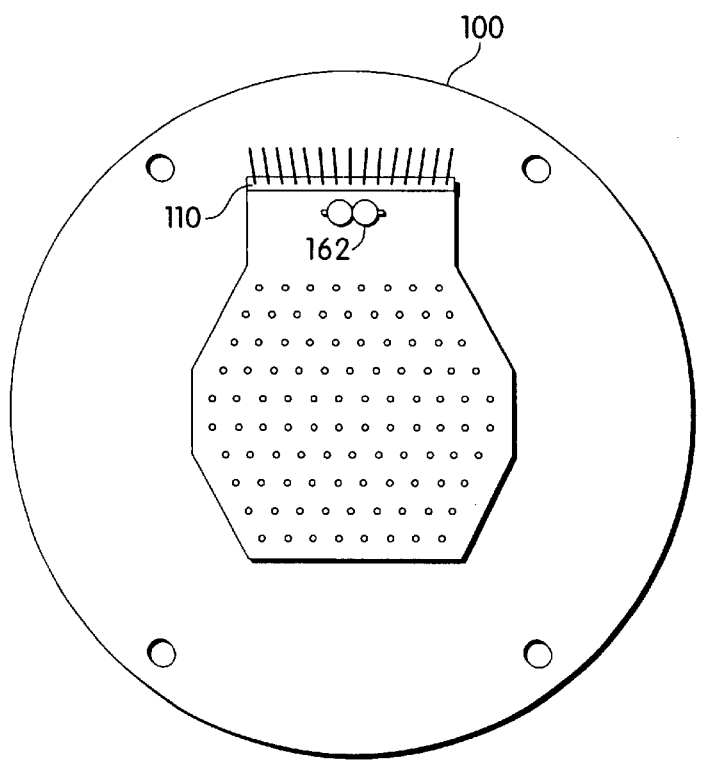
FIG. 5 depicts a power module in an embodiment of the invention.

Turning to FIG. 3, shown is an electrical schematic representation of the light module 100 in one embodiment of the present invention. FIGS. 4 and 5 show the LED-containing side and the electrical connector side of an exemplary embodiment of such a light module 100. Light module 100 may be constructed, in an embodiment, as a self-contained module that is configured to be a standard item interchangeable with any similarly constructed light module. Light module 100 contains a ten-pin electrical connector 110 of the general type. In this embodiment, the connector 110 contains male pins adapted to fit into a complementary ten-pin connector female assembly, to be described below. Pin 180 is the power supply. A source of DC electrical potential enters light module 100 on pin 180. Pin 180 is electrically connected to the anode end of light emitting diode (LED) sets 120, 140 and 160 to establish a uniform high potential on each anode end.

LED system 120 includes a set 121 of red LEDs, a set 140 of blue LEDs, and a set 160 of green LEDs. The LEDs may be conventional LEDs, such those obtainable from the Nichia America Corporation. These LEDs are primary colors, in the sense that such colors when combined in preselected proportions can generate any color in the spectrum. While use of three primary colors is preferred, it will be understood that the present invention will function nearly as well with only two primary colors to generate a wide variety of colors in the spectrum. Likewise, while the different primary colors are arranged herein on sets of uniformly colored LEDS, it will be appreciated that the same effect may be achieved with single LEDs containing multiple color-emitting semiconductor dies. LED sets 121, 140 and 160 each preferably contains a serial/parallel array of LEDs in the manner described by Okuno in U.S. Pat. No. 4,298,869, incorporated herein by reference. In the present embodiment, LED system 120 includes LED set 121, which contains three parallel connected rows of nine red LEDs (not shown), as well as LED sets 140 and 160, which each contain five parallel connected rows of five blue and green LEDS, respectively (not shown). It is understood by those in the art that, in general, each red LED drops the potential in the line by a lower amount than each blue or green LED, about two and one-tenth V, compared to four volts, respectively, which accounts for the different row lengths. This is because the number of LEDs in each row is determined by the amount of voltage drop desired between the anode end at the power supply voltage and the cathode end of the last LED in the row. Also, the parallel arrangement of rows is a fail-safe measure that ensures that the light module 100 will still function even if a single LED in a row fails, thus opening the electrical circuit in that row. The cathode ends of the three parallel rows of nine red LEDs in LED set 121 are then connected in common, and go to pin 128 on connector 110. Likewise, the cathode ends of the five parallel rows of five blue LEDs in LED set 140 are connected in common, and go to pin 148 on connector 110. The cathode ends of the five parallel rows of five green LEDs in LED set 160 are connected in common, and go to pin 168 on connector 110. Finally, on light module 100, each LED set in the LED system 120 is associated with a programming resistor that combines with other components, described below, to program the maximum current through each set of LEDS. Between pin 124 and 126 is resistor 122, six and two-tenths ohms. Between pin 144 and 146 is resistor 142, four and seven-tenths ohms. Between pin 164 and 166 is resistor 162, four and seven-tenths ohms. Resistor 122 programs maximum current through red LED set 121, resistor 142 programs maximum current through blue LED set 140, and resistor 162 programs maximum current through green LED set 160. The values these resistors should take are determined empirically, based on the desired maximum light intensity of each LED set. In the embodiment depicted in FIG. 3, the resistances above program red, blue and green currents of seventy, fifty and fifty mA, respectively.

Figure 6:
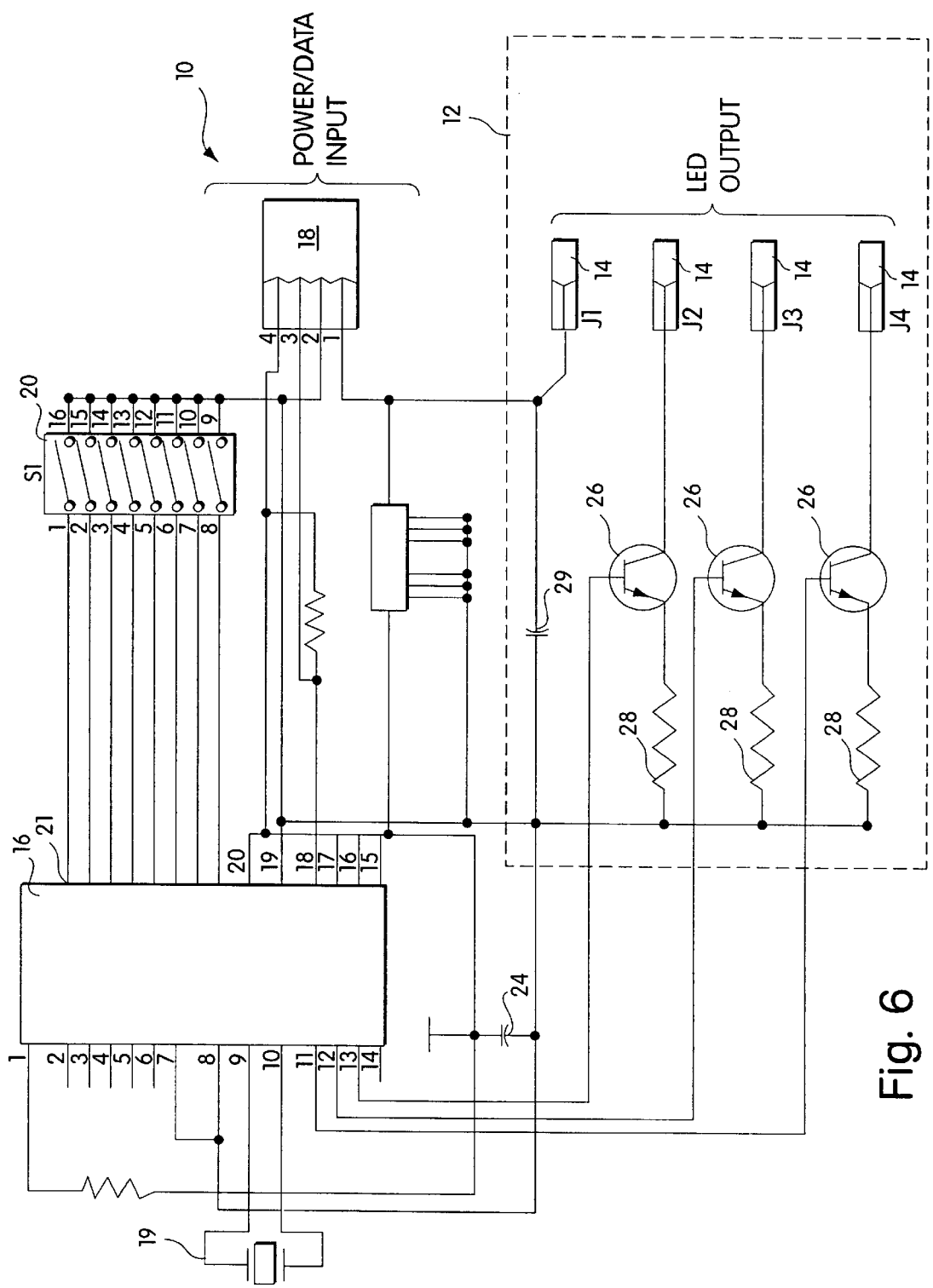
FIG. 6 depicts a circuit design for an embodiment of a light module.

As shown in FIG. 6, a circuit 10 for a digitally controlled LED-based light includes an LED assembly 12 containing LED output channels 14, which are controlled by the processor 16. Data and power are fed to the circuit 10 via power and data input unit 18. The address for the processor 16 is set by switch unit 20 containing switches which are connected to individual pins of pin set 21 of processor 16. An oscillator 19 provides a clock signal for processor 16 via pins 9 and 10 of the same.

In an embodiment of the invention, data and power input unit 18 has four pins, including a power supply 1, which may be a twenty-four volt LED power supply, a processor power supply 2, which may be a five volt processor power supply, a data in line 3 and a ground pin 4. The first power supply 1 provides power to LED channels 14 of LED assembly 12. The second processor power supply 2 may be connected to power supply input 20 of processor 16 to provide operating power for the processor 16 and also may be connected to a pin 1 of the processor 16 to tie the reset high. A capacitor 24, such as a one-tenth microfarad capacitor, may be connected between the processor power supply 2 and ground. The data line 3 may be connected to pin 18 of processor 16 and may be used to program and dynamically control the processor 16. The ground may be connected to pins 8 and 19 of the processor 16.

LED assembly 12 may be supplied with power from the LED power supply 1 and may contain a transistor-controlled LED channel 14. The LED channel 14 may supply power to at least one LED. As shown in FIG. 1, the LED assembly 12 may supply multiple LED channels 14 for different color LEDs (e.g., red, green and blue), with each LED channel 14 individually controlled by a transistor 26. However, it is possible that more than one channel 14 could be controlled by a single transistor 26

Figure 7:
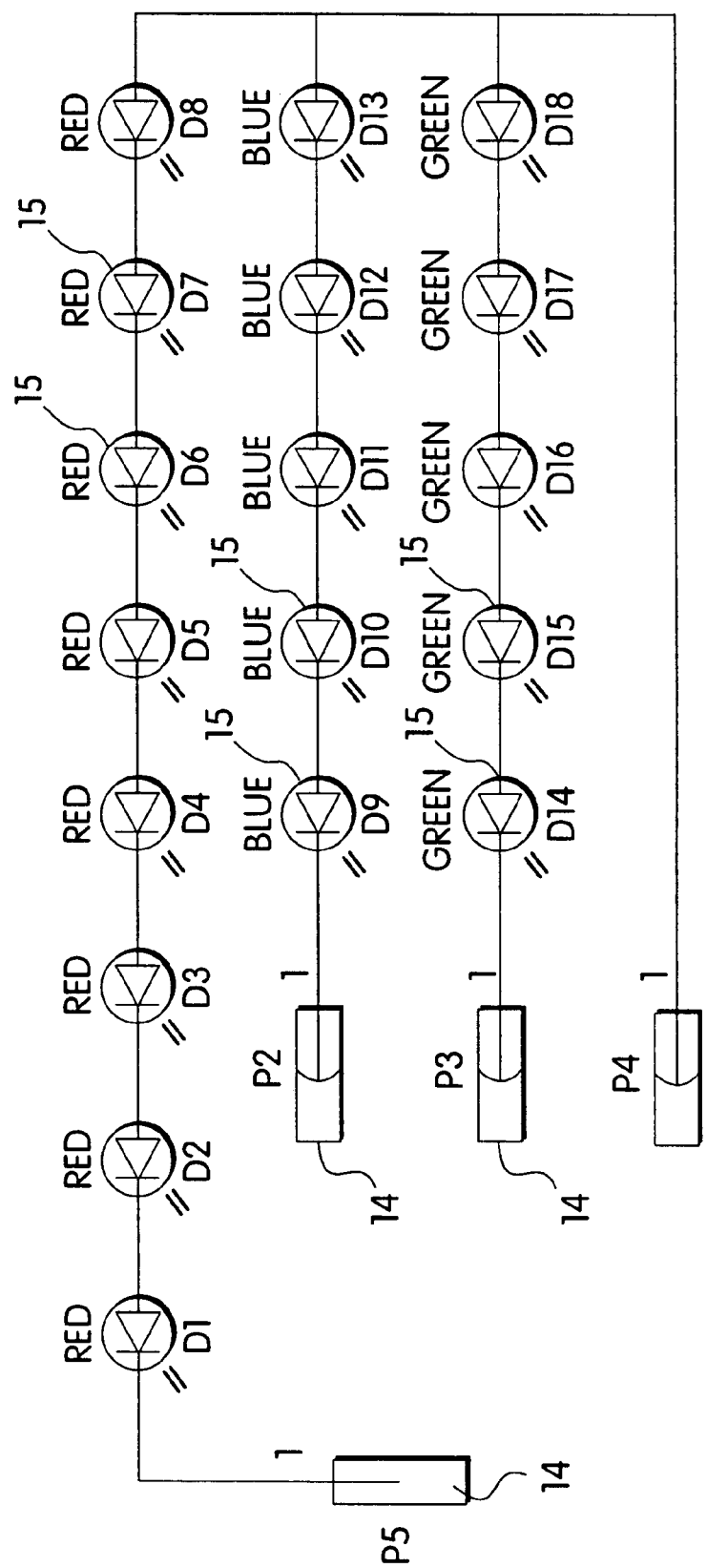
FIG. 7 depicts a circuit design for an array of LEDs in a light module in an embodiment of the invention.

As shown in FIG. 7, LEDs 15 may be arrayed in series to receive signals through each of the LED channels 14. In the embodiment depicted in FIG. 7, a series of LEDs of each different color (red, green and blue) is connected to an output LED channel 14 from the circuit 10 of FIG. 6. LEDs 15 may also be arrayed to receive data according to a protocol such as the DMX-512 protocol, so that many individual LEDs 15 may be controlled through programming the processor 16.

Referring again to FIG. 6, gates of transistors 26 are controlled by processor 16 to thereby control operation of the LED channels 14 and the LEDs 15. In the illustrated example, the output of the microprocessor appears on pins 12, 13 and 14 of processor 16, which are then connected to the gates of the LED channels 14 of the LEDs 15. Additional pins of processor 16 could be used to control additional LEDs. Likewise, different pins of processor 16 could be used to control the illustrated LEDs 15, provided that appropriate modifications were made to the instructions controlling operation of processor 16.

A resistor 28 may be connected between transistor 26 and ground. In the illustrated example, resistor 28 associated with the red LED has a resistance value of sixty-two ohms, and the resistors associated with the green and blue LEDs each have a resistance of ninety ohms. A capacitor 29 may be connected between the first LED power supply 1 and ground. In the illustrated embodiment, this capacitor has a value of one-tenth of a microfarad.

Processor 16 may be connected to an oscillator 19. One acceptable oscillator is a crystal tank circuit oscillator which provides a twenty megaHertz clock. This oscillator may be connected to pins 9 and 10 of processor 16. It is also possible to use an alternative oscillator. Primary considerations associated with selection of an oscillator are consistency, operating speed and cost.

In an embodiment of the invention, processor 16 is a programmable integrated circuit, or PIC chip, such as a PIC 16C63 or PIC 16C66 manufactured by Microchip Technology, Inc. A complete description of the PIC 16C6X series PIC chip (which includes both the PIC 16C63 and PIC 16C66) is attached to the U.S. Provisional Patent Application filed on Dec. 17, 1997, entitled Digitally Controlled Light Emitting Diode Systems and Methods, to Mueller and Lys, and is incorporated by reference herein. Although the PIC 16C66 is currently the preferred microprocessor, any processor capable of controlling the LEDs 15 of LED assembly 12 may be used. Thus, for example, an application specific integrated circuit (ASIC) may be used instead of processor 16. Likewise, other commercially available processors may also be used without departing from this invention.

Figure 8:
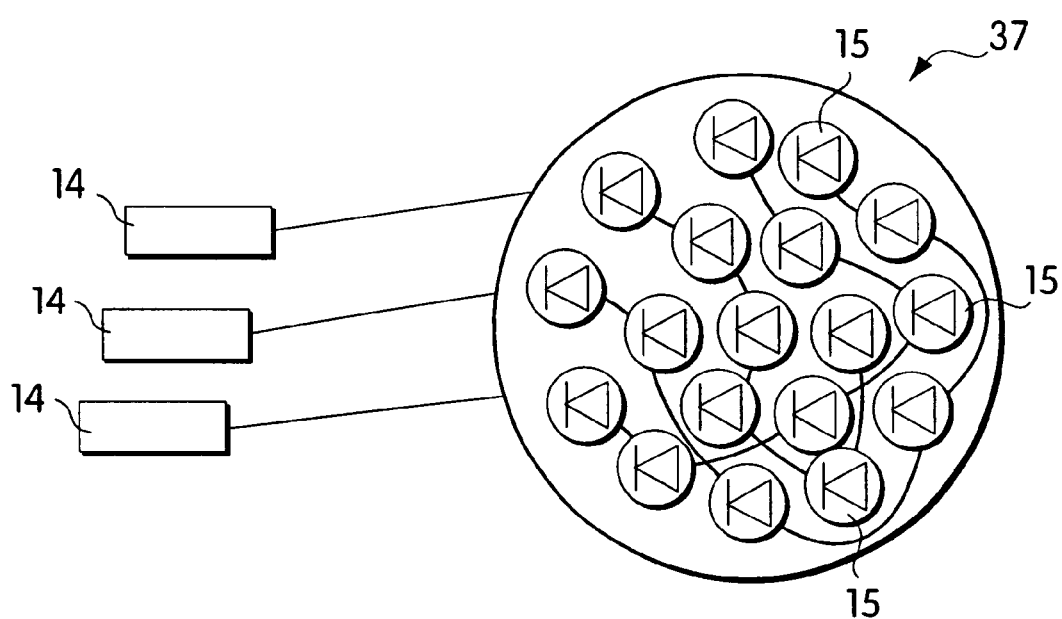
FIG. 8 depicts an array of LEDs that may be associated with a circuit such as that of FIG. 6.

In an embodiment of the invention depicted in FIG. 8, a total of eighteen LEDs 15 are placed in three series according to color, and the series are arranged to form a substantially circular array 37. The processor 16 can be used to separately control the precise intensity of each color series of the LEDs 15, so that any color combination, and thus any color, can be produced by the array 37.

The responsiveness of LEDs to changing electrical signals permits computer control of the LEDs via control of the electrical impulses delivered to the LEDs. Thus, by connecting the LED to a power source via a circuit that is controlled by a processor, the user may precisely control the color and intensity of the LED. Due to the relatively instantaneous response of LEDs to changes in electrical impulses, the color and intensity state of an LED may be varied quite rapidly by changes in such impulses. By placing individual LEDs into arrays and controlling individual LEDs, very precise control of lighting conditions can be obtained through use of a microprocessor. The processor 16 may be controlled by conventional means, such as a computer program, to send the appropriate electrical signals to the appropriate LED at any given time. The control may be digital, so that precise control is possible. Thus, overall lighting conditions may be varied in a highly controlled manner.

Figure 9:
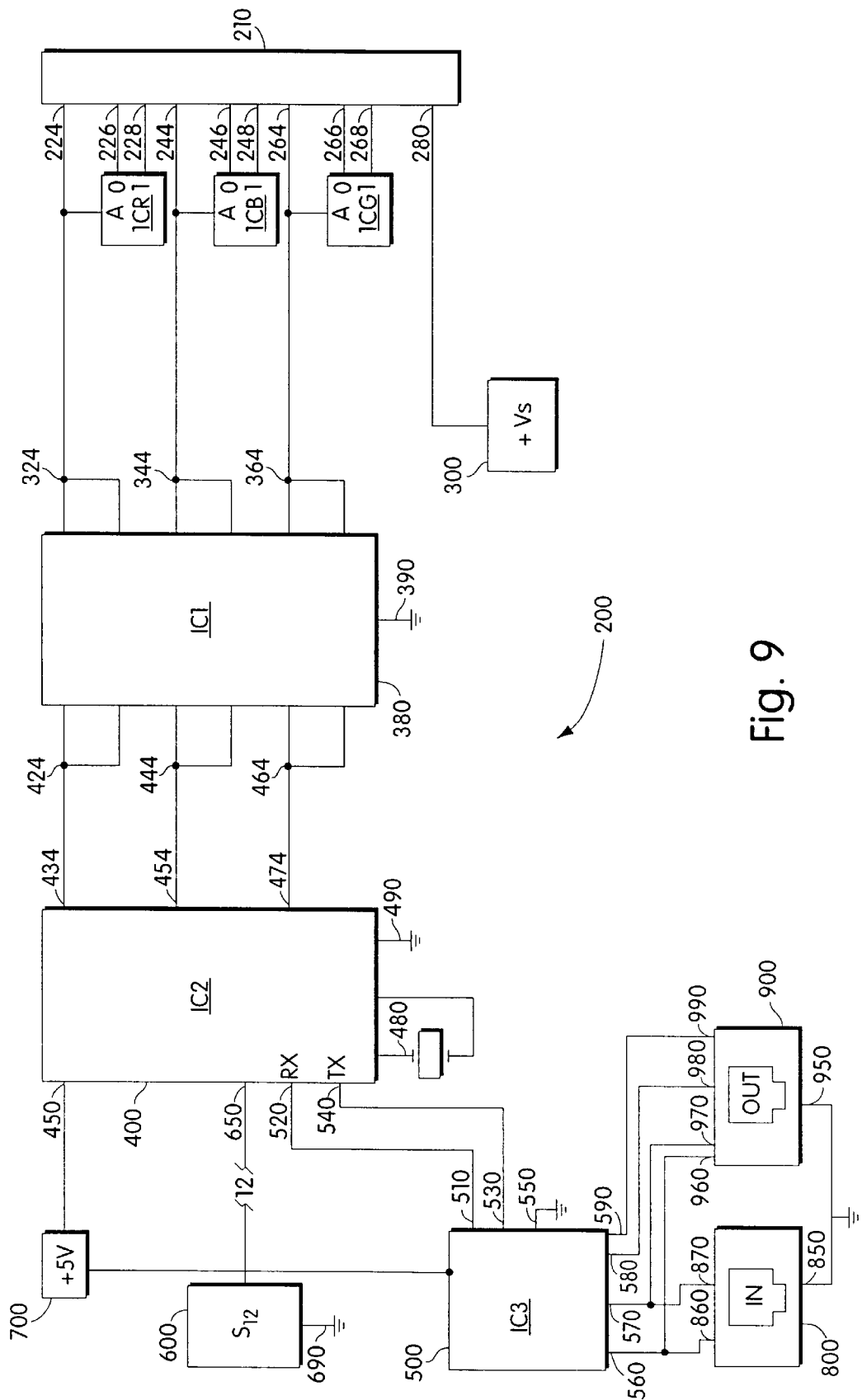
FIG. 9 depicts a schematic of the electrical design of an embodiment of a light module.
Figure 10:
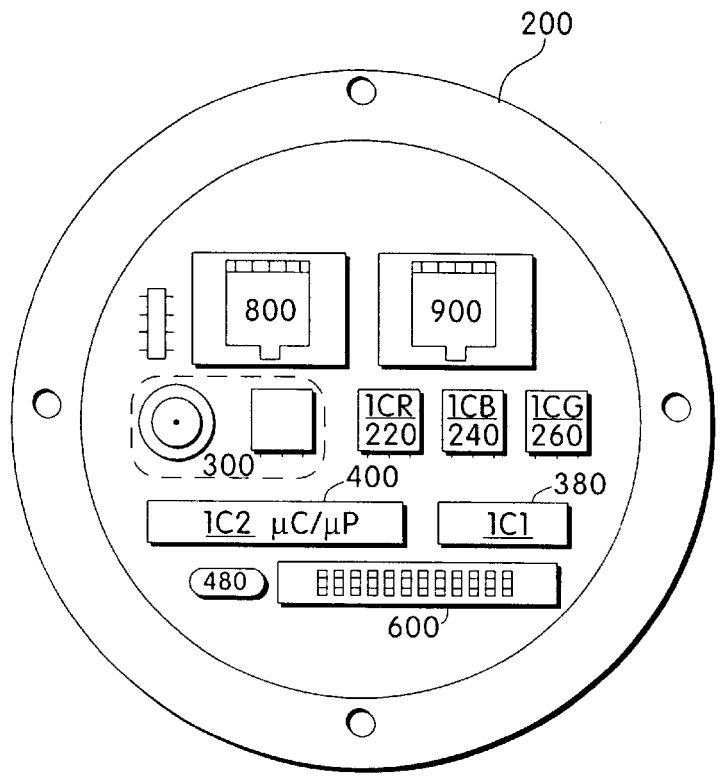
FIG. 10 depicts a power module for a light module of the invention.
Figure 11:
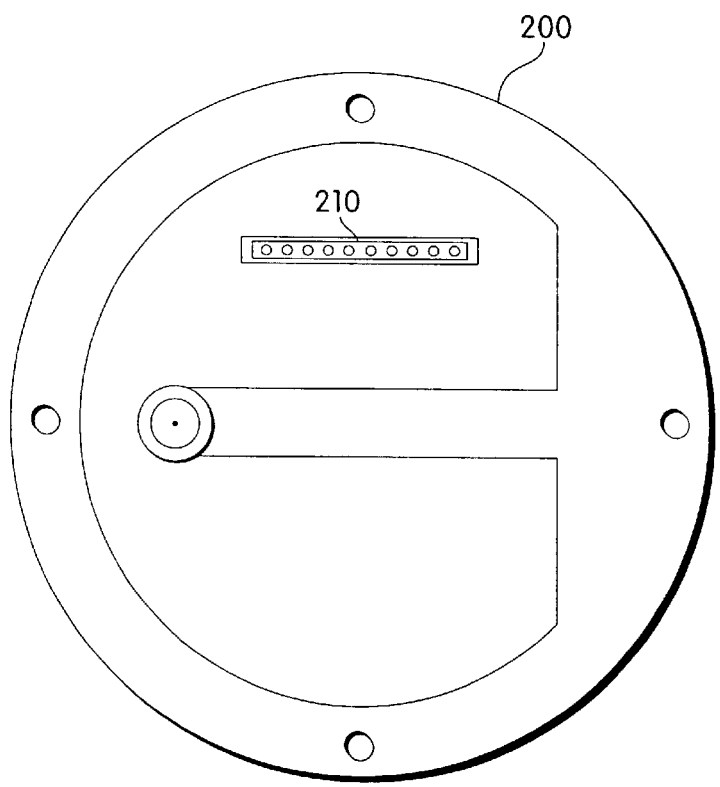
FIG. 11 depicts another view of the power module of FIG. 10.

With the electrical structure of an embodiment of light module 100 described, attention will now be given to the electrical structure of an example of a power module 200 in one embodiment of the invention, shown in FIG. 9. FIGS. 10 and 11 show the power terminal side and electrical connector side of an embodiment of power module 200. Like light module 100, power module 200 may be self contained. Interconnection with a male pin set 110 is achieved through complementary female pin set 210. Pin 280 connects with pin 180 for supplying power, delivered to pin 280 from supply 300. Supply 300 is shown as a functional block for simplicity. In actuality, supply 300 can take numerous forms for generating a DC voltage. In the present embodiment, supply 300 provides twenty-four volts through a connection terminal (not shown), coupled to pin 280 through transient protection capacitors (not shown) of the general type. It will be appreciated that supply 300 may also supply a DC voltage after rectification and/or voltage transformation of an AC supply, as described more fully in U.S. Pat. No. 4,298,869.

Also connected to pin connector 210 are three current programming integrated circuits, ICR 220, ICB 240 and ICG 260. Each of these may be a three terminal adjustable regulator, such as part number LM317B, available from the National Semiconductor Corporation, Santa Clara, Calif. The teachings of the LM317 datasheet are incorporated herein by reference. Each regulator contains an input terminal, an output terminal and an adjustment terminal, labeled I, O, and A, respectively. The regulators function to maintain a constant maximum current into the input terminal and out of the output terminal. This maximum current is pre-programmed by setting a resistance between the output and the adjustment terminals. This is because the regulator will cause the voltage at the input terminal to settle to whatever value is needed to cause one and twenty-five hundredths volts to appear across the fixed current set resistor, thus causing constant current to flow. Since each functions identically, only ICR 220 will now be described. First, current enters the input terminal of ICR 220 from pin 228. Pin 228 in the power module is coupled to pin 128 in the light module and receives current directly from the cathode end of the red LED system 121. Since resistor 122 is ordinarily disposed between the output and adjustment terminals of ICR 220 through pins 224/124 and 226/126, resistor 122 programs the amount of current regulated by ICR 220. Eventually, the current output from the adjustment terminal of ICR 220 enters a Darlington driver. In this way, ICR 220 and associated resistor 122 program the maximum current through red LED system 120. Similar results are achieved with ICB 240 and resistor 142 for blue LED set 140, and with ICG 260 and resistor 162 for green LED set 160.

The red, blue and green LED currents enter another integrated circuit, ICI 380, at respective nodes 324, 344 and 364. ICI 380 may be a high current/voltage Darlington driver, such as part no. DS2003, available from the National Semiconductor Corporation, Santa Clara, Calif. ICI 380 may be used as a current sink, and may function to switch current between respective LED sets and ground 390. As described in the DS2003 datasheet, incorporated herein by reference, ICI contains six sets of Darlington transistors with appropriate on-board biasing resistors. As shown, nodes 324, 344 and 364 couple the current from the respective LED sets to three pairs of these Darlington transistors, in the well known manner to take advantage of the fact that the current rating of ICI 380 may be doubled by using pairs of Darlington transistors to sink respective currents. Each of the three on-board Darlington pairs is used in the following manner as a switch. The base of each Darlington pair is coupled to signal inputs 424, 444 and 464, respectively. Hence, input 424 is the signal input for switching current through node 324, and thus the red LED set 121. Input 444 is the signal input for switching current though node 344, and thus the blue LED set 140. Input 464 is the signal input for switching current through node 364, and thus the green LED set 160. Signal inputs 424, 444 and 464 are coupled to respective signal outputs 434, 454 and 474 on microcontroller IC2 400, as described below. In essence, when a high frequency square wave is incident on a respective signal input, ICI 380 switches current through a respective node with the identical frequency and duty cycle. Thus, in operation, the states of signal inputs 424, 444 and 464 directly correlate with the opening and closing of the power circuit through respective LED sets 121, 140 and 160.

The structure and operation of microcontroller IC2 400 in the embodiment of FIG. 9 will now be described. Microcontroller IC2 400 is preferably a MICROCHIP brand PIC16C63, although almost any properly programmed microcontroller or microprocessor can perform the software functions described herein. The main function of microcontroller IC2 400 is to convert numerical data received on serial Rx pin 520 into three independent high frequency square waves of uniform frequency but independent duty cycles on signal output pins 434, 454 and 474. The FIG. 9 representation of microcontroller IC2 400 is partially stylized, in that persons of skill in the art will appreciate that certain of the twenty-eight standard pins have been omitted or combined for greatest clarity. Further detail as to a similar microcontroller is provided in connection with FIG. 12 for another embodiment of the invention.

Microcontroller IC2 400 is powered through pin 450, which is coupled to a five volt source of DC power 700. Source 700 is preferably driven from supply 300 through a coupling (not shown) that includes a voltage regulator (not shown). An exemplary voltage regulator is the LM340 3-terminal positive regulator, available from the National Semiconductor Corporation, Santa Clara, Calif. The teachings of the LM340 datasheet are hereby incorporated by reference. Those of skill in the art will appreciate that most microcontrollers, and many other independently powered digital integrated circuits, are rated for no more than a five volt power source. The clock frequency of microcontroller IC2 400 is set by crystal 480, coupled through appropriate pins. Pin 490 is the microcontroller IC2 400 ground reference.

Switch 600 is a twelve position dip switch that may be alterably and mechanically set to uniquely identify the microcontroller IC2 400. When individual ones of the twelve mechanical switches within dip switch 600 are closed, a path is generated from corresponding pins 650 on microcontroller IC2 400 to ground 690. Twelve switches create twenty-four possible settings, allowing any microcontroller IC2 400 to take on one of four thousand ninety-six different IDs, or addresses. In the embodiment of FIG. 9, only nine switches are actually used because the DMX-512 protocol is employed.

Once switch 600 is set, microcontroller IC2 400 "knows" its unique address ("who am "), and "listens" on serial line 520 for a data stream specifically addressed to it. A high speed network protocol, such as a DMX protocol, may be used to address network data to each individually addressed microcontroller IC2 400 from a central network controller (not shown). The DMX protocol is described in a United States Theatre Technology, Inc. publication entitled "DMX512/1990 Digital Data Transmission Standard for Dimmers and Controllers," incorporated herein by reference. Basically, in the network protocol used herein, a central controller (not shown) creates a stream of network data consisting of sequential data packets.

Each packet first contains a header, which is checked for conformance to the standard and discarded, followed by a stream of sequential characters representing data for sequentially addressed devices. For instance, if the data packet is intended for light number fifteen, then fourteen characters from the data stream will be discarded, and the device will save character number fifteen. If as in the preferred embodiment, more than one character is needed, then the address is considered to be a starting address, and more than one character is saved and utilized. Each character corresponds to a decimal number zero to two hundred fifty-five, linearly representing the desired intensity from Off to Full. (For simplicity, details of the data packets such as headers and stop bits are omitted from this description, and will be well appreciated by those of skill in the art.) This way, each of the three LED colors is assigned a discrete intensity value between zero and two hundred fifty-five. These respective intensity values are stored in respective registers within the memory of microcontroller IC2 400 (not shown). Once the central controller exhausts all data packets, it starts over in a continuous refresh cycle. The refresh cycle is defined by the standard to be a minimum of one thousand one hundred ninety-six microseconds, and a maximum of one second.

Microcontroller IC2 400 is programmed continually to "listen" for its data stream. When microcontroller IC2 400 is "listening," but before it detects a data packet intended for it, it is running a routine designed to create the square wave signal outputs on pins 434, 454 and 474. The values in the color registers determine the duty cycle of the square wave. Since each register can take on a value from zero to two hundred fifty five, these values create two hundred fifty six possible different duty cycles in a linear range from zero percent to one hundred percent. Since the square wave frequency is uniform and determined by the program running in the microcontroller IC2 400, these different discrete duty cycles represent variations in the width of the square wave pulses. This is known as pulse width modulation (PWM).

In one embodiment of the invention, the PWM interrupt routine is implemented using a simple counter, incrementing from zero to two hundred fifty-five in a cycle during each period of the square wave output on pins 434, 454 and 474. When the counter rolls over to zero, all three signals are set high. Once the counter equals the register value, signal output is changed to low. When microcontroller IC2 400 receives new data, it freezes the counter, copies the new data to the working registers, compares the new register values with the current count and updates the output pins accordingly, and then restarts the counter exactly where it left off. Thus, intensity values may be updated in the middle of the PWM cycle. Freezing the counter and simultaneously updating the signal outputs has at least two advantages. First, it allows each lighting unit to quickly pulse/strobe as a strobe light does. Such strobing happens when the central controller sends network data having high intensity values alternately with network data having zero intensity values at a rapid rate. If one restarted the counter without first updating the signal outputs, then the human eye would be able to perceive the staggered deactivation of each individual color LED that is set at a different pulse width. This feature is not of concern in incandescent lights because of the integrating effect associated with the heating and cooling cycle of the illumination element. LEDS, unlike incandescent elements, activate and deactivate essentially instantaneously in the present application. The second advantage is that one can "dim" the LEDs without the flickering that would otherwise occur if the counter were reset to zero. The central controller can send a continuous dimming signal when it creates a sequence of intensity values representing a uniform and proportional decrease in light intensity for each color LED. If one did not update the output signals before restarting the counter, there is a possibility that a single color LED will go through nearly two cycles without experiencing the zero current state of its duty cycle. For instance, assume the red register is set at 4 and the counter is set at 3 when it is frozen. Here, the counter is frozen just before the "off part" of the PWM cycle is to occur for the red LEDS. Now assume that the network data changes the value in the red register from four to two and the counter is restarted without deactivating the output signal. Even though the counter is greater than the intensity value in the red register, the output state is still "on", meaning that maximum current is still flowing through the red LEDS. Meanwhile, the blue and green LEDs will probably turn off at their appropriate times in the PWM cycle. This would be perceived by the human eye as a red flicker in the course of dimming the color intensities. Freezing the counter and updating the output for the rest of the PWM cycle overcomes these disadvantages, ensuring the flicker does not occur.

The microprocessors that provide the digital control functions of the LEDs of the present invention may be responsive to any electrical signal; that is, external signals may be used to direct the microprocessors to control the LEDs in a desired manner. A computer program may control such signals, so that a programmed response to given input signals is possible. Thus, signals may be generated that turn individual LEDs on and off, that vary the color of individual LEDs throughout the color spectrum, that strobe or flash LEDs at predetermined intervals that are controllable to very short time intervals, and that vary the intensity of light from a single LED or collection of LEDs. A variety of signal-generating devices may be used in accordance with the present invention to provide significant benefits to the user. Input signals can range from simple on-off or intensity signals, such as that from a light switch or dial, or from a remote control, to signals from detectors, such as detectors of ambient temperature or light. The precise digital control of arrayed LEDs in response to a wide range of external signals permits applications in a number of technological fields in accordance with the present invention.

The network interface for microcontroller IC2 400 will now be described. Jacks 800 and 900 are standard RJ-45 network jacks. Jack 800 is used as an input jack, and is shown for simplicity as having only three inputs: signal inputs 860, 870 and ground 850. Network data enters jack 800 and passes through signal inputs 860 and 870. These signal inputs are then coupled to IC3 500, which is an RS-485/RS-422 differential bus repeater of the standard type, preferably a DS96177 from the National Semiconductor Corporation, Santa Clara, Calif. The teachings of the DS96177 datasheet are hereby incorporated by reference. The signal inputs 860, 870 enter IC3 500 at pins 560, 570. The data signal is passed through from pin 510 to pin 520 on microcontroller IC2 400. The same data signal is then returned from pin 540 on IC2 400 to pin 530 on IC3 500. Jack 900 is used as an output jack and is shown for simplicity as having only five outputs: signal outputs 960, 970, 980, 990 and ground 950. Outputs 960 and 970 are split directly from input lines 860 and 870, respectively. Outputs 980 and 990 come directly from IC3 500 pins 580 and 590, respectively. It will be appreciated that the foregoing assembly enables two network nodes to be connected for receiving the network data. Thus, a network may be constructed as a daisy chain, if only single nodes are strung together, or as a tree, if two or more nodes are attached to the output of each single node.

From the foregoing description, one can see that an addressable network of LED illumination or display units can be constructed from a collection of power modules each connected to a respective light module. As long as at least two primary color LEDs are used, any illumination or display color may be generated simply by preselecting the light intensity that each color LED emits. Further, each color LED can emit light at any of 255 different intensities, depending on the duty cycle of PWM square wave, with a full intensity generated by passing maximum current through the LED. Further still, the maximum intensity can be conveniently programmed simply by adjusting the ceiling for the maximum allowable current using programming resistances for the current regulators residing on the light module. Light modules of different maximum current ratings may thereby be conveniently interchanged.

Figure 12:
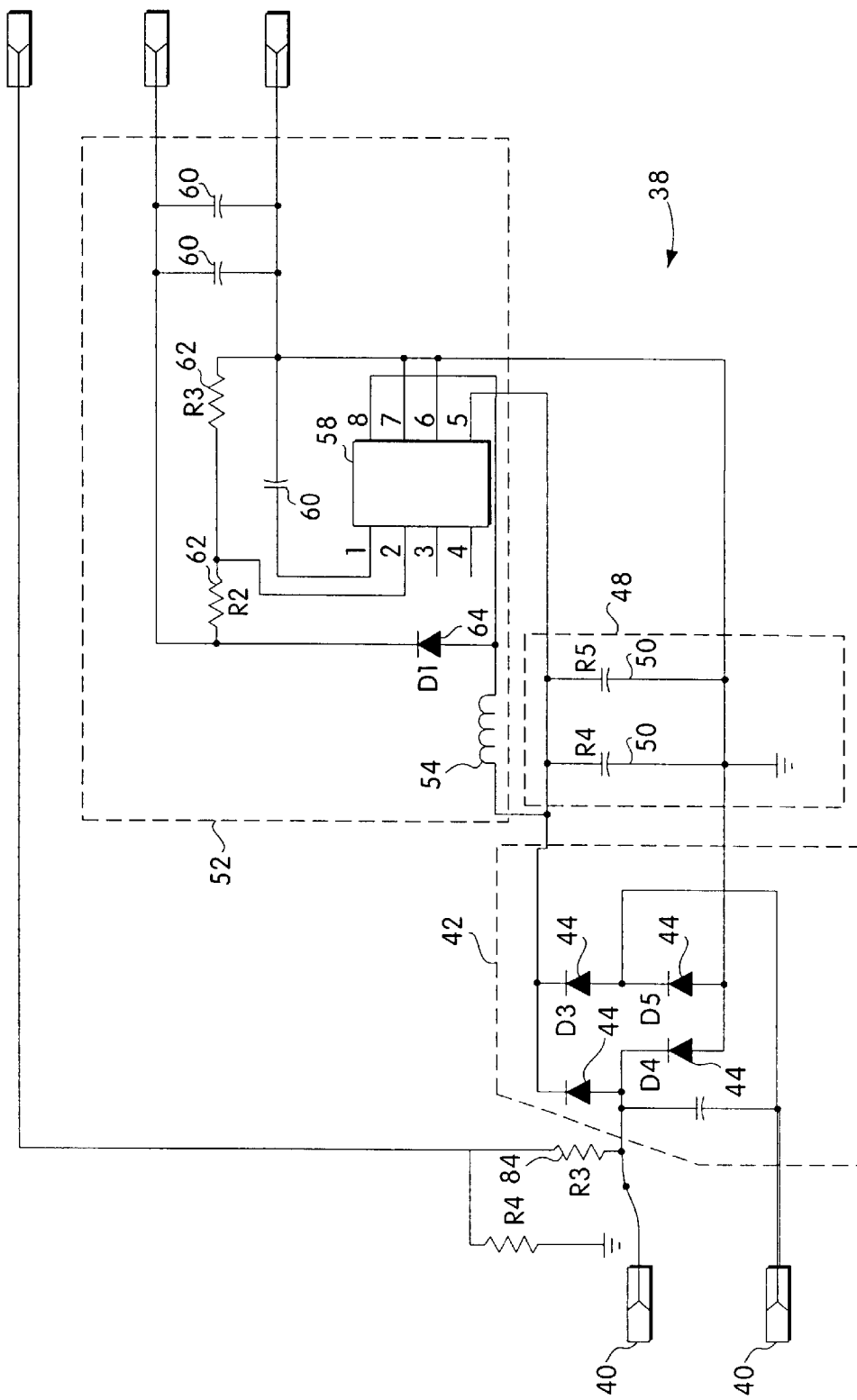
FIG. 12 depicts a circuit for a power supply for a light module of the invention.

In an alternative embodiment of the invention, a special power supply module 38 is provided, as depicted in FIG. 12. The power supply module 38 may be disposed on any platform of the light module 100, such as, for example, the platform of the embodiment depicted in FIGS. 4 and 5. The output of the power supply module 38 supplies power to a power and data input, such as the power and data input 18 of the circuit 10 of FIG. 6. The power supply module 38 is capable of taking a voltage or current input in a variety of forms, including an intermittent input, and supplying a steady, clean source of power to the circuit 10. In the embodiment depicted in FIG. 12, the power supply module includes inputs 40, which may be incoming electrical signals that would typically be of alternating current type. Incoming signals are then converted by a rectifying element 42, which in an embodiment of the invention is a bridge rectifier consisting of four diodes 44. The rectifying element 42 rectifies the alternating current signal into a clean direct current signal. The power supply module 38 may further include a storage element 48, which may include one or more capacitors 50. The storage element stores power that is supplied by the rectifying element 42, so that the power supply module 38 can supply power to the input 18 of the circuit 10 of FIG. 6, even if power to the input 40 of the power supply module 38 is intermittent. In the illustrated example, one of the capacitors is an electrolytic capacitor with a value of three hundred thirty microfarads.

The power supply module 38 may further include a boost converter 52. The boost converter takes a low voltage direct current and boosts and cleans it to provide a higher voltage to the DC power input 18 of the circuit 10 of FIG. 6. The boost converter 52 may include an inductor 54, a controller 58, one or more capacitors 60, one or more resistors 62, and one or more diodes 64. The resistors limit the data voltage excursions in the signal to the processor of the circuit 10. The controller 58 may be a conventional controller suitable for boost conversion, such as the LTC1372 controller provided by Linear Technology Corporation. The teachings of the LTC1372 data sheet are incorporated by reference herein.

In the illustrated embodiment, the boost converter 52 is capable of taking power at approximately ten volts and converting it to a clean power at twenty-four volts. The twenty-four volt power can be used to power the circuit 10 and the LEDs 15 of FIG. 6.

In certain embodiments of the invention, power and data are supplied to the circuit 10 and the LEDs 15 by conventional means, such as a conventional electrical wire or wires for power and a separate wire, such as the RS-485 wire, for data, as in most applications of the DMX-512 protocol. For example, in the embodiment of FIG. 4 and FIG. 5, a separate data wire may provide data to control the LEDs 15, if the platform 30 is inserted into a conventional halogen fixture 34 that has only electrical power.

In another embodiment, electrical power and serial data are simultaneously supplied to the device, which may be a lighting device such as the LED-based lighting device of FIG. 1 or may be any other device that requires both electrical power and data. Electrical power and data may be supplied to multiple lighting devices on a single pair of wires. In particular, in this embodiment of the invention, power is delivered to the device (and, where applicable, through the power supply module 38) along a two wire data bus such as the type normally used for lighting in applications where high power is required, such as halogen lamps.

Figure 13:
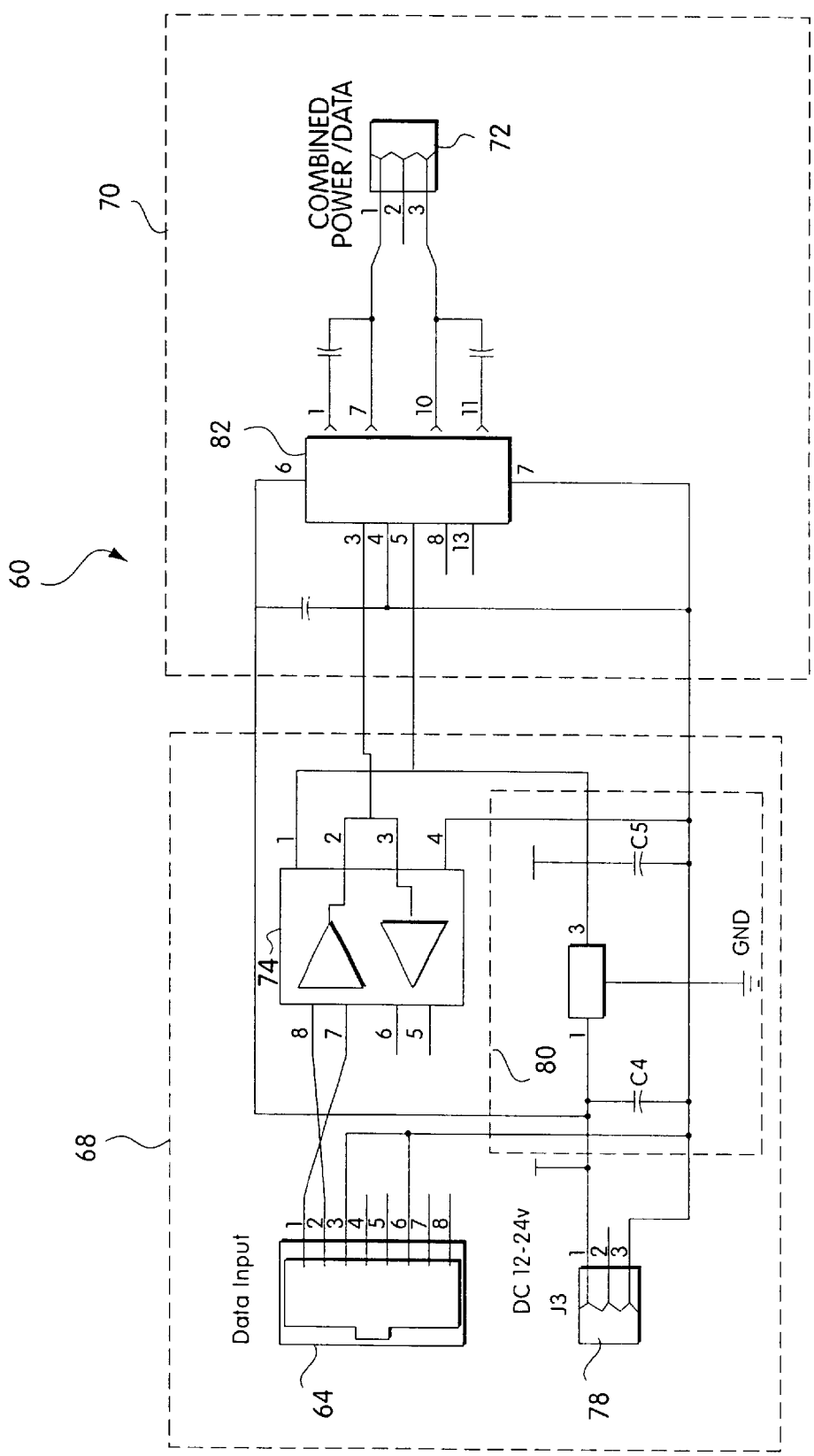
FIG. 13 depicts a circuit for a power/data multiplexor.

In an embodiment of the invention, the power supply module 38 recovers power from data lines. In order to permit power recovery from data lines, a power data multiplexer 60 is provided, which amplifies an incoming data stream to produce logical data levels, with one or more of the logical states having sufficient voltage or current that power can be recovered during that logical state. Referring to FIG. 13, in an embodiment of the invention, a data input 64 is provided, which may be a line driver or other input for providing data. In embodiment of the invention, the data is DMX-512 protocol data for control of lighting, such as LEDs. It should be understood that the power data multiplexer 60 could manipulate data according to other protocols and for control of other devices.

The power data multiplexer 60 may include a data input element 68 and a data output element 70. The data output element 70 may include an output element 72 that supplies combined power and data to a device, such as the power supply module 38 of FIG. 12, or the input 18 of the circuit 10 of FIG. 6. The data input element 68 may include a receiver 74, which may be an RS-485 receiver for receiving DMX-512 data, or any other conventional receiver for receiving data according to a protocol. The data input element 68 may further include a power supply 78 with a voltage regulator 80, for providing regulated power to the receiver 74 and the data output element 70. The data input element 68 supplies a data signal to the data output element 70. In the illustrated embodiment of FIG. 12, a TTL data signal is supplied. The data output element 70 amplifies the data signal and determines the relative voltage direction of the output. In the illustrated embodiment, a chip 82 consists of a high speed PWM stepper motor driver chip that amplifies the data signal to a positive signal of twenty four volts to reflect a logical one and to negative signal of twenty four volts to reflect a logical zero. It should be understood that different voltages could be used to reflect logical ones and zeros. For example, zero volts could represent logical zero, with a particular positive or negative voltage representing a logical one.

In this embodiment, the voltage is sufficient to supply power while maintaining the logical data values of the data stream. The chip 82 may be any conventional chip capable of taking an input signal and amplifying it in a selected direction to a larger voltage. It should be understood that any circuit for amplifying data while maintaining the logical value of the data stream may be used for the power data multiplexer 60.

The embodiments of FIGS. 12 and 13 should be understood to encompass any devices for converting a data signal transmitted according to a data protocol, in which certain data are represented by nonzero signals in the protocol, into power that supplies an electrical device. The device may be a light module 100, such as that depicted in FIG. 1.

In an embodiment of the invention, the data supplied to the power data multiplexer 60 is data according to the USITT DMX-512 protocol, in which a constant stream of data is transmitted from a console, such as a theatrical console, to all devices on the DMX-512 network. DMX-512 formats are enforced upon the data. Because of this one can be assured that the power data multiplexer 60, either in the embodiment depicted in FIG. 13, or in another embodiment, can amplify the DMX-512 signal from the standard signal voltage and/or electrical current levels to higher voltages, and usually higher electrical currents.

The resulting higher power signal from the power data multiplexer 60 can be converted back into separated power by the power supply module 38, or by another circuit capable of providing rectification with a diode and. filtering with a capacitor for the power.

The data stream from the power data multiplexor 60 can be recovered by simple resistive division, which will recover a standard data voltage level signal to be fed to the input 18. Resistive division can be accomplished by the resistors 84 of FIG. 12.

The power data multiplexer 62, when combined with the power supply module 38 and the array 37 mounted on a modular platform 30, permits the installation of LED-based, digitally controlled lighting using already existing wires and fixtures. As the system permits the device to obtain power and data from a single pair of wires, no separate data or power wires are required. The power data multiplexor 60 can be installed along a conventional data wire, and the power supply module 38 can be installed on the platform 30. Thus, with a simple addition of the power data multiplexor 60 and the insertion of the modular platform 30 into a conventional halogen fixture, the user can have LED based, digitally controlled lights by supplying DMX-512 data to the power data multiplexer 60.

It should be understood that the power supply module 38 can be supplied with standard twelve volt alternating current in a non-modified manner. That is, the power supply module can supply the array 37 from alternating current present in conventional fixtures, such as MR-16 fixtures. If digital control is desired, then a separate data wire can be supplied, if desired.

Figure 14:
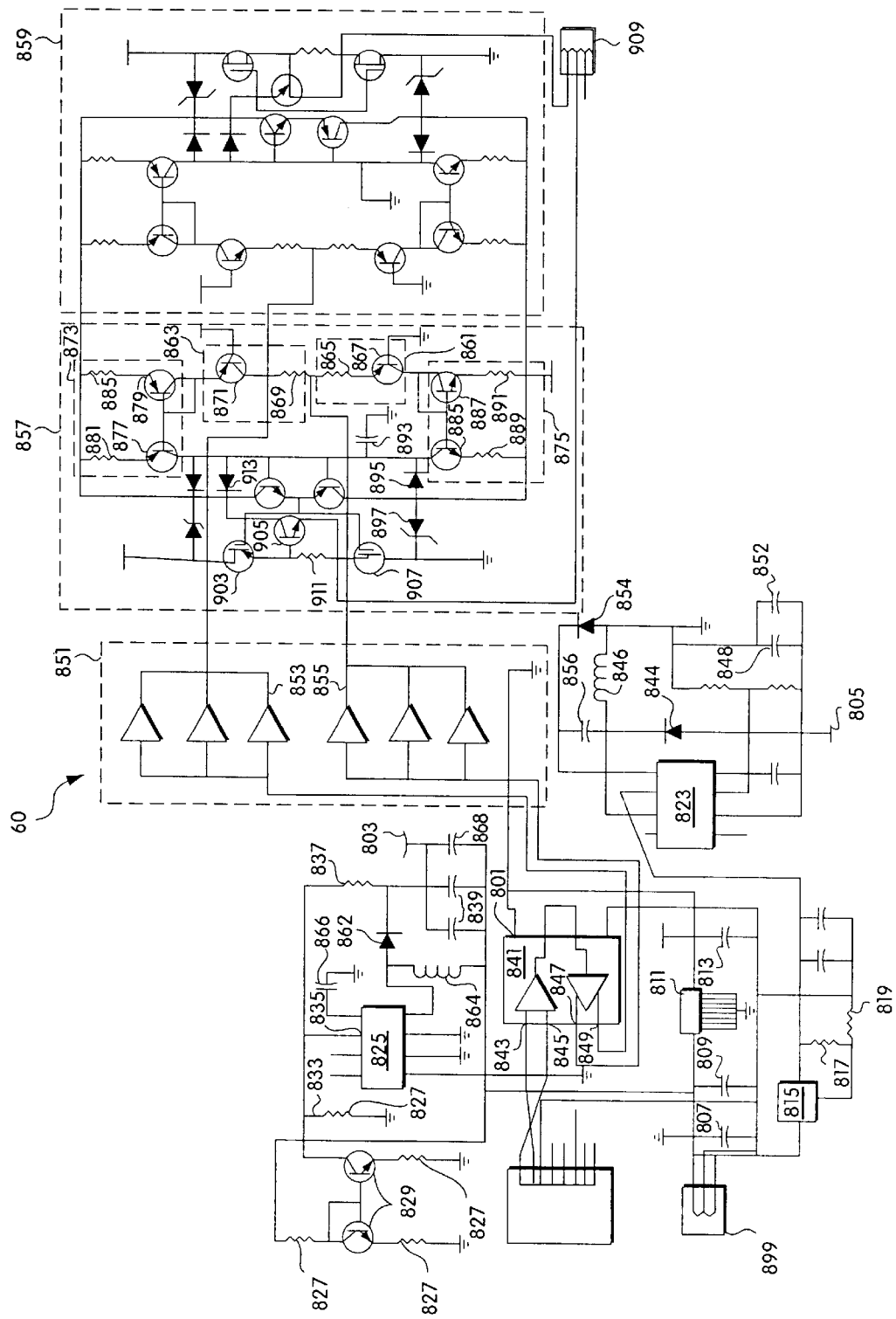
FIG. 14 depicts a circuit for another embodiment of a power/data multiplexor.

Another embodiment of a power data multiplexor 60 is depicted in FIG. 14. In this embodiment, a power supply of between twelve and twenty-four volts is used, connected to input terminals 899.

The voltage at 803 is eight volts greater than the supply voltage. The voltage at 805 is about negative eight volts. The voltage at 801 is five volts. The power data multiplexor 60 may include decoupling capacitors 807 and 809 for the input power supply. A voltage regulator 811 creates a clean, five volt supply, decoupled by capacitor 813. A voltage regulator 815, which may be an LM317 voltage regulator available from National Semiconductor, forms an eighteen volt voltage regulator with resistors 817 and 819, decoupled by capacitors 821 and 823. The teachings of the LM317 data sheet are incorporated by reference herein. This feeds an adjustable step down regulator 823, which may be an LT1375 step down regulator available from Linear Technology of Milpitas Calif., operated in the voltage inverting configuration. The teachings of the LT1375 data sheet are incorporated by reference herein. The resistances of resistors 817 and 819 have been selected create negative eight volts, and a diode 844 is a higher voltage version than that indicated in the data sheet, inductor 846 is may be any conventional inductor, for example, one with a value of one hundred uH to allow a smaller and cheaper capacitor to be used for the capacitor 848, supply has been further bypassed with capacitor 852. Diode 854 may be a plastic packaged version 1N914, and frequency compensating capacitor 856 sized appropriately for changes in other components according to data sheet formulas. The circuit generates negative eight volts at 805.

Also included may be a step up voltage regulator 825, which may be an LT1372 voltage regulator available from Linear Technology of Milpitas, Calif. The teachings of the LT1372 data sheet are incorporated by reference herein. The step up voltage regulator may be of a standard design. Diode 862 may be a diode with higher voltage than that taught by the data sheet. Inductor 864 and capacitor 839 may be sized appropriately according to data sheet formulas to generate eight volts more than input voltage over the range between input voltages of twelve and twenty-four volts. Capacitor 866 may be sized for frequency compensation given values of inductor 864 and capacitor 868 as per data sheet guidelines. A set of resistors 827, 833, 837, along with transistors 829 form the voltage feedback circuit. Resistors 833 and 837 form a voltage divider, producing a voltage in proportion to the output voltage 803 at the feedback node pin 835. Resistors 827 and transistors 829 form a current mirror, drawing a current from the feedback node at 835 in proportion to the input voltage. The voltage at feedback pin 835 is thus proportional to the output voltage minus the input voltage. The ratio of resistor 833 to that of resistor 837, which may need to be equal to resistor 827 for the subtraction to work, is chosen to produce eight volts. Capacitors 839 may be used to further bypass the supply.

Incoming data, which may be in the form of an incoming RS-485 protocol data stream, is received by a receiver chip 841 at the pins 843 and 845, buffered, and amplified to produce true and complement data signals at pins 847 and 849 respectively. These signals are further buffered and inverted by element 851 to produce true and complement data signals with substantial drive capabilities at pins 853 and 855, respectively.

Each of the signals from the pins 853 and 855 is then processed by an output amplifier. There are two output amplifiers 857 and 859, which may be substantially identical in design and function. In each case, the data signal entering the amplifier connected to two switched cascode type current sources 861 and 863, the first composed of resistor 865 and transistor 867, the second composed of resistor 869 and transistor 871, at the junction of the two resistors 865 and 869. The current source 863 will sink a current of approximately 20 milliamps when the signal entering the amplifier is low, such as at zero volts, and will sink no current when the signal is high, for example at positive five volts. The other current source 861 will source approximately twenty milliamperes when the signal is high, but not when low. These currents are fed to two current mirrors 873 and 875, composed of transistors 877 and 879 and resistors 881 and 883 for current source 863 and transistors 885 and 887 and resistors 889 and 891 for current source 861, which are of a standard design, familiar to analog circuit designers. The collectors of transistors 877 and 885 are connected together, forming a current summing node. The net current delivered to this node by these transistors will be about twenty milliamps in either the sourcing direction (flowing into the node) if the input signal is low, or the sinking direction (flowing out of the node) if the signal is high. When a transition from the low state to the high state occurs at the input signal, the resulting twenty milliampere sinking current will cause capacitor 893 (and the parasitic capacitance at this node) to discharge at a controlled rate of approximately fifty volts per microsecond, until the voltage at the node reaches approximately negative five volts, at which time diodes 895 and 897 will begin to conduct, clamping the negative excursion of the node voltage at negative five volts, and preventing the saturation of transistor 885. Transistors 899 and 901 form a bi-directional Class B voltage follower of a standard design, and the voltage at the junction of their emitters follows the transition at the node connected to capacitor 893. Specifically transistor 899 turns off and transistor 901 conducts, causing the voltage at the gates of transistors 903 and 907 to decrease, switching off transistor 903 and slowly turning on transistor 907, causing current to flow from the output pin 909 to ground. Field effect transistors 903 and 907, which may be of the type available from National Semiconductor of Santa Clara, Calif., also form a Class B Voltage follower, of standard design. When the voltage at the current summing node is clamped at negative five volts, the voltage at the gate of 903 will reach negative four and four-thenths volts, and transistor 907 will remain on so long as the input signal remains high.

Once the input signal goes low, the current at the summing node will change direction, and capacitor 893 will charge at the same rate, eventually being clamped to a value of the input voltage plus five volts. Transistor 899 will cause the voltage at the gates of transistor 903 and transistor 905 to rise, turning off transistor 903 and turning, on transistor 907, sourcing current from the input supply to the output through resistor 911. It will take approximately five hundred nanoseconds for the voltage at the summing node, and hence the output, to fully switch between zero and twenty-four volts (if the power input is the maximum of twenty four volts), or approximately two hundred fifty nanoseconds to move between zero and twelve volts (if the power input is twelve volts). Transistor 905 and resistor 911 form a short circuit protection circuit, limiting the current flowing through 903 to approximately six amperes. Diode 913 isolates the short circuit protector circuit when transistor 903 is not on. No protection is provided for transistor 907, because the expected short circuit paths would be either to ground or to the other amplifier channel. In the first case no current could flow through transistor 907, while in the second, the other amplifier's short circuit protection would protect transistor 907.

Because of the bridge rectifier at the input to the device, as disclosed in connection with the description of the embodiment of FIG. 6, the power data multiplexor circuits depicted in FIGS. 13 and 14 supply power to the device during both the data=1 and data=0 states and does not rely on any data format at the input to maintain sufficient power to the device. The data is extracted as in other embodiments of the invention.

The circuit of FIG. 14 produces a controlled slew rate; that is, the power and data generated have relatively smooth transitions between a logical zero state and a local one state. The controlled slew rate produced by the circuit of FIG. 14 decreases the magnitude of the radio frequency interference generated, as described more particularly below in connection with the data track embodiment of the invention.

The lamps themselves auto terminate the line, as their input looks substantially similar to the terminating circuit in the track embodiment described below, having the same effect as that terminating circuit. This eliminates any need for terminators on the line. Additional termination is only needed in the case of a device that is commanded to be off, with actual data wire impedance low, with a long wire, and where there are many transitions going by. Since this is a very unlikely combination of factors, the configuration with an additional terminator is not needed as a practical matter.

For the embodiment of FIG. 14, six amperes of power runs forty eight lights at twenty-four volts or twenty four lights at twelve volts.

Figure 15:
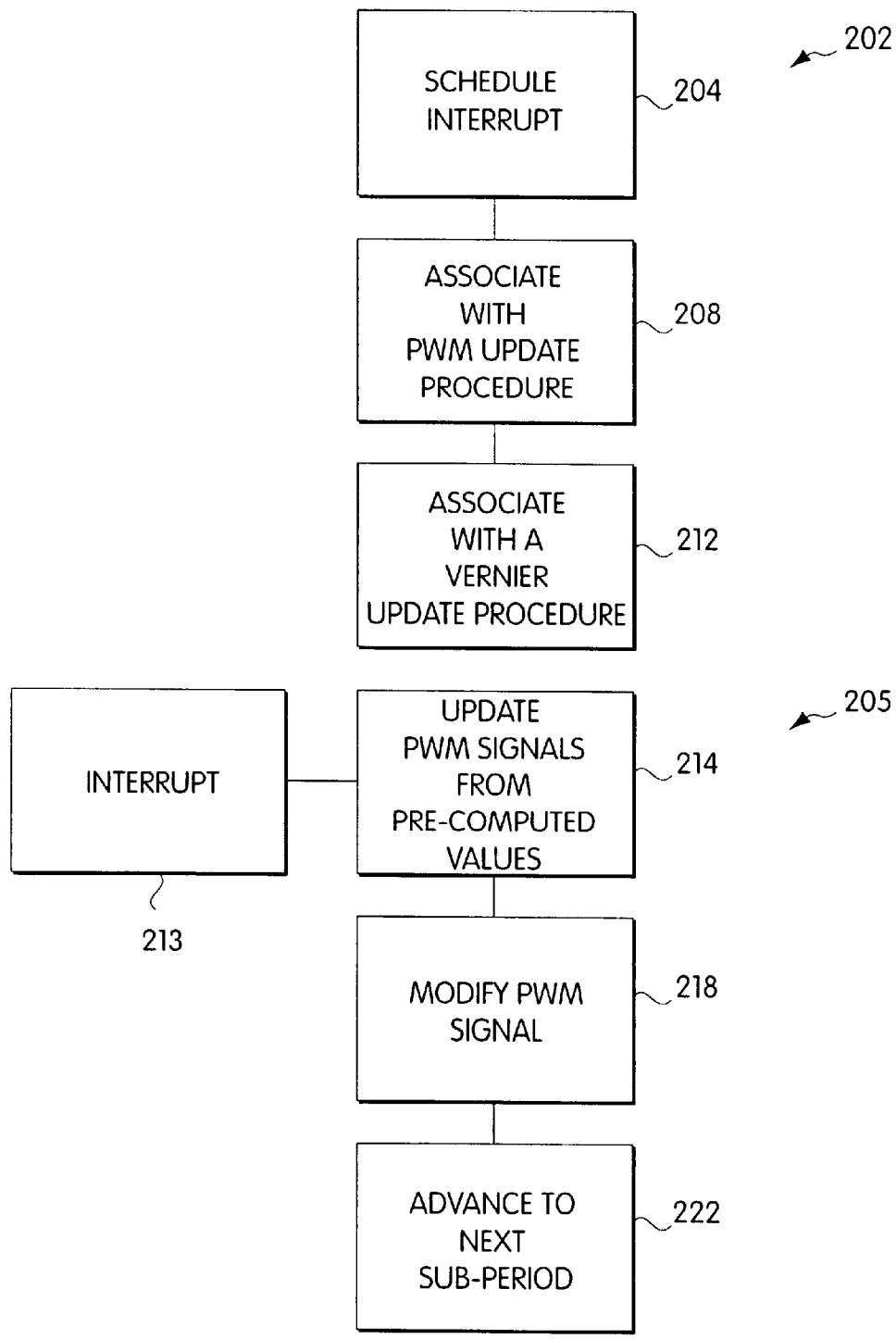
FIG. 15 depicts flow charts depicting steps in a modified pulse width modulation software routine.

In an embodiment of the invention, a modified method and system is provide to provide multiple simultaneous high speed pulse width modulated signals. The method may be accomplished by computer software coding of the steps depicted in the flow charts 202 and 205 of FIG. 15, or by computer hardware designed to accomplish these functions. To generate a number, N, of PWM signals, in a step 204 the processor schedules an interrupt of at least N possibly equal (as in this embodiment) sub-periods. In this embodiment this interrupt is generated by a counter, interrupting the processor every two hundred fifty-six processor clock cycles. In step 208 each sub-period's coarse PWM values are computed. In step 212, the vernier value for each PWM channel is computed. The sub-periods may be denoted $P_i$ where the first sub-period is one, etc.

In each sub-period, which begins with an interrupt at a step 213, the interrupt routine executes the steps of the flow chart 205. In a step 214, all PWM signals are updated from pre-computed values corresponding to this specific sub-period. In most cases this entails a single read from an array of pre-computed values, followed by a single write to update the multiple I/O pins on which the PWM signals are generated.

In a step 218, one of the PWM signals is then modified. The step 218 is accomplished by executing a write to the I/O pins, executing a series of instructions consuming the desired amount of time, and then executing another update (I/O) write.

In a step 222, the processor advances the sub-period bookkeeping value to point to the next sub-period.

The vernier in the step 218 can reduce or increase the amount of time that the PWM signal is on, by changing the state of the signal for up to one-half of the sub-period. There are two possible cases. Either the coarse update places the signal in the "off" state and the vernier routine turns it "on" for a time period of up to one-half of the sub period, or the coarse update is "on" and the vernier routine turns the signal "off" for a period of time of up to one-half of the sub period.

Using this method, each PWM signal can change multiple times per PWM period. This is advantageous because software can use this property to further increase the apparent PWM frequency, while still maintaining a relatively low interrupt rate.

The method disclosed thus far consumes a maximum of approximately half of the processor time compared to conventional PWM routines.

As an example: consider two signals A and B with a resolution of twenty counts programmed to seven and fourteen counts respectively. These signals could be generated as follows:

A: |+v_v++++++|_____|
B: |++++++++++|_^++^_____|
Pi: ^1 ^2

In this example the pre-computed update value at $P_i=1$ is both signals on. Signal A then spends some time in the on state, while the interrupt routine continues to execute. A then goes off in the vernier step at the first "v", and the interrupt routine executes time delay code during the time before restoring the signal to the on state at the second "v".

The actual time between the multiple update at the beginning of the sub period and the vernier update need not be known, so long as the time spent between the vernier updates is the desired time. While the vernier updates are occurring, signal B, which was switched on, remains on and unaffected. When the second interrupt occurs, both signals are switched off, and the vernier routine now adds four additional counts to the period of signal B. In this example only thirty-five percent of the processor time plus the time required for two interrupts has been consumed.

Since only one vernier period is required per signal generated, increasing the number of periods per PWM cycle can generate non-uniform PWM waveforms at frequencies higher than those possible on most microprocessors' dedicated hardware PWM outputs for a large number of possible PWM channels. The microprocessor still executes interrupts at fixed intervals.

To change the duty cycles of the signals produced, the software can asynchronously update any or all of the coarse or vernier values, in any order, without having to worry about synchronization with the interrupt routine, and more importantly, without stopping it. The interrupt routine never changes any variables which the main code changes or vice-versa. Thus there is no need for interlocks of any kind.

This software routine can thus utilize a single timer to generate multiple PWM signals, with each signal ultimately having the resolution of a single processor cycle. On a Microchip PIC microprocessor, this allows three PWM signals to be generated with a resolution of two hundred fifty-six counts, each corresponding to only a four instruction delay. This allows a PWM period of just one thousand twenty four instruction cycles, i.e four thousand eight hundred eighty two Hertz at a twenty megaHertz clock.

Furthermore, for counts between sixty-four and one hundred ninety-two, the PWM waveform is a non-uniform nine thousand seven hundred sixty-five Hertz signal, with much lower noise than a conventional PWM generator in such a processor.

As described above, the LED arrays of the present invention are responsive to external electrical signals and data. Accordingly, it is desirable to have improved data and signal distribution mechanisms in order to take full advantage of the benefits of the present invention. In an embodiment of the invention, the data connection 500 can be a DMX or lighting data network bus disposed in a track on which conventional lights or LEDs are located. Thus, a track capable of delivering data signals may be run inside a track lighting apparatus for LEDs or conventional lights. The data signals may then be controlled by a microprocessor to permit intelligent individual control of the individual lamps or LEDs. It is within the scope of the present invention to provide distributed lights that are responsive to both electrical and data control.

The LEDs of the present invention are highly responsive to changes the input signal. Accordingly, to take advantage of the features of the invention, rapid data distribution is desirable. In embodiment of the invention, a method for increasing the communication speed of DMX-512 networks is provided. In particular, DMX 512-networks send data at two hundred fifty-thousand baud. All receivers are required by the DMX standard to recognize a line break of a minimum of eighty-eight microseconds. After the mark is recognized, all devices wait to receive a start code and ignore the rest of the packet if anything other than zero was received. If a non-zero start code is sent prior to sending data at a higher baud rate, the devices are able to respond more quickly to the higher baud rate. Alternatively channels above a certain number could be assigned to the high baud rate, and other devices would not be deprived of necessary data as they would already have received their data from that frame. It may be desirable to frame several characters with correct stop bits to prevent loss of synchronization.

The present invention may also include an automation system chassis that consists of a mother board that communicates with a network and/or bus using the DMX, Ethernet or other protocol to control a wide range of electrical devices, including the LED arrays of the present invention.

In another embodiment of the invention, the input signals for the microprocessor can be obtained from a light control network that does not have a direct electrical circuit connection. A switch that is mounted on a wall or a remote control can transmit a programmed infrared, radio frequency or other signal to a receiver which can then transmit the signal to the microprocessor.

Another embodiment provides a different track lighting system. Present track lighting systems use both the physical and electrical properties of a track of materials, which typically consist of an extruded aluminum track housing extruded plastic insulators to support and house copper conductors. A conventional track lighting system delivers power and provides a mechanical support for light fixtures, which can generally be attached to the "track" at any location along its length by a customer without tools.

In the simplest form, a track provides only two conductors, and all fixtures along the track receive power from the same two conductors. In this situation, all fixtures attached to the track are controlled by a single control device. It is not possible to control remotely (switch on or off, or dim) a subset of the fixtures attached to the track without affecting the other fixtures.

Track systems have generally included more than two conductors, primarily because of the requirements of the Underwriters Laboratories for a separate ground conductor. Many systems have also endeavored to provide more than just two current-carrying conductors. The purpose of additional current-carrying conductors is typically either to increase the total power carrying capacity of the track, or to provide separate control over a subset of fixtures. Tracks with up to four "circuits," or current-carrying conductors, are known.

Even with four circuits however, full flexibility may not be achieved with conventional tracks, for a number of reasons. First, a fixture is assigned to a subset at the time of insertion into the track. Thus, that fixture will be affected by.

signals for the particular subset. If there are more lights than circuits, it is not possible to control lights individually with conventional systems. Also, the fixture typically only receives power, which can be modified somewhat (i.e. dimmed), but cannot easily be used to send substantial quantities of data. Further, information cannot be returned easily from the fixtures.

The track embodiment disclosed herein provides individual control of a large number of lighting fixtures installed on a track and allows robust bi-directional communication over that track, while complying with regulatory requirements pertaining to both safety and pertaining to elimination of spurious radio frequency emissions. Disclosed herein are methods and systems for creating electrical signals for delivering data to a multitude of lighting fixtures attached to a track, a track capable of delivering the signals to the fixtures, and specialized termination devices for ensuring that the signals do not cause excessive spurious reflections.

Figure 16:
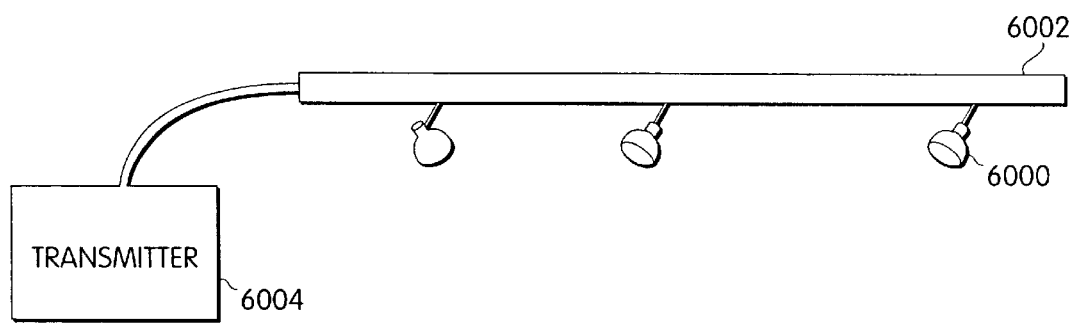
FIG. 16 depicts a data delivery track lighting system.

Referring to FIG. 16, in an embodiment, a user may wish to send lighting control data over a track 6002 to a fixture 6000, preferably using an industry standard. The fixture 6000 could be a light module 100, such as that disclosed herein, or it could be any other conventional fixture capable of connection to a conventional track lighting track. In an embodiment, the data control standard is the DMX-512 standard described herein.

DMX-512 specifies the use of RS-485 voltage signaling levels and input/output devices. However, use of RS-485 presents certain problems in the track lighting applications described herein, because it requires that the network to which the fixture 6000 is attached be in the form of a bus, composed of lengths of controlled impedance media, and it requires that the network be terminated at each bus endpoint. These properties are not provided in typical track lighting systems, which generally do not contain controlled impedance conductor systems. Furthermore, track installations often contain branches or "Ts" at which one section of track branches to multiple other sections, and it is undesirable to electrically regenerate signals at such points, for cost, reliability and installation reasons. Because of this, each section cannot be "terminated" with its characteristic impedance to achieve a properly terminated network for purposes of RS-485.

It is possible however, through the present invention, to send signals conforming to a modification of the RS-485 specification, which can be received by currently available devices that conform to the RS-485 specification.

To deliver data effectively in this environment, a new data transmitter 6004 is needed. In order to negate the transmission line effect created by the multiple sections of track, a controlled waveshape driver is utilized as the data transmitter 6004. The design of this driver may be further optimized to minimize the amount of unintended radio frequency radiation, to allow conformance to FCC and CE regulatory requirements. To further ensure signal integrity, a specialized termination network may be utilized.

Certain characteristics of the track system are relevant. First, multiple sections of track can be viewed as a collection of individual transmission lines, each with some (generally unknown) characteristic impedance, and with some unknown length. Fixtures attached to the track present some load along the transmission line's length. The RS-485 standard specifies that the minimum impedance of such loads shall be not less than ten and five-tenths kilo-ohms, and that the added capacitance must not exceed fifty picofarads. In a large lighting network, it is possible to envision a track system comprised of several dozen sections, each up to several meters long. The total number of fixtures can easily exceed two hundred in just a single room. Thus the total load presented by the controlled devices alone can be below fifty ohms and contain an added ten thousand picofarads of capacitance. Furthermore, crosstalk between the power conductors and signal conductors in the track can also occur. The track itself may present upwards of twenty-five picofarads per foot of additional capacitance.

It is generally understood that transmission lines shorter than one-fourth of the wavelength of the highest frequency signal transmitted on them can be analyzed and viewed as a lumped load; i.e., their transmission line effects can be effectively ignored. Thus any combination of loads and track sections can be viewed as a single lumped load, so long as the maximum length from any one terminus to any other terminus is less than one-fourth of the wavelength of the highest frequency signal delivered to it. For a digital signal, the highest frequency component is the edge, at which the signal transitions between the two voltage states representing a logical one and a logical zero. The DMX-512 lighting control protocol specifies a data transmission rate of two hundred fifty thousand bits per second. The signal edge transition time required to reliably transmit such a signal is at least five times faster than that rate; i.e., the transition must occur in no longer than eight hundred nanoseconds, in order to assure reliable data transmission. If we assume that a data driver capable of creating electrical signals which transition at this rate can be constructed, that the speed of light is three times ten to the eighth meters per second, and that the velocity of propagation in track is approximately seventy percent of the speed of light, then a conservative limit on the maximum network length is about forty-two meters. This is an adequate length for most applications. Assuming that the total length of a branched network might be as much as two such forty-two meter track sections, a total capacitance added by the track itself could be as much as another seven thousand picofarads, for a total load of seventeen thousand picofarads.

Figure 17:
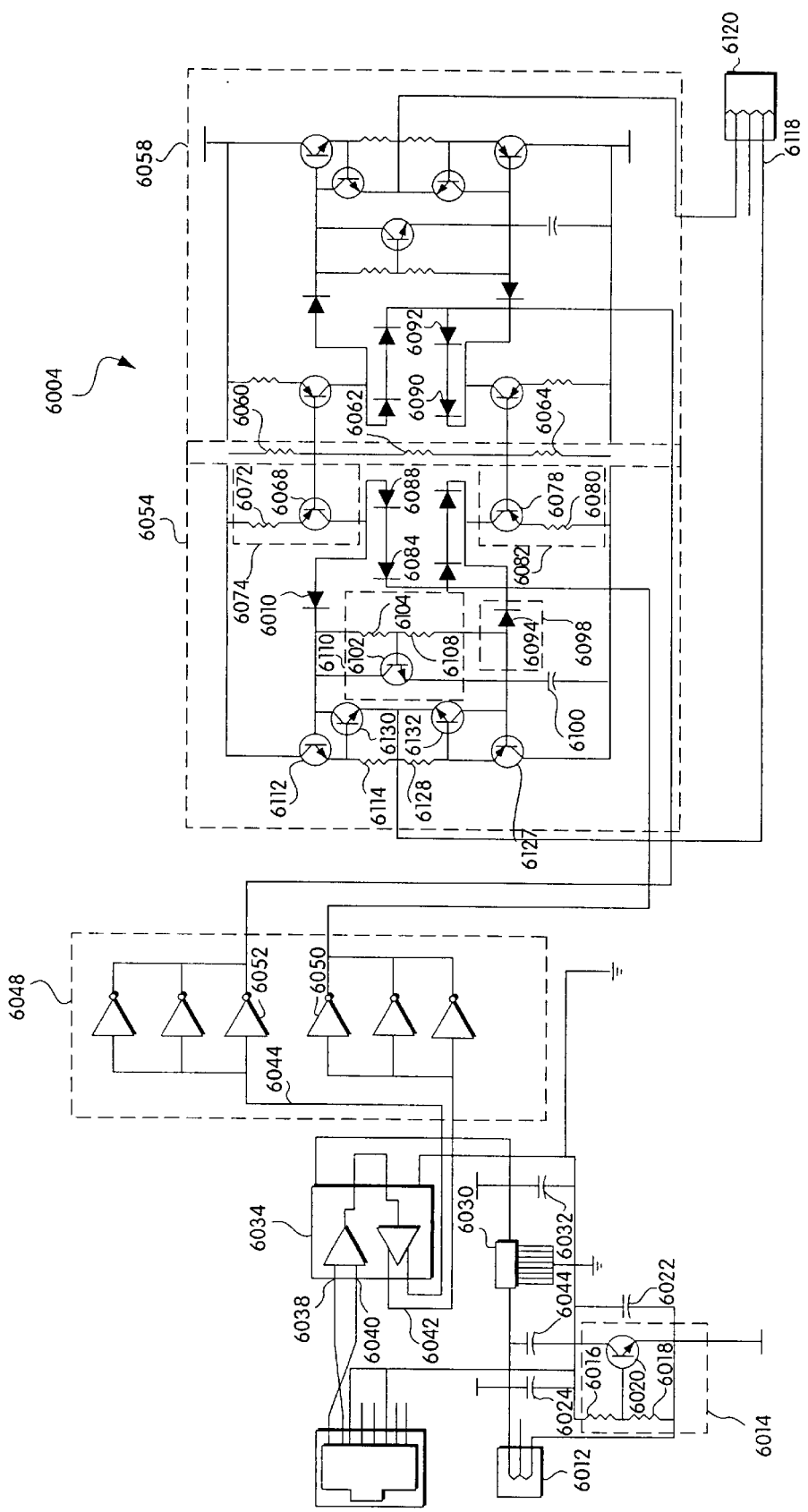
FIG. 17 depicts a circuit design for a data driver for the track system of FIG. 16.

In order to effectively transmit data into such a network, a driver with significantly more power than a driver for the current RS-485 standard is required. To achieve a five volt transition, for a highly loaded network as described above, the driver is preferably capable of supplying at least one hundred milliamps continuously for the resistive portion of the load, and at least one hundred milliamps additionally during the transition period, which will be absorbed by the capacitive load. Thus the driver output current is preferably at least two hundred milliamps to ensure adequate margin. A circuit design for a driver 6004 which meets these criteria is illustrated in FIG. 17. It is important to note that transitions faster than eight hundred nanoseconds will still not cause the network to fail, but will cause the current needed during the transient to increase, will cause excessive ringing at lightly loaded track endpoints, and will substantially increase the spurious radio frequency generated from the system. All of these effects are undesirable. At an eight hundred nanosecond transition time, most spurious harmonics generated by the system fall well below the thirty megahertz starting frequency for CE testing, and higher order harmonics do not have sufficient energy to violate the requirements.

In order to effectively propagate signals along the length of a track, the track's data conductors should have a low resistance per unit length, ideally less than that needed to deliver one and one-half volts of signal to all receivers as specified in the RS-485 standard. In a highly loaded network (with all loads being at the end), this is approximately nine one-hundredths ohms per foot. This includes the intermediate connectors, so the track conductor's resistance should ideally be much lower than this figure. The track's inductive effect will also contribute to signal degradation.

Figure 18:
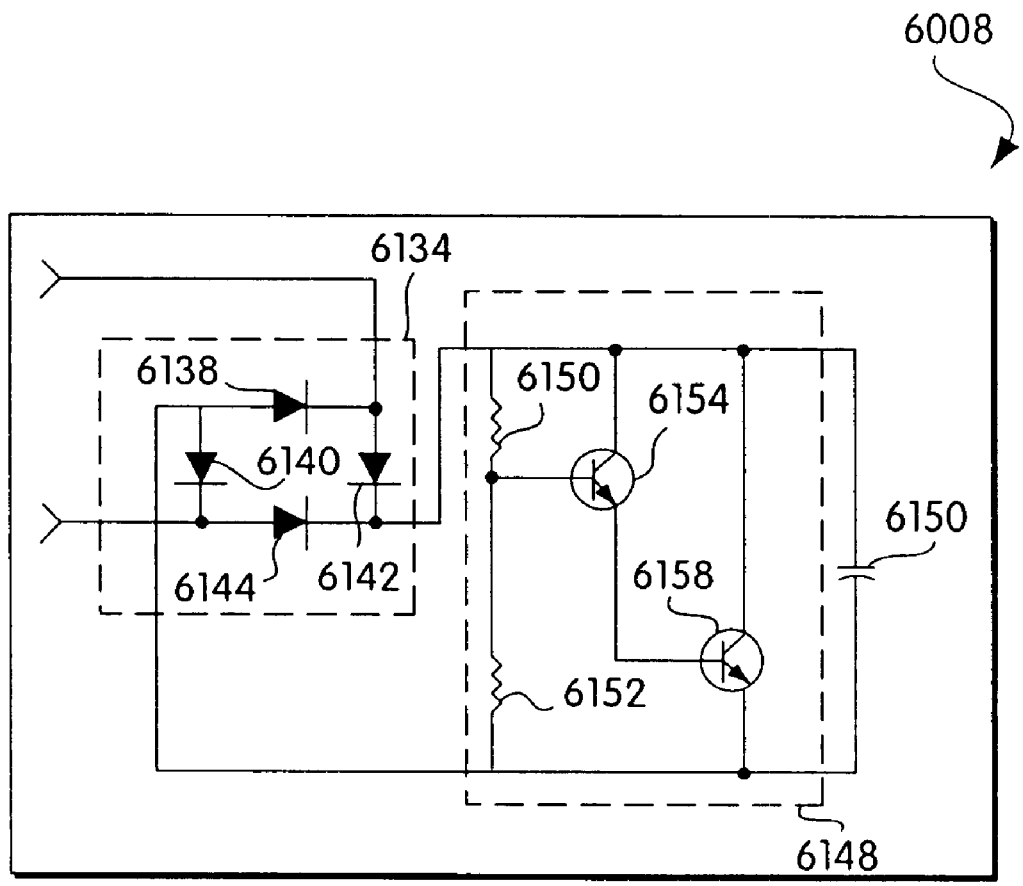
FIG. 18 depicts a circuit design for a terminator for a track system of FIG. 16.

In order to compensate for the inductive effect of the track, limited termination may be provided at the endpoint of each branch. This termination is preferably not purely resistive, but rather compensates only for the inductive effect of the track. A circuit design for a suitable terminator 6008 is shown in FIG. 18. This circuit effectively clamps the voltage between the data+ and data− connections to plus or minus five volts. Any overshoot of the signal may thus be absorbed by a shunt regulator 6148 of FIG. 18. The terminator 6008 effectively terminates the line, without drawing power constantly from the data lines.

Recovering data from the track then becomes a matter of attaching (using any of the commonly used attachment methods, e.g., spring clips) to the electrical and mechanical attachment points of the track itself Many examples of track lighting attachment are well known to those of ordinary skill in the art. One example is the Halo Power Track provided by Cooper Lighting.

Once both the power and data are available on a wire, for example, we can use the network version of the light modules 100 described above, or any digitally controlled dimmer, to achieve individual control over the lighting unit. The data can correspond not only to light intensity, but also to control effects, such as moving a yoke, gobo control, light focus, or the like. Moreover, the system can be used to control non-lighting devices that are RS-485 compliant.

It is further possible, by using this embodiment, to create devices which can respond over the same data conductors or over a separate pair, using substantially similar drivers, possibly with added circuitry to allow the driver(s) to be electrically disconnected from the data conductors during times when the device is not selected for a response, i.e., to allow bus sharing. Units can send status information to the driver, or information can be provided to the units through other means, such as radio frequency, infrared, acoustic, or other signals.

Referring again to FIG. 17, a circuit design for the data driver 6004 includes a connector 6012 through which power, which may nominally be positive twelve volts of unregulated power, is delivered to the data driver 6004. The power may be split into positive eight and one-half volts of unregulated supply and negative three and one-half volts of regulated supply by a shunt regulator 6014 consisting of a resistor 6016, a resistor 6018, and a transistor 6020. Decoupling may be provided by capacitors 6022, 6024 and 6028. The shunt regulator 6014 may be of a standard design familiar to analog circuit designers. The eight and one-half volt supply is further regulated to produce a five volt supply by a voltage regulator 6030, which may be an LM78L05ACM voltage regulator available from National Semiconductor Corporation, Santa Clara, Calif., and may be decoupled by capacitor 6032. The teachings of the data sheet for the LM78L05ACM are incorporated herein by reference.

The incoming RS-485 data stream may be received by the RS-485 receiver chip 6034 at pins 6038 and 6040. The data stream may be further buffered by the receiver chip 6034 to produce a clean, amplified true and complement data signals at pins 6042 and 6044, respectively. These signals are further buffered and inverted by buffer 6048 to produce true and complement data signals with substantial drive capabilities at pins 6050 and 6052 respectively. Each of these signals is then processed by an output amplifier. There are two output amplifiers 6054 and 6058, identical in design and function.

Each amplifier 6054 and 6058 draws power from the previously described power supplies, and both amplifiers share the bias voltage generator network composed of resistors 6060, 6062 and 6064. Amplifier 6054 is composed of all parts to the left of this network on FIG. 17, while amplifier 6058 is composed of all parts to the right of this bias network. Only amplifier 6054 will be described, as amplifier 6058 is substantially identical, with the exception that its input is an inverted copy of the input to amplifier 6054.

The bias network generates two bias voltages, nominally positive six and four-tenths volts, and negative one and four-tenths volts, appearing at the base of transistors 6068 and 6070, respectively. Transistor 6068 and resistor 6072 form a constant current source 6074, sourcing a current of approximately twenty milliamps from the collector of transistor 6068. Similarly transistor 6078 and resistor 6080 provide a current sink 6082 to sink a current of twenty milliamps from the collector of transistor 6078. Diodes 6010, 6084, 6088, 6090, 6092 and 6094 form a current steering network 6098 and steer the twenty milliamp currents alternately into the incoming data line, or capacitor 6100 (through the one volt shunt regulator composed of transistor 6102, resistor 6104 and resistor 6108 if the current is from transistor 6068). If the incoming data line switches from the low state of zero volts to the high state of positive five volts, current sink 6082 will sink current from the incoming data line, through diodes 6090 and 6092, because the voltage at the anode of 6090 will be greater than the voltage at the anode of diode 6094. Diodes 6084 and 6088 will be reverse-biased, and current will flow through 6010 and the shunt regulator 6110 comprised of transistor 6102 and resistors 6104 and 6108. The circuit node at the anode of diode 6094 will not immediately follow the transition, as capacitor 6100 must slowly charge from the current provided by transistor 6068. Capacitor 6100 will charge at a rate of approximately six and sixty-seven hundredths volts per microsecond, and will reach approximately four volts approximately seven hundred fifty nanoseconds later. At that time the voltage at the collector of transistor 6068 will become large enough to forward bias diodes 6084 and 6088, causing the current source 6074 to be steered into the input data line. As long as this data line is held in a high state (at five volts), no more current will flow through diode 6010, the shunt regulator 6110 and into capacitor 6100. The cathode of diode 6010 will remain at approximately five and five-tenths volts until the data line changes state to the low state of zero volts. During the switching as described, transistor 6112 acts as a common collector current buffer and will source as much current as is required into resistor 6114. This current will flow into the output at pin 6118 of output device 6120. The voltage at the output will thus be a slowly rising signal, whose slope is regulated by the charging of capacitor 6100 from current source 6074. A small base current will be drawn from transistor 6068 by transistor 6112, but its effect on the transition timing will be negligible.

When the incoming data line transitions to the low state, diodes 6084, 6088 and 6094 will be forward-biased, diodes 6090, 6092 and 6010 will be reverse-biased, and capacitor 6100 will discharge through diode 6094 through the current sink 6082 at similar rates to the positive transition described above. Current from current source 6074 will flow into the data line, now held at zero volts. The voltage at the anode of diode 6094 will reach negative five-tenths volts, and current will again flow through 6090 and 6092, instead of diode 6094 and transistor 6078, completing the downward transition. During this period transistor 6129 will sink as much current as necessary through resistor 6128, from the output at pin 6118 of device 6120, to cause it to follow the voltage at the anode of diode 6094. A small base current will be drawn by transistor 6129 from transistor, but its effect on the transition timing will be negligible. Transistors 6130 and 6132 in combination with resistors 6114 and 6128 protect transistors 6112 and 6129 respectively in case of a short circuit at the output, limiting the maximum possible output current (and hence the current through transistors 6112 and 6130) to approximately two hundred fifty milliamps.

The wave-shaping performed by this circuit can be implemented by a variety of different circuits. The embodiment depicted in FIG. 17 is only one example of a circuit for producing a desirable wave shape. Any circuit which slows the rising and falling transitions of the data signal can be considered to be an implementation of a wave-shaping circuit as disclosed herein.

Referring to FIG. 18, the terminating circuit is composed of a bridge rectifier 6134 composed of diodes 6138, 6140, 6142 and 6144 and a shunt regulator 6148 composed of resistors 6150, 6152 and transistors 6154 and 6158. This circuit is a bi-directional voltage limiter and clamps the voltage between the input terminals at approximately five and three-tenths volts, regardless of the polarity of the applied input. Both the shunt regulator 6148 and the bridge rectifier 6134 are of a standard design, known by those familiar with analog circuit design. Capacitor 6150 improves the transient response of the voltage limiter.

Excess energy stored in a transmission line would normally cause voltage excursions above five and three-tenths volts. The termination circuit 6008 of FIG. 18 will absorb the excess energy as it clamps the voltage at the terminus of the transmission line to five and three-tenths volts. Approximately ninety-five percent of the reflected energy may be absorbed by the circuit, and the resulting oscillation will be of insignificant amplitude.

The transistors disclosed herein may be of a conventional type, such as those provided by Zetex. The diodes may be of industry standard type. Buffer 6048 may be of industry standard type, and may be 74HC04 type. The receiver chip 6034 may be a MAX490 receiver chip made by Maxim Inc. of Sunnyvale, Calif. Other receiver chips may be used.

Figure 19:
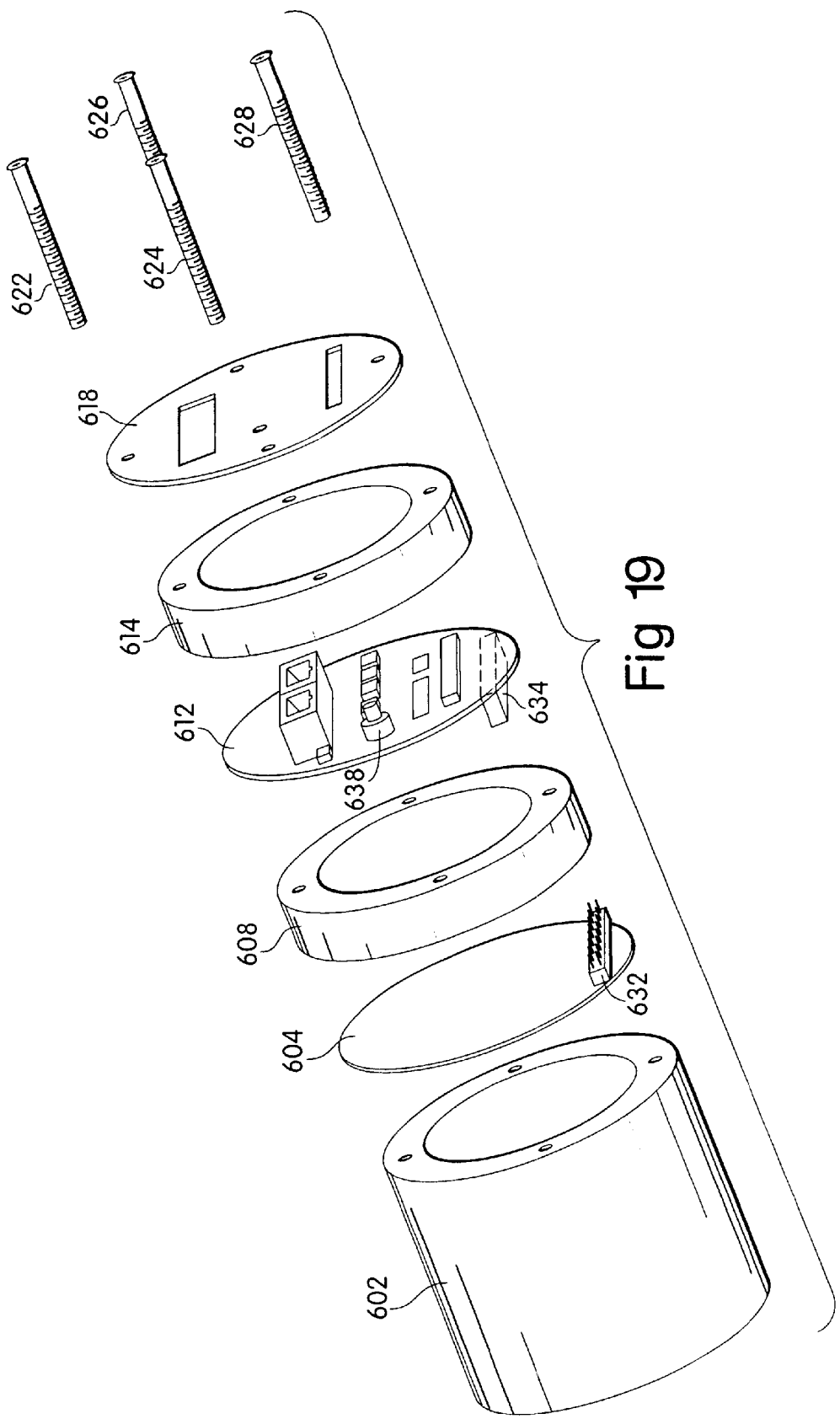
FIG. 19 depicts an embodiment of a light module in which a cylindrical housing houses the light module.

The foregoing embodiments may reside in any number of different housings. Turning now to FIG. 19, there is shown an exploded view of an illumination unit of the present invention comprising a substantially cylindrical body section 602, a light module 604, a conductive sleeve 608, a power module 612, a second conductive sleeve 614, and an enclosure plate 618. It is to be assumed here that the light module 604 and the power module 612 contain the electrical structure and software of light module 100 and power module 200, described above, or other embodiments of the light module 100 or other power modules disclosed herein. Screws 622, 624, 626, 628 allow the entire apparatus to be mechanically connected. Body section 602, conductive sleeves 604 and 614 and enclosure plate 618 are preferably made from a material that conducts heat, such as aluminum. Body section 602 has an open end, a reflective interior portion and an illumination end, to which module 604 is mechanically affixed. Light module 604 is disk-shaped and has two sides. The illumination side (not shown) comprises a plurality of LEDs of different primary colors. The connection side holds an electrical connector male pin assembly 632. Both the illumination side and the connection side are coated with aluminum surfaces to better allow the conduction of heat outward from the plurality of LEDs to the body section 602. Likewise, power module 612 is disk shaped and has every available surface covered with aluminum for the same reason. Power module 612 has a connection side holding an electrical connector female pin assembly 634 adapted to fit the pins from assembly 632. Power module 612 has a power terminal side holding a terminal 638 for connection to a source of DC power. Any standard AC or DC jack may be used, as appropriate.

Interposed between light module 602 and power module 612 is a conductive aluminum sleeve 608, which substantially encloses the space between modules 602 and 612. As shown, a disk-shaped enclosure plate 618 and screws 622, 624, 626 and 628 seal all of the components together, and conductive sleeve 614 is thus interposed between enclosure plate 618 and power module 612. Once sealed together as a unit, the illumination apparatus may be connected to a data network as described above and mounted in any convenient manner to illuminate an area. In operation, preferably a light diffusing means will be inserted in body section 602 to ensure that the LEDs on light module 604 appear to emit a single uniform beam of light.

Figure 20:
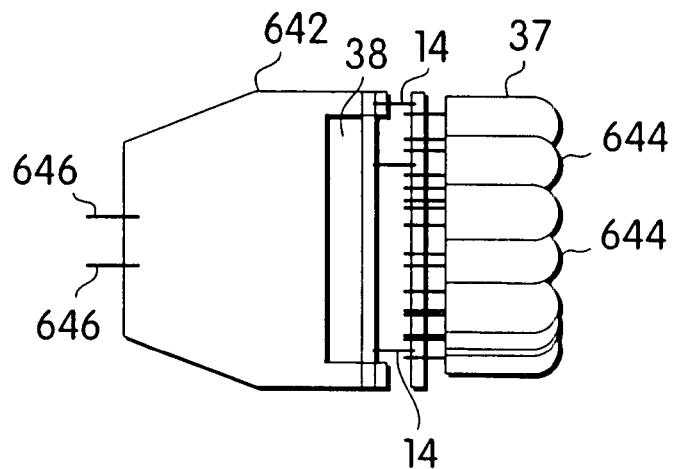
FIG. 20 depicts a modular light module.

Another embodiment of a light module 100 is depicted in FIG. 20. One of the advantages of the array 37 is that it can be used to construct an LED-based light that overcomes the problem of the need for different fixtures for different lighting applications. In particular, in an embodiment of the invention illustrated in FIG. 20, an array of LEDs 644, which can be the circular array 37 depicted in FIG. 8 or another array, may be disposed on a platform 642 that is constructed to plug into a fixture, such as an MR-16 fixture for a conventional halogen lamp. In other embodiments of the invention, the platform 642 may be shaped to plug, screw or otherwise connect into a power source with the same configuration as a conventional light bulb, halogen bulb, or other illumination source. In the embodiment of FIG. 20, a pair of connectors 646 connect to a power source, such as an electrical wire, in the same manner as connectors for a conventional halogen bulb in an MR-16 fixture.

Figure 21:
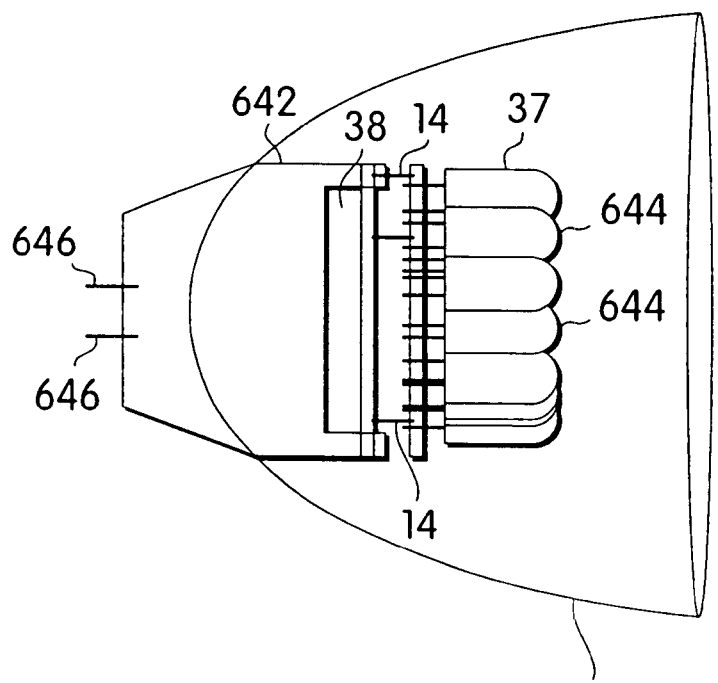
FIG. 21 depicts a modular light module constructed to fit a halogen socket.

In an embodiment of the invention depicted in FIG. 21, the platform 642 bearing the LED array 644 can be plugged into a conventional halogen fixture. Thus, without changing wiring or fixtures, a user can have LED based lights by simply inserting the modular platform 642. The user can return to conventional lights by removing the modular platform 642 and installing a conventional halogen bulb or other illumination source. Thus, the user can use the same fixtures and wiring for a wide variety of lighting applications, including the LED system 120, in the various embodiments disclosed herein.

Figure 22:
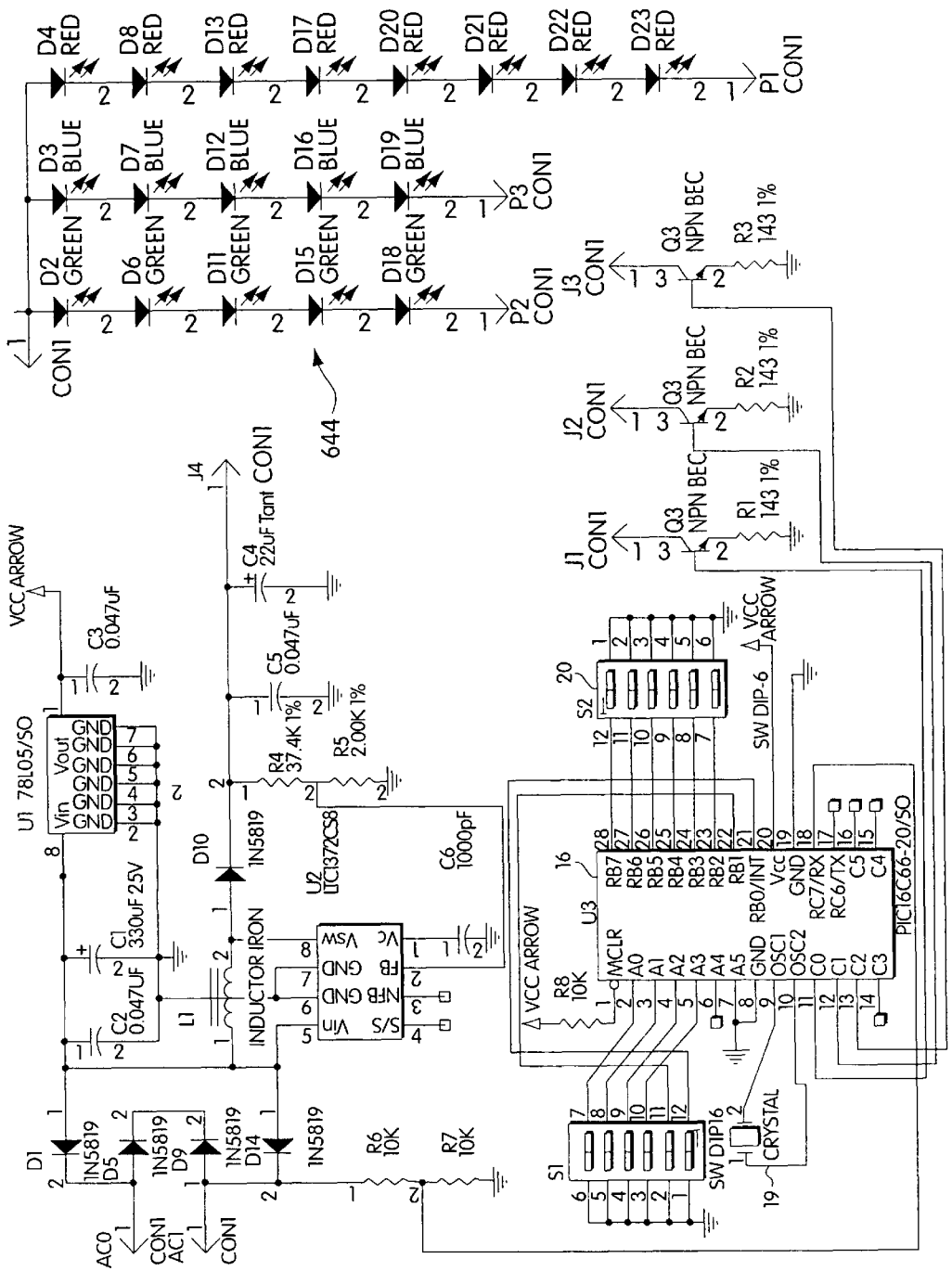
FIG. 22 depicts a circuit design for an embodiment of a light module.

Referring to FIG. 22, a schematic is provided for a circuit design for a light module 100 suitable for inclusion in a modular platform, such as the platform 642 of FIG. 20. An LED array 644 consists of green, blue and red LEDs. A processor 16 provides functions similar to the processor 16 described in connection with FIG. 6. Data input pin 20 provides data and power to the processor 16. An oscillator 19 provides clock functions. The light module 100 includes other circuit elements for permitting the processor 16 to convert incoming electrical signals that are formatted according to a control protocol, such as a DMX-512 protocol, into control signals for the LEDs of the array 644 in a manner similar to that disclosed in connection with other embodiments disclosed above.

Figure 23:
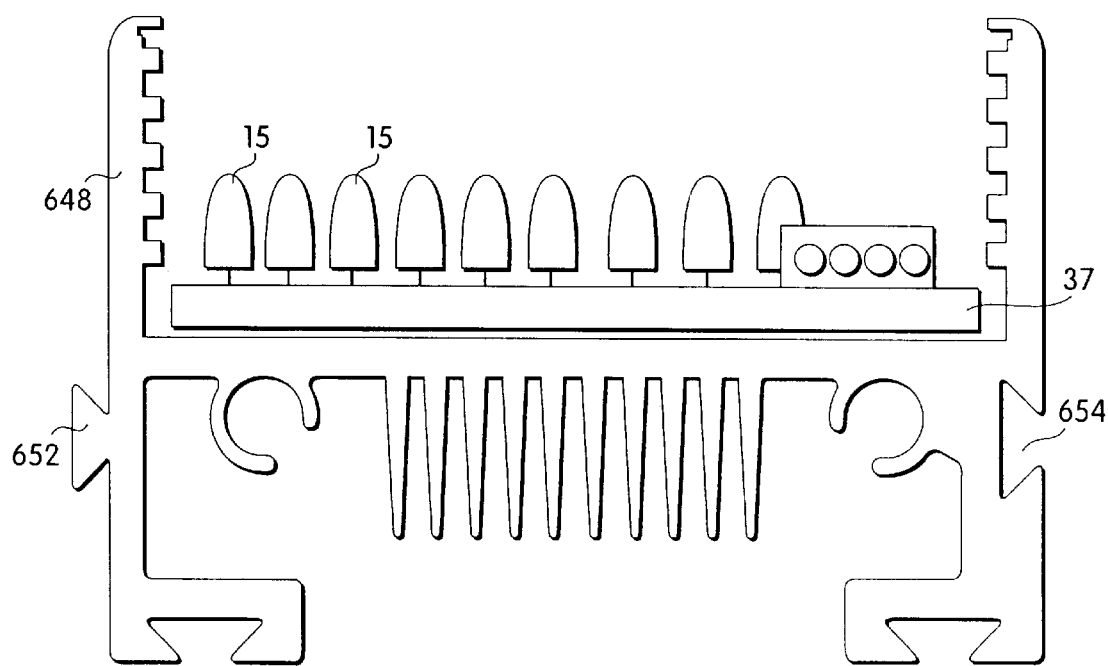
FIG. 23 depicts a modular housing for a light module.

In a further embodiment of the invention, depicted in FIG. 23, a modular platform 648 is provided on which a digitally controlled array 37 of LEDs 15, which may be an LED system 120 of a light module 100 according to the other embodiments disclosed herein, is disposed. The modular platform 648 may be made of clear plastic or similar material, so that the platform 648 is illuminated to whatever color is provided by the array 37. The modular platform 648 may include extrusions 652 and intrusions 654, so that modular blocks can be formed that interconnect to form a variety of three-dimensional shapes. A wall, floor, ceiling, or other object can be constructed of blocks, with each block being illuminated to a different color by that block's array 37 of LEDs 15. The blocks 648 can be interconnected. Such an object can be used to create signage; that is, the individual blocks of such an object can be illuminated in the form of symbols, such as letters, numbers, or other designs. For example, a wall can be used as a color display or sign. Many different shapes of modular blocks 648 can be envisioned, as can many different interlocking mechanisms. In fact, light modules 100 may be disposed in a variety of different geometric configurations and associated with a variety of lighting environments, as further disclosed herein.

In another embodiment of the present invention, an arrayed LED is mounted on a pan or tilt platform, in a manner similar to conventional theater lights. Known robotic lights shine a conventionally produced light beam from a bulb or tube onto a pan or tilt mirror. The arrayed LEDs of the present invention may be placed directly on the pan or tilt platform, avoiding the necessity of precisely aligning the light source with the pan or tilt mirror. Thus, an adjustable pan/tilt beam effect may be obtained similar to a mirror-based beam, without the mirror. This embodiment permits pan/tilt beam effects in more compact spaces than previously possible, because there is not a need for a separation between the source and the mirror.

Also provided is an LED based construction tile, through which a wall, floor or ceiling may be built that includes an ability to change color or intensity in a manner controlled by a microprocessor. The tile may be based on modularity similar to toy plastic building blocks. Multicolor tiles can be used to create a multicolor dance floor or shower, or a floor, wall or bathroom tile.

Also provided is a modular lighting system which allows the creation of various illuminating shapes based on a limited number of subshapes. In this embodiment of the present invention, a plurality of light emitting squares (or other geometric shapes) may be arranged into larger shapes in one, two or three dimensions. The modular blocks could communicate through physical proximity or attachment. Modular multicolor lighting blocks can be configured into different formats and shapes.

As described above, embodiments of the present invention may be utilized in a variety of manners. By way of examples, the following discussion provides different environments within which the LEDs of the present invention may be adapted for lighting and/or illumination.

Figure 24:
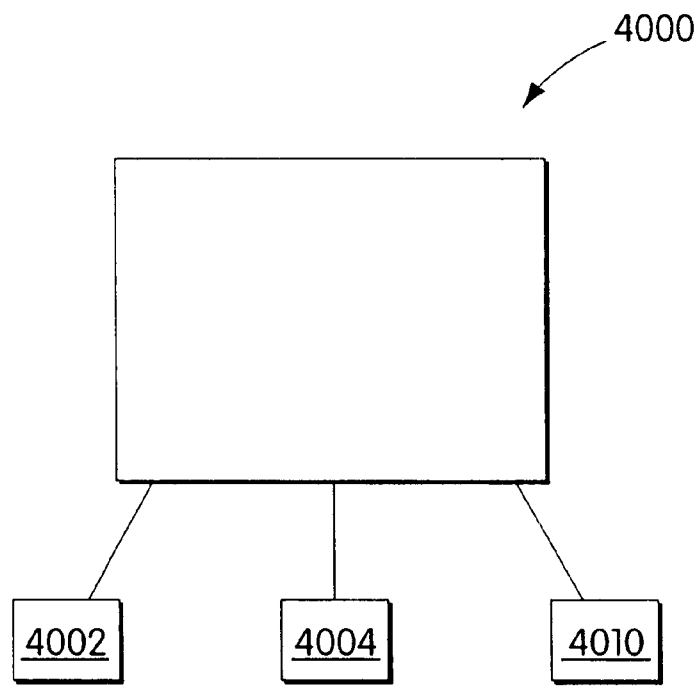
FIG. 24 is a schematic illustration of a modular LED unit in accordance with one embodiment of the present invention.
Figure 25:
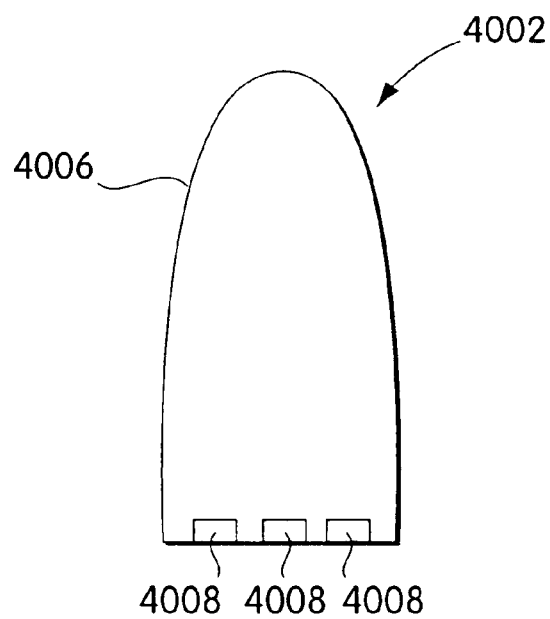
FIG. 25. illustrates a light module in accordance with one embodiment of the present invention.

Looking now at FIG. 24, a modular LED unit 4000, is provided for illumination within an environment. Modular unit 4000 comprises a light module 4002, similar to item 120 discussed in connection with FIG. 1, and a processor 4004, similar to item 16 discussed in connection with FIG. 1. The light module 4002 may include, as illustrated in FIG. 25, an LED 4006 having a plurality of color-emitting semiconductor dies 4008 for generating a range of radiation within a spectrum, for example, a range of frequencies within the visible spectrum. Each color-emitting die 4008 preferably represents a primary color and is capable of individually generating a primary color of varying intensity. When combined, the primary colors from each of dies 4008 can produce a particular color within the color spectrum. The processor 4004, on the other hand, may be provided for controlling an amount of electrical current supplied to each of the semiconductor die 4008. Depending on the amount of electrical current supplied to each die, a primary color of a certain intensity may be emitted therefrom. Accordingly, by controlling the intensity of the primary color produced from each die, the processor 4004, in essence, can control the particular color illuminated from the LED 4006. Although FIG. 25 shows three color-emitting semiconductor dies 4002, it should be appreciated that the use of at least two color emitting dies may generate a range of radiation within a spectrum.

The modular unit 4000 may further include a mechanism (not shown) for facilitating communication between a generator of control signals and the light module 4002. In one embodiment, the mechanism may include a separate transmitter and receiver, as discussed above in connection with FIG. 2. However, it should be appreciated that the transmitter and receiver may be combined into one mechanism. The modular unit 4000 may also include a power module 4010, as discussed in connection with FIG. 9, for providing an electrical current from a power source, for example, an electrical outlet or a battery, to the light module 4002. To permit electrical current to be directed from the power module 4010 to the light module 4002, an electrical connector, similar to complementary male pin set 632 and female pin set 634 in FIG. 19, may be provided. In this manner, the electrical connector may be designed to removably couple the light module 4002 to the power module 4010.

Figure 26:
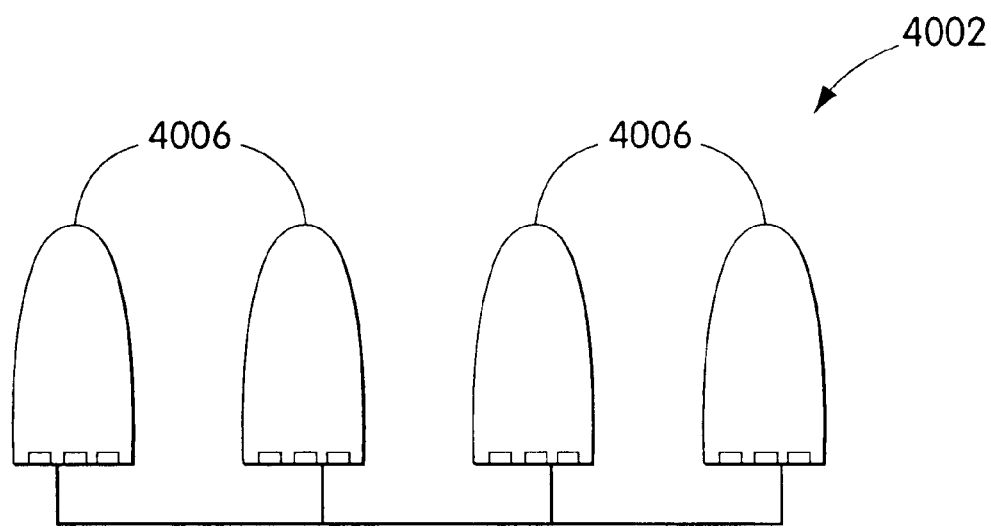
FIG. 26 illustrates a light module in accordance with another embodiment of the present invention.

In an alternate embodiment, the light module 4002, as shown in FIG. 26, may include a plurality of LEDs 4006 illustrated in FIG. 25. Each LED 4006 may be part of a light module 4002, which may be provided with a data communication link 4014, similar to item 500 described above in connection with FIG. 2, for communication with a control signal generator, or, in certain embodiments of the invention, with other light modules 4002. In this manner, data such as the amount of electrical current controlled by processor 4004 may be supplied to the plurality of semiconductor dies 4008 in each of the LEDs 4006, so that a particular color may be generated.

Figure 27:
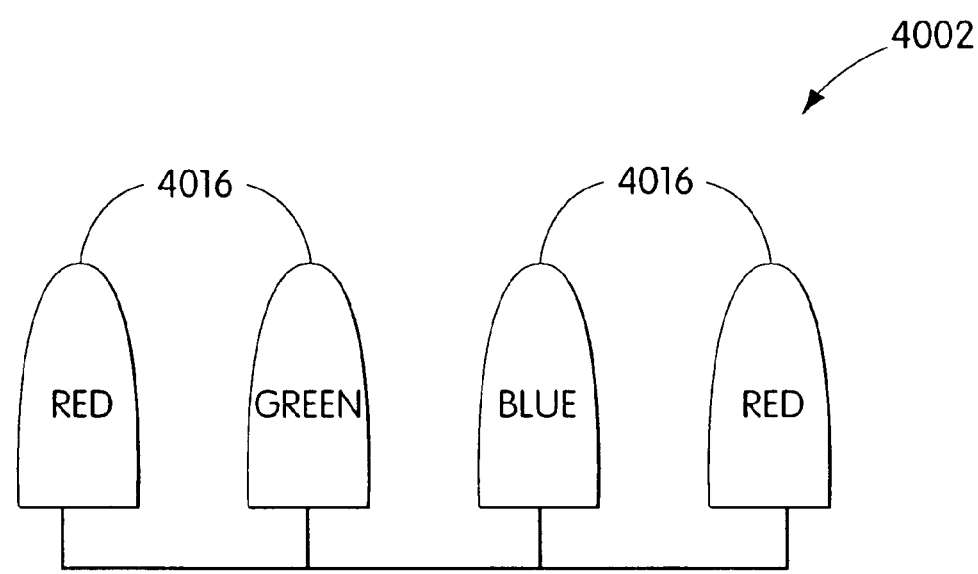
FIG. 27 illustrates a light module in accordance with a further embodiment of the present invention.

In another embodiment, the light module 4002, as shown in FIG. 27, may include a plurality of conventional light emitting diodes (LEDs) 4016. The conventional LEDs 4016 may be representative of primary colors red, blue and green. Thus, when the primary color from each of the LED 4016 is generated, the combination of a plurality of LEDs 4016 can produce any frequency within a spectrum. It should be understood, that similar to the semiconductor dies 4008, the intensity and/or illumination of each LED 4016 may be varied by processor 4004 to obtain a range of frequencies within a spectrum. To facilitate communication amongst the plurality of LEDs 4016 and with the processor 4004, data communication link 4014 may be provided.

Figure 28A:
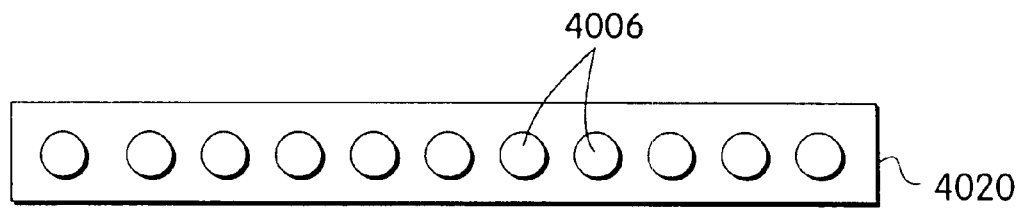
FIGS. 28A–C illustrate a plurality of LEDs arranged within the various configurations for use with the modular LED unit of the present invention.
Figure 28B:
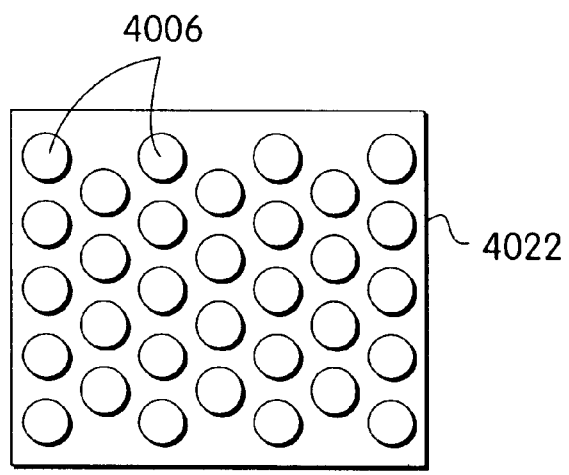
Figure 28C:
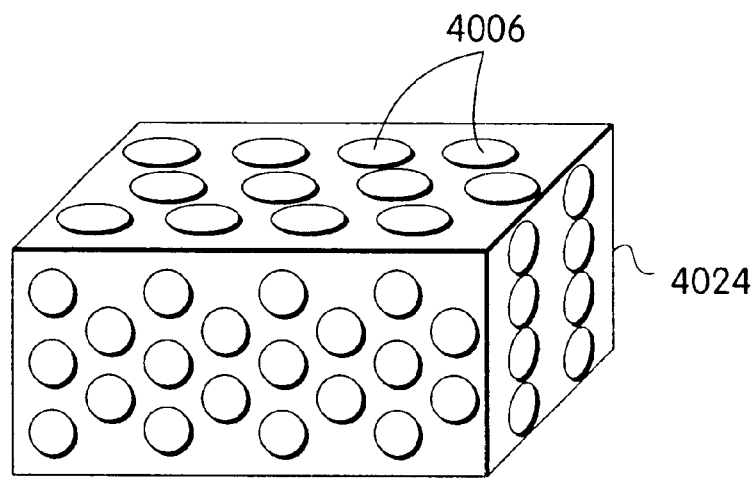

The modular LED unit 4000, in certain embodiments, may be interconnected to form larger lighting assemblies. In particular, the light module 4002 may include LEDs 4006 or 4016 arranged linearly in series within a strip 4020 (FIG. 28A). The LEDs 4006 or 4016 may also be arranged within a two dimensional geometric panel 4022 (FIG. 28B) or to represent a three-dimensional structure 4024 (FIG. 28C). It should be appreciated that the strip 4020, the geometric panel 4022 or the three-dimensional structure 4024 need not adhere to any particular design, and may be flexible, so as to permit the light module 4002 to conform to an environment within which it is placed.

In one embodiment of the invention, the strip 4020, the geometric panel 4022 and the three-dimensional structure 4024 may be provided with a coupling mechanism (not shown) to permit coupling between modular LED units 4000. Specifically, the coupling mechanism may permit a plurality of strips 4020 to be stringed together, or a plurality of geometric panels 4022 to be connected to one another, or a plurality of three-dimensional structures 4024 to be coupled to one another. The coupling mechanism may also be designed to permit interconnection of one of a strip 4020, a geometric panel 4022, and a three-dimensional structure 4024 to another of a strip 4020, a geometric panel 4022, and a three-dimensional structure 4024. The coupling mechanism can permit either mechanical coupling or electrical coupling between the modular LED units 4000, but preferably permits both electrical and physical coupling between the modular LED units 4000. By providing an electrical connection between the modular LED units 4000, power and data signals may be directed to and between the modular LED units 4000. Moreover, such connection permits power and data to be provided at one central location for distribution to all of the modular LED units 4000. In an embodiment of the invention, data may be multiplexed with the power signals in order to reduce the number of electrical connections between the modular LED units 4000. The mechanical coupling, on the other hand, may simply provide means to securely connect the modular LED units 4000 to one another, and such function may be inherent through the provision of an electrical connection.

The modular LED unit 4000 of the present invention may be designed to be either a "smart" or "dumb" unit. A smart unit, in one embodiment, includes a microprocessor incorporated therein for controlling, for example, a desired illumination effect produced by the LEDs. The smart units may communicate with one another and/or with a master controller by way of a network formed through the mechanism for electrical connection described above. It should be appreciated that a smart unit can operate in a stand-alone mode, and, if necessary, one smart unit may act as a master controller for other modular LED units 4000. A dumb unit, on the other hand, does not include a microprocessor and cannot communicate with other LED units. As a result, a dumb unit cannot operate in a stand-alone mode and requires a separate master controller.

The modular LED unit 4000 may be used for illumination within a range of diverse environments. The manner in which the LED unit may be used includes initially placing the modular LED unit 4000 having a light module 4002, such as those provided in FIGS. 25–27, within an environment, and subsequently controlling the amount of electrical current to at least one LED, so that a particular amount of current supplied thereto (i.e., the semiconductor dies 4008 or the plurality of conventional LEDs) generates a corresponding frequency within a spectrum, for instance, the visible spectrum.

Figure 29:
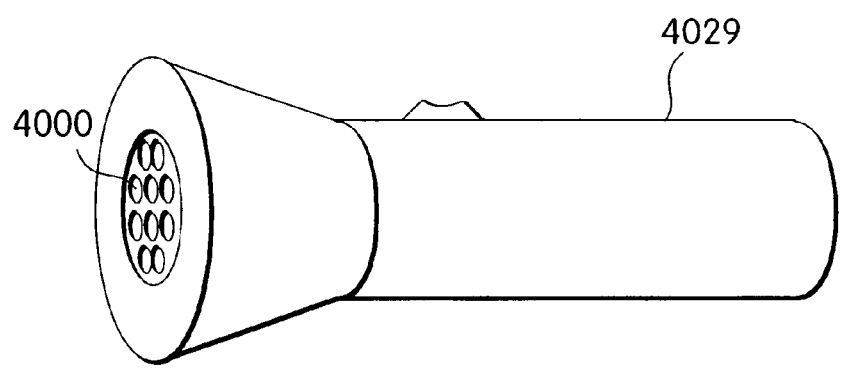
FIGS. 29–68 illustrate the various environments within which the modular LED unit of the present invention may illuminate.
Figure 30:
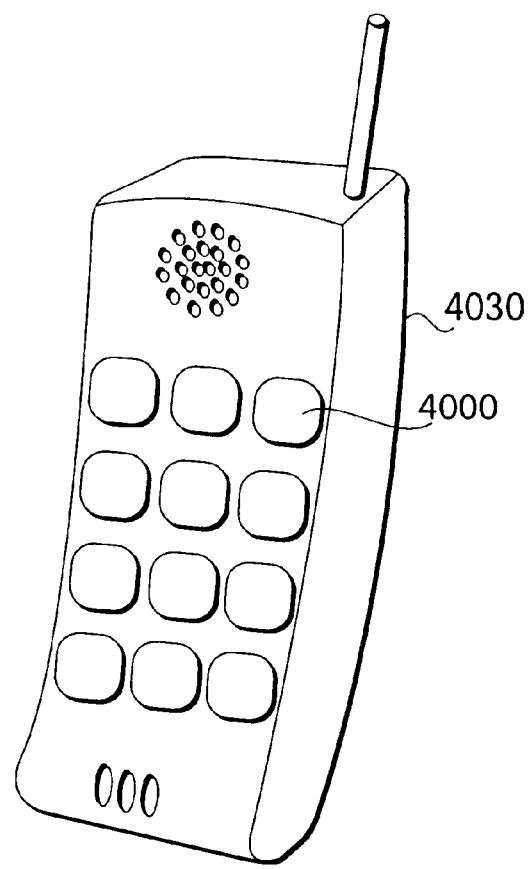
Figure 31:
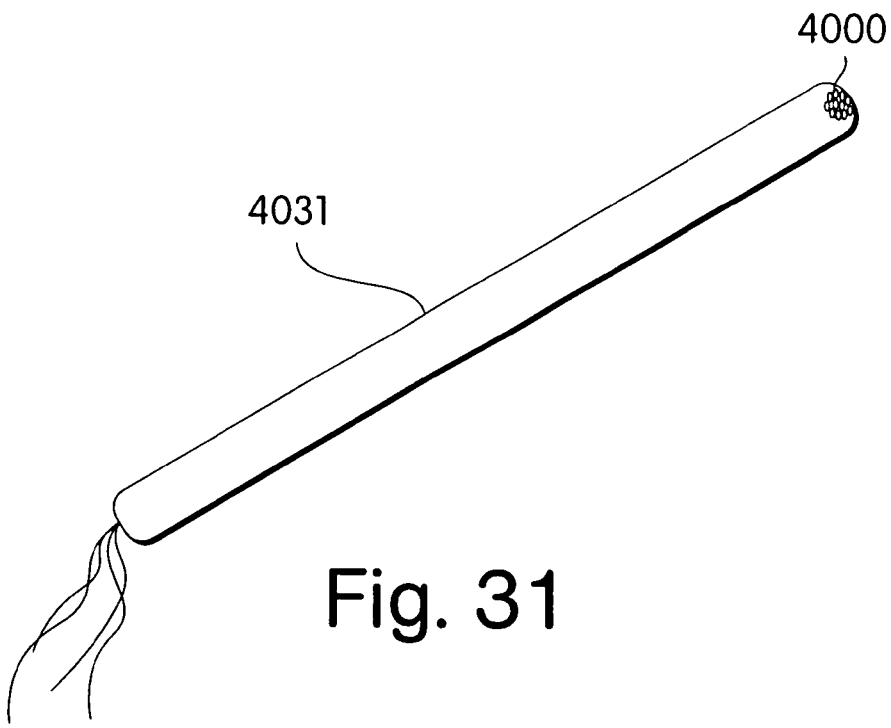
Figure 32:
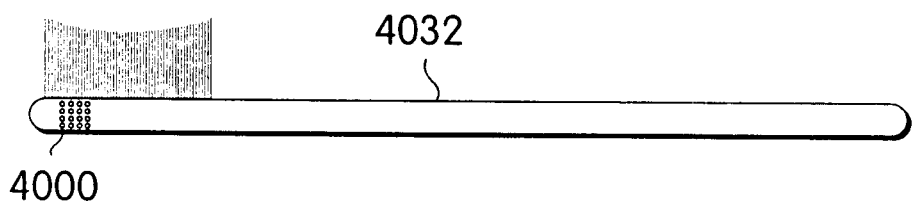

An environment within which the modular LED unit 4000 may illuminate includes a handheld flashlight 4029 (FIG. 29) or one which requires the use of an indicator light. Examples of an environment which uses an indicator light include, but are not limited to, an elevator floor button, an elevator floor indication display or panel, an automobile dashboard, an automobile ignition key area, an automobile anti-theft alarm light indicator, individual units of a stereo systems, a telephone pad button 4030 (FIG. 30), an answering machine message indicator, a door bell button, a light status switch, a computer status indicator, a video monitor status indicator, and a watch. Additional environments within which the modular LED unit 4000 may illuminate can include (i) a device to be worn on a body, examples of which include, an article of jewelry, an article of clothing, shoes, eyeglasses, gloves and a hat, (ii) a toy, examples of which include, a light wand 4031 (FIG. 31), a toy police car, fire truck, ambulance, and a musical box, and (iii) a hygienic product, examples of which include, a tooth brush 4032 (FIG. 32) and a shaver.

Figure 33:
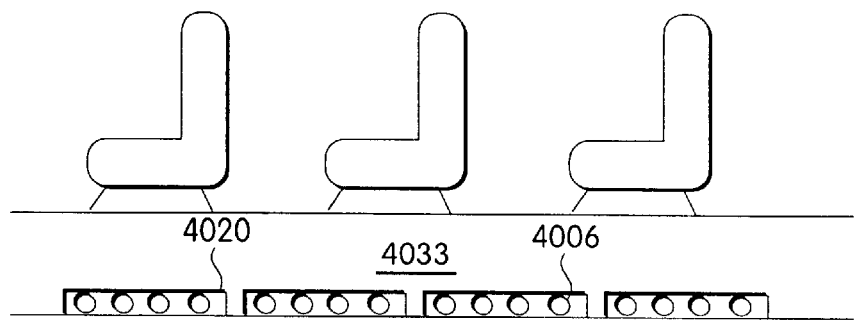

In accordance with another embodiment of the invention, a modular LED unit 4000 having a plurality of LEDs 4006 or 4016 arranged linearly in series within a strip 4020 may be also be used for illumination within an environment. One such environment, illustrated in FIG. 33, includes a walkway 4033, for instance, an airplane aisle, a fashion show walkway or a hallway. When used in connection with a walkway, at least one strip 4020 of LEDs 4006 or 4016 may be positioned along one side of the walkway 4033 for use as a directional indicator.

Figure 34:
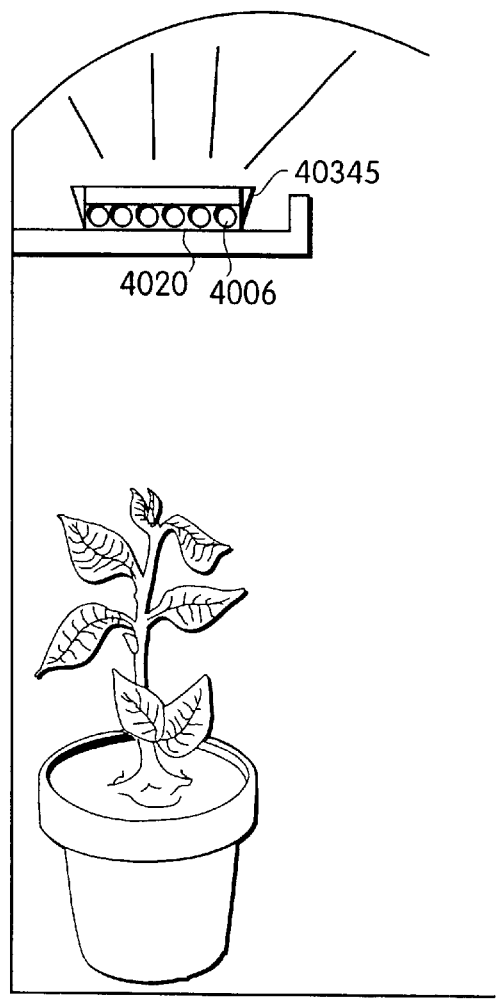

Another such environment, illustrated in FIG. 34, includes a cove 4034. When used in connection with a cove, at least one strip 4020 of LEDs 4006 or 4016 may be positioned adjacent the cove 4034, such that the strip of LEDs may illuminate the cove. In one embodiment, the strip 4020 of LEDs 4006 or 4016 may be placed within a housing 40345, which housing is then placed adjacent the cove 4034.

Figure 35:
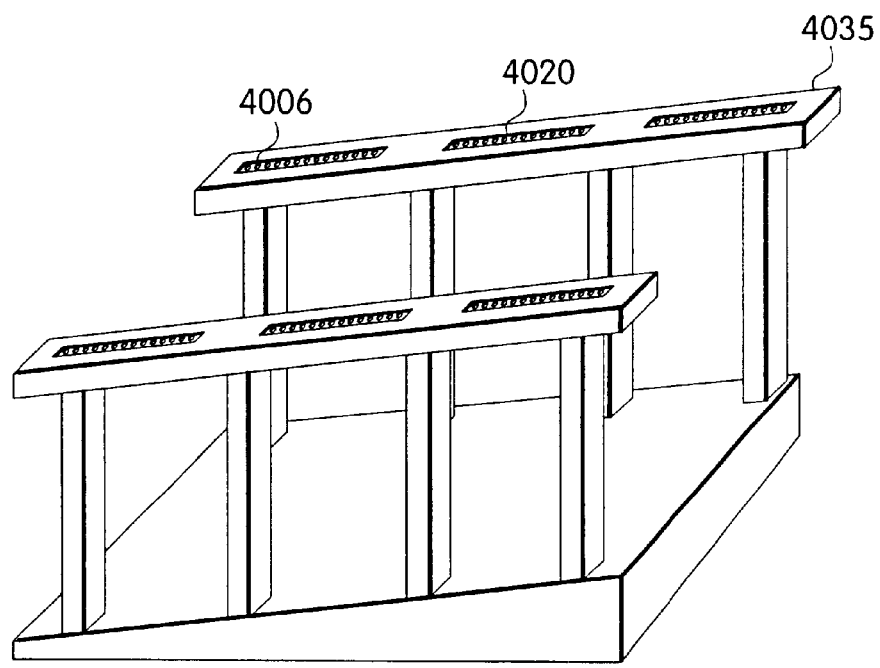

Another such environment, illustrated in FIG. 35, includes a handrail 4035. When used in connection with a handrail, such as that in a dark movie theater, at least one strip 4020 of LEDs 4006 or 4016 may be positioned on a surface of the handrail 4035 to direct a user to the location of the handrail.

Figure 36:
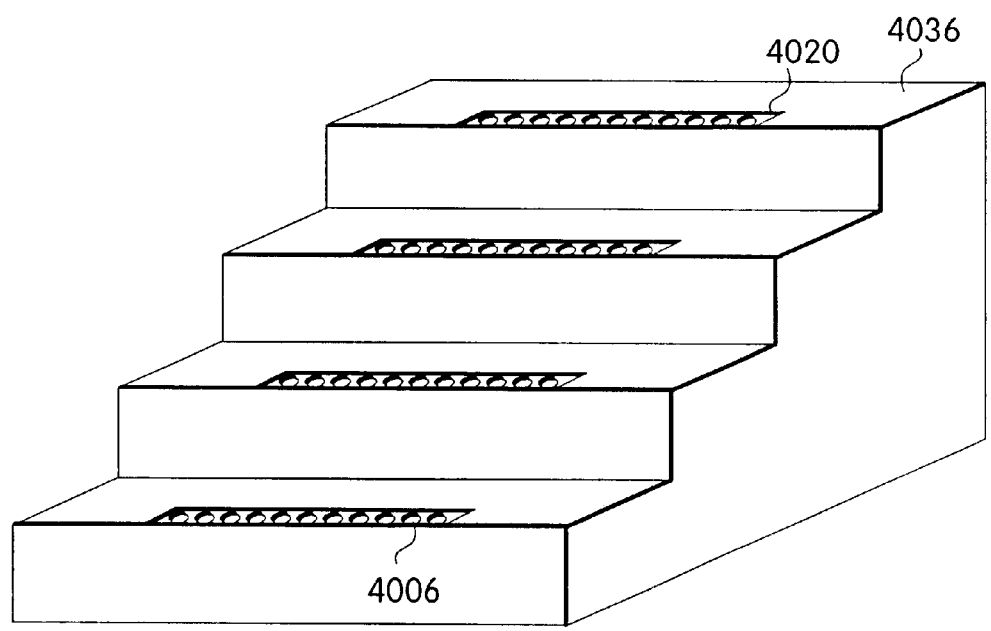

Another such environment, illustrated in FIG. 36, includes a plurality of steps 4036 on a stairway. When used in connection with a plurality of steps, at least on strip 4020 of LEDs 4006 or 4016 is positioned at an edge of a step 4036, so that at night or in the absence of light, a user may be informed of the location of the step.

Figure 37:
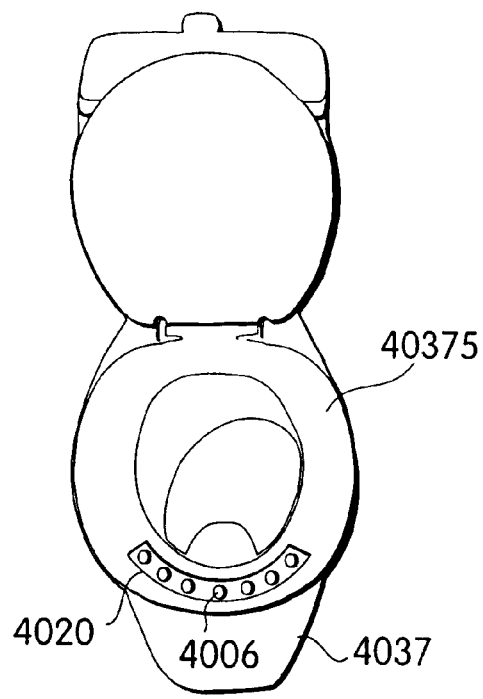

Another environment, illustrated in FIG. 37, includes a toilet bowl 4037. When used in connection with a toilet bowl, at least one strip 4020 of LEDs 4006 or 4016 may be positioned about a rim of the bowl 4037 or the seat 40375, so that in the absence of light in the bathroom, a user may be informed of the location of the bowl or the seat.

Figure 38:
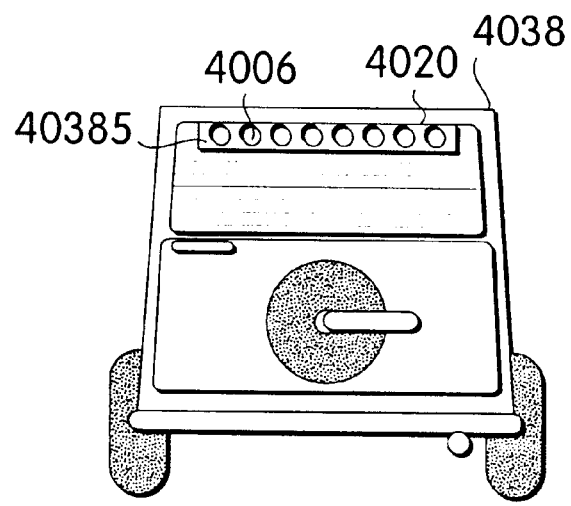

Another environment, illustrated in FIG. 38, includes an elevated brake light 4038 located in the rear of an automobile. When used in connection with an elevated brake light, at least one strip 4020 of LEDs 4006 or 4016 may be positioned within a previously provided housing 40385 for the brake light.

Figure 39:
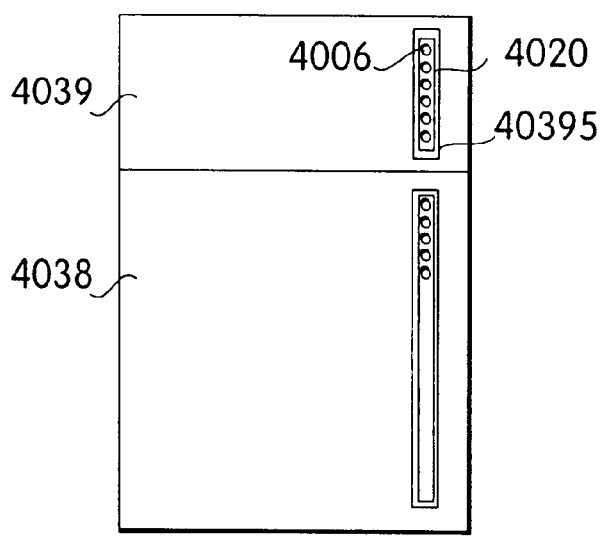

Another environment, illustrated in FIG. 39, includes a refrigerator door 4039. When used in connection with a refrigerator door, at least one strip 4020 of LEDs 4006 or 4016 may be positioned on a refrigerator door handle 40395, so that in the absence of light in, for example, the kitchen, a user may quickly locate the handle for opening the refrigerator door 4039.

Figure 40:
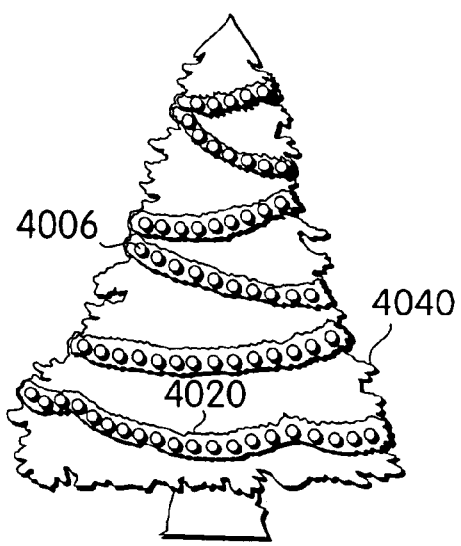

Another environment, illustrated in FIG. 40, includes a tree 4040. When used in connection with a tree, at least one strip 4020 of LEDs 4006 or 4016 may be positioned on the tree 4040, so as to permit illumination thereof. The tree 4040 could be a Christmas tree or other ornamental tree, such as an artificial white Christmas tree. By strobing the LEDs 4006 between different colors, the tree 4040 can be caused to change color.

Figure 41:
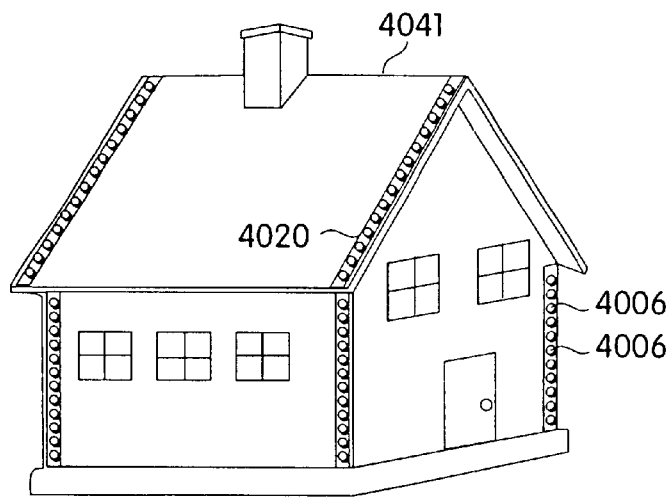

Another environment, illustrated in FIG. 41, includes a building 4041. When used in connection with a building, at least one strip 4020 of LEDs 4006 or 4016 may be positioned along a surface of the building 4041, so that illumination of the LEDs may attract attention from an observer.

Figure 42:
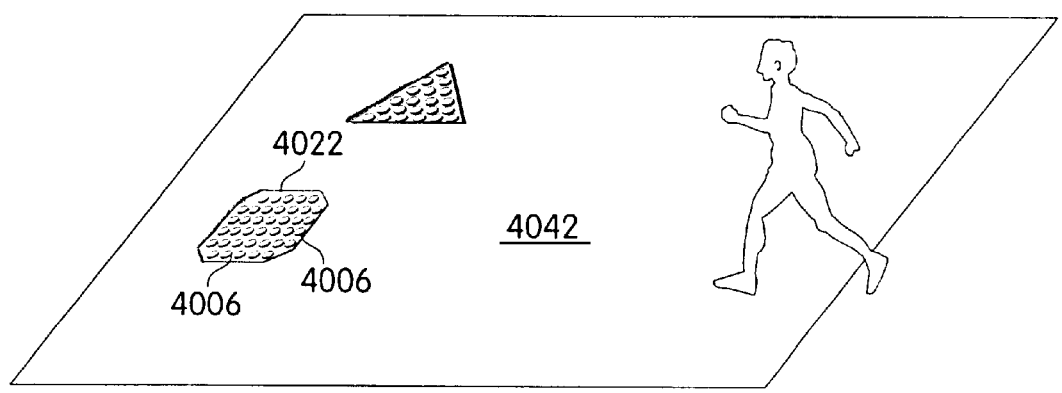

In accordance with another embodiment of the invention, a modular LED unit 4000 having a plurality of LEDs 4006 or 4016 arranged within a geometric panel 4022 may be also be used for illumination within an environment. One such environment, illustrated in FIG. 42, includes a floor 4042. When used in connection with a floor, at least one geometric panel 4022 of LEDs 4006 or 4016 may be positioned within at least one designated area in the floor 4042 to provide illumination thereof.

Figure 43:
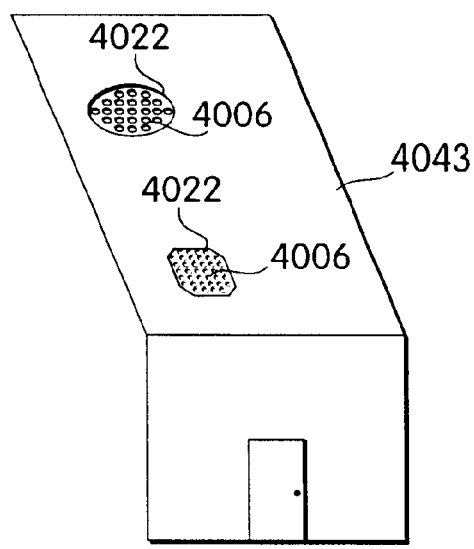

Another environment within which a geometric panel 4022 of LEDs 4006 or 4016 may be used includes a ceiling 4043, as illustrated in FIG. 43. When used in connection with a ceiling, at least one geometric panel 4022 may be positioned within at least one designated area on the ceiling 4043 to provide illumination thereof.

Figure 44:
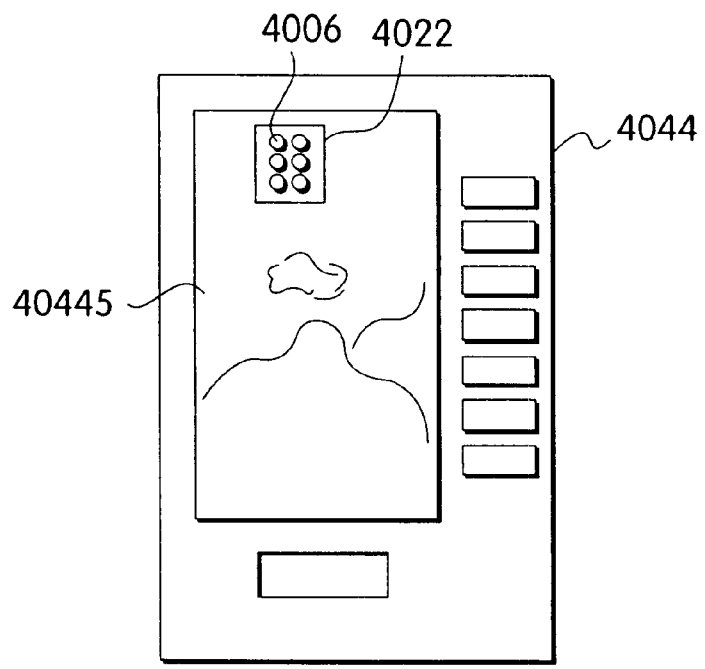

Another environment within which a geometric panel 4022 of LEDs 4006 or 4016 may be used includes a vending machine 4044, as illustrated in FIG. 44. When used in connection with a vending machine, at least one geometric panel 4022 may be positioned posterior to a frontal display 40445 of the vending machine, so as to provide illumination of illustration on the frontal display.

Figure 45:
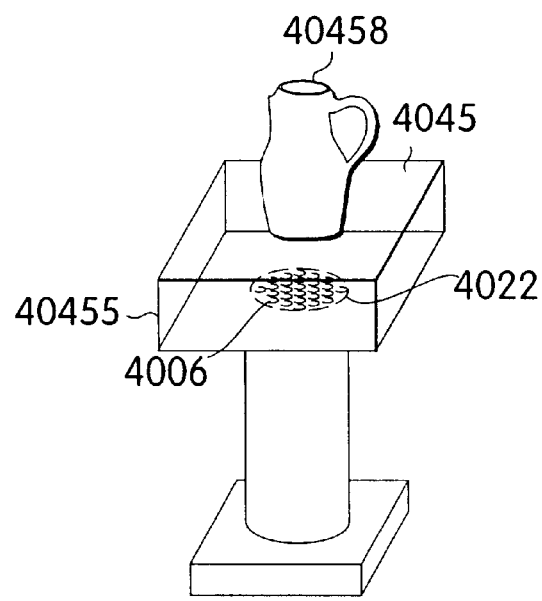

Another environment within which a geometric panel 4022 of LEDs 4006 or 4016 may be used includes an illuminating surface 4045, as illustrated in FIG. 45. When used in connection with an illuminating surface 4045, at least one geometric panel 4022 may be positioned posterior to the surface to provide illumination of a graphical illustration on the surface or illumination of an object placed on the surface. Examples of such an illuminating surface may include an advertisement sign of the type typically seen at an airport, or a transparent surface of a stand 40455 for displaying an object 40458.

Figure 46:
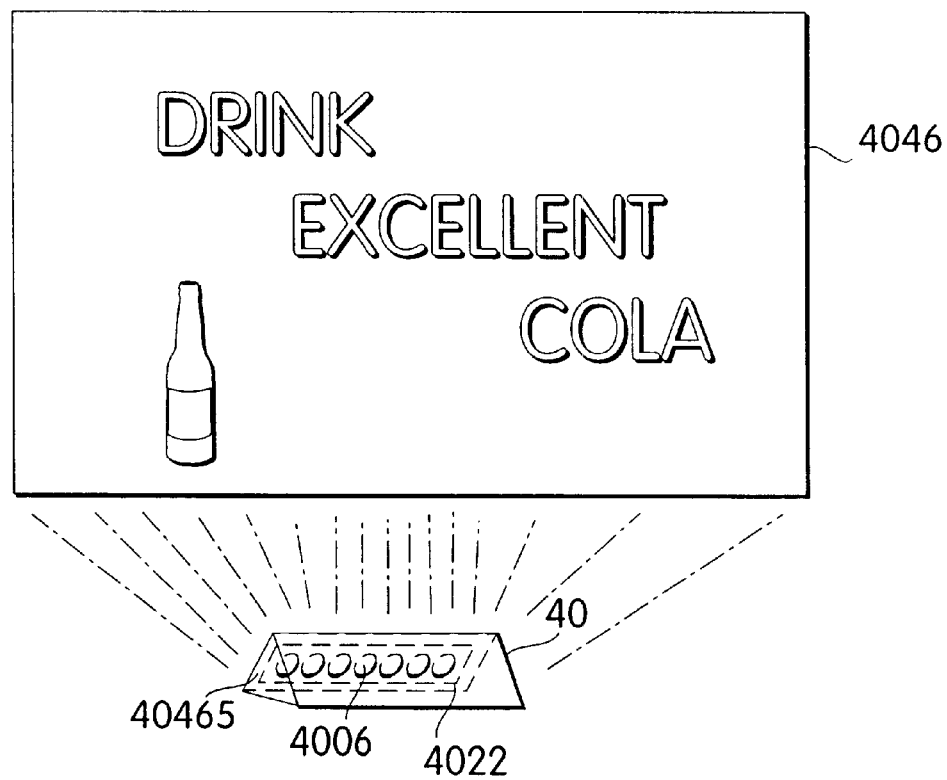

Another environment within which a geometric panel 4022 of LEDs 4006 or 4016 may be used includes a displayment sign 4046, as illustrated in FIG. 46. When used in connection with a displayment sign, such as a billboard or a advertisement board, at least one geometric panel 4022 may be positioned within a housing 40465 located, for example, in front of the sign to provide illumination of illustration thereon.

Figure 47:
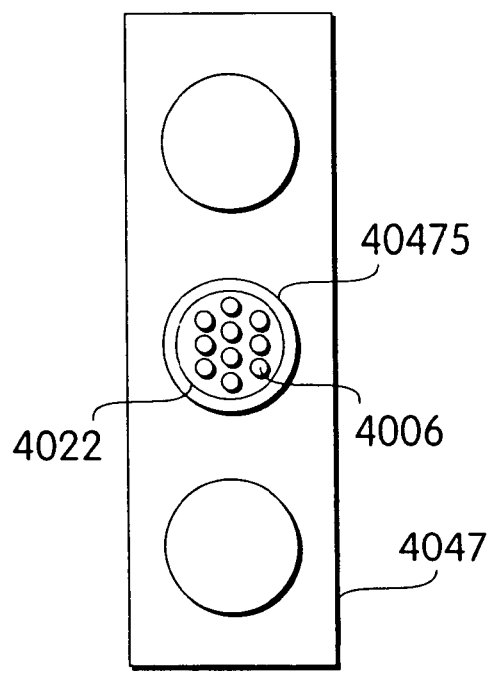

Another environment within which a geometric panel 4022 of LEDs 4006 or 4016 may be used includes a traffic light 4047, as illustrated in FIG. 47. When used in connection with a traffic light, at least one geometric panel 4022 may be positioned within a housing 40475 for at least one of the lights. It should be noted that on a conventional traffic light, a geometric panel 4022 may be needed for each of the three lights. However, since the modular LED unit of the present invention may generate a range of colors, including red, yellow and green, it may be that a new traffic light might be designed to include placement for only one modular LED unit. A variety of different colors could be provided within each signal light, so that an adequate signal is provided for different users, including those with red/green color blindness.

Figure 48:
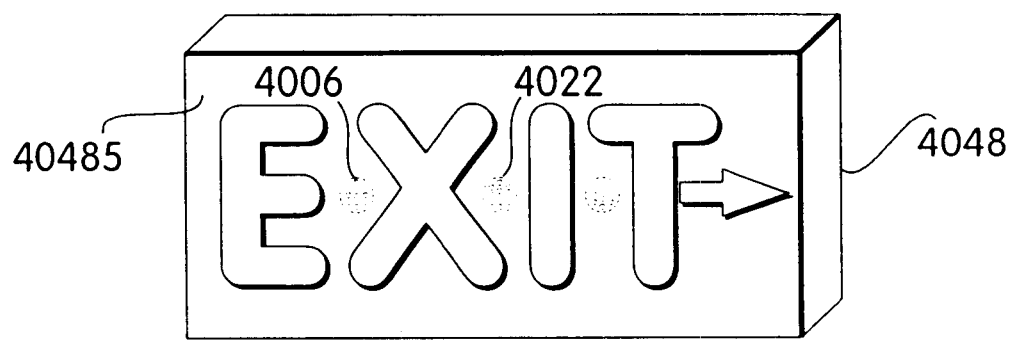

Another environment within which a geometric panel 4022 of LEDs 4006 or 4016 may be used includes a directional display sign 4048, as illustrated in FIG. 48. When used in connection with a directional display sign, at least one geometric panel 4022 may be positioned within a housing 40485 for the directional display sign.

Figure 49:
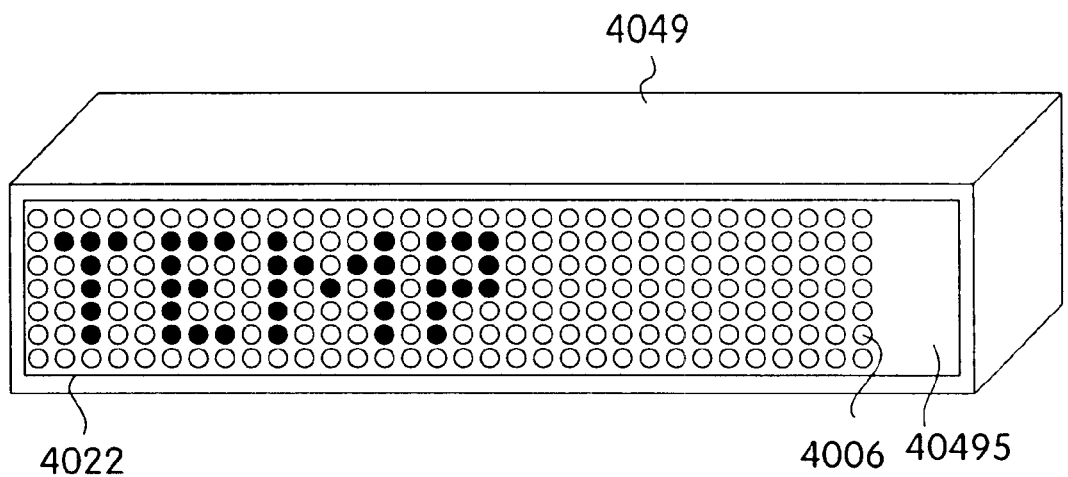

Another environment within which a geometric panel 4022 of LEDs 4006 or 4016 may be used includes an information board 4049, as illustrated in FIG. 49. When used in connection with an information board, at least one geometric panel 4022 may be positioned on a front side of the board 4049, so that informational data may be provided to the reader. In one embodiment of the invention, the information board includes, but is not limited to, a traffic information sign, a silent radio 40495, a scoreboard, a price board, an electronic advertisement board, and a large public television screen.

Figure 50:
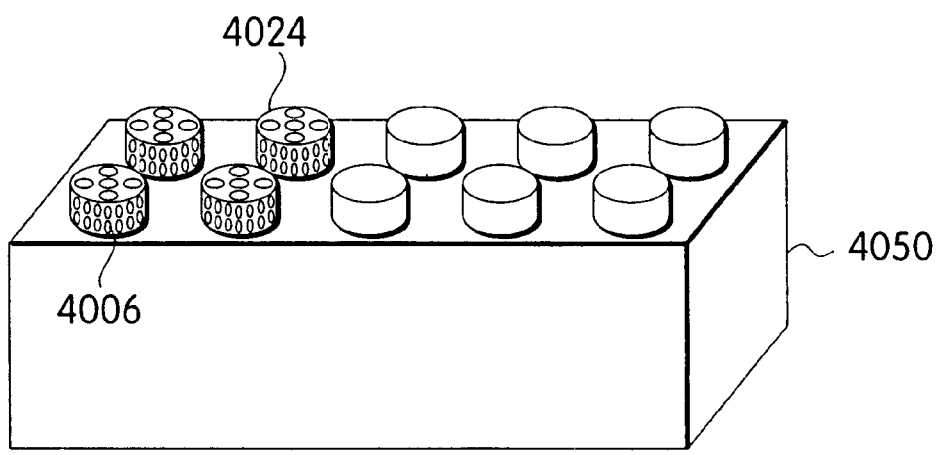

In accordance with another embodiment of the invention, a modular LED unit 4000 having a plurality of LEDs 4006 or 4016, arranged to represent a three-dimensional structure 4024, may be also be used for illumination within an environment. One such environment, illustrated in FIG. 50, includes a toy construction block 4050. When used in connection with a toy construction block, at least one three-dimensional structure 4024 of LEDs 4006 or 4016 may be positioned on or within the toy construction block 4050 to provide illumination thereof It should be appreciated that the three-dimensional structure of LEDs can be design to represent any desired three-dimensional object.

Figure 51:
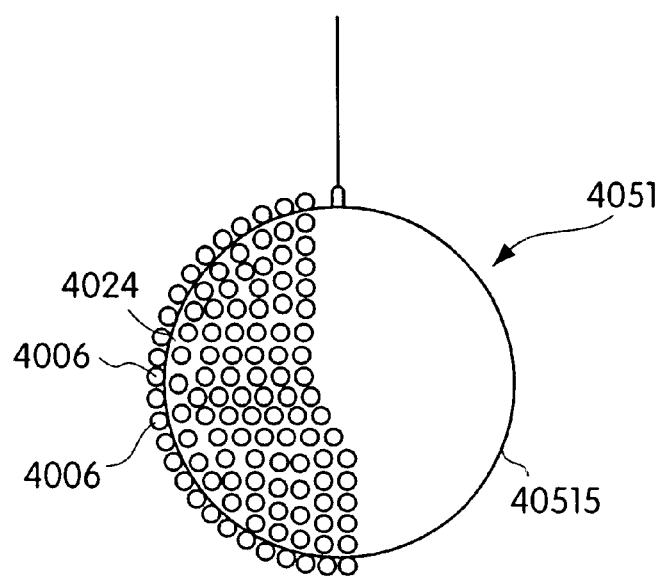

A further environment within which the three-dimensional structure 4024 of LEDs 4006 or 4016 may be utilized includes, as shown in. FIG. 51, an ornamental display 4051. Since the three-dimensional structure 4024 of LEDs, as indicated, can be designed to represent any three-dimensional object, the structure may be formed into the ornamental display 4051 of interest, so that illumination of the LEDs provides an illuminated representation of the object. Examples of an ornamental display 4051 can include a Christmas tree ornament, an animal-shaped figure, a discotheque ball 40515, or any natural or man-made object capable of being represented.

Figure 52:
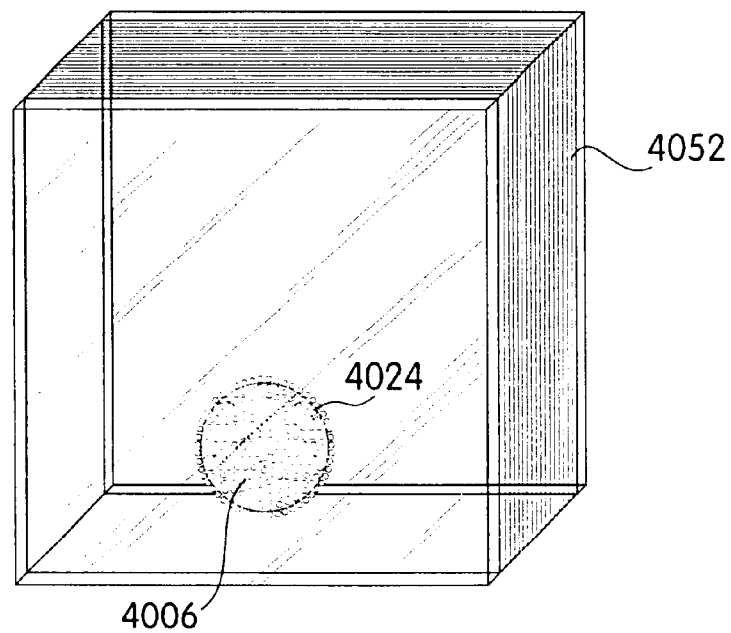
Figure 53:
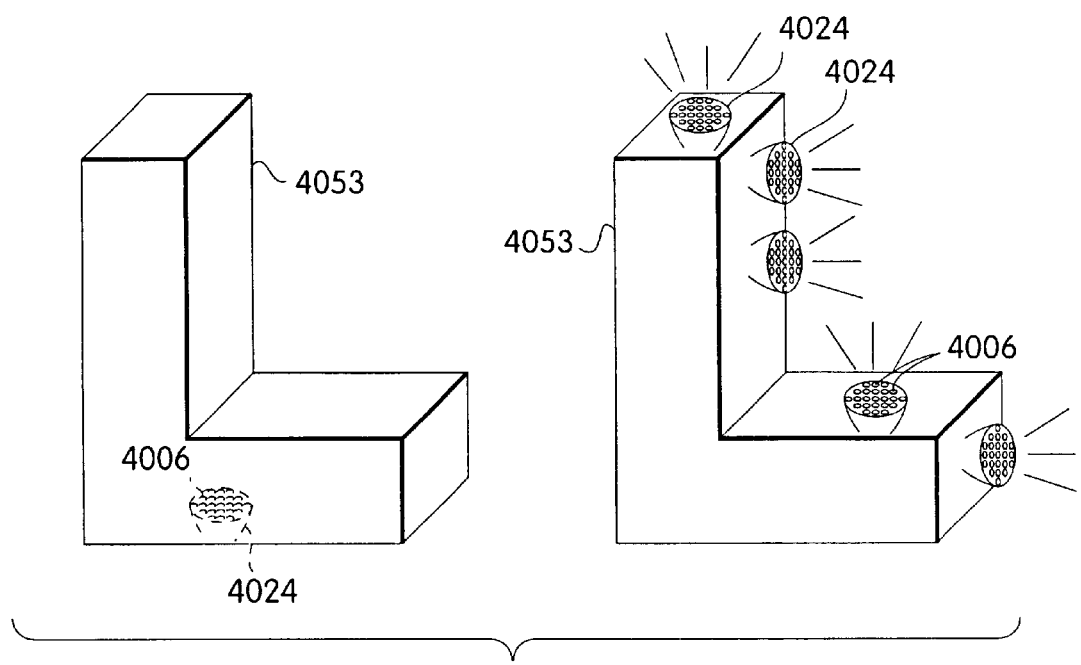

A further environment within which the three-dimensional structure 4024 of LEDs 4006 or 4016 may be utilized includes an architectural glass block 4052, as shown in FIG. 52, or large letters 4053, as shown in FIG. 53. To utilize the three-dimensional structure 4024 in connection with the glass block, at least one three-dimensional structure 4024 may be positioned within the glass block 4052 for illumination thereof. To utilize the three-dimensional structure 4024 in connection with the large letter 4053, at least one three-dimensional structure 4024 may be positioned on the letter, or if the letter 4053 is transparent, within the letter.

Figure 54:
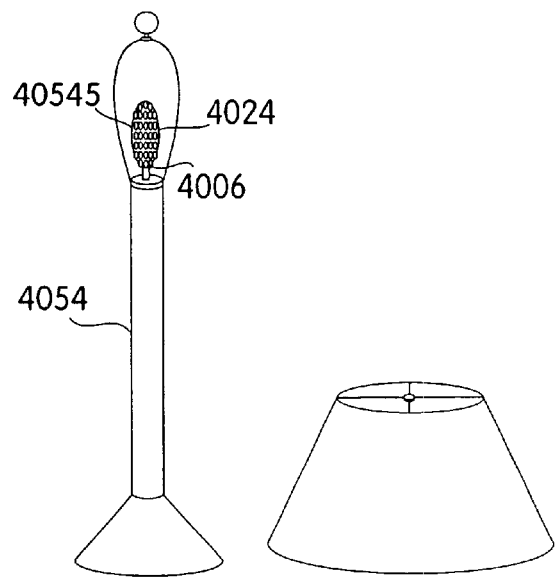

A further environment within which the three-dimensional structure 4024 of LEDs 4006 or 4016 may be utilized includes a traditional lighting device 4054, as shown in FIG. 54. To utilize the three-dimensional structure 4024 in connection with the traditional lighting device 4054, at least one three-dimensional structure 4024, in the shape of, for example, a conventional light bulb 40545, may be positioned within a socket for receiving the conventional light bulb.

Figure 55:
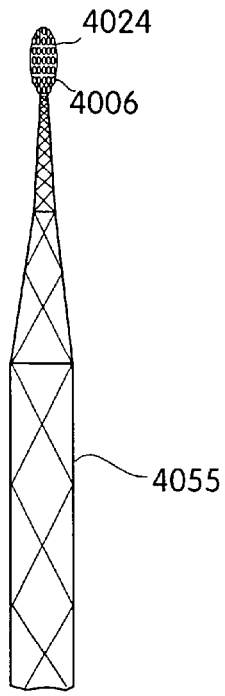

A further environment within which the three-dimensional structure 4024 of LEDs 4006 or 4016 may be utilized includes a warning tower 4055, as shown in FIG. 55. To utilize the three-dimensional structure 4024 in connection with the warning tower, at least one three-dimensional structure 4024 may be positioned on the tower 4055 to act as a warning indicator to high flying planes or distantly located vessels.

Figure 56:
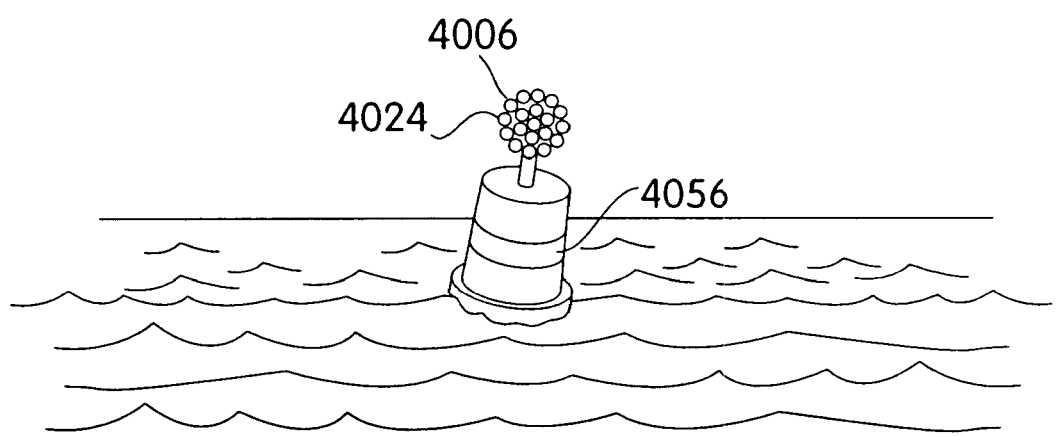

A further environment within which the three-dimensional structure 4024 of LEDs 4006 or 4016 may be utilized includes a buoy 4056, as shown in FIG. 56. To utilize the three-dimensional structure 4024 in connection with the buoy, at least one three-dimensional structure 4024 may be positioned on the buoy 4056 for illumination thereof.

Figure 57:
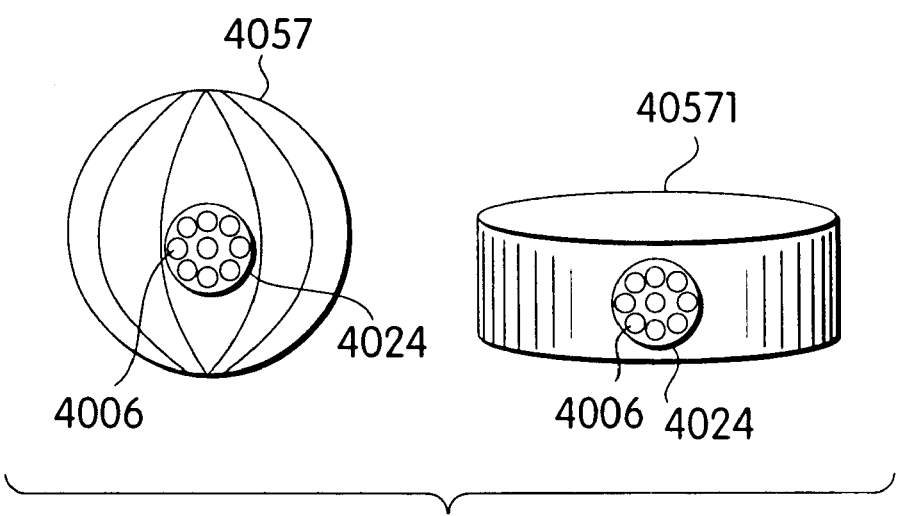

A further environment within which the three-dimensional structure 4024 of LEDs 4006 or 4016 may be utilized includes a ball 4057 or puck 40571, as shown in FIG. 57. To utilize the three-dimensional structure 4024 in connection with the ball or puck, at least one three-dimensional structure 4024 may be positioned within the ball 4057 or puck 40571 to enhance visualization of the ball or puck.

Figure 58:
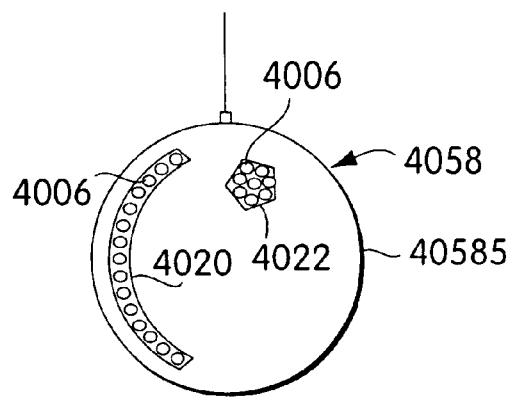

In accordance with another embodiment of the invention, two or more of the modular LED unit 4000 having a plurality of LEDs 4006 or 4016, arranged linearly in a strip 4020, in a geometric panel 4022 or as a three-dimensional structure 4024, may be used for illumination within an environment. One such environment, illustrated in FIG. 58, includes an ornamental display 4058. When used in connection with an ornamental display, at least one strip 4020 of LEDs 4006 or 4016 and one of a geometric panel 4022 and three-dimensional structure 4024 of LEDs 4006 or 4016 may be positioned along a surface to provide illumination of the ornamental display. Examples of an ornamental display 4058 can include a Christmas tree ornament 40585, an animal-shaped figure, a discotheque ball, or any natural or man-made object capable of being represented.

Figure 59:
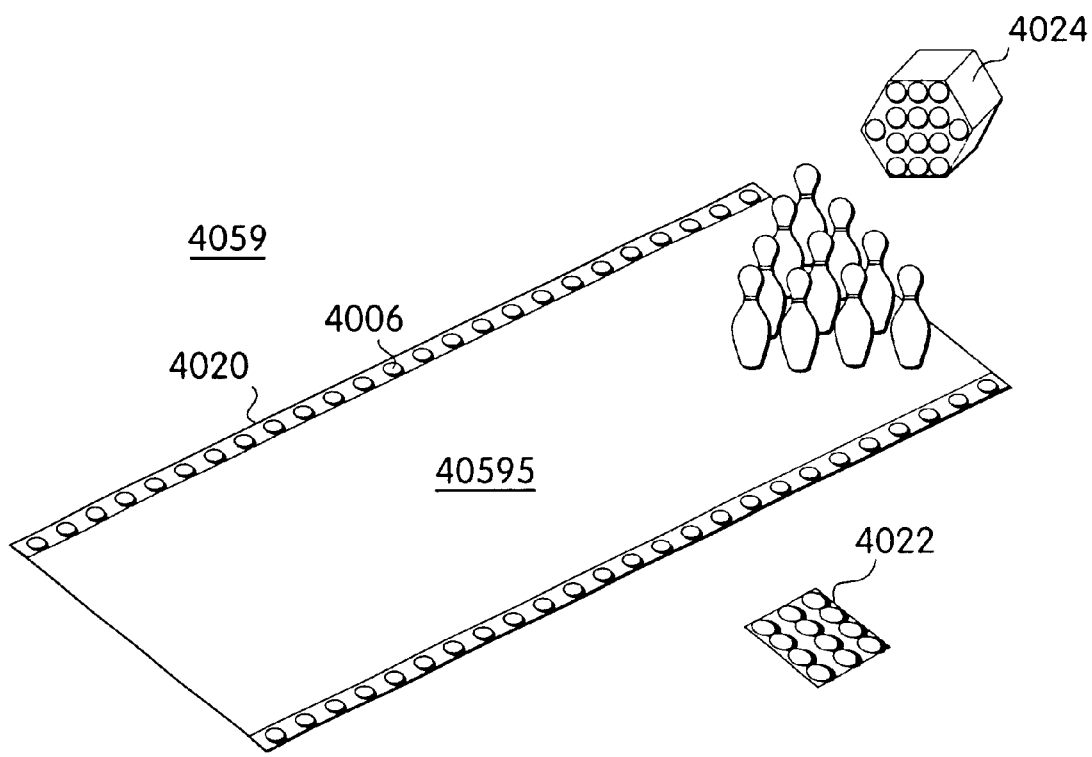

Another such environment, illustrated in FIG. 59, includes a bowling alley 4059. When used in connection with a bowling alley, one of a strip 4020, a geometric panel 4022, and a three-dimensional structure 4024 of LEDs 4006 or 4016 may be positioned along a lane 40595, and one of a strip 4020, a geometric panel 4022, and a three-dimensional structure 4024 of LEDs 4006 or 4016 may be positioned on a ceiling, a floor or a wall of the bowling alley.

Figure 60:
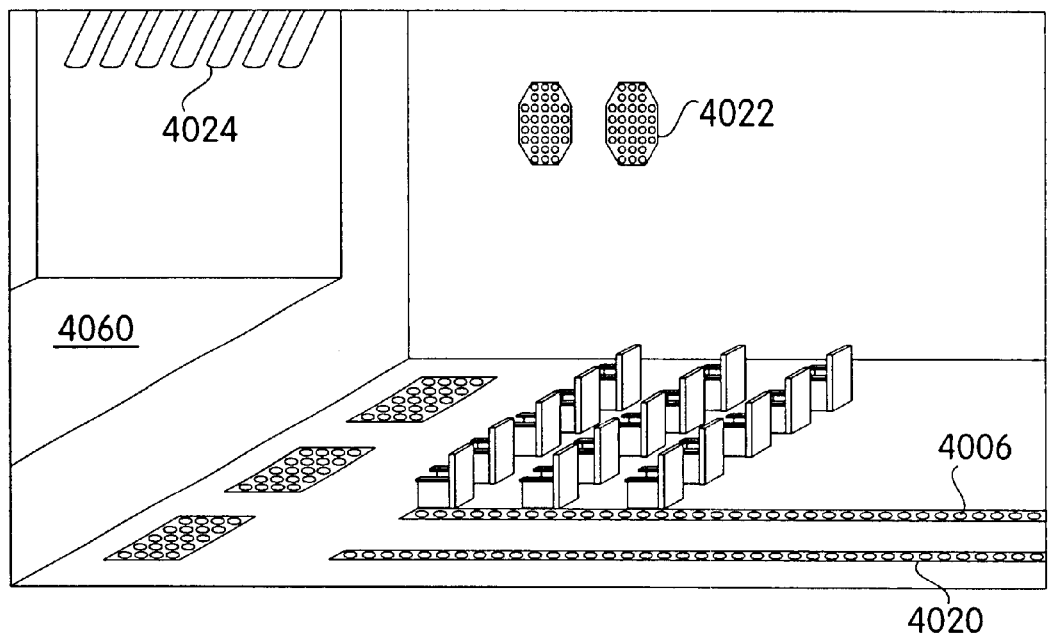

Another such environment, illustrated in FIG. 60, includes a theatrical setting. When used in connection with a theatrical setting, one of a strip 4020, a geometric panel 4022, and a three-dimensional structure 4024 of LEDs 4006 or 4016 may be positioned on a ceiling, a floor, or a wall of a theater 4060, and one of a strip 4020, a geometric panel 4022, and a three-dimensional structure 4024 of LEDs 4006 or 4016 may be positioned on the remainder of the ceiling, the floor or the wall of the theater.

Figure 61:
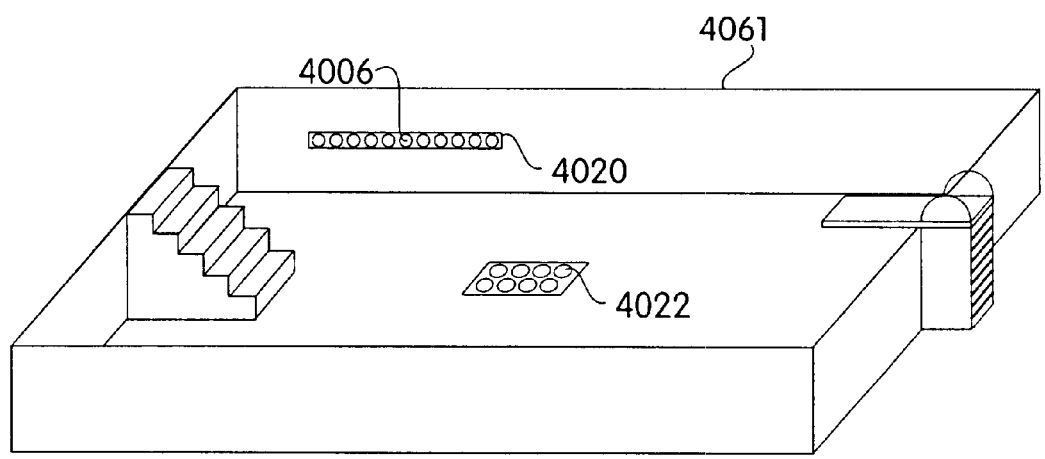

Another such environment, illustrated in FIG. 61, includes a swimming pool 4061. When used in connection with a swimming pool, one of a strip 4020, a geometric panel 4022, and a three-dimensional structure 4024 of LEDs 4006 or 4016 may be positioned on a floor or a wall of the swimming pool 4061, and one of a strip 4020, a geometric panel 4022, and a three-dimensional structure 4024 of LEDs 4006 or 4016 may be positioned on the other of the floor or the wall of the swimming pool.

Figure 62:
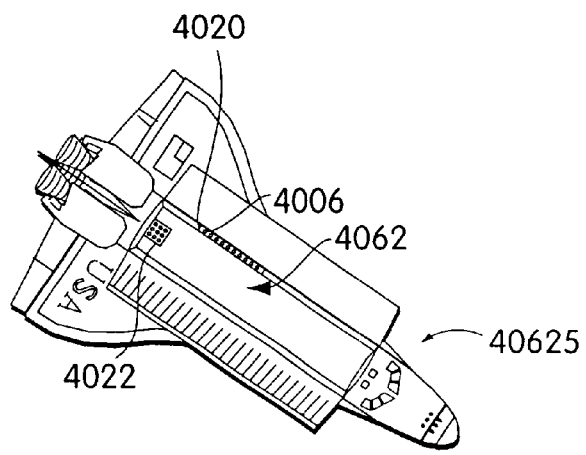

Another such environment, illustrated in FIG. 62, includes a cargo bay 4062 of a spacecraft 40625. When used in connection with the cargo bay of a spacecraft, one of a strip 4020, a geometric panel 4022, and a three-dimensional structure 4024 of LEDs 4006 or 4016 may be positioned on a ceiling, a floor, or a wall of the cargo bay 4062, and one of a strip 4020, a geometric panel 4022, and a three-dimensional structure 4024 of LEDs 4006 or 4016 may be positioned on the remainder of the ceiling, the floor or the wall of the cargo bay 4062.

Figure 63:
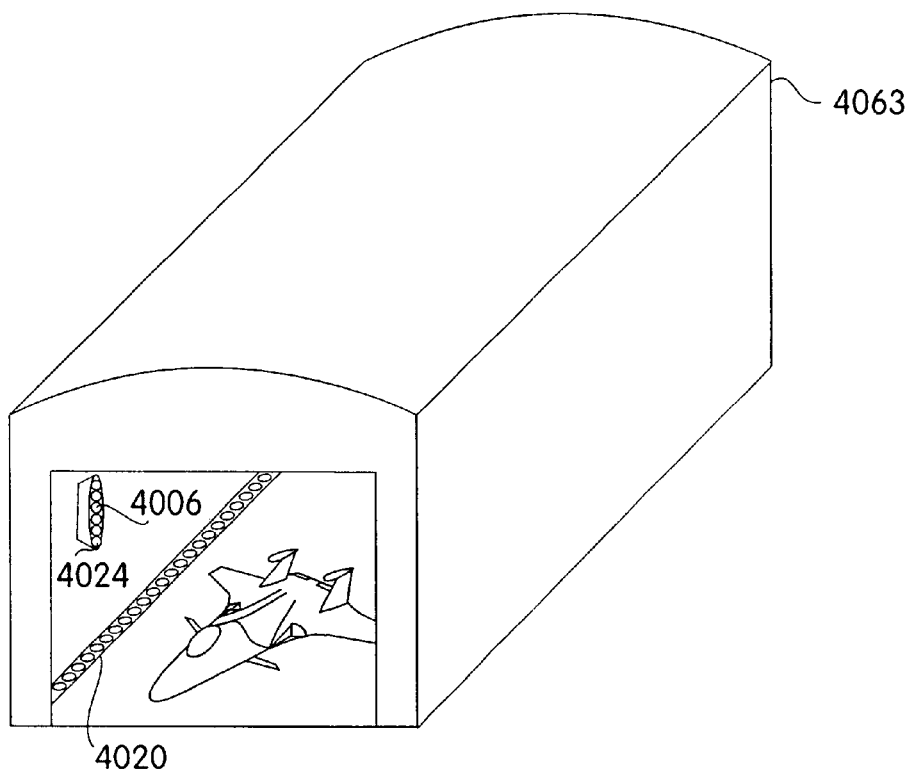

Another such environment, illustrated in FIG. 63, includes an aircraft hangar 4063. When used in connection with an aircraft hangar, one of a strip 4020, a geometric panel 4022, and a three-dimensional structure 4024 of LEDs 4006 or 4016 may be positioned on a ceiling a floor, or a wall of the hangar 4063, and one of a one of a strip 4020, a geometric panel 4022, and a three-dimensional structure 4024 of LEDs 4006 or 4016 may be positioned on the remainder of the ceiling, the floor or the wall of the hangar.

Figure 64:
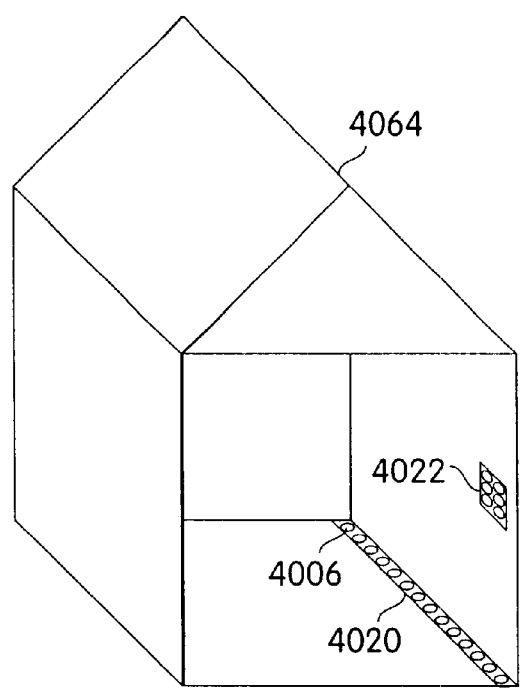

Another such environment, illustrated in FIG. 64, includes a warehouse 4064. When used in connection with a warehouse, one of a strip 4020, a geometric panel 4022, and a three-dimensional structure 4024 of LEDs 4006 or 4016 may be positioned on a ceiling, a floor, or a wall of the warehouse 4064, and one of a one of a strip 4020, a geometric panel 4022, and a three-dimensional structure 4024 of LEDs 4006 or 4016 may be positioned on the remainder of the ceiling, the floor or the wall of the warehouse.

Figure 65:
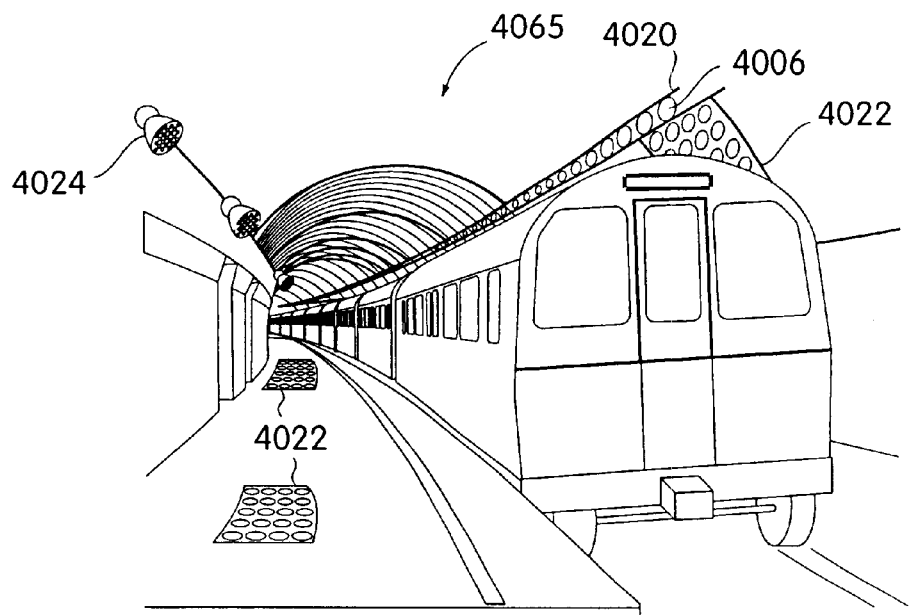

Another such environment, illustrated in FIG. 65, includes a subway station 4065. When used in connection with a subway station, one of a strip 4020, a geometric panel 4022, and a three-dimensional structure 4024 of LEDs 4006 or 4016 may be positioned on a ceiling, a floor, or a wall of the subway station 4065, and one of a one of a strip 4020, a geometric panel 4022, and a three-dimensional structure 4024 of LEDs 4006 or 4016 may be positioned on the remainder of the ceiling, the floor or the wall of the subway station.

Figure 66:
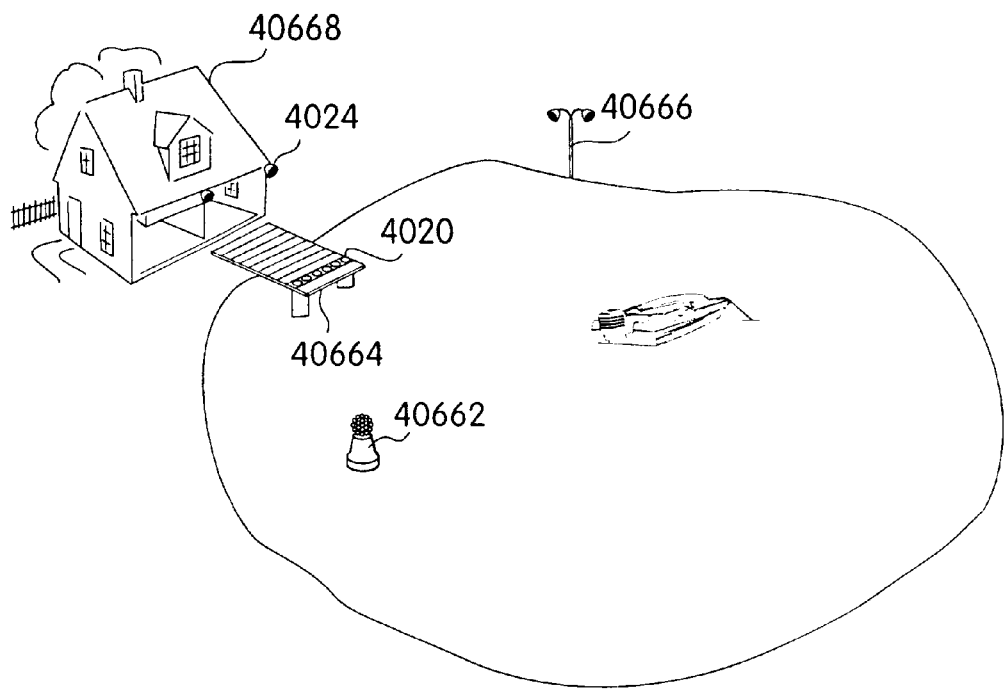

Another such environment, illustrated in FIG. 66, includes a marina 6066. When used in connection with a marina, one of a strip 4020, a geometric panel 4022, and a three-dimensional structure 4024 of LEDs 4006 or 4016 may be positioned on a buoy 40662, a dock 40664, a light fixture 40666, or a boathouse 40668, and one of a one of a strip 4020, a geometric panel 4022, and a three-dimensional structure 4024 of LEDs 4006 or 4016 may be positioned on the remainder of the buoy, the dock, the light fixture, or the boathouse.

Figure 67:
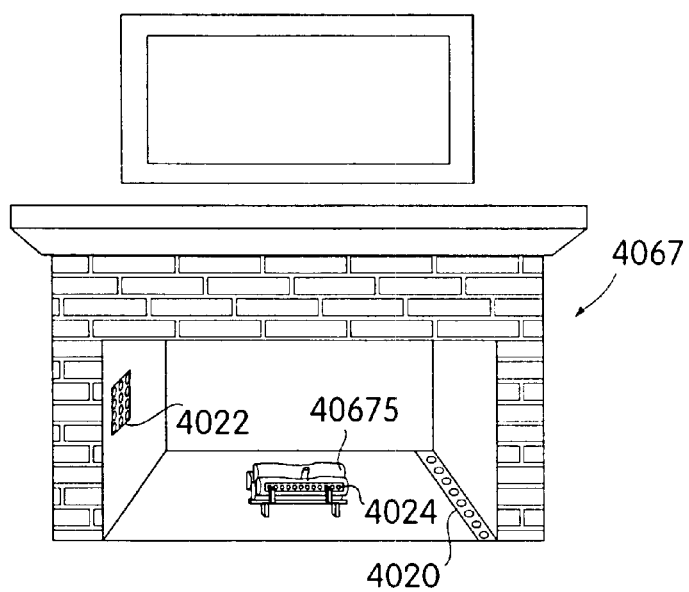

Another such environment, illustrated in FIG. 67, includes a fireplace 4067. When used in connection with a fireplace, one of a strip 4020, a geometric panel 4022, and a three-dimensional structure 4024 of LEDs 4006 or 4016 may be positioned on a simulated fire log 40675, a wall, or a floor of the fireplace 4067, and one of a one of a strip 4020, a geometric panel 4022, and a three-dimensional structure 4024 of LEDs 4006 or 4016 may be positioned on the remainder of the simulated log, the wall, or the floor of the fireplace, such that when frequencies within the spectrum are generated, an appearance of fire is simulated.

Figure 68:
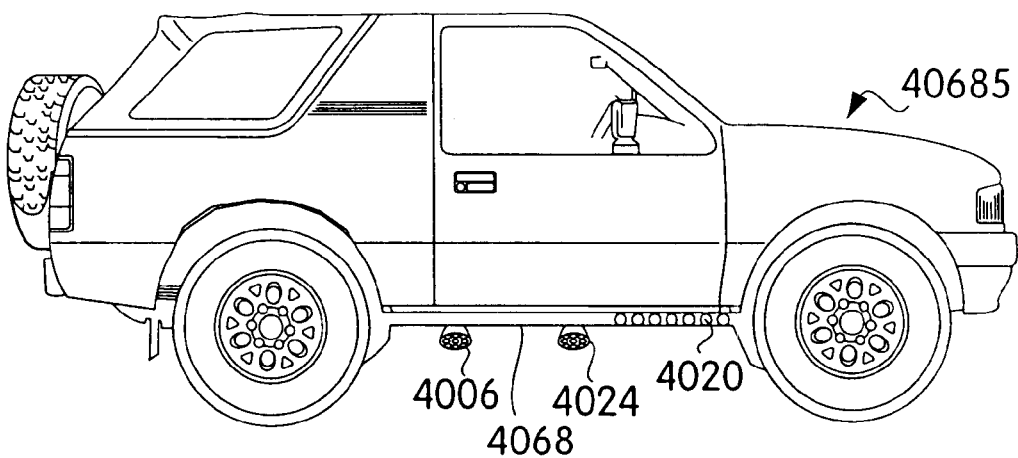

Another such environment, illustrated in FIG. 68, includes an underside 4068 of a car 40685. When used in connection with the underside of a car, one of a strip 4020, a geometric panel 4022, and a three-dimensional structure 4024 of LEDs 4006 or 4016 may be positioned on the underside of the car to permit illumination of a road surface over which the car passes.

Although certain specific embodiments of the light module 4002 in the modular LED unit 4000 have been discussed in connection with particular environments, it should be understood that it would be apparent to those of skilled in the art to use light modules similar to those discussed within many different environments, as well as combinations of light module and environment not yet discussed, but readily conceivable.

From the foregoing, it will be appreciated that PWM current control of LEDs to produce multiple colors may be incorporated into countless environments, with or without networks. Certain embodiments of the invention are described herein, but it should be understood that other embodiments are within the scope of the invention.

Another use of the present invention is as a light bulb. Using appropriate rectifier and voltage transformation means, the entire power and light modules may be placed in any traditional lightbulb housing, such as an Edison-mount (screw-type) light bulb housing. Each bulb can be programmed with particular register values to deliver a particular color bulb, including white. The current regulator can be preprogrammed to give a desired current rating and thus preset light intensity. Naturally, the lightbulb may have a transparent or translucent section that allows the passage of light into the ambient.

Figure 69:
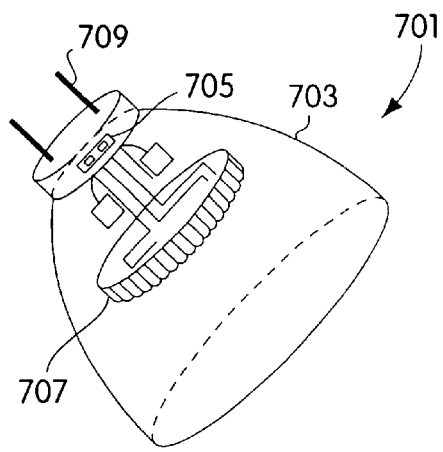
FIG. 69 depicts a smart light bulb embodiment of the invention.

Referring to FIG. 69, in one embodiment of the invention a smart light bulb 701 is provided. The smart light bulb may include a housing 703 in which are disposed a processor 705 and an illumination source 707. The housing may include a connector 709 for connection to a power source. The connection may also serve as a connection to a data source, such as the data connection 500 disclosed in connection with certain other embodiments herein. The processor may be a processor 16 such as that disclosed elsewhere herein. The smart light bulb 701 may form one embodiment of a light module 100 that may be used in the various embodiments disclosed or encompassed herein.

In an embodiment the housing 703 may be configured to resemble the shape of housing for a conventional illumination source, such as a halogen light bulb. In one embodiment, depicted in FIG. 69, connector 709 is configured to fit into a conventional halogen socket, and the illumination source 707 is an LED system, such as the LED system 120 disclosed above in connection with FIG. 1.

Processor 705 may be similar to the processor 16 disclosed in connection with the discussion of FIG. 1 above and further described elsewhere herein. That is, in one embodiment of the invention, the smart light bulb 701 consists of a light module 100 such as that disclosed above. However, it should be understood that the smart light bulb may take a variety of other configurations. For example, the housing 703 could be shaped to resemble an incandescent light bulb, in which case the connector 709 could be a set of threads for screwing into a conventional incandescent light slot, and the illumination source 707 could be an incandescent light source. The housing 703 could be configured to resemble any conventional light bulb or fixture, such as a headlamp, a flashlight bulb, an alarm light, a traffic light, or the like. In fact, the housing 703 could take any geometric configuration appropriate for a particular illumination or display environment.

The processor 705 may be used to control the intensity of the illumination source, the color of the illumination source 707 and other features or elements included in the housing 703 that are capable of control by a processor. In an embodiment of the invention the processor 705 controls the illumination source 707 to produce any color in the spectrum, to strobe rapidly between different colors, and to otherwise produce any desired illumination condition. Illumination sources that could disposed in a housing 703 and made subject to the processor 705 could include any type of illumination source, including the range of such sources disclosed above.

Figure 70:
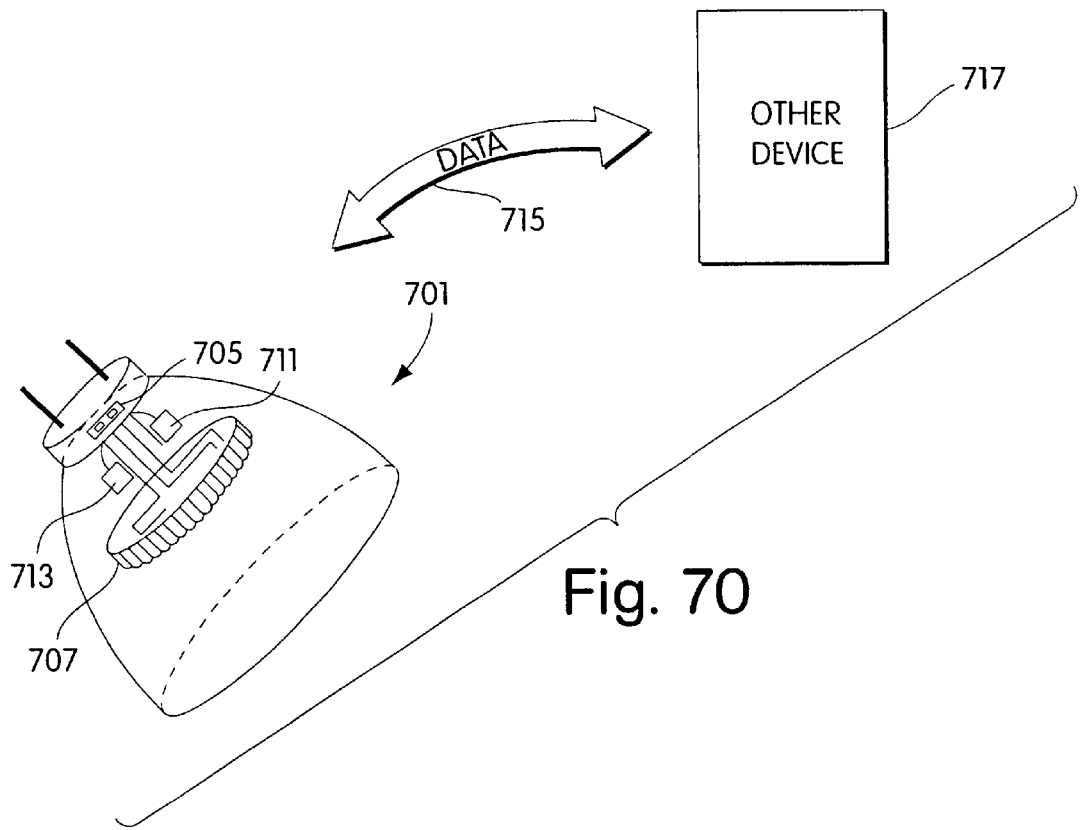
FIG. 70 depicts the embodiment of FIG. 69 in data connection with another device.

In an embodiment of the invention depicted in FIG. 70, the smart light bulb 701 may be equipped with a receiver 711 and/or a transmitter 713, which may be connected to the processor 705. The receiver 711 may be capable of receiving data signals and relaying them to the processor 705. It should be understood that the receiver 711 may be merely an interface to a circuit or network connection, or may be a separate component capable of receiving other signals. Thus, the receiver may receive signals by a data connection 715 from another device 717. In an embodiment of the invention, the other device is a laptop computer, the data connection is a DMX data track, and the data is sent according to the DMX-512 protocol to the smart light bulb 701. Processor 705 then processes the data to control the illumination source 707 in a manner similar to that described above in connection with other embodiments of the invention. The transmitter 713 may be controlled by the processor 705 to transmit the data from the smart light bulb 701 over the data connection 715 to another device 717. The other device may be another smart light bulb 701, a light module 100 such as disclosed above, or any other device capable of receiving a signal data connection 715. Thus, the data connection 715 could be any connection of among the types disclosed above. That is, any use of the electromagnetic spectrum or other energy transmission mechanism for the communication link could provide the data connection 715 between the smart light bulb 701 and another device 717. The other device 717 could be any device capable of receiving and responding to data, such as an alarm system, a VCR, a television, an entertainment device, a computer, an appliance, or the like.

Figure 71:
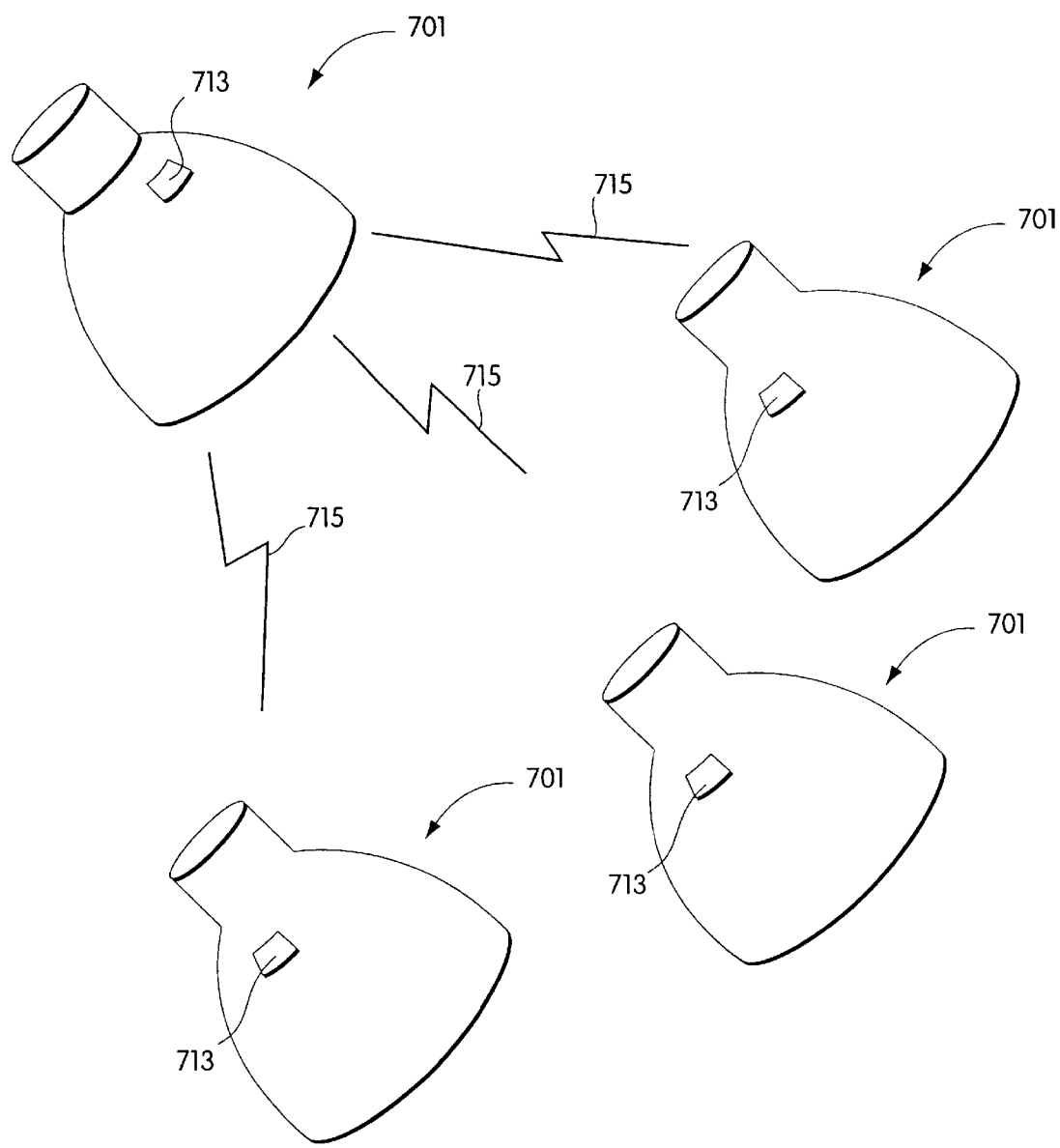
FIG. 71 depicts the embodiment of FIG. 69 in connection with other smart light bulbs.

Referring to FIG. 71, the smart light bulb 701 could be part of a collection of smart light bulbs similarly configured. One smart light bulb could through use of the transmitter 711 transmit data to the receiver 713 of one or more other smart light bulbs 701. In this manner, a plurality of smart light bulbs 701 may be established in a master/slave arrangement, whereby the master smart light bulb 701 controls the operation of one or more other slave smart light bulbs 701. The data connection 715 between the smart light bulbs 701 could be any type of data connection 715, including any of those described in connection with FIG. 70.

Figure 72:
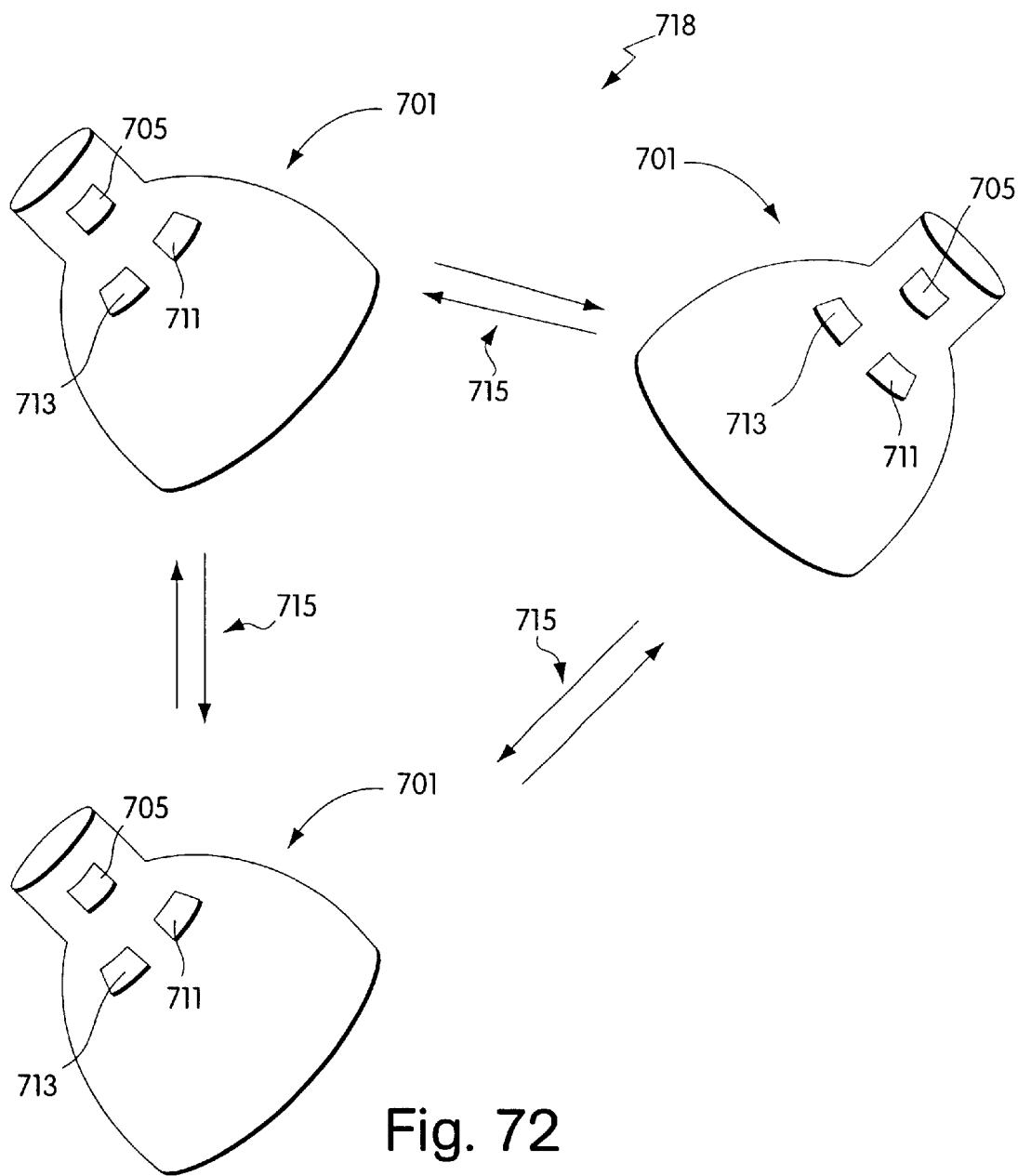
FIG. 72 depicts a network of smart light bulbs in data connection with each other.

The smart light bulb 701 may be part of a network of such smart light bulbs 701 as depicted in FIG. 72. Through use of the transmitter 711 and the receiver 713 of each of the smart light bulbs 701, as well as the processor 705, each smart light bulb 701 in a network 718 may send and receive queries over a data connection 715 similar to that disclosed in connection with the description of FIG. 70. Thus, the smart light bulb 701 can determine the configuration of the network in which the smart light bulb 701 is contained. For example, the smart light bulb 701 can process signals from another smart light bulb 701 to determine which of the light bulbs is the master and which is the slave in a master/slave relationship.

Figure 73:
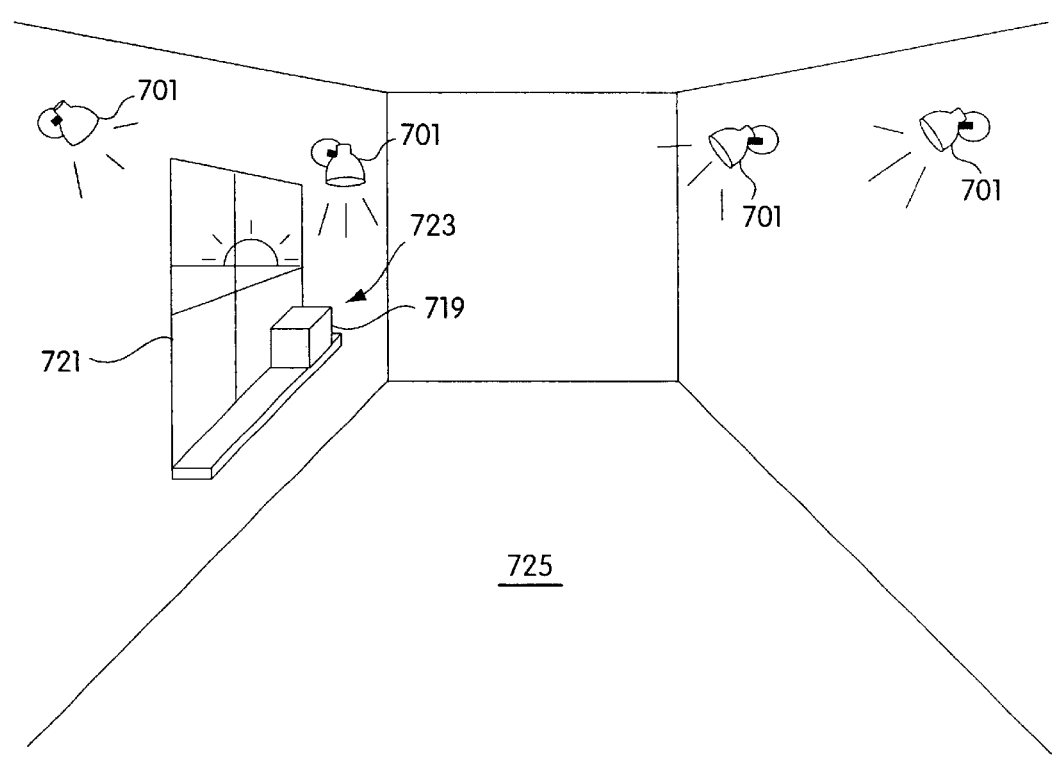
FIG. 73 depicts a light buffer sensor/feedback application using a smart light bulb.

Additional processing capabilities may be included in each smart light bulb 701. For example, each smart light bulb 701 may be made responsive to an external data signal for illumination control. For example, in the embodiment depicted in FIG. 73, a light sensor 719 may be disposed in proximity to a window 722 for sensing external illumination conditions. The light sensor 719 may detect changes in the external illumination conditions and send a signal 723 to one or more smart light bulbs 701 to alter the illumination in an interior space 725, to compensate for or otherwise respond to the external illumination conditions sensed by the light sensor 719. Thus, the room lights in the exterior space 725 can be made to turn on or change color at sunrise or sunset, in response to changes in the external illumination conditions at those times. The light sensor 719 could also be made to measure the color temperature and intensity of the external environment and to send a signal 723 that instructs the light module 701 to produce a similar color temperature and intensity. Thus, the room lights could mimic an external sunset with an internal sunset in the internal space 725. Thus, the smart light bulb 701 maybe used in a wide variety of sensor and feedback applications as disclosed in connection with other embodiments described herein.

Figure 74:
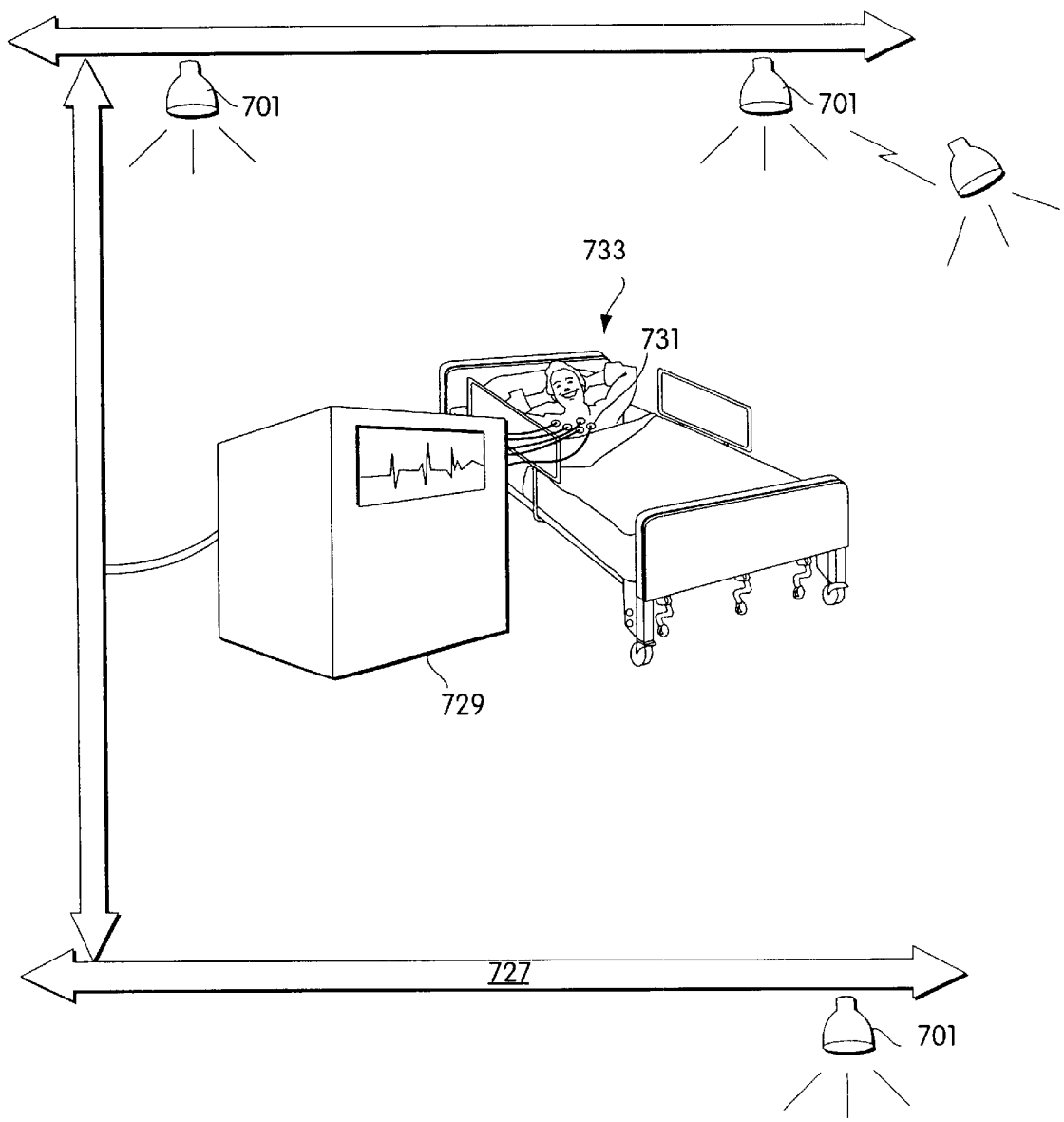
FIG. 74 depicts an EKG sensor/feedback environment using a smart light bulb.

Referring to FIG. 74, in another embodiment a. plurality of smart light bulbs 701 may be disposed on a data network 727. The data network may carry signals from a control device 729. The control device may be any device capable of sending a signal to a data network 727. The control device in the embodiment depicted in FIG. 74 is an electrocardiogram (EKG) machine. The EKG machine 729 has a plurality of sensors 731 that measure the electrical activity of the heart of a patient 733. The EKG machine 729 may be programmed to send control data over the network 727 to the smart light bulb 701 in instances in which the EKG machine 729 measures particular states of the electrical activity measured by the sensors 731. Thus, for example, the light bulbs could illuminate with a particular color, such as green, for normal cardiac activity, but could change to a different color to reflect particular cardiac problems. For example, arrhythmia could be reflected by a flashing red illumination signal to the smart light bulb 701, a rapid pulse could be reflected by a yellow signal to the smart light bulbs 701, or the like.

A smart light bulb such as depicted in FIG. 70 can be programmed to operate in a stand alone mode as well. Thus, preprogrammed instructions may cause the smart light bulb 701 to change colors at intensities in a designed way, thus, the light may be designed to shine a particular color at a particular time of day, or the like. The smart light bulb 701 may also include algorithms for altering the illumination from the smart light bulb 701 to reflect the state of the smart light bulb 701. For example, the light bulb could display a particular illumination pattern if the LED system 707 is near the end of its life, if there is a problem with the power supply, or the like.

Figure 75:
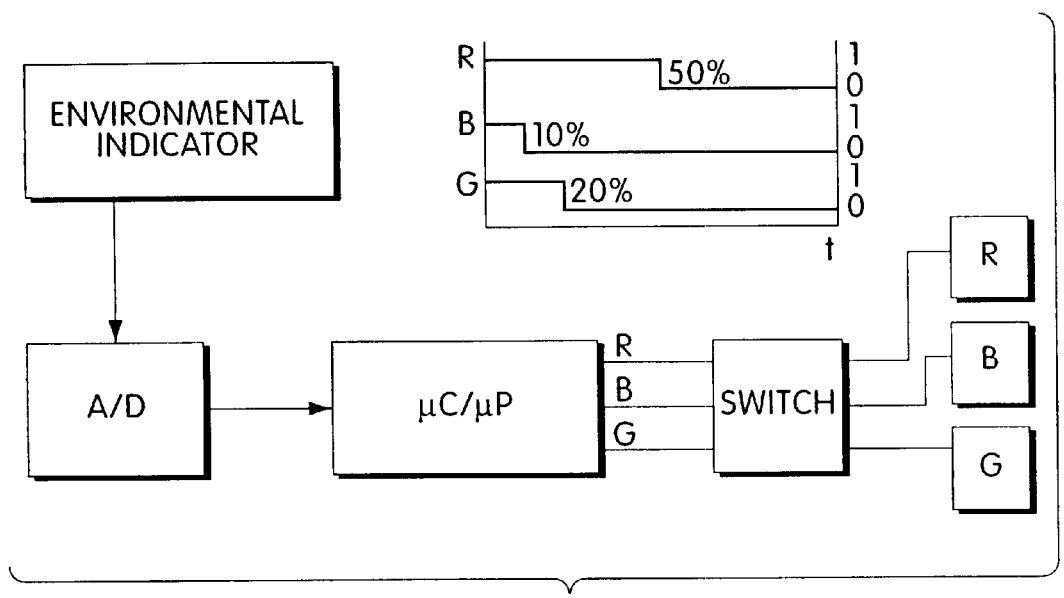
FIG. 75 depicts a schematic diagram of a sensor/feedback application.

The present invention may be used as a general indicator of any given environmental condition. FIG. 75 shows the general functional block diagram for such an apparatus. Shown within FIG. 75 is also an exemplary chart showing the duty cycles of the three color LEDs during an exemplary period. As one example of an environmental indicator, the power module can be coupled to an inclinometer. The inclinometer measures general angular orientation with respect to the earth's center of gravity. The inclinometer's angle signal can be converted through an A/D converter and coupled to the data inputs of the processor 16 in the power module. The processor 16 can then be programmed to assign each discrete angular orientation a different color through the use of a lookup table associating angles with LED color register values. Another indicator use is to provide an easily readable visual temperature indication. For example, a digital thermometer can be connected to provide the processor 16 a temperature reading. Each temperature will be associated with a particular set of register values, and hence a particular color output. A plurality of such "color thermometers" can be located over a large space, such as a storage freezer, to allow simple visual inspection of temperature over three dimensions.

In another embodiment of the invention, the signal-generating device may be a detector of ambient conditions, such as a light meter or thermometer. Thus, lighting conditions may be varied in accordance with ambient conditions. For example, arrayed LEDs may be programmed to increase room light as the external light entering the room from the sun diminishes at the end of the day. LEDs may be programmed to compensate for changes in color temperature as well, through a feedback mechanism.

When coupled to transducers, many embodiments of the present invention are possible that associate some ambient condition with an LED system. As used herein, the term "transducer" should be understood to encompass all methods and systems for converting a physical quantity into an electrical signal. Electrical signals, in turn, can be manipulated by electronic circuits, digitized by analog to digital converters, and sent for processing to a processor, such as a microcontroller or microprocessor. The processor could then send out information to dictate the characteristics of the light emitted by the LED system of the present invention. In such manner, physical conditions of the environment involving external forces, temperature, particle number, and electromagnetic radiation, for example, can be made to correspond to a particular LED system. We also note that other systems involving liquid crystal, fluorescence, and gas discharge could also be used.

In a specific embodiment, a temperature transducer such as a thermocouple, thermistor, or integrated circuit (IC) temperature sensor and the light module 100 of the present invention can be used to make a color thermometer. As mentioned above, such a thermometer would emit a particular set of colors from the LED system to indicate the ambient temperature. Thus the inside of an oven or freezer having such an LED system could emit different colored lights to indicate when certain temperatures have been reached.

Figure 76:
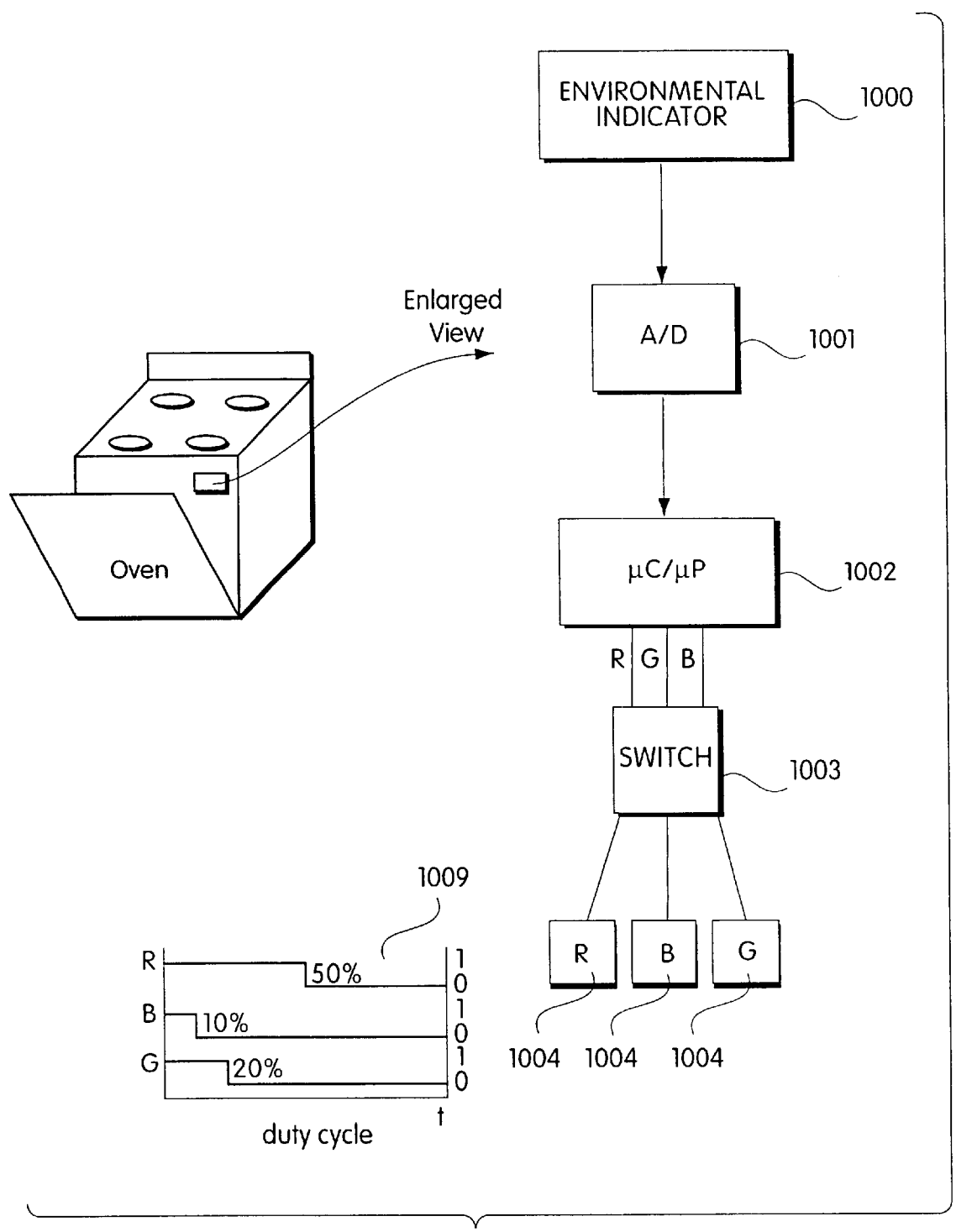
FIG. 76 depicts a general block diagram relevant to a color thermometer.

FIG. 76 shows a general block diagram relevant to the color thermometer. Item 1000 is an IC temperature sensor like the LM335. This is a two-terminal temperature sensor with an accuracy of approximately ±1° C. over the range −55° C. to 125° C. Further information pertaining to the LM335 may be found in the monograph The Art of Electronics, by Paul Horowitz and Winfield Hill. The entire disclosure of such monograph is hereby incorporated. Item 1001 is an analog to digital (A/D) converter that converts the voltage signal from the IC temperature sensor to binary information. As mentioned above, this is fed to a microcontroller or microprocessor 1002 such as a MICROCHIP brand PIC16C63 or other processor, such as the processor 16 mentioned above. Output from the microcontroller or microprocessor 1002 proceeds to a switch 1003 which can be a high current/voltage Darlington driver, part no. DS2003, available from the National Semiconductor Corporation, Santa Clara, Calif. as mentioned above. Element 1003 switches current from LED system 1004. Shown within FIG. 76 as item 1009 is also an exemplary chart showing the duty cycles of the three color LEDs during an exemplary period.

The enlargement of FIG. 76 is a general diagram that is also applicable to other embodiments that follow. Each of these embodiments are similar to the extent that they associate the different environmental conditions mentioned above with an LED system. The different embodiments differ from each other because they possess different transducers appropriate to the environmental condition that is being indicated. Thus, in the embodiments that follow, the temperature sensor 1000 is replaced by another appropriate transducer.

The power module (not shown in FIG. 76) can be included in the color thermometer. The signal from the temperature transducer 1000 can be converted by the A/D converter 1001 and coupled to the data inputs of the microcontroller 1002 in the power module. The microcontroller can then be programmed to assign a range of temperatures to a different color through the use of a lookup table associating temperatures with LED color register values.

Figure 77:
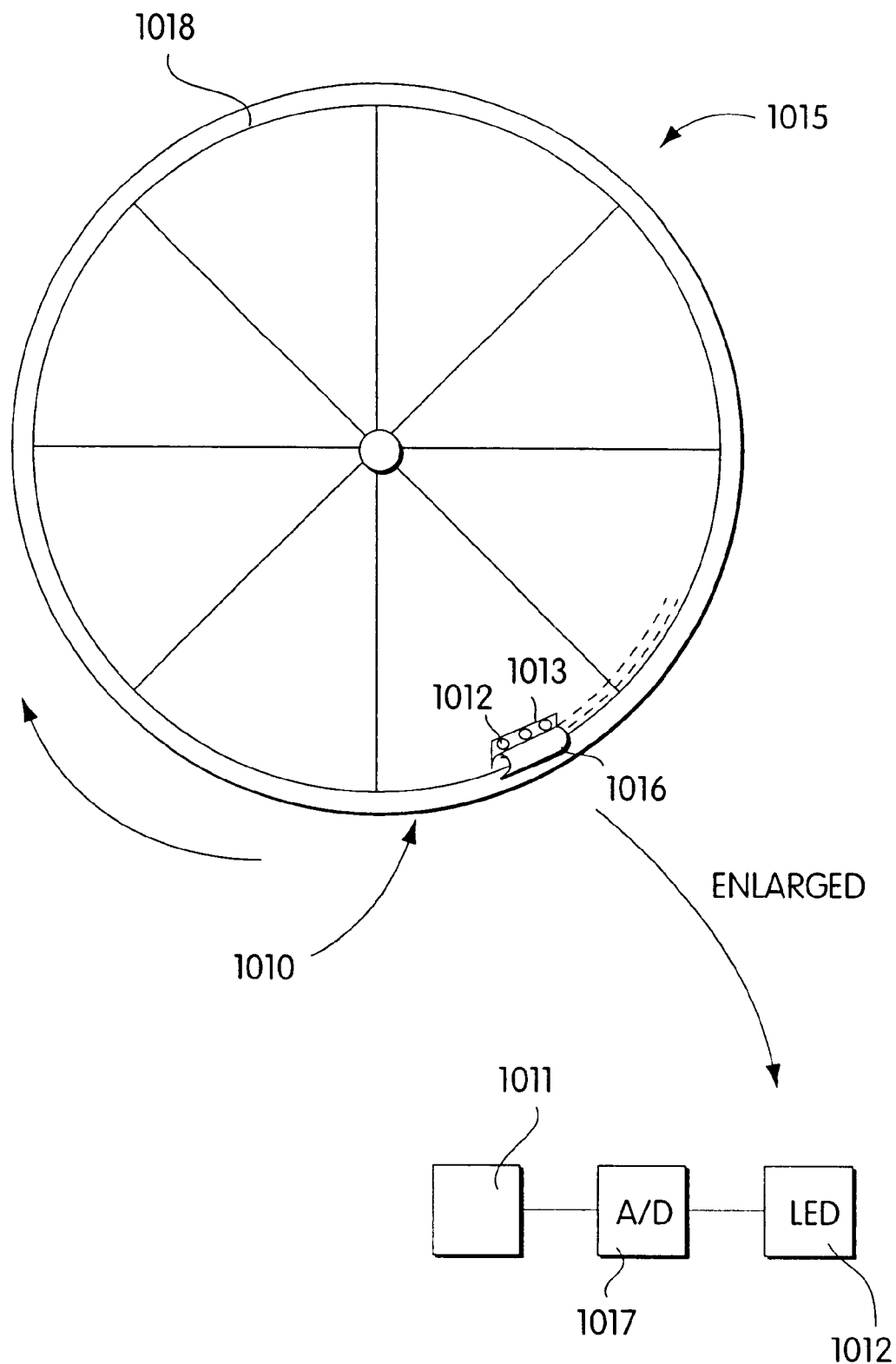
FIG. 77 depicts a color speedometer.

In another specific embodiment, a force transducer such as a differential transformer, strain gauge, or piezoelectric device and the LED system of the present invention can be used to associate a range of forces with a corresponding LED system. FIG. 77 shows a color speedometer 1010 having a force transducer 1011, such as a linear variable differential transformer (LVDT), coupled to an A/D converter 1017 which is in turn coupled to an LED system 1012 of the present invention. A housing 1013 encloses the force transducer 1011 and the LED system 1012. The housing possesses a fastener to affix the housing and contents to a rotating object like a bicycle wheel 1015. The fastener shown in FIG. 77 is a clamp 1016, although other fasteners such as screws, or rivets could also be used that permit the color speedometer to become affixed to a wheel rim 1018.

Such a color speedometer 1010 could be used to "see" the angular speed of various rotating objects. Thus, as in the example of FIG. 77, the LED system 1012 coupled to the force transducer 1011 could be mounted to the bicycle wheel 1015 at a distance r from the center of the wheel 1015. A reference mass m in the transducer (not shown) could exert a force $m\omega^2 r$ from which the angular speed $\omega$ could be ascertained. Each distinct force or range of forces would result in a particular color being emitted from the LED system 1012. Thus the wheel rim 1018 would appear in different colors depending on the angular speed.

Figure 78:
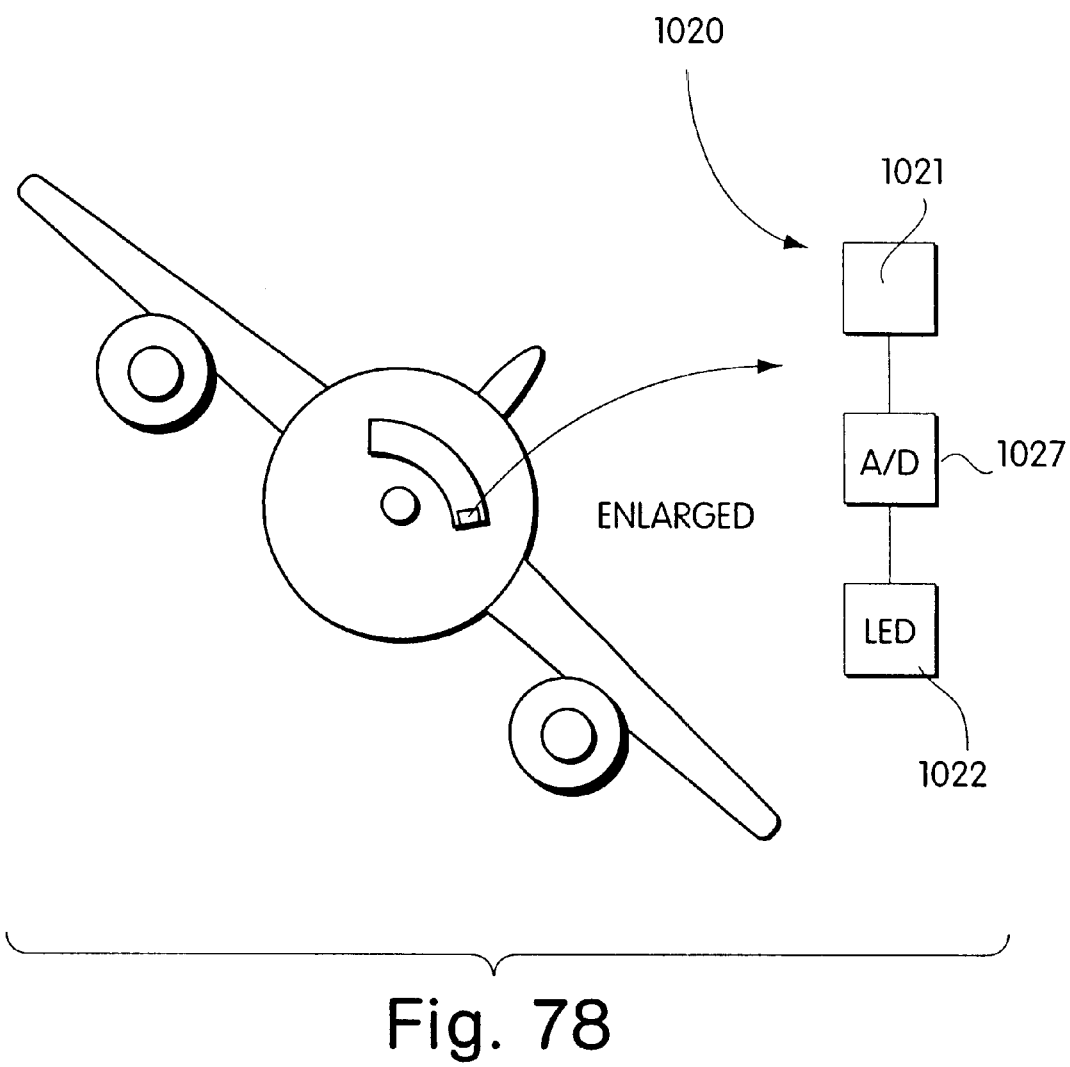
FIG. 78 depicts a color inclinometer.

Another specific embodiment comprising a force transducer appears in FIG. 78 where an color inclinometer 1020 is shown. The inclinometer 1020 possesses a force transducer 1021 such as a linear variable differential transformer (LVDT) coupled to an A/D converter 1027 which is in turn coupled to an LED system 1022 of the present invention. A housing (not shown) encloses the force transducer 1021 and the LED system 1022. The housing possesses a fastener (not shown) to affix the housing and contents to an object whose inclination one wants to determine such as an airplane. The fastener could, for example, consist of screws, clamps, rivets, or glue to secure the inclinometer 1020 to an airplane console, for example.

A power module (not shown) can be coupled to the inclinometer. The inclinometer 1020 measures general angular orientation with respect to the earth's center of gravity. The inclinometer's angle signal can be converted by the A/D converter 1027 and coupled to the data inputs of the microcontroller in the power module. The microcontroller can then be programmed to assign angular orientations to different color through the use of a lookup table associating angles with LED color register values. The color inclinometer may be used for safety, such as in airplane cockpits, or for novelty, such as to illuminate the sails on a sailboat that sways in the water.

Figure 79:
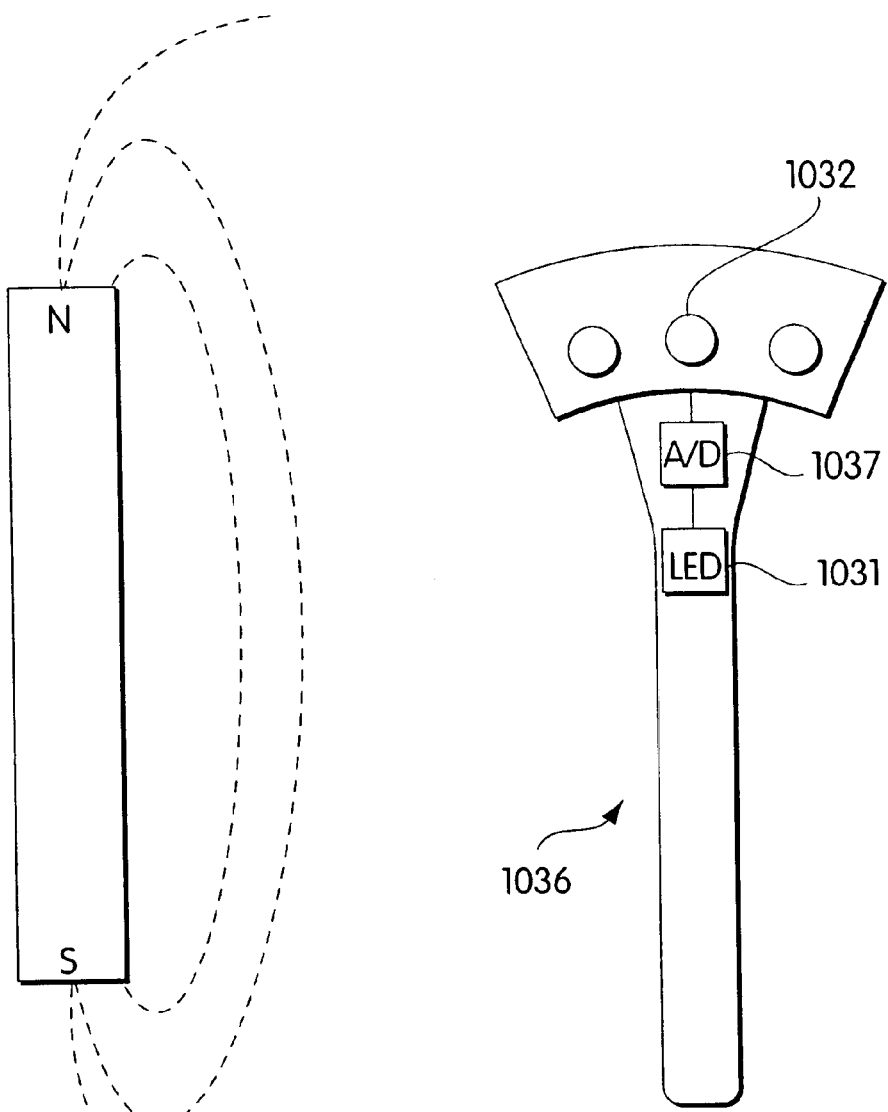
FIG. 79 depicts a color magnometer.

In another embodiment, the light module 100 of the present invention can be used in a color magnometer as an indicator of magnetic field strength. FIG. 79 shows such a magnometer 1036 having a magnetic field transducer 1031 coupled to an LED system 1032 via an A/D converter 1037. The magnetic field transducer can include any of a Hall-effect probe, flip coil, or nuclear magnetic resonance magnometer.

The magnetic field transducer 1031 changes a magnetic field strength into an electrical signal. This signal is, in turn, converted to binary information by the A/D converter 1037. The information can then be sent as input to the microcontroller controlling the LED system 1032 to cause to shine lights of various colors that correspond to the magnetic field strength. This embodiment could find wide use in the fields of geology and prospecting, as well as in the operation of instruments that rely on magnetic fields to operate such as magnetic resonance devices, magnetrons, and magnetically focused electron devices.

Figure 80:
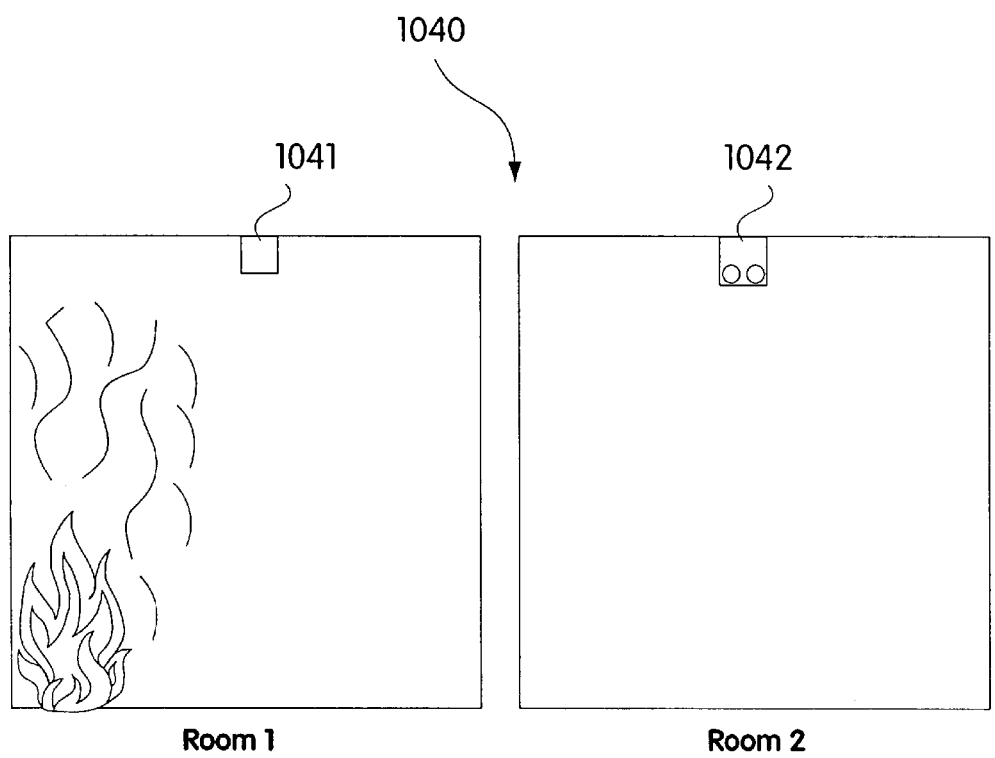
FIG. 80 depicts a smoke alert system.

In another embodiment, the light module 100 of the present invention can be used for a smoke alert system shown in FIG. 80. The smoke alert system 1040 comprises a smoke detector 1041, either of the ionization or optical (photoelectric) variety, electrically coupled to an LED system 1042 of one embodiment of the present invention via an A/D converter (not shown). The LED system 1042 need not be proximal to the detector 1041. In particular, the smoke detector 1041 can be in one room where a fire might ignite, while the LED system 1042 might be in another room where it would be advantageous to be alerted, the bedroom or bathroom for example.

As those of ordinary skill in the art would appreciate, the smoke detector 1041 can be of either of two types: ionization or optical (photoelectric). If the latter is used, a detection chamber in the smoke detector 1041 is employed whose shape normally prevents a light sensitive element (e.g., a photocell) from "seeing" a light source (e.g., an LED). When smoke from a fire enters the chamber, it scatters light so that the light sensitive element can now detect the light. In a smoke detector 1041 employing ionization technology, radioactive materials ionize air molecules between a pair of electrodes in a detection chamber. The resultant charged air molecules permit a current to be conducted between the electrodes. The presence of smoke in the chamber, however, diminishes the amount of charged air particles and thus diminishes the current. In both types of smoke detectors, therefore, the strength of a current is indicative of the concentration of smoke particles in the detection chamber. The strength of this current can be converted by the A/D converter into binary information that can be sent to the microprocessor controlling the LED system 1042. By using a look-up table, this binary information can dictate the range of frequencies, corresponding to various smoke concentrations, that is emitted from the LED system 1042. For example, a green or red light can be emitted if the concentration of smoke particles is below or above a certain threshold. This invention could alert a person to a potential fire even if that person is incapable of hearing the smoke detector's alarm. (The person may be deaf, listening to music, or in the shower, for example.) Also, conventional detectors convey only two pieces of information: the alarm is either off, or, if sufficient smoke is in the detection chamber, on. The smoke alert system of the present invention would also convey information about the amount of smoke present by emitting characteristic colors.

Smoke is but one type of particle whose concentration can be indicated by the light module 100 of the present invention. With the use of other particle detectors such as an ionization chamber, Geiger counter, scintillator, solid-state detector, surface-barrier detector, Cerenkov detector, or drift chamber, concentrations of other types of particles such as alpha particles, electrons, or energetic photons represented by x-rays or gamma rays, can be manifested by different colored LED lights.

Figure 81:
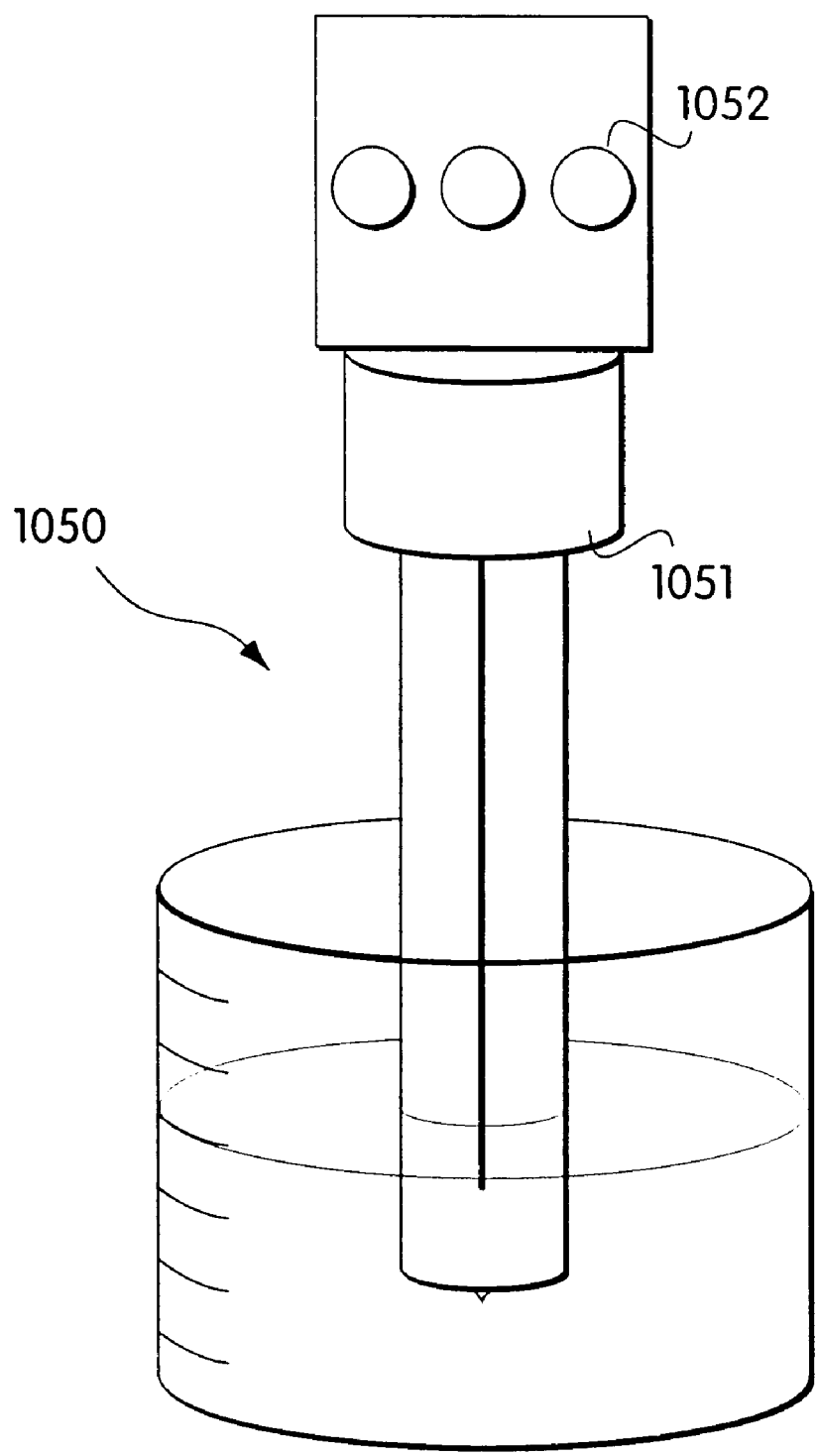
FIG. 81 depicts a color pH meter.

In another specific embodiment of the present invention, the light module 100 of the present invention can be used to build an electronic pH color meter for indicating the acidity of solutions by displaying colored lights. FIG. 81 depicts a color pH meter 1050 comprising a pH meter 1051 electrically coupled to an LED system 1052 via an A/D converter (not shown).

The electronic pH meter can be of a variety known to those of ordinary skill in the art. A possible example of an electronic pH meter that can be used is Corning pH Bench Meter Model 430, which provides digital measurements and automatic temperature compensation. The meter produces an analog recorder output, which can be converted to a digital signal by the A/D converter. The signal can then be sent to a microcontroller controlling the LED system 1052 which can emit colors corresponding to various pH levels.

Besides the aforementioned pH meter, meters having ion-specific electrodes that produce an analog signal corresponding to the concentration of a particular species in solution can also be used. These meters measure voltages developed between a reference electrode, typically silver-coated with silver chloride immersed in a concentrated solution of potassium chloride, and an indicator electrode. The indicator electrode is separated from an analyte by a membrane through which the analyte ions can diffuse. It is the nature of the membrane that characterizes the type of ion-specific electrode. Electrode types include glass, liquid-ion exchanger, solid state, neutral carrier, coated wire, field effect transistor, gas sensing, or a biomembrane. The reference electrode can communicate with the solution whose concentration one is trying to determine via a porous plug or gel. As described above, an embodiment of an LED system of the present invention can be electrically coupled to such meters to associate a particular ion concentration with the emission of light of various colors.

Figure 82:
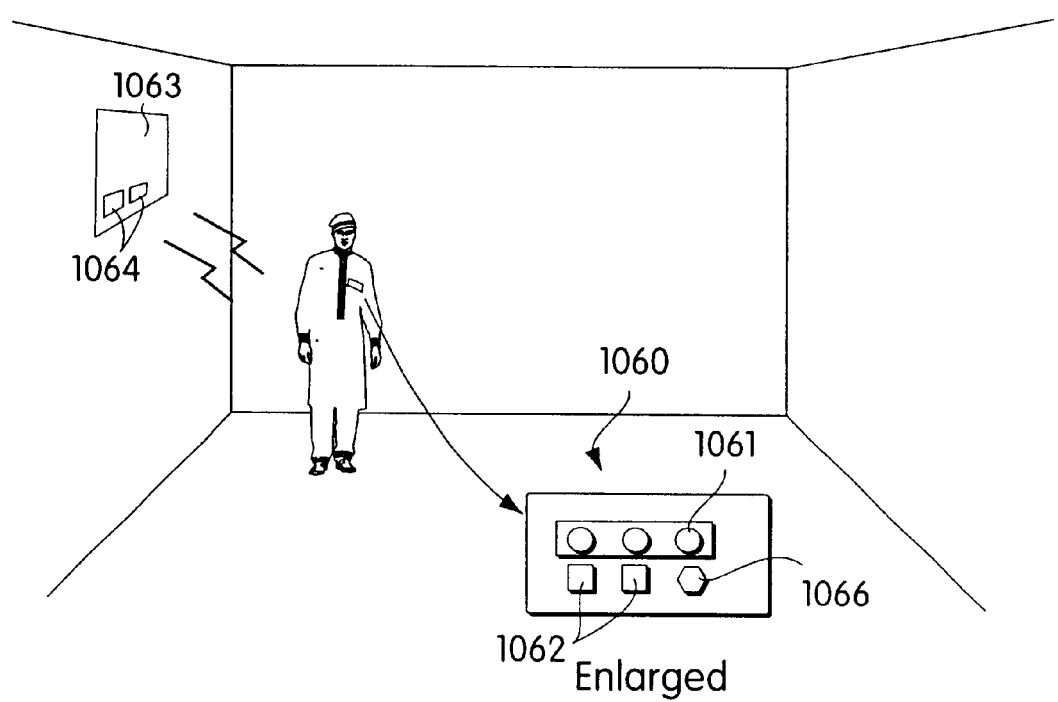
FIG. 82 depicts a security system to indicate the presence of an object.

In another specific embodiment, the light module 100 of the present invention could be used to produce a security system to indicate the presence of an object. FIG. 82 shows such a system comprising an identification badge 1060, an LED system 1061 of the present invention, a transmitter and receiver 1062 together with an electromagnetic radiation detector 1066 coupled to an A/D converter (not shown), and a security clearance network 1063 having a receiver and transmitter 1064 of electromagnetic signals to the badge 1060.

The security clearance network 1063 responsive to the transmitter and receiver 1062 may identify the individual as having the appropriate security clearance for the room at a given time. The badge 1060 itself may include the transmitter and receiver 1062, the electromagnetic radiation detector 1066, coupled to the A/D converter, and the LED system 1061 responsive to the security clearance network 1063, so that the badge 1060 changes color depending on whether the individual has clearance to be in proximity to a particular receiver or not. The ID badge 1060 with the LED system 1061 on it may change color in response to a control network depending on whether the person wearing it is "authorized" to be in a certain area, so that others will know if that person is supposed to be there. This could also tell others if the person must be "escorted" around the area or can roam freely. The advantages include time of day based control, zone based control and the concept of moving control zones or rapid zone modification. For example, maintenance staff could be allowed in an area only when another object is not present. For example, in a military aircraft hangar, cleaning might be allowed only when the plane is not there. As another example, security zones in a factory may be used for the purpose of keeping people safe, but when the factory is shut down, much larger areas may be accessible.

Figure 83:
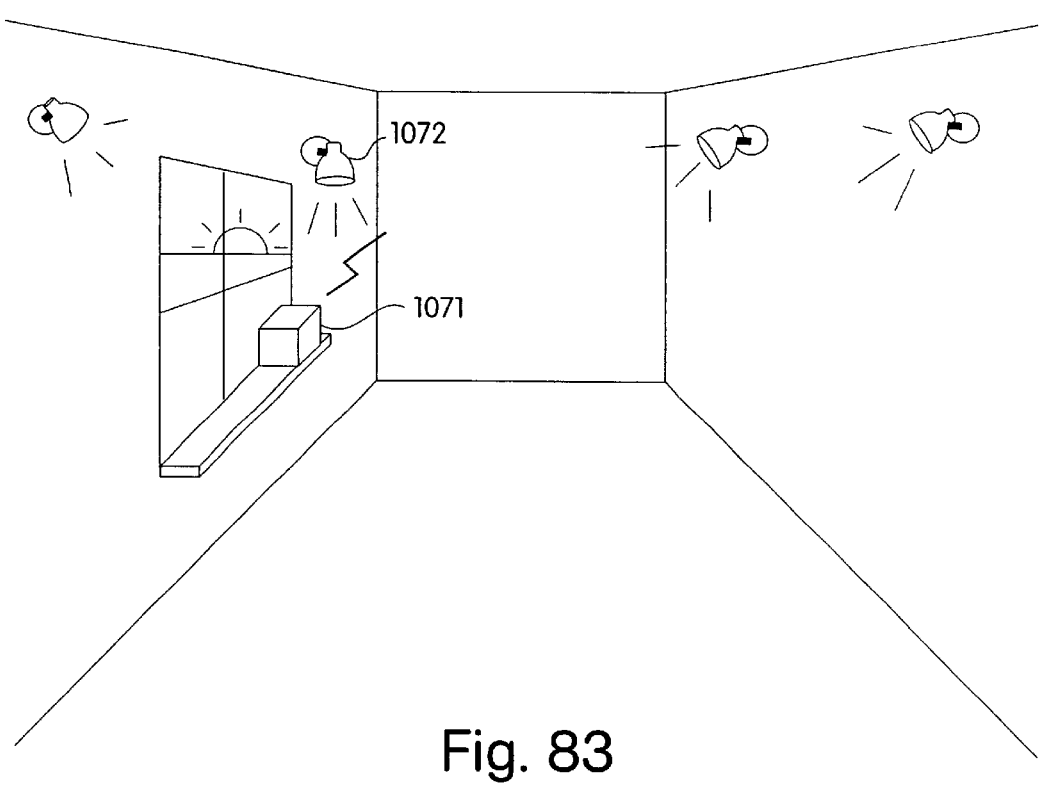
FIG. 83 depicts an electromagnetic radiation detector.

In another embodiment, the light module 100 of the present invention can be used to change the lighting conditions of a room. FIG. 83 depicts an electromagnetic radiation detector 1071 such as a photodiode, phototransistor, photomultiplier, channel-plate intensifier, charge-coupled devices, or intensified silicon intensifier target (ISIT) coupled to an A/D converter (not shown), which in turn is electrically coupled to an LED system 1072.

The light module 100 may be programmed to increase room light as the external light entering the room from the sun diminishes at the end of the day and to compensate for changes in color temperature as well, through a feedback mechanism. In particular, a user may measure the color temperature of particular lighting conditions with the electromagnetic radiation detector 1071, identify the signal from the electromagnetic radiation detector 1071 under desired conditions, connect the microprocessor of the present invention to the electromagnetic radiation detector 1071 and strobe the LED system 1072 of the present invention through various lighting conditions until the signal from the electromagnetic radiation detector 1071 indicates that the desired conditions have been obtained. By periodically strobing the LED system 1072 and checking the signal from the electromagnetic radiation detector 1071, the light module 100 may be programmed to maintain precise lighting conditions in a room.

Figure 84:
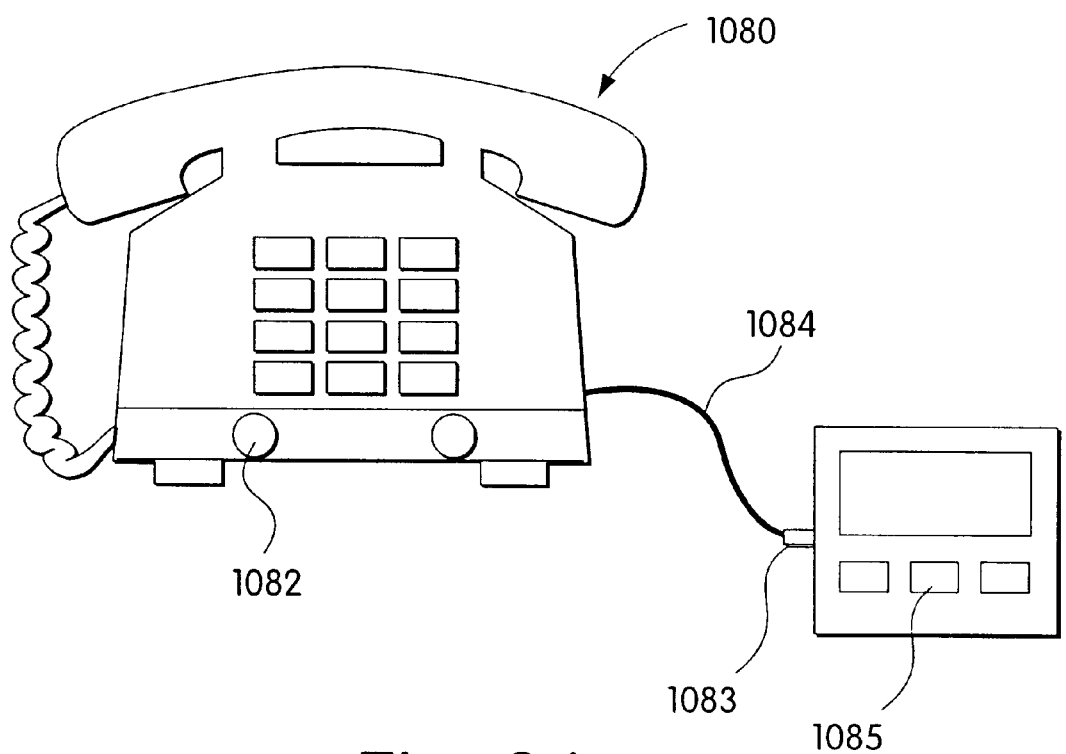
FIG. 84 depicts a color telephone indicator.

In another embodiment, room or telephone lights could help identify the source or intent of a telephone call. FIG. 84 shows a color telephone indicator 1080 comprising an LED system 1082 of the present invention, an output port 1083 that can be either serial or parallel and a connection wire 1084 connecting the system to a caller ID box 1085.

By emitting a characteristic color, it would be possible to determine whence a telephone call is being placed. Thus, one could program the light module 100 to cause the LED system 1082 to emit a red light, for example, if the call is being placed from a certain telephone. Alternatively, a caller's wish to designate a call as being urgent could be conveyed to a receiver by a particular color display. Thus, one could program the light module 100 to cause the LED system 1082 to emit a red light, for example, if a caller has designated the call to be an emergency. Still another telephone application involves displaying a range of colors to indicate to the receiver the length of time that a caller has been on hold. For example, the LED system 1082 could emit a green, amber, or red light depending on whether the caller has been on hold for less than one minute, between one and two minutes, and more than two minutes, respectively. This last feature would be especially useful if the telephone has more than one line, and it is important to keep track of various people who have been put on hold.

The foregoing disclosure has dealt with physical conditions that could be indicated by using the LED system of the present invention. Also capable of being indicated in this manner are other such conditions which include acceleration, acoustic, altitude, chemical, density, displacement, distance, capacitance, charge, conduction, current, field strength, frequency, impedance, inductance, power, resistance, voltage, heat, flow, friction, humidity, level, light, spectrum, mass, position, pressure, torque, linear velocity, viscosity, wind direction, and wind speed.

In an embodiment of the invention, the signal-generating device is a remote control of a conventional type used to control electronic devices through radio frequency or infrared signals. The remote control includes a transmitter, control switches or buttons, and a microprocessor and circuit responsive to the controls that causes the transmitter to transmit a predetermined signal. In this embodiment of the invention, the microprocessor or microprocessors that control the LEDs is connected to a receiver via a circuit and is capable of processing and executing instructions from the remote control according to the transmitted signal. The remote control may include additional features, such as illuminated buttons or controls that are formed of LEDs and that change color or intensity in correspondence to the change in the signal sent from the remote control. Thus a lever that is depressed to cause the color of a controlled room light to strobe from red to violet may itself strobe in correspondence to the room light. This effect permits the user to control lights in conditions where the actual LEDs may not be visible, or where interference from other sources makes the true color of the controlled LED difficult to see.

In other embodiments of the invention, the input device for the signals that control the microprocessor may be a light switch for control and mood setting. In particular, the physical mechanism of the light switch, such as a dial, slide bar, lever or toggle, may include one or more LEDs that are responsive to the external signal generated by the switch, so that using the switch to change a microprocessor controlled array of LEDs, such as room lights, causes the switch itself to change colors in a way that matches the changes in the room. The signal could be used to control a multi-color light, monitor, television, or the like. Any control switch, dial, knob or button that changes color in association with the output light that is controlled by the same is within the scope of the present invention.

In another embodiment of the present invention, the input control device may constitute a badge, card or other object associated with an individual that is capable of transmitting a radio frequency, infrared, or other signal to a receiver that controls the microprocessor that controls the arrayed LEDs of the present invention. The badge thus constitutes an interface to the color settings in a room. The badge or card may be programmed to transmit signals that reflect the personal lighting preferences of the individual to the microprocessor, so that room lights or other illumination may be changed, in color or intensity, when the person is in proximity to the receiver for the lights. The desired lighting environment conditions are automatically reproduced via the lighting network in the room. The badge could also include other data associated with the individual, such as music preferences, temperature preferences, security preferences and the like, so that the badge would transmit the data to receivers associated with networked electronic components that are responsive to the signals. Thus, by walking into a room, the individual could cause the lights, music and temperature to be changed automatically by microprocessors controlling arrayed LEDs or other lights, a compact disc player or similar music source, and a thermostat.

In another embodiment of the present invention, the arrayed LEDs may be placed in the floor, ceiling or walls of an elevator, and the LEDs may be made responsive to electrical signals indicating the floor. Thus, the color of the light in the elevator (or of a floor, ceiling or wall lit by the light) may be varied according to the floor of the elevator.

Figure 85:
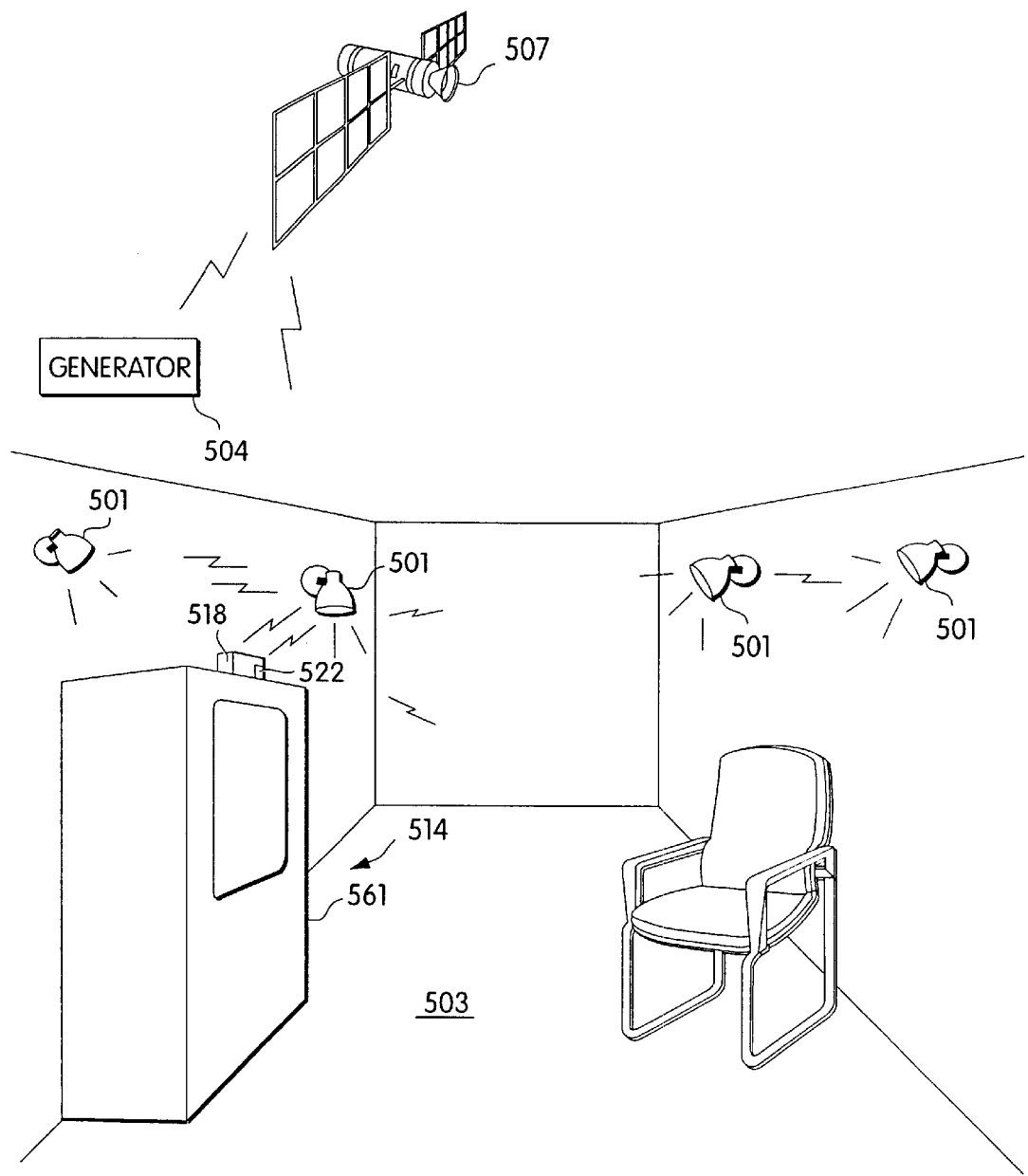
FIG. 85 depicts a lighting system using a light module of the present invention in association with an entertainment device.

In another embodiment of the present invention, depicted in FIG. 85, the signal-generating device 504 may be a generator of a television, stereo, or other conventional electronic entertainment signal. That is, the lighting control signal can be embedded in any music, compact disc, television, videotape, video game, computer web site, cybercast or other broadcast, cable, broadband or other communications signal. Thus, for example, the signal for the microprocessor may be embedded into a television signal, so that when the television signal is processed by the receiver, a microprocessor processes certain portions of the bandwidth of the television signal for signals relating to the room lights. In this embodiment, the color and intensity of room lights, as well as other lighting effects, may be directly controlled through a television signal. Thus, a television signal may instruct the room lights to dim at certain points during the presentation, to strobe to different colors at other points, and to flash at other points. The signals are capable of controlling each LED, so that a wide variety of effects, such as those more particularly described herein, may be obtained. Among other things, selected color washes may enhance visual effects during certain television or movie scenes. For example, the explosion scene in a movie or on a computer game, could cause lights in the room to flash a sequence or change to a specified color. A sunset in a movie scene could be imitated by a sunset generated by the room lights. Alternatively, a music CD, DVD disk, audio tape, or VHS tape could contain room color, intensity or lighting positional data. The present invention may be embodied not only in television signals, but in any other signal-based source, such as music, film, a website, or the like, so that the lighting environment, or specific lights, whether in the home, at work, or in a theater, can be matched to the entertainment source.

Figure 86:
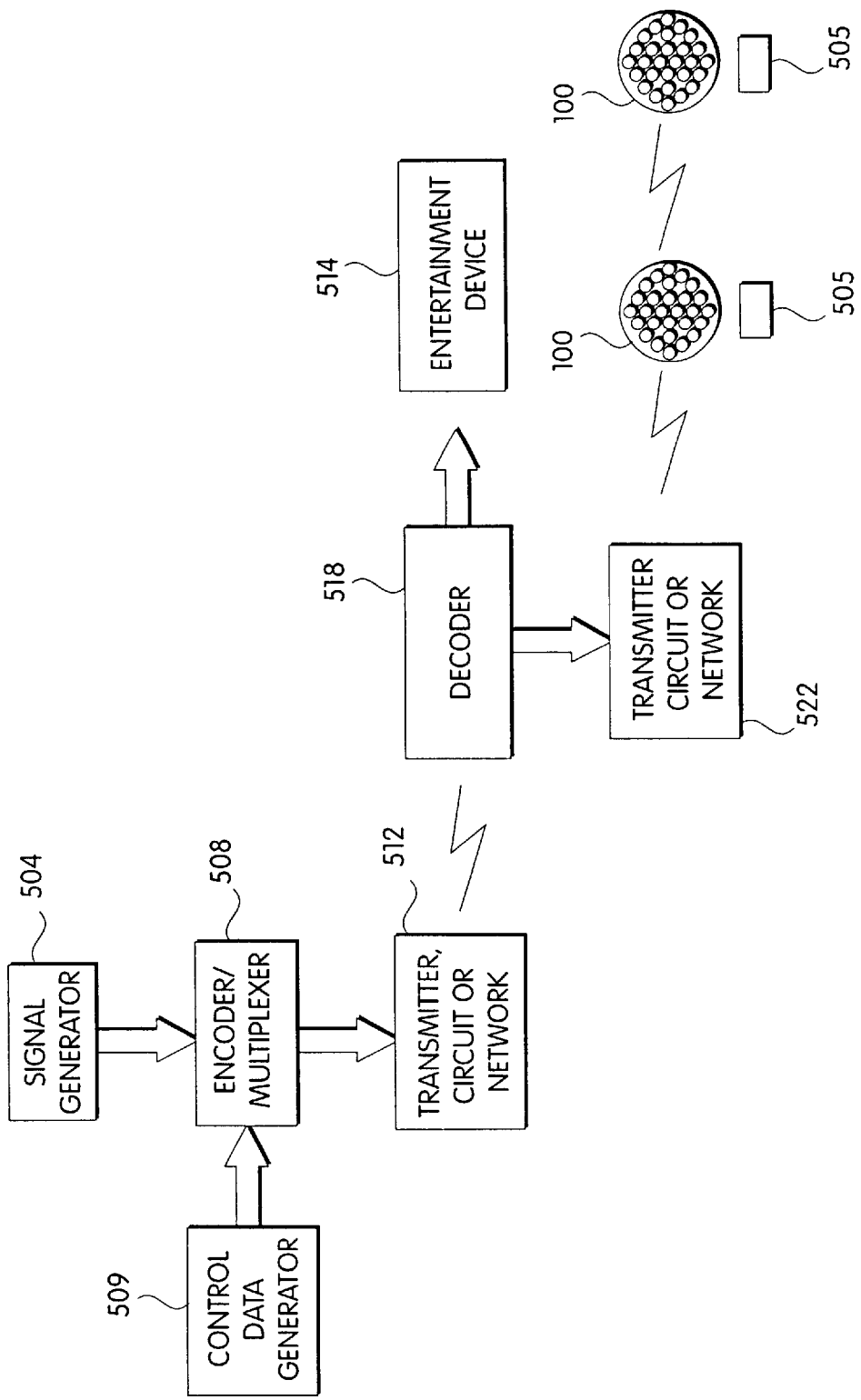
FIG. 86 depicts a schematic of the system of FIG. 85.

Referring to FIG. 85, a signal generator 504 may be any device capable of generating an entertainment signal, such as a television broadcast camera. Referring to FIG. 86, lighting control data may be added to the signal generated by the signal generator through use of a data encoder or multiplexor 508. Methods and systems for adding data to television signals and other entertainment signals are known to those or ordinary skill in the art; for example, standards exist for insertion of closed-captioning data into the vertical blanking interval of a television broadcast signal, in order to have captioned text for the hearing-impaired appear on a portion of a television screen. Similar techniques can be used to insert lighting control data into the same or similar portions of the television signal. In an embodiment of the invention, a multiplexor may detect a horizontal sync pulse that identifies the beginning of the television line, count a pre-determined amount of time after the pulse, and replace or supplement the television signal data for a pre-determined amount of time after the pulse. Thus, a combined signal of control data superimposed on the television signal may be produced. Similar techniques may be used for other types of signals.

Once the signal is encoded, the signal may be transmitted by a data connection 512, which may be a transmitter, circuit, telephone line, cable, videotape, compact disk, DVD, network or other data connection of any type, to the location of the user's entertainment device 514. A decoder 518 may be designed to separate the lighting control data from the entertainment signal. The decoder 518 may be a decoder box similar to that used to decode closed-captioning or other combined signals. Such a decoder may, for example, detect the horizontal sync pulse, count time after the horizontal sync pulse and switch an output channel between a channel for the entertainment device 514 and a different channel dedicated to lighting control data, depending on the time after the horizontal sync pulse. Other techniques for reading or decoding data from a combined signal, such as optical reading of black and white pixels superimposed onto the television screen, are possible. Any system adding and extracting lighting control data to and from an entertainment signal may be used. The entertainment signal may then be relayed to the entertainment device 514, so that the signal may be played in a conventional manner. The lighting control data, once separated from the entertainment signal by the decoder 518, may be relayed to a lighting module or modules 100 for controlled illumination. The signal may be relayed to the light modules 100 by a data connection 522 by any conventional data connection, such as by infrared, radio, or other transmission, or by a circuit, network or data track.

Systems and methods provided herein include an system for combining illumination control with another signal. One such embodiment is an entertainment system, which is disclosed herein. It should be understood that other signals, such as those used for informational, educational, business or other purposes could be combined with illumination control signals in the manner described herein, and are within the scope of the disclosure, notwithstanding the fact that the depicted embodiment is an entertainment system.

The entertainment system may include an illumination source 501, which may be part of a group of such illumination sources 501. The illumination source 501, in this embodiment of the invention, may be a light module 100 such as that disclosed above. Referring to FIG. 85, the illumination source 501 may be disclosed about a space 503 in which an entertainment system 561 is located. The illumination system may include the illumination sources 501, as well as an entertainment device 514. The illumination source 501 may include a receiver 505 for receiving a control signal to control the illumination source 501. The control signal can be any type of control signal capable of controlling a device, such as a radio frequency signal, an electrical signal, an infrared signal, an acoustic signal, an optical signal, or any other energy signal.

The entertainment system 561 may include a decoder 518 that is capable of decoding an incoming signal and transmitting the signal by a transmitter 522 to the illumination sources 501. The illumination system may further include a signal generator 504, which is depicted in schematic form in FIG. 86 and FIG. 85. The signal generator 504 may generate any form of entertainment signal, whether it be a video signal, an audio signal, a data packet, or other signal. In an embodiment, as depicted in FIG. 85, a signal generator 504 generates a television signal that is transmitted to a satellite 507. Referring to FIG. 86, the signal generator 504 may be associated with an encoder 508 which may include a multiplexor and which may combine a signal from a signal generator 504 with control data from a control data generator 509. The encoded signal 508 may then be transmitted by a transmitter 512 to the decoder 518. Once decoded by the decoder 518, the signal may be split back into the entertainment signal component and the illumination control data component. The entertainment signal may be sent to the entertainment device 514 by a circuit or other conventional means. The control data may be sent by a transmitter, circuit, network or other conventional connection 522 to the illumination sources, which in the embodiment depicted in 86 are light modules 100 such as disclosed above. As a result, illumination control may be associated with an entertainment signal, so that the illumination produced by the illumination sources 501 can be matched to the entertainment signal played on the entertainment device 514. Thus, for example, the room lights may be synchronized and controlled to create different conditions simultaneously with events that occur in programs that are being displayed on a television.

It should be recognized that any type of entertainment signal could be combined or multiplexed with the control signal to permit control of the illumination sources 501 with the entertainment device 514. For example, the entertainment device could be a television, a computer, a compact disc player, a stereo, a radio, a video cassette player, a DVD player, a CD-ROM drive, a tape player, or other device. It should be understood that the entertainment device 514 could be a device for display for one or more of the above signals for purposes other than entertainment. Thus, educational, informational, or other purposes and devices should be understood to be within the scope disclosed herein, although the embodiment depicted is an entertainment device 514. It should be understood that the particular system for combining the data, transmitting the data, and decoding the data for use by the device 514 and the illumination sources 501 will depend on the particular application. Thus, the transmitter used in the embodiment depicted in FIGS. 85 and 86 could be replaced with a circuit, a network, or other method or system for connecting or transmitting a decoded signal. Similarly the connection between the decoder 518 and the illumination sources 501 could be a transmitter, circuit, network, or other connection method of delivering data to the illumination sources 501.

The illumination control driver 509 that generates control data can be any data generator capable of generating data for controlling the illumination sources 501. In an embodiment of the invention, the control driver is similar to that disclosed in connection with FIG. 6 hereof, and the illumination sources a light module 100. In this case, the data would be sent according to the DMX-512 protocol.

Figure 87:
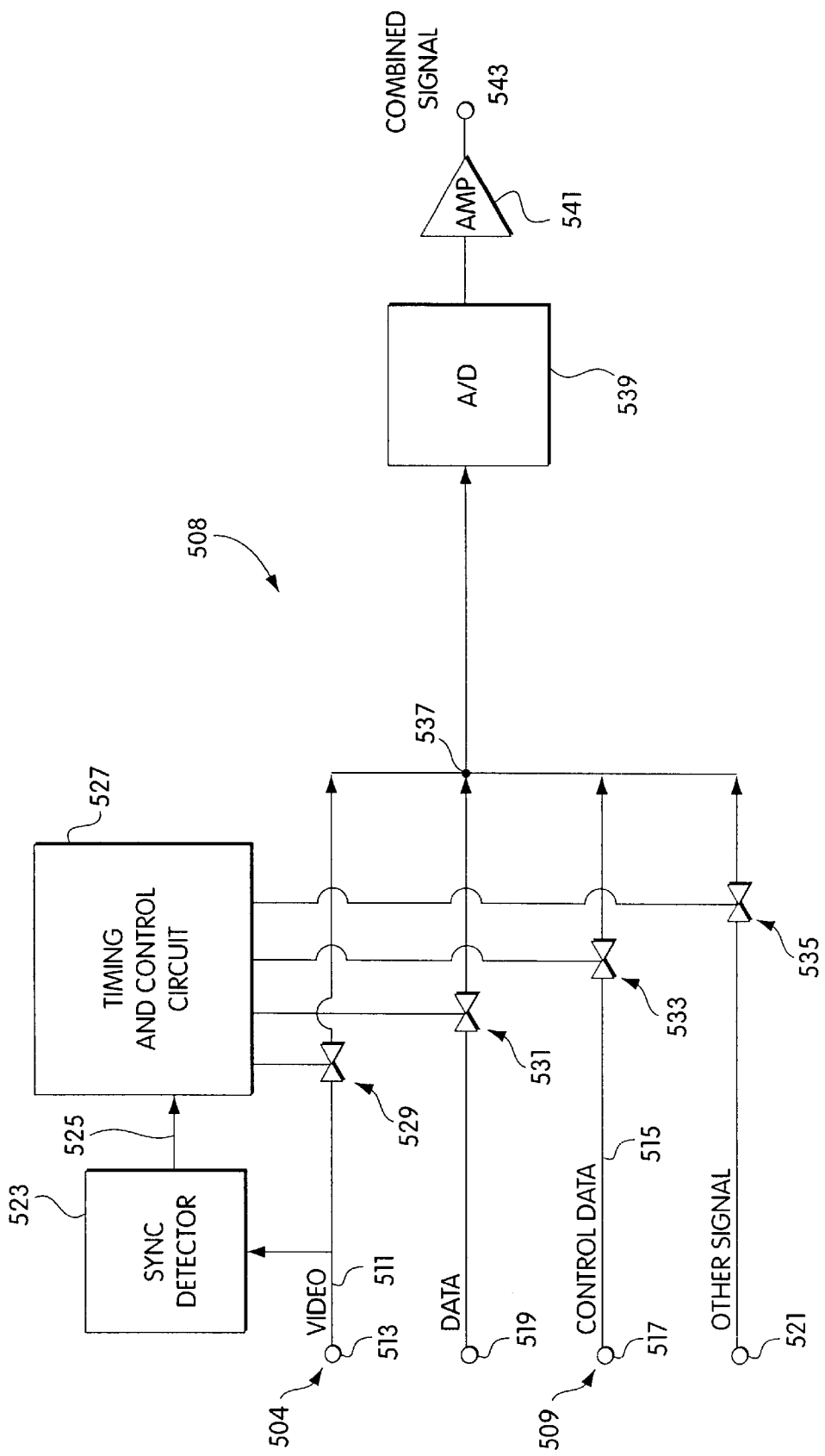
FIG. 87 depicts a schematic of an encoder for the system of FIG. 85.

In an embodiment of the invention depicted in FIG. 87, an encoder 508 is depicted in schematic form in an embodiment where the signal is a television signal. In this embodiment, a video signal 511 enters the device at 513 from the signal generator 504. Control data 515 may enter the encoder 508 at 517 from the illumination control driver 509. Other data or signals may enter at 519 and 521. These other signals may be used to control the encoder 508, to change the operation mode of the controller 508, or for other purposes. The other signal 521 could also be some other form of piggyback signal that is related to the video signal 511. For example, the other signal 521 could be closed-caption or teletext data that would be multiplexed with the video signal. The encoder 508 may include a sync detector 523. The sync detector 523 may detect the horizontal sync pulse in the video signal 511. The sync detector may then send a signal 525 to a timing and control circuit 527.

The timing and control circuit 527 may count a predetermined amount of time after the horizontal sync pulse detected by the sync detector 523 and control a series of gates or switches 529, 531, 533 and 535. In particular, the timing and control circuit 527 may be used to open one of the gates 529, 531, 533 and 535 while keeping the other gates closed. Thus, the signal at the node 537 of FIG. 87 represents the particular selected signal among the signals 511, 515, 519 and 521 that has an open gate among the gates 529, 531, 533 and 535. By opening and closing different gates at different times, the timing and control circuit 527 can generate a combined signal at 537 that captures different data at different points of the output signal.

In an embodiment the invention may include an analog to digital converter 539, an amplifier 541, or other component or components to convert the signal to appropriate format or to provide an adequate signal strength for use. The end result is an output combined signal 543 that reflects multiple types of data. In an embodiment, the combined signal combines a video signal 511 with illumination control data 515 that is capable of controlling the illumination sources 501 depicted in FIG. 85.

Figure 88:
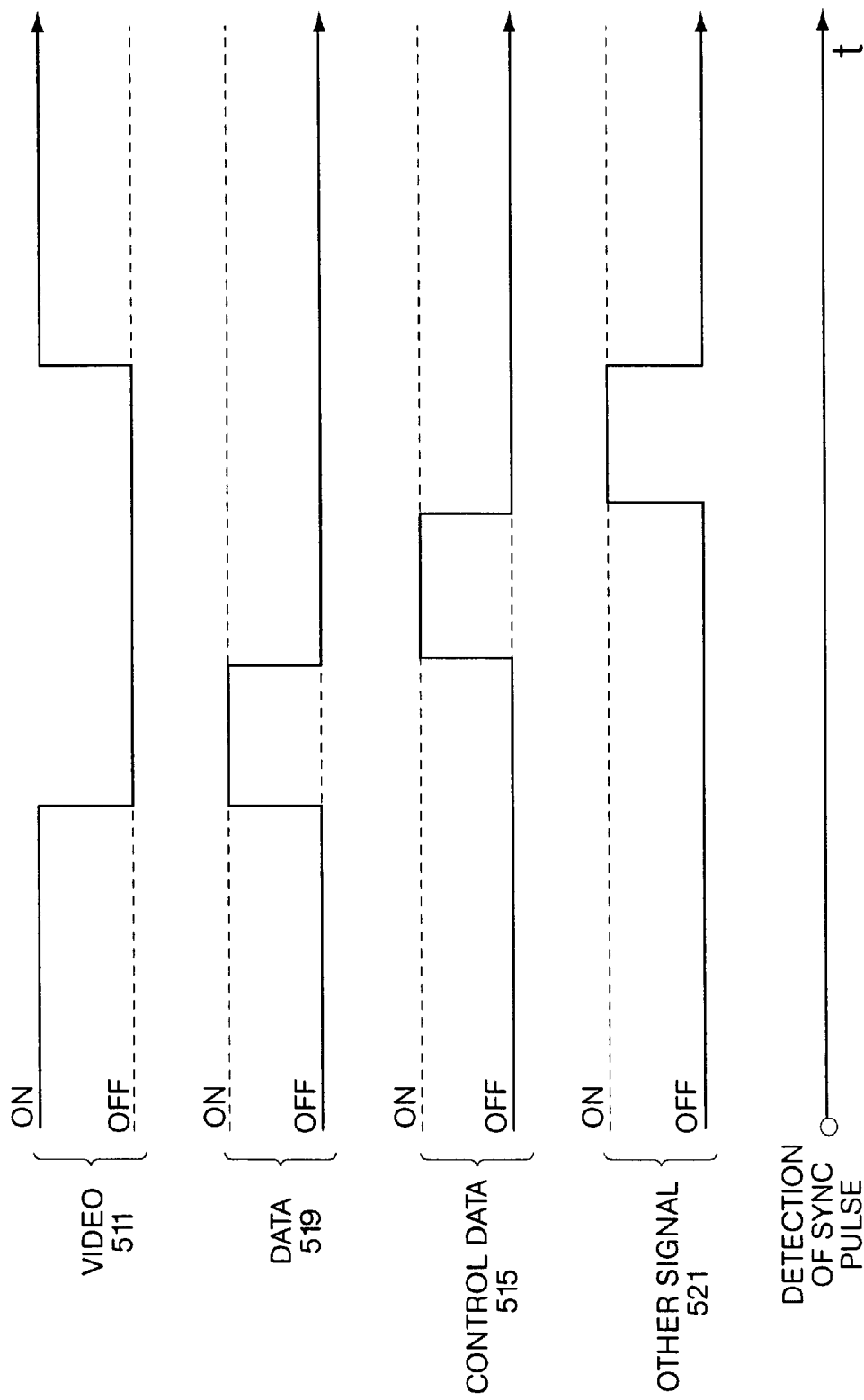
FIG. 88 depicts a schematic of an encoding method using the encoder of FIG. 87.

Referring to FIG. 88, a depiction of the operation of the timing and control circuit 527 is provided. For each of the signals 511, 519, 515 and 521 the gate for the signal may be kept on or off (i.e., open or closed) at a predetermined time after detection of the sync pulse by the sync detector 523. The timing and control circuit may thus allocate the time periods after detection of the sync pulse to be different signals, with only one of the gates 529, 531, 533 and 535 open at any particular time. Thus, the gate for the video signal 511 is open for the time immediately after detection of the sync pulse and for a time after the gates have been opened and closed. The gate for the data signal 519, the control data 515 and the other signal 521 can be opened in sequence, with no single gate open at the same time as any other gate. This approach, as reflected by the schematics of FIG. 87 and FIG. 88, establishes a combined signal without interference between the constituent signals 511, 519, 515 and 521.

Figure 89:
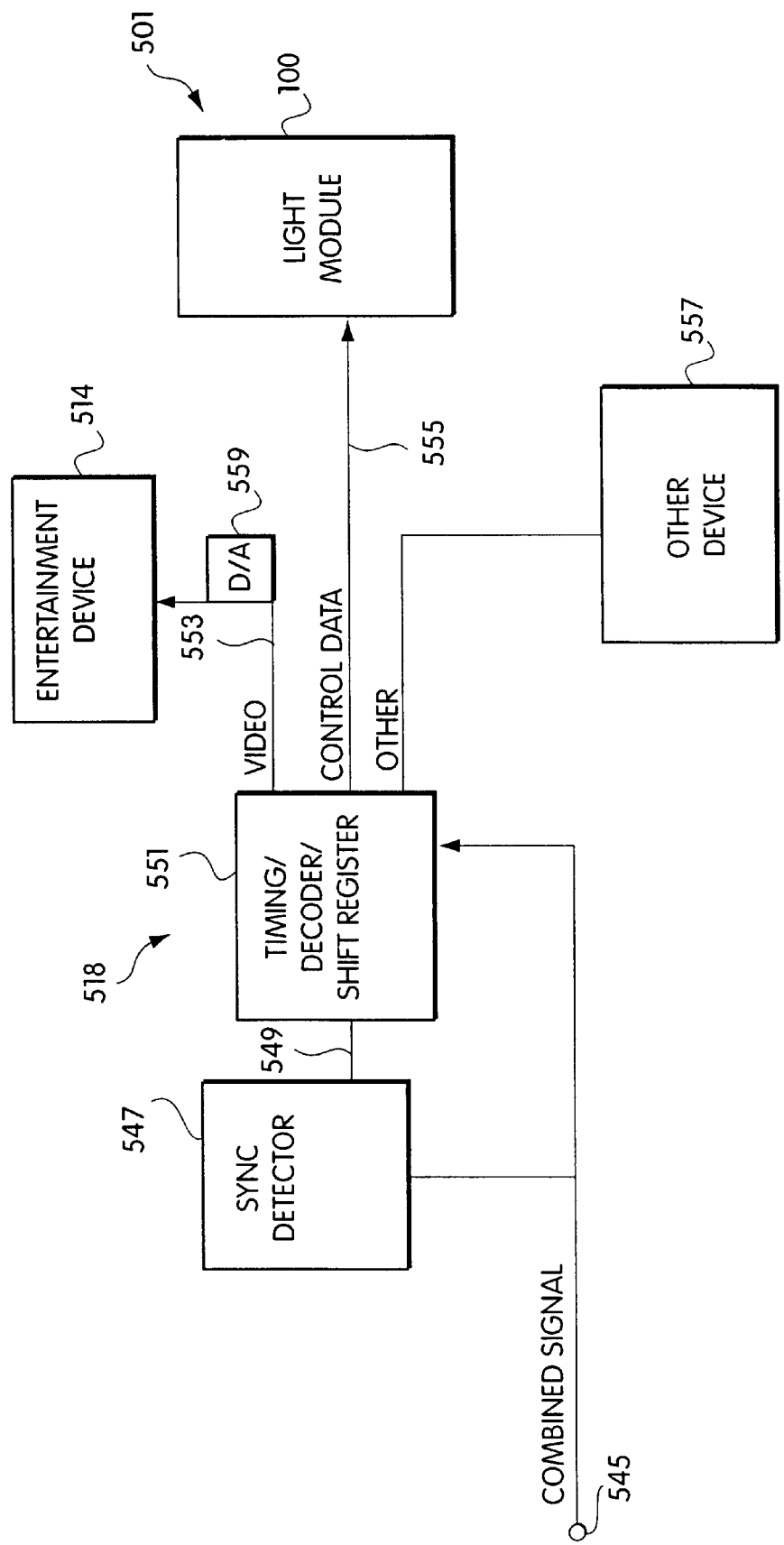
FIG. 89 depicts a schematic of a decoder of the system of FIG. 85.

Referring to FIG. 89, an embodiment of a decoder 518 is provided. In this embodiment, the decoder 518 is a decoder box for a video signal. The incoming signal at 545 may be the combined signal produced by the encoder 508 of FIG. 87. A detector 547 may detect the horizontal or other sync pulse in the combined signal 545 and send a signal 549 to a control circuit 551 to establish the timing of the control circuit 551. The combined signal 545 may be also be sent to the timing and control circuit 551, which may process the incoming combined signal 545 according to the time of arrival, or using other information. In one embodiment, the decoder may separate the incoming signal according to the time of arrival as determined by the sync detector 547. Therefore, by coding the timing of the opening of the gates as depicted in FIG. 88, the timing and control circuit 551 can separate video, control data, and other data according to the time of arrival. Thus, the timing and control circuit 551 can send a video signal 553 to the entertainment device 514. The timing and control circuit 551 can similarly send control data 555 to the illumination source 501, which may be a light module 100 such as that depicted above. The other data can be sent to another device 557.

Other elements can be included between the timing and control circuit 551 and the respective device; for example, a digital to analog converter 559 could be disposed between the timing and control circuit 551 and the entertainment device 514 to permit use of an analog signal with the entertainment device 514. It should be understood that the timing and control approach depicted in the schematic FIG. 89 is only one of many approaches of decoding a combined signal. For example, the signal could be a data packet, in which case the packet could include specific information regarding the type of signal that it is, including information that specifies which illumination source 501 it is intended to control. In this case the timing and control 551 could include a shift register for accepting and outputting data packets to the appropriate devices.

The embodiments depicted in FIGS. 85–89 are merely illustrative, and many embodiments of circuits or software for producing such a system would be readily apparent to one of ordinary skill in the art. For example, many systems and methods for inserting data into signals are known. For example, systems are provided for including closed-caption data, vertical interval time code data, non-real time video data, sample video data, North American Basic Teletex specification data, World System Teletex data, European broadcast union data and Nielsen automated, measurement and lineup data, and entry video signals. One such system is disclosed in U.S. Pat. No. 5,844,615 to Nuber et al., the disclosure of which is incorporated by reference herein. Systems and methods for nesting signals within a television signal are also known. One such system is disclosed in U.S. Pat. No. 5,808,689 to Small, the entire disclosure of which is incorporated by reference herein. Other applications include surround sound, in which certain sound data is combined with a signal, which may be a motion picture, music, or video signal. Such surround sound systems are known to those skilled in the art. One such system is disclosed in U.S. Pat. No. 5,708,718 to Ambourn et al., the entire disclosure of which is incorporated by reference herein. Any system for superimposing data onto a signal or combining data with a signal for controlling a device wherein the system is capable of also carrying illumination control information produced by an illumination control driver for controlling an illumination source should be understood to be within the scope of the invention.

In the television embodiment, different portions of the television signal are used for different purposes. One portion of the signal is used for the visible image that appears on the screen. Another portion is used for audio signals. Another is the overscan area. Another portion is the vertical blanking interval. Another portion is the horizontal blanking interval. Any portion of the signal can be used to carry data. In an embodiment, the data is located in one of the portions, such as the horizontal blanking interval or the vertical blanking interval, that does not interfere with the display on the screen. However, it is known that a typical television does not display all of the display portion of the television signal. Therefore, the initial part of the television display signal could also be replaced with the illumination control data without substantially interfering with the appearance of the picture to the user of the entertainment device 514.

In embodiments, a user may measure the color temperature of particular lighting conditions with a light sensor, identify the signal from the light sensor under desired conditions, connect the processor of the present invention to the light sensor and strobe the arrayed LEDs of the present invention through various lighting conditions until the signal from the light sensor indicates that the desired conditions have been obtained. By periodically strobing the LEDs and checking the signal from the light sensor, the arrayed LEDs of the present invention may thus be programmed to maintain precise lighting conditions in a room. This light compensation feature may be useful in a number of technological fields. For example, a photographer could measure ideal conditions, such as near sunset when warm colors predominate, with a light sensor and reestablish those exact conditions as desired with the arrayed LEDs of the present invention. Similarly, a surgeon in an operating theater could establish ideal lighting conditions for a particular type of surgery and reestablish or maintain those lighting conditions in a controlled manner. Moreover, due to the flexible digital control of the arrayed LEDs of the present invention, any number of desired lighting conditions may be programmed for maintenance or reestablishment. Thus, a photographer may select a range of options, depending on the desired effect, and the surgeon may select different lighting conditions depending on the surgical conditions. For example, different objects appear more or less vividly under different colors of light. If the surgeon is seeking high contrast, then lighting conditions can be preprogrammed to create the greatest contrast among the different elements that must be seen in the surgery. Alternatively, the surgeon, photographer, or other user may strobe the lighting conditions through a wide range until the conditions appear optimal.

The ability to vary lighting conditions, continuously or discretely, at short time intervals and over a wide range of colors, permits a number of technological advances in fields that depend on controlled illumination. Certain embodiments of the invention in the area of controlled illumination are set forth as follows.

In the embodiments depicted below, LED systems are used to generate a range of colors within a spectrum. "LED system," as the term is used herein, refers to an array of color-emitting semiconductor dies. Color emitting semiconductor dies are also termed light emitting diodes or LEDs. The array of color-emitting semiconductor dies can include a plurality of color-emitting semiconductor dies grouped together in one structural unit. Alternatively, the array of color-emitting semiconductor dies can comprise a plurality of structural units, each comprising at least one color-emitting semiconductor die. An LED system can further comprise a plurality of structural units, each unit comprising a plurality of color-emitting semiconductor dies. It is understood that as long as at least two primary color LEDs are used, any illumination or display color may be generated simply by preselecting the light intensity that each color LED emits. Further, as described in part in the foregoing specification, each color LED can emit light at any of a large number of different intensities, depending on the duty cycle of PWM square wave, with a full intensity pulse generated by passing maximum current through the LED. The term brightness, as used herein, is understood to refer to the intensity of a light. As an example, described in part above, the maximum intensity of an LED or of the LED system can be conveniently programmed simply by adjusting the ceiling for the maximum allowable current using programming resistances for the processors residing on the light module.

In one embodiment of the present invention, a multicolor illuminating system is provided for illuminating a material. The terms "illumination" and "illuminate" as used herein can refer to direct illumination, indirect illumination or transillumination. Illumination is understood to comprise the full spectrum radiation frequencies, including, visible, ultraviolet, and infrared, as well as others. Illumination can refer to energy that comprises any range of spectral frequencies. Illumination can be viewed or measured directly, whereby the reflected light regarded by the viewer or sensor is reflected at an angle relative to the surface substantially equivalent to the angle of the incident light. Illumination can be viewed or measured indirectly, whereby the reflected light regarded by the viewer or sensor is reflected at an angle relative to the surface that is different than the angle of the incident light. Direct or indirect illumination can be directed at the surface of a material. A surface can be a naturally occurring surface such as a body part or a geological formation. Alternatively, the surface can be a face of an apparatus. A surface can have a three-dimensional topography. A surface can have a plurality of objects affixed to it.

The term "material" as used herein encompasses the full range of materials that can be targets for illumination. The term "transillumination" refers to an illumination method whereby light is directed at least in part through a material, wherein the characteristics of the light are regarded by a viewer or a sensor after the light has passed through the material. As an example of transillumination, illumination from a gastroscope can be directed through the wall of the stomach and through the overlying soft tissues so that a site can be identified for placement of a percutaneous endoscopic gastrostomy tube. As another example of transillumination, a light can be directed at a surface of a tissue mass to determine whether it is cystic or solid. A cystic mass is said to transilluminate, this term referring to the fact that light passes through the mass to be perceptible by an observer at a site remote from the site of the incident light.

Figure 90A:
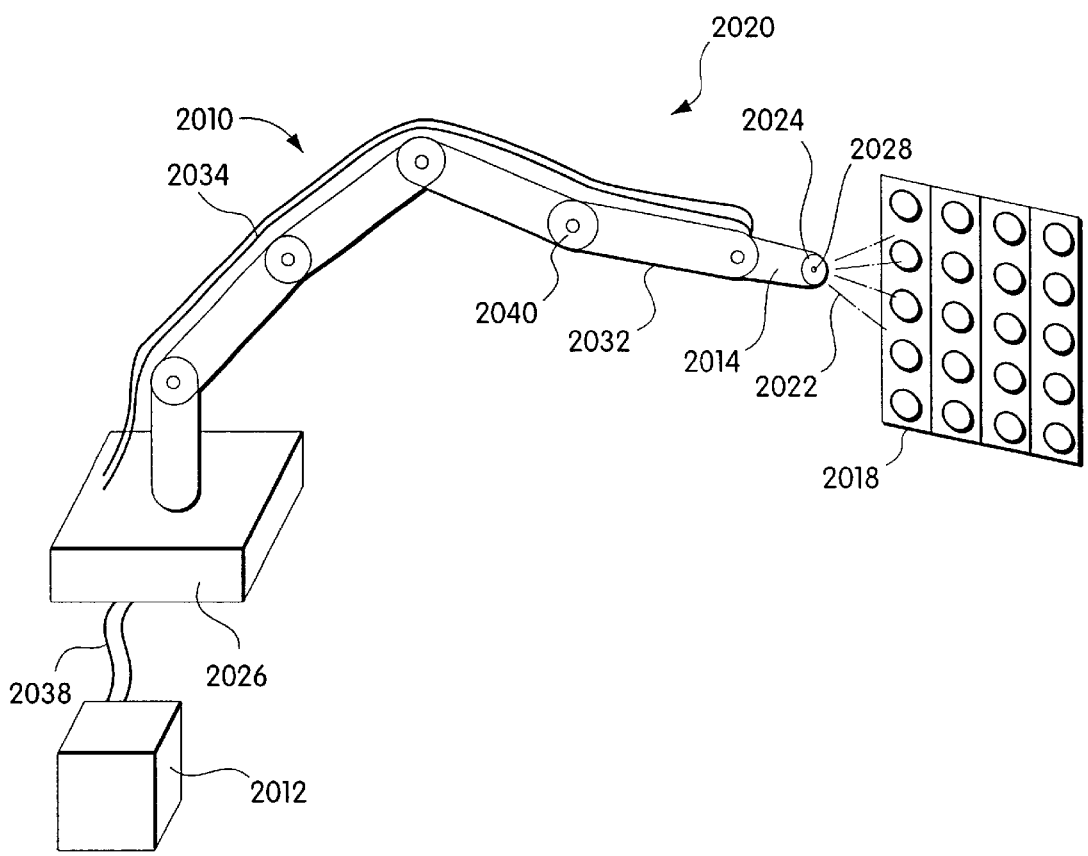
FIG. 90A depicts an embodiment of a system for precision illumination.

FIG. 90A depicts an embodiment of an illumination system 2020. The embodiment illustrated in FIG. 90A shows a positioning system 2010, a control module 2012, an LED assembly 2014 and a target material 2018. In the embodiment illustrated in FIG. 90A, the target material 2018 is represented as a surface of an apparatus. It will be apparent to those of ordinary skill in the relevant arts that the target material 2018 can be any material, and is not limited to the illustrated embodiment. In FIG. 90A, an embodiment of the illumination system 2020 is shown directing incident light 2022 at material 2018. FIG. 90A further illustrates a LED assembly 2014, comprising a sensor system 2024 and an LED system 2028. In one embodiment, a plurality or an array of LEDs comprises the LED system 2028, each LED being controlled by the control module 2012. An LED system 2028 is understood to comprise a plurality of color-emitting semiconductor dies for generating a range of colors within a spectrum. The LED system 2028 can comprise the light module 100 or the smart light bulb 701 disclosed above. In the embodiment illustrated in FIG. 90A, the sensor system 2024 is capable of providing a signal related to the characteristics of the light reflected to the sensor system 2024 from the material 2018. In an alternate embodiment, a sensor system 2024 can be responsive to other features of the material 2018. A sensor system 2024 can be affixed to the LED system housing, or a sensor system 2024 can be positioned in juxtaposition to the LED system 2028. Other placements of the sensor system 2024 relative to the LED system 2028 can be readily envisioned by those of ordinary skill in these arts. Alternately, an embodiment can provide no sensor system.

FIG. 90A further depicts a positioning arm 2032, a control module 2012 and a LED cable 2034 through which can pass the electrical signal to the LED system 2028, and the data signal to the LED system 2028. Optionally, a data signal can pass to the sensor module (not shown) from the sensor system 2024. The LED cable 2034 can carry these sensor signals. The control module 2012 in the illustrated embodiment can contain the processor for the LED system, the power source for the LED system, the sensor module for the sensor system and a processor for relating the signals received by the sensor system 2024 to the processor, so that signals received by the sensor module affect the output characteristics of the LED system 2028. The control module can further include a position controller (not shown). In the illustrated embodiment the positioning system 2010 comprises the positioning arm 2032, the position controller and a positioning cable 2038. This depiction of a positioning system is merely illustrative. As the term is used herein, a positioning system is understood to include any system capable of positioning the LED system in a spatial relationship with the material being illuminated whereby the LED system illuminates the material. A positioning system, therefore, can include an apparatus of any kind capable of positioning the LED system. A positioning system can comprise a human operator who is capable of positioning the LED system in a spatial relationship with the material being illuminated whereby the LED system illuminates the material. A positioning system can further comprise the LED cable if the LED cable is adapted for positioning the LED system in a spatial relationship with the material being illuminated.

A plurality of positioning systems can be envisioned by practitioners in these arts that will conform to the features of the particular material being illuminated. For example, a positioning system adapted for microsurgery can be mounted on an operating microscope and can be controlled by a control module suitable for receiving positioning input from the microsurgeons. As one option for a positioning system to be used in microsurgery or other surgical procedures, a foot pedal system can provide positioning input, either using a foot-operated button, pedal or slide. As an alternative option, a manual control can be adapted for placement in the sterile field by convering the manual control with a sterile plastic bag or sheet so the microsurgeon can manipulate the control manually without compromising sterile technique.

As an example of a positioning system, a standard surgical light fixture can be equipped with an LED system as disclosed herein. The standard surgical light fixture is capable of positioning the LED system in a spatial relationship with the material being illuminated whereby the LED system illuminates the material. This positioning system can be adjusted manually in the standard fashion well-known to surgical practitioners. Alternatively, the positioning system can be controlled in response to signals input from a separate control module. The positioning system can change its position to illuminate materials designated by the operator, either in response to direct input into the control module or as a response to signals transmitted to a sensor apparatus. Other embodiments of positioning systems can be envisioned by those skilled in these arts. The scope of the term "positioning system" is not to be limited by the embodiment illustrated in this figure. A plurality of other positioning systems can be envisioned consistent with the systems and methods described herein.

FIG. 90A illustrates an embodiment of a positioning system 2010 where the LED assembly 2014 is located at the distal end of the positioning arm 2032. In this embodiment, the position controller can transmit signals to the positioning arm 2032 to adjust its spatial position. These signals can be carried through the positioning cable 2038. Alternatively, the signals can be transmitted by infrared, by radio frequency, or by any other method known in the art. Remote access to the control module 2012 can permit the illumination system 2020 to be controlled from a great distance, for example in undersea or aerospace applications. Remote access also permits control of the illumination system 2020 when the illumination system 2020 is operating in hostile or inhospitable environments. Remote access to the control module is understood to comprise remote control. Techniques for remote control are familiar to practitioners in these arts.

In the illustrated embodiment, the positioning arm 2032 has a plurality of articulations 2040 permitting its three-dimensional motion. In the illustrated embodiment, the articulations 2040 are arranged to provide the flexibility required by a particular technical application. Positioning can be accomplished with other mechanisms besides those depicted in FIG. 90A. These mechanisms will be familiar to practitioners in the art. As depicted in FIG. 90A, the proximal end of the positioning arm 2032 is anchored to a base 2026. The articulation connecting the positioning arm 2032 to the base 2026 can be arranged to permit motion along an axis parallel to or perpendicular to the axes of motion permitted by the other articulations 2040.

The positioning system depicted in FIG. 90A is merely one embodiment of the systems described herein. A plurality of other embodiments are available, as will be realized by practitioners of ordinary skill in the relevant arts. In one embodiment, the positioning system 2010 can be configured for large-scale applications, such as the evaluation of sheet metal or structural steel. Alternatively, the positioning system 2010 can be adapted for microscopic adjustments in position. It is understood that the light provided by the illumination system can be used for a plurality of precision applications. Fine three-dimensional control of the illumination pattern can direct the light to an exact three-dimensional position. In an alternate embodiment, signals from the sensor module can be used to control or to activate the position controller, so that the positioning system 2010 can be directed to move the LED assembly 2014 in response to received sensor data. The illumination system comprising the LED system 2028 allows the selection of a colored light predetermined to facilitate visualization of the target material 2018. The strobing effect provided by an embodiment of the illumination system can permit freeze-frame imaging of dynamic processes, or can enhance the resolution of images acquired using conventional imaging modalities.

An embodiment of the illumination system can be used for taking photomicrographs. In another embodiment of the present invention, the illumination system 2020 may be used to improve the quality of robotic vision applications. In many robotic vision applications, such as location of semiconductor chips during the manufacturing process, reading of bar code matrices, location of robotic devices during manufacturing, or the like, a robotic camera is required to identify shapes or contrasts and to react accordingly. Different lighting conditions can have a dramatic effect on such vision systems. A method for improving the accuracy of such systems includes creating a color image via a sequence of multiple black and white images taken under multiple different strobed illuminating sequences. For example, the user may strobe a red strobe to get the red frame, a green strobe to get the green frame, and a blue strobe to get the blue frame. The strobing effect permits a higher resolution by the robotic camera of the image required for robotic vision. Other embodiments can be envisioned by those of ordinary skill in the art without departing from the scope of the present invention.

Figure 90B:
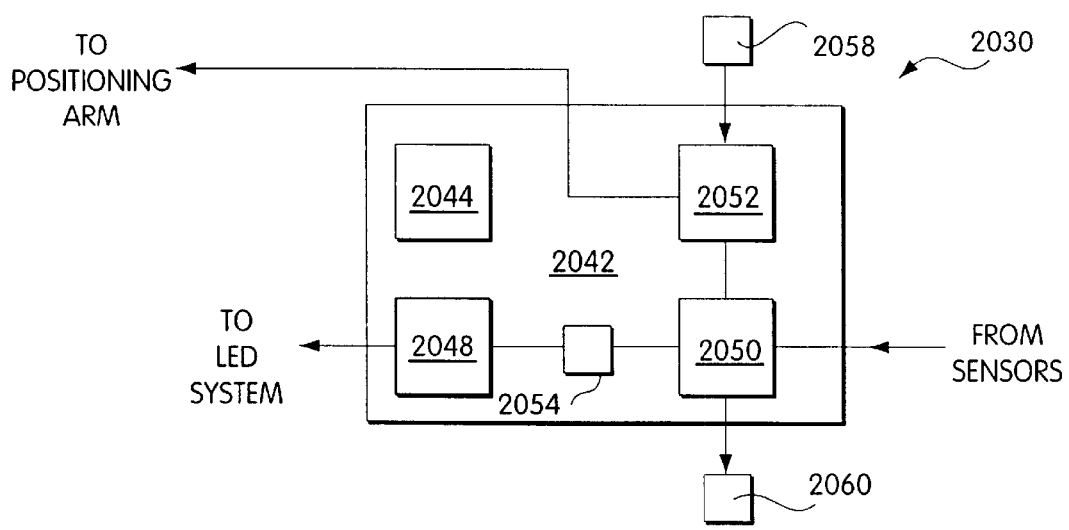
FIG. 90B depicts a block diagram of a control module for the precision illumination system of FIG. 90A.

FIG. 90B shows in more detail a schematic diagram of the control module 2012. In the illustrated embodiment, the control module 2012 provides a housing 2042 that contains a power source 2044, a first microprocessor 2048 for the LED, a sensor module 2050 adapted for receiving signals from the sensors affixed to the distal end of the position arm, and a position controller 2052. The illustrated embodiment features a second microprocessor 2054 for relating data received by the sensor module 2050 to data for controlling the LED system. The position controller 2052 is adapted for adjusting the three-dimensional position of the positioning arm. The position controller 2052 can include an input device 2058 for receiving signals or data from an outside source. As an example, data can be input through a control panel operated by an operator. Data can be in the form of 3-D coordinates to which the position system is directed to move, or in any other form that can be envisioned by practitioners of these arts. Data can also be provided through computer programs that perform calculations in order to identify the 3-D coordinates to which the position system is directed to move. The input device 2058 can be configured to receive data received through a computer-based 3-dimensional simulator or virtual reality apparatus. Further examples of input devices 2058 can be envisioned by those of ordinary skill in the art without departing from the scope of this invention. The control module 2030 depicted in FIG. 90B further shows a sensor module 2050 adapted for receiving signals from the sensors affixed to the distal end of the position arm. The sensor module 2050 can be configured to receive any type of signal, as described in part above. A sensor module 2050 can comprise a light meter for measuring the intensity of the light reflected by the surface being illuminated. A sensor module 2050 can comprise a calorimeter, a spectrophotometer or a spectroscope, although other sensor modules and sensor systems can be employed without departing from the scope of the invention. A spectrophotometer is understood to be an instrument for measuring the intensity of light of a specific wavelength transmitted or reflected by a substance or a solution, giving a quantitative measure of the amount of material in the substance absorbing the light. Data received in the sensor module 2050 can be used to evaluate features of a material. In one embodiment, sensor module 2050 can be configured to provide data output to an output device 2060. The output data can include values that can be compared to a set of known values using algorithms familiar to those skilled in these arts. The relationship between the output data and the set of known values can be determined so as to yield meaningful information about the material being illuminated by the illumination system.

FIG. 91 depicts an embodiment of an illumination system 2056 capable of being directed by a part of an operator's body. The embodiment shown in FIG. 91 depicts an illumination system 2056 held in the operator's hand 2062. In the illustrated embodiment, the LED system 2064 is positioned at the distal end of a handheld wand 2068 that can be disposed in the operator's hand 2062 and directed towards a material 2070. The LED cable 2072 connects the LED system 2064 to a power source (not shown). The LED cable 2072 transmits power signals and data signals to the LED system 2064. In an alternate embodiment, sensors can be positioned at the distal end of the handheld wand 2068 to provide sensing data as described above. The signals from the sensors can be transmitted through the LED cable 2072 in one embodiment. In yet another embodiment, the handheld wand 2068 can include an imaging system for video imaging. This imaging system can permit display of real-time images, for example on a video screen. Alternatively, this imaging system can permit capture of still or motion images through appropriate software and hardware configurations. Illuminating the material 2070 with a variety of colors can result in significantly different images, as described in part above. Strobing the light provided by the illumination system 2056 can allow capture of still images and can allow improved improved resolution. The handheld system can be used for any application where using an operator's hand 2062 is advantageous in positioning the illumination system. In an embodiment, the system can be entirely handheld, as illustrated in FIG. 91. In an alternate embodiment, a wand bearing the LED can be affixed to a framework that supports it, whereby the positioning of the wand is facilitated by direct manipulation by the operator's hand. In yet another embodiment, the illumination system can be borne on the operator's hand by a band or a glove, so that the position of the illumination system can be directed by the movements of the operator's hand. In other embodiments, the illumination system can be affixed to or retained by other body parts, to be directed thereby.

In another embodiment of the present invention, the LEDs are displayed in proximity to the workpiece that requires illumination. Thus, an improved flashlight, light ring, wrist band or glove may include an array of LEDs that permit the user to vary the lighting conditions on the workpiece until the ideal conditions are recognized. This embodiment of the invention may be of particular value in applications in which the user is required to work with the user's hands in close proximity to a surface, such as in surgery, mechanical assembly or repair, particularly where the user cannot fit a large light source or where the workpiece is sensitive to heat that is produced by conventional lights.

In one practice of a method for illuminating a material, a LED system, as described above, can be used. According to this practice, an LED system and a processor are provided. The practice of this method can then involve positioning the LED system in a spatial relationship with the material to be illuminated. The positioning can take place manually or mechanically. The mechanical placement can be driven by input from an operator. Alternately, mechanical placement can be driven by a data set or a set of algorithms provided electronically. A first microprocessor can be provided for controlling the LED system. In an embodiment, a second microprocessor can be provided for positioning the positioning system in relation to the material to be illuminated. In yet another embodiment, a third microprocessor can be provided for processing data input from a sensor system or input from a control panel. Each microprocessor can be related to each other microprocessor, so that changes in one function can be related to changes in other functions.

In one practice, the method can further comprise providing an image capture system for recording an image of the material. An image capture system, as the term is used herein, comprises techniques using film-based methods, techniques using digital methods and techniques using any other methods for image capture. An image capture system further comprises methods that record an image as a set of:electronic signals. Such an image can exist, for example, in a computer system. In the current arts, images can be captured on film, on magnetic tape as video or in digital format. Images that are captured using analog technologies can be converted to digital signals and captured in digital format. Images, once captured, can be further manipulated using photomanipulative software, for example Adobe Photoshop™. Photomanipulative software is well-known in the art to permit modification of an image to enhance desirable visual features. An image once captured can be published using a variety of media, including paper, CD-ROM, floppy disc, other disc storage systems, or published on the Internet. The term recording as used herein refers to any image capture, whether permanent or temporary. An image capture system further includes those technologies that record moving images, whether using film-based methods, videotape, digital methods or any other methods for capturing a moving image. An image capture system further includes those technologies that permit capture of a still image from moving images. An image, as the term is used herein, can include more than one image. As one embodiment, a photography system can be provided whereby the material being illuminated is photographed using film-based methods. In this embodiment, the LED system can be strobed to permit stop-action photography of a moving material.

In an alternative embodiment, a sensor system can be arranged to identify the characteristics of light reflected by a material and the LED system can be controlled to reproduce a set of desired light characteristics so that the material will be optimally illuminated to achieve a desired photographic effect. This effect may be an aesthetic one, although industrial and medical effects can be achieved. For example, a set of characteristics for ambient light in the operating room can be identified by surgical personnel and replicated during surgery. Certain types of lighting conditions can be more suitable for certain operations. As another example, photography can be carried out using the LED system to provide certain characteristics for the photographic illumination. As is well-known in the art, certain light tones and hues highlight certain colors for photography. Different light systems used for photography can cause different tones and hues to be recorded by the photograph. For example, incandescent light is known to produce more reddish skin tones, while fluorescent light is known to produce a bluish skin tone. The LED system can be used to provide consistent tones and hues in a photographic subject from one lighting environment to another. Other desired photographic effects can be envisioned by those skilled in the relevant arts.

As one practice of a method for illuminating a material, a predetermined range of colors can be selected within the spectrum. The LED system can then be controlled to generate these colors and to illuminate the material thereby. The material to be illuminated can be an inanimate entity. In one embodiment, a chemical reaction or its component reagents can be illuminated according to this method, whereby the illumination is understood to influence the characteristics of the chemical reaction. In another embodiment, the method of illumination can be directed to a biological entity. The term biological entity as used herein includes any entity related to biology. The term biology refers to the science concerned with the phenomena of life and living organism. Hence, a biological entity can comprise a cell, a tissue, an organ, a body part, a cellular element, a living organism, a biological product, a chemical or an organic material produced by a biological entity or through biotechnology, or any other entity related to biology. Further, though, the term biological entity can refer to a substance that was once part of a living organism, including a substance extracted from a living organism and including a substance that is no longer alive. Pathological specimens are encompassed by the term biological entity. A living organism is called out as a particular embodiment of a biological entity, but this usage is not intended to narrow the scope of the term biological entity as it is used herein. In one practice of a method for illuminating a biological entity, that biological entity can be a living organism. A living organism can include cells, microorganisms, plants, animals or any other living organism.

As a practice of a method for illuminating a material, a predetermined desired illumination condition can be selected, and a material can be illuminated with a range of colors until the desired condition is attained. A range of colors can be selected according to this method, whereby the selected colors are capable of producing the desired condition. Optionally, an additional step of this practice comprises illuminating the material with the selected colors, so as to bring about the desired effect. This method can be applied to non-living or biological entities.

It is understood that a method for illuminating a living organism can have specific effects upon its structure, physiology or psychology. As embodiments of a method for illuminating a living organism, these technologies can be directed towards cells, microorganisms, plants or animals. These practices can comprise, without limitation, microbiological applications, cloning applications, cell culture, agricultural applications, aquaculture, veterinary applications or human applications. As an example, plant growth can be accelerated by precisely controlling the spectrum of light they are grown in. FIG. 92A shows a practice of this method, whereby a plurality of LED systems 2074 provide illumination to fruitbearing plants 2078 being grown in a greenhouse environment. The size and number of fruit 2080 on these plants 2078 are understood to compare advantageously to the results of the method illustrated in FIG. 92B, wherein the fruitbearing plants 2078 illuminated with natural light 2082 are observed to bear smaller and fewer fruits 2080. As a further example, cellular growth in culture can be improved by illuminating the cells or the media with light having certain spectral qualities. As another example, optimal breeding and animal health can be achieved by illuminating the subjects with a range of colors within the spectrum. As yet another example, replicating for a marine species in an aquarium the spectrum of light in its waters of origin can significantly increase its lifespan in captivity. For example, it is understood that the spectrum in the Red Sea is distinctly different from the spectrum in the waters of Cape Cod. According to a practice of this method, the illumination conditions of the Red Sea can be reproduced in an aquarium containing Red Sea species, with salubrious effect. As an additional example, an organism's circadian rhythms can be evoked by illuminating the subject creature with light of varying spectral characteristics.

As a practice of a method for illumination, a material can be evaluated by selecting an area of the material to be evaluated, illuminating that area with an LED system, determining the characteristics of the light reflected from that area and comparing those characteristics of color and/or intensity with a set of known light parameters that relate to a feature of the material being evaluated. The feature being evaluated can be a normal feature or an abnormal feature of the material. As an example, the integrity of a tooth can be evaluated by directing light of a particular color at the tooth to identify those areas that are carious. Structural conditions of materials can be evaluated by illuminating those materials and looking for abnormalities in reflected light. A practice of this method can be applied to biological entities. In forensic pathology, for example, various kinds of fillings for teeth can be distinguished by the way in which they reflect light of particular spectra. This allows identifications to be made based on dental records for forensic purposes. An embodiment of this method related to biological entities is adapted for use in a variety of medical applications, as will be described in more detail hereinafter.

In another embodiment of the present invention, as described in part above, a multicolor illuminator is provided for surgical illumination. Different body organs are typically low in relative color contrast. By changing color conditions in a controlled manner, the surgeon or assistant can increase this relative contrast to maximize the visibility of important surgical features, including internal organs and surgical instruments. Thus, if the surgeon is trying to avoid nerve tissue in a surgery, a light that is designed to create the maximum apparent contrast between nerve tissue color and other tissue will permit the greatest precision. Surgical lights of the present invention can be of any conventional configuration, such as large theater lights, or can be attached to surgical instruments, such as an endoscope, surgical gloves, clothing, or a scalpel.

Figure 93A:
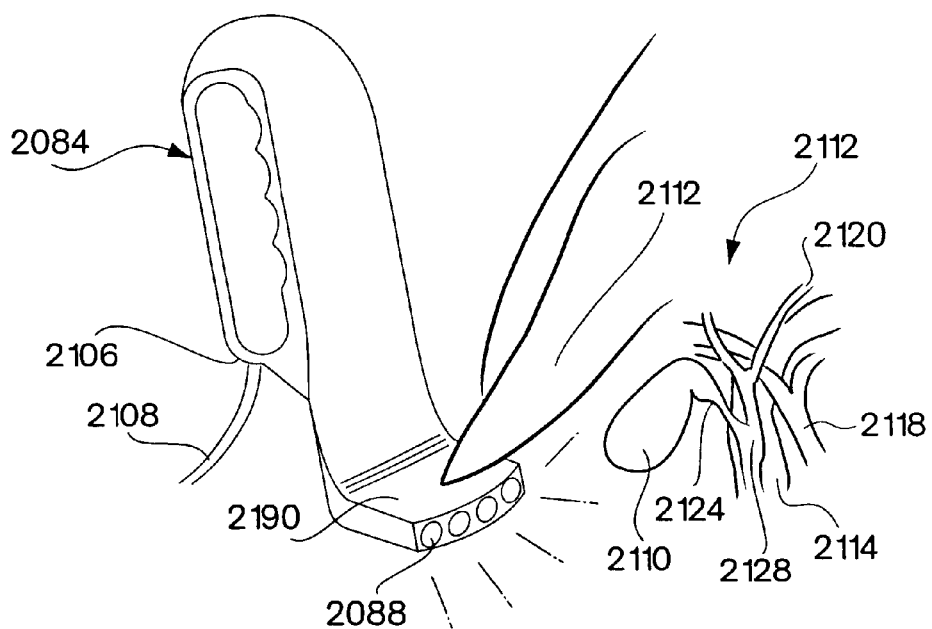
FIG. 93A is a generally schematic view illustrating the anatomy of the porta hepatis as illuminated by an embodiment of an LED system affixed to a medical instrument.

FIG. 93A depicts one embodiment of a system for illuminating a body part according to the present invention. This illustration shows a medical instrument for positioning the LED system in proximity to a body part, here a conventional surgical retractor 2084 with the LED system 2088 affixed to the anterior aspect of its retracting face 2090. The illustrated surgical retractor 2084 resembles a Richardson-type retractor, well-known in the art. Other medical instruments can be employed to bear the LED system 2088 without departing from the scope of these systems and methods. Medical instruments bearing LED systems can be used for illuminating a body part.

In the embodiment depicted in FIG. 93A, a conventional surgical retractor 2084 is shown elevating a segment of body tissue, here depicted as the edge of the liver 2104. The illumination from the LED system 2088 is directed at a body part, here the gallbladder 2110 and porta hepatis 2112. As used herein, the term body part refers to any part of the body. The term is meant to include without limitation any body part, whether that body part is described in anatomic, physiologic or topographic terms. A body part can be of any size, whether macroscopic or microscopic. The term body part can refer to a part of the body in vivo or ex vivo. The term ex vivo is understood to refer to any body part removed from body, whether that body part is living or is non-living. An ex vivo body part may comprise an organ for transplantation or for replantation. An ex vivo body part may comprise a pathological or a forensic specimen. An ex vivo body part can refer to a body part in vitro. The term body part shall be further understood to refer to the anatomic components of an organ. As an example, the appendix is understood to be an anatomic component of the organ known as the intestine.

In the illustrated embodiment, the porta hepatis 2112 is an anatomic region that is a body part. The porta hepatis 2112 is understood to bear a plurality of other body parts, including the portal vein 2114, the hepatic artery 2118, the hepatic nerve plexus, the hepatic ducts and the hepatic lymphatic vessels. The hepatic ducts 2120 from the liver 2104 and the cystic duct 2124 from the gallbladder 2110 converge to form the common bile duct 2128; all these ducts are body parts as the term is used herein. Distinguishing these body parts from each other can be difficult in certain surgical situations. In the depicted embodiment, the LED system 2088 is directed at the porta hepatis 2112 during a gallbladder procedure to facilitate identification of the relevant body parts. Directing lights of different colors at the discrete body parts can allow the operator more readily to decide which body part is which, a decision integral to a surgical operation.

A plurality of other applications of these illumination systems can be readily envisioned by those of ordinary skill in the relevant arts. While the embodiment depicted in FIG. 93A shows a handheld retractor 2084 being used in an open surgical procedure, the illumination systems described herein can also be applied to endoscopic surgery, thoracoscopy or laparoscopy. Discrimination among the various body parts in a region such as the porta hepatis 2112 can be particularly difficult during a laparoscopic procedure. As an alternate embodiment, the relevant anatomic structures can be illuminated using an LED system affixed to the instrumentation for laparoscopy, thereby facilitating the identification of the structures to be resected and the structures to be preserved during the laparoscopic procedure.

Other endoscopic applications will be apparent to those skilled in the art. As illustrative embodiments, an LED system can be combined with endoscopic instrumentation for the evaluation of intraluminal anatomy in gastrointestinal organs, in cardiovascular organs, in tracheobronchial organs or in genitourinary organs. A lumen is understood to be a body part, within the meaning of the latter term. The term lumen is understood to refer to a space in the interior of a hollow tubular structure. The term body part further comprises the wall of a hollow tubular structure surrounding the lumen. Subcutaneous uses of the illumination system can be envisioned to allow identification of body parts during endoscopic musculocutaneous flap elevation. Such body parts identified can include nerves, blood vessels, muscles and other tissues. Other embodiments can be readily envisioned by skilled practitioners without departing from the scope of the systems disclosed herein.

In FIG. 93A, the LED system 2088 is shown arrayed at the distal edge of the retractor 2084 mounted on the undersurface of the retracting face 2090 of the retractor 2084. This arrangement interposes the retracting face 2090 of the retractor 2084 between the body tissue, here the edge of the liver 2104, and the LED system 2088 so that a retracting force on the body tissue, here the edge of the liver 2104, does not impinge upon the LED system 2088. The LED system 2088 in the illustrated embodiment is arranged linearly along the retracting face 2090 of the retractor. Here the power cord 2108 is shown integrated with the handle 2106 of the retractor 2084. The systems described herein can be adapted for a plurality of medical instruments without departing from the scope of the invention. For example, a malleable retractor or a Deaver retractor can bear the LED system. Other types of retractors for specialized surgical applications can similarly be adapted to bear the LED system in any arrangement with respect to the retracting face system that fits the particular surgical need. As an example, an LED system can be mounted on a flexible probe for illuminating a particular tissue where the probe does not serve the function of retraction. In an embodiment, an LED system can be directed at lymph nodes in the axilla or in the inguinal region following percutaneous access and subcutaneous dissection, illuminating these lymph nodes with a light color selected to illuminate a feature of the lymph nodes preferentially, such as their replacement with the melanotic tissue of malignant melanoma; the illumination of the lymph nodes can be simultaneously evaluated through endoscopy or videoendoscopy using minimally invasive techniques, thereby reducing the need for full operative lymphadenectomy with its consequent sequelae. This example is offered as an illustration of an embodiment of an application of the technologies described herein, but other examples and illustrations can be devised by those of ordinary skill in these arts that fall within the scope of the invention.

A plurality of arrangements of LEDs can be envisioned by those of ordinary skill in these arts without departing from the scope of the invention. The LED array is capable of being placed in proximity to the target organ by a surgical instrument. The term proximity as used herein refers to the degree of propinquity such that the illumination directed at the target body part is effective in accomplishing the clinical purpose intended by the operator. Thus, the proximity to the target body part is determined by the medical judgment of the operator. Since the LED system does not produce heat, it can be positioned extremely close to the target body parts and other body parts without damaging the tissues. In an embodiment, the illumination assembly is capable of being directed at microsurgical structures without causing heat damage. The intensity of the light available from an LED system is a feature that influences how close the LED system needs to be positioned in order to accomplish the operator's clinical purpose.

Figure 93B:
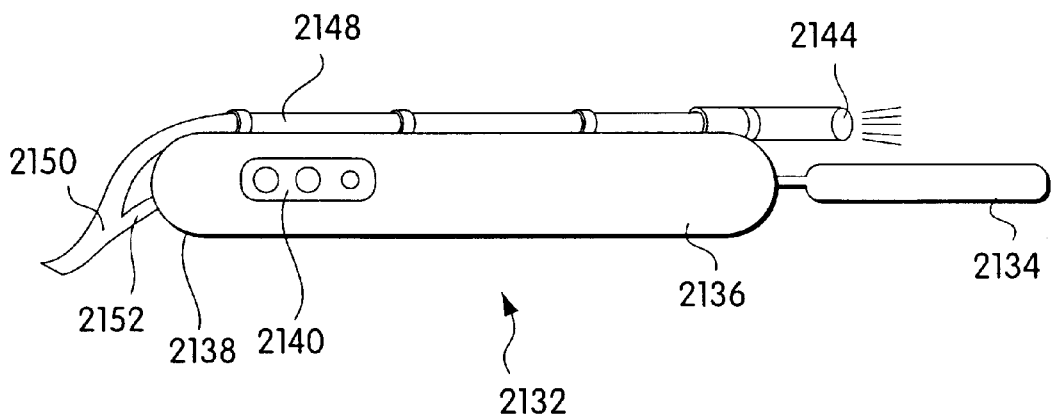
FIG. 93B depicts an embodiment of an LED system affixed to a medical instrument.

As an alternative embodiment, the LED system can be combined with other features on a medical instrument. The term medical instrument as used herein comprises surgical instruments. For example, the LED system can be combined with a cautery apparatus or a smoke aspirator to be used in surgery. FIG. 93B depicts one embodiment of a surgical instrument that combines several other pieces of apparatus with the LED system. In FIG. 93B, a Bovie cautery assembly 2132 is depicted, well-known in the surgical art. The cautery assembly 2132 includes a cautery tip 2134 and a handheld wand 2138. Imbedded in the wand 2138 in standard fashion is an array of control buttons 2140, an arrangement familiar to those in the art. At the distal tip of the handheld wand 2138 is a LED system 2144. The power and data signals to the LED system 2144 are carried through a LED cable 2148 affixed to the superior aspect of the handheld wand 2138. The LED, cable 2148 joins with the Bovie power cord 2152 at the proximal end of the instrument to form a single united device cable 2150. In an alternate embodiment, the LED cable can be contained within the Bovie wand housing 2136 in proximity to the Bovie power cord 2152.

The depicted embodiment permits the surgeon to direct LED light at a particular structure to identify it anatomically as part of cautery dissection. The spectral capacity of the LED system 2144 is useful in identifying blood vessels, for example. Blood vessels embedded in tissues can be especially difficult to identify. The surgeon can dissect with the cautery tip 2134 of the illustrated embodiment while directing a light from the LED that is selected to highlight vascular structures. The tissues themselves would be distinguishable from the vascular structures based on the response of each set of structures to the light illumination from the LED system 2144. The contrast between tissues requiring dissection and blood vessels to be preserved would be highlighted by the light illumination from the LED system 2144. The surgeon, therefore, would be able to identify what structures are safe to transgress with cautery dissection. In this way, the surgeon could preserve blood vessels more readily, as required by the surgical procedure. Alternatively, the surgeon could identify blood vessels imbedded in tissues and take precautions to coagulate or ligate them effectively before transgressing them. The illustrated embodiment represents only one possible arrangement of combined surgical instrumentation that employs an LED system. Other arrangements can be envisioned by those of ordinary skill in these arts. For specialized surgical applications, specialized combinations can be required. For example, particular instruments are employed in neurosurgery and in microsurgery. The same principles illustrated in the depicted embodiment of FIG. 93B can be applied in the fabrication of surgical instruments appropriate for these purposes.

Figure 93C:
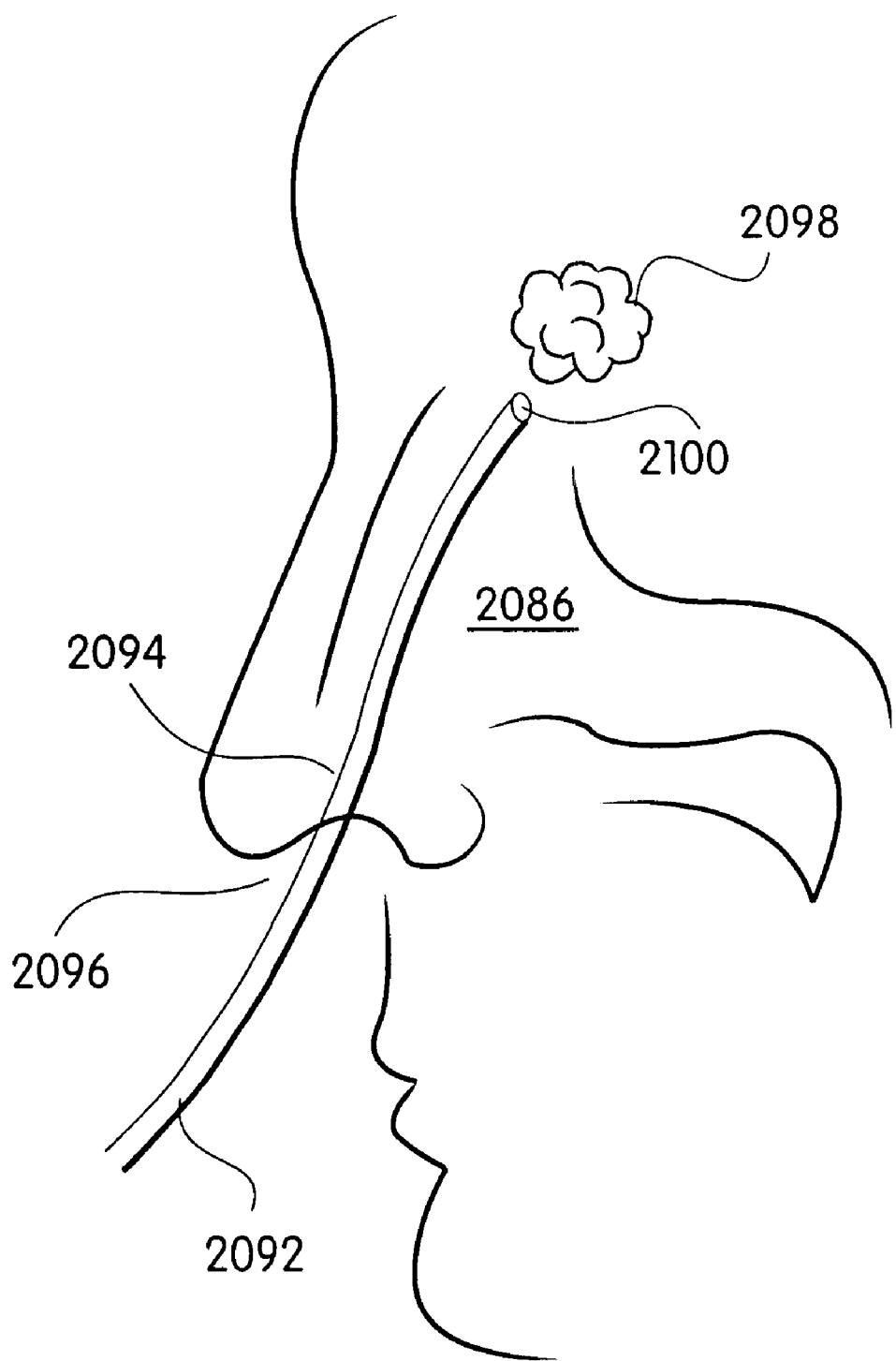
FIG. 93C depicts an embodiment of an LED system affixed to an endoscope.

As an alternate embodiment, the LED system can be combined with a sensor system that provides signals that correlate with some characteristic of the body part being illuminated. As an example, FIG. 93C shows an LED assembly 2100 affixed to a nasal endoscope 2092 being inserted transnasally 2094 to evaluate an intranasal or a pituitary tumor 2098. The endoscope 2092 is shown in this figure entering through the naris 2096 and being passed through the nasal airway 2086. The tumor 2098 is here shown at the superior aspect of the nasal airway 2086. The LED assembly 2100 can comprise an LED system (not shown) and a sensor system (not shown). The LED system can illuminate the intranasal and intrasellar structures with a range of colors, while the sensor system can provide data relating to the characteristics of the reflected light. The tumor 2098 can be identified by how it reflects the range of light being used to illuminate it. The sensor system can provide information about the characteristics of the reflected light, permitting the operator to identify the tumor 2098 in these remote locations. Further, such an endoscope 2092 can be combined with means familiar to practitioners in these arts for resecting or ablating a lesion.

The illumination system described herein is available for both direct illumination and transillumination. Transillumination is understood to refer to the method for examining a tissue, an anatomical structure or a body organ by the passage of light through it. For example, transilluminating a structure can help determine whether it is a cystic or a solid structure. One embodiment of an illumination system can employ LEDs to direct light of differing colors through a structure, whereby the appearance of the structure when subjected to such transillumination can contribute to its identification or diagnosis. Transillumination using LED light can be directed to a plurality of structures. In addition to soft tissues and organs, teeth can be transilluminated to evaluate their integrity. An additional embodiment can employ a LED as an indwelling catheter in a luminal structure such as a duct. Illuminating the structure's interior can assist the surgeon in confirming its position during surgery. For example, in certain surgical circumstances, the position of the ureter is difficult to determine. Transilluminating the ureter using an LED system placed within its lumen can help the surgeon find the ureter during the dissection and avoid traumatizing it. Such an LED system could be placed cystoscopically, for example, as a catheter in a retrograde manner before commencing the open part of the operative procedure. In this embodiment, the LED system is particularly useful: not only can the color of the LED be varied in order to maximize the visibility of the transilluminated structure, but also the LED avoids the tissue-heating problem that accompanies traditional light sources.

Evaluation of a tissue illuminated by an embodiment of the illuminating system described herein can take place through direct inspection. In an alternative embodiment, evaluation can take place through examining the tissues using videocameras. In an illustrative embodiment, the tissues would be visualized on a screen. Color adjustments on the video monitor screen can enhance the particular effect being evaluated by the operating team. As an alternative embodiment, the illuminating system can be combined with a sensor module, as partially described above, whereby the intensity of the reflected light can be measured. As examples, a sensor module could provide for spectroscopic, colorometric or spectrophotometric analysis of the light signals reflected from the illuminated area. Other types of sensor modules can be devised by those skilled in the relevant arts. A sensor module can be combined with direct inspection for evaluating tissues. Alternatively, a sensor module can provide a means for remote evaluation of tissues in areas not available for direct inspection as a substitute for or as an adjunct to video visualization. Examples of such areas are well-known in the surgical arts. Examples of such areas can include transnasal endoscopic access to the pituitary, endoscopic evaluation of the cerebral ventricles, and intraspinal endoscopy, although other areas can be identified by those familiar with the particular anatomic regions and relevant methods of surgical access. In addition to the abovementioned embodiments for use in living tissues, embodiments can be devised to permit evaluation of forensic tissues or pathology specimens using the illuminating systems disclosed herein.

Figure 93D:
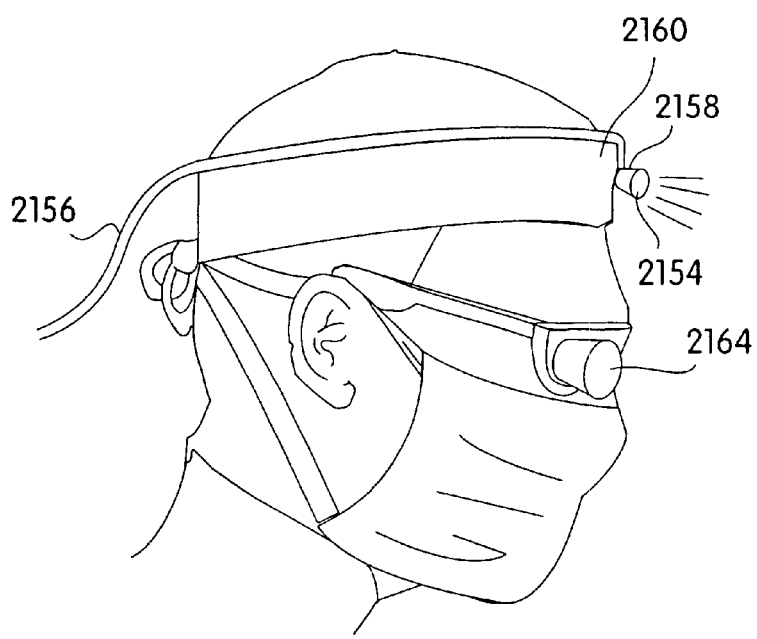
FIG. 93D depicts an embodiment of an LED system affixed to a surgical headlamp.

FIG. 93D depicts an embodiment of the illumination system wherein the LED system 2154 is mounted within a traditional surgical headlamp 2158 apparatus. In the illustrated embodiment, the LED system 2154 is affixed to the headband 2160 using methods of attachment well-known to practitioners. Advantageously, however, the LED system 2154 of the illustrated embodiment can be considerably lighter in weight than traditional headlamps. This reduces strain for the wearer and makes the headlamp apparatus more comfortable during long procedures. As depicted herein, the LED system 2154 is connected to a power cord 2156. In distinction to traditional headlamp apparatus, however, the power cord 2156 for the LED system 2154 is lightweight and non-bulky. The power cord 2156 can therefore be deployed around the headband 2160 itself, without having to be carried above the surgeon's head in a configuration that predisposes to torquing the headband and that collides with pieces of overhead equipment in the operating room. Furthermore, the power cord employed by the LED system avoids the problems inherent in the fiberoptic systems currently known in the surgical arts. In the traditional surgical headlamp as employed by practitioners in these arts, light is delivered to the lamp through a plurality of fiberoptic filaments bundled in a cable. With the systems known presently in the art, individual fiberoptic filaments are readily fractured during normal use, with a concomitant decrease in the intensity of the light generated by the headlamp. By contrast, the power cord 2156 for the LED system 2154 does not contain fiberoptic elements but rather contains a wire carrying power to the LED system 2154. This provides a more durable illumination unit than those known in the present art. Furthermore, the LED system 2154 is sufficiently lightweight that it is capable of being integrated with the surgeon's magnifying loupes 2164.

Figure 93E:
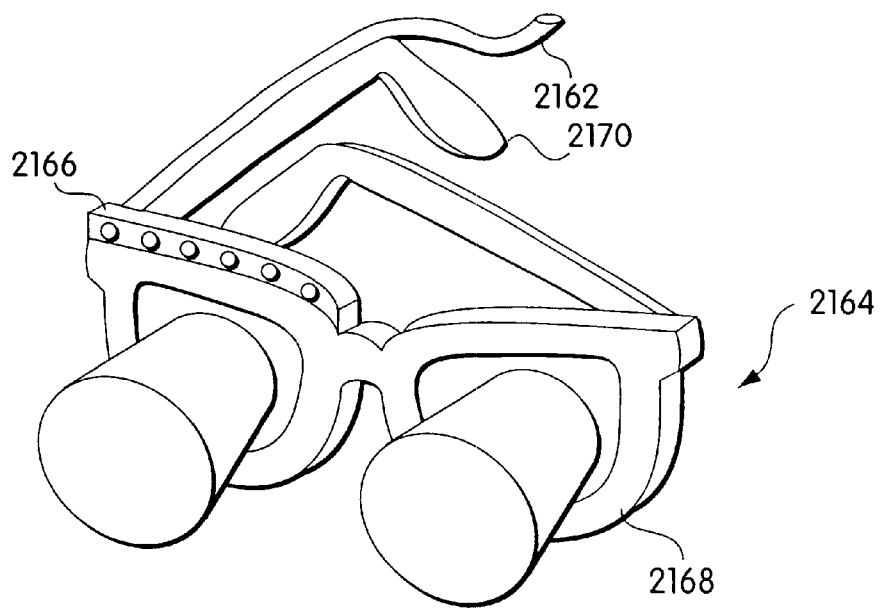
FIG. 93E depicts an embodiment of an LED system affixed to surgical loupes.

Although the LED system in the illustrated embodiment is affixed to a headband 2160, an alternative embodiment can permit eliminating the headband 2160 entirely and integrating the LED system 2154 in the surgeon's spectacles or magnifying loupes 2164. FIG. 93E depicts an embodiment of this latter arrangement. In this embodiment, an LED system 2166 is shown integrated with the frame 2168 of the loupes 2164. The LED system 2166 can be situated superiorly on the frame 2168 as depicted in this figure, or it can be arranged in any spatial relation to the frame 2168 that is advantageous for illuminating aspects of the surgical field. In this embodiment, the power cord 2162 can be positioned to follow the templepiece 2170 of the loupes 2164.

The methods of the present invention comprise methods for diagnosing a condition of a body part. The methods for diagnosing a condition of a body part comprise selecting an area of the body part for evaluation, illuminating the area with an LED system, determining characteristics of the light reflected from the body part, and comparing the characteristics with known characteristics, wherein the known characteirstics relate to the condition of the body part. These methods can be applied to normal, nonpathological conditions of a body part. Alternatively, these methods can be used to identify pathological conditions of the body part.

It is understood that different body parts reflect light differently, depending upon their anatomic or physiological condition. For example, when subjected to room light, an ischemic body part can be perceived to be a purplish color, a color termed "dusky" or "cyanotic" by practitioners in these arts. Ischemia can therefore be at times diagnosed by direct inspection under room light. However, a multitude of situations exist where the vascular status of a body part cannot be evaluated by inspection under room light. For example, ischemia can be hard to see in muscles or in red organs. Further, skin ischemia is difficult to evaluate in room light in people with dark skins. The methods of the present invention include practices that permit the diagnosis of ischemia to be made by illuminating a body part with an LED system and comparing the reflected light with known light characteristics indicative of ischemia. These methods further can permit this diagnosis to be made at an earlier stage, when room light may not reveal color changes but when LED system illumination can permit the perception of more subtle color changes. A spectrometer or another sort of sensor system can be optionally employed to evaluate the color and/or the intensity of the light reflected from the illuminated body part. For example, the systems and methods of the present invention can be adapted for the diagnosis of early circulatory compromise following vascular procedures. Common vascular procedures which can be complicated by circulatory compromise include surgical vascular reconstructions or revascularizations, surgical replantations, free tissue transfers, embolectomies, percutaneous angioplasties and related endovascular procedures, and medical thrombolytic therapies. The systems and methods disclosed herein can be adapted for the evaluation of tissues within the body by providing an LED system capable of implantation and removal and by providing a sensor system capable of implantation and removal, the former system adapted for directing illumination at a body part within the body and the latter system adapted for receiving color data from the light that is reflected or absorbed by the target body part. Systems and methods adapted for the evaluation of internal body parts can be advantageous in the monitoring of buried free flaps, for example. The lack of heat generated by the LED system makes it feasible to implant it without subjecting the surrounding tissues to heat trauma. Practitioners skilled in the relevant arts can identify other conditions besides ischemia that can be diagnosed using the methods disclosed herein. The full spectrum of light available from the LED systems disclosed herein is particularly advantageous for diagnosis of a plurality of conditions.

As a further example of the methods described herein, the LED system can be used to illuminate the retina for ophthalmological examination. Variation in light color can facilitate ophthalmological examination, for example the diagnosis of retinal hemorrhage or the evaluation of the retinal vessels. Practitioners of these arts will be able to envision other forms of retinopathy that are suitable for diagnosis using these methods. In one embodiment, an LED system can be integrated in a slit lamp apparatus for ophthalmological examination. In an additional embodiment, the LED system can be adapted for use in ophthalmological surgery. As an example, the LED system is capable of assisting in the localization of mature and hypermature cataracts, and is capable of assisting in the surgical extraction of cataracts.

One practice of these methods for diagnosing a condition of a body part can comprise administering an agent to the patient that will be delivered to the body part, whereby the agent alters the characteristic of the light reflected from the body part. An agent is any bioactive substance available for administration into the patient's tissues. An agent can include a drug, a radioisotope, a vitamin, a vital dye, a microorganism, a cell, a protein, a chemical, or any other substance understood to be bioactive. An agent can be administered by any route which will permit the agent to be delivered to the body part being evaluated. Administration can include intravenous injection, intramuscular injection, intraarterial injection, ingestion, inhalation, topical application, intrathecal delivery, intraluminal or intravesical delivery, subcutaneous delivery or any other route. The full spectrum of light provided by the systems and methods disclosed herein is advantageously employed in conjunction with certain administered agents.

An example of an agent known to alter the characteristic of light reflected from a body part is fluoroscein, a vital dye applied topically for ophthalmic purposes or injected intravenously to evaluate vascular perfusion. When illuminated by a Wood's lamp, fluoroscein glows green. Wood's lamp, though, is not adaptable to many surgical situations because of its physical configuration. Fluoroscein administered to remote body parts cannot be illuminated by a Wood's lamp, nor can the fluorescence be seen in a body part too remote to inspect. Illuminating the tissues with an LED system after the administration of a vital dye such as fluoroscein can produce a characteristic pattern of reflected light. This reflected light can be evaluated by direct visualization, by remote visualization or by a light sensor system. Other agents will be familiar to those of skill in these arts, whereby their administration permits the evaluation of a body part subjected to LED illumination.

As one example, gliomas are understood to have a different uptake of vital dye than other brain tissues. Directing an LED system at a glioma after the administration of vital dye can permit more complete excision of the tumor with preservation of surrounding normal brain tissue. This excision can be performed under the operating microscope, to which can be affixed the LED system for illuminating the brain tissues. The lack of heat generation by the LED system makes it particularly advantageous in this setting. As an additional example, the LED system can be combined with fluoroscein dye applied topically to the surface of the eye for ophthalmological evaluation. As yet another example, the LED system combined with fluoroscein can permit diagnosis of ischemia in patients whose skin pigmentation may prevent the evaluation of skin ischemia using traditional methods such as Wood's lamp illumination. As disclosed in part above, these systems and methods can advantageously be directed towards body parts within the human body for evaluation of those body parts after the administration of an agent taken up by the body part.

The methods according to the present invention can be directed towards effecting a change in a material. In a practice of these methods, a change in a material can be effected by providing an LED system, selecting a range of colors from the spectrum that are known to produce the change in the material being illuminated, and illuminating the material with the LED system for a period of time predetermined to be effective in producing that change. The methods disclosed herein are directed to a plurality of materials, both non-biological materials and biological entities. A biological entity can include a living organism. A living organism can include a vertebrate. A living organism can include an invertebrate. A biological entity can be treated with light exposure in order to effect a change in its structure, physiology or psychology. For example, persons afflicted with the depressive syndrome termed seasonal affective disorder are understood to be benefited psychologically by exposure to illumination with light of known characteristics for predetermined periods of time. The illumination can be provided directly to the living organism, for example to the person with seasonal affective disorder. Alternatively, the illumination can be provided to the environment surrounding the person. For example, illumination can be provided by a room light comprising an LED system that can provide light with the predetermined characteristics.

As a practice of these methods, a condition of a patient can be treated. This practice can comprise providing an LED system, selecting a set of colors that produce a therapeutic effect and illuminating an area of the patient with the set of colors. A therapeutic effect is understood to be any effect that improves health or well-being. According to this practice, a pathological condition can be treated. Alternatively, a normal condition can be treated to effect an enhanced state of well-being. The area being illuminated can include the external surface of the patient, to wit, the skin or any part of the skin. The external surface of the patient can be illuminated directly or via ambient illumination in the environment. These methods can be likewise applied to internal body parts of a patient.

Figure 94:
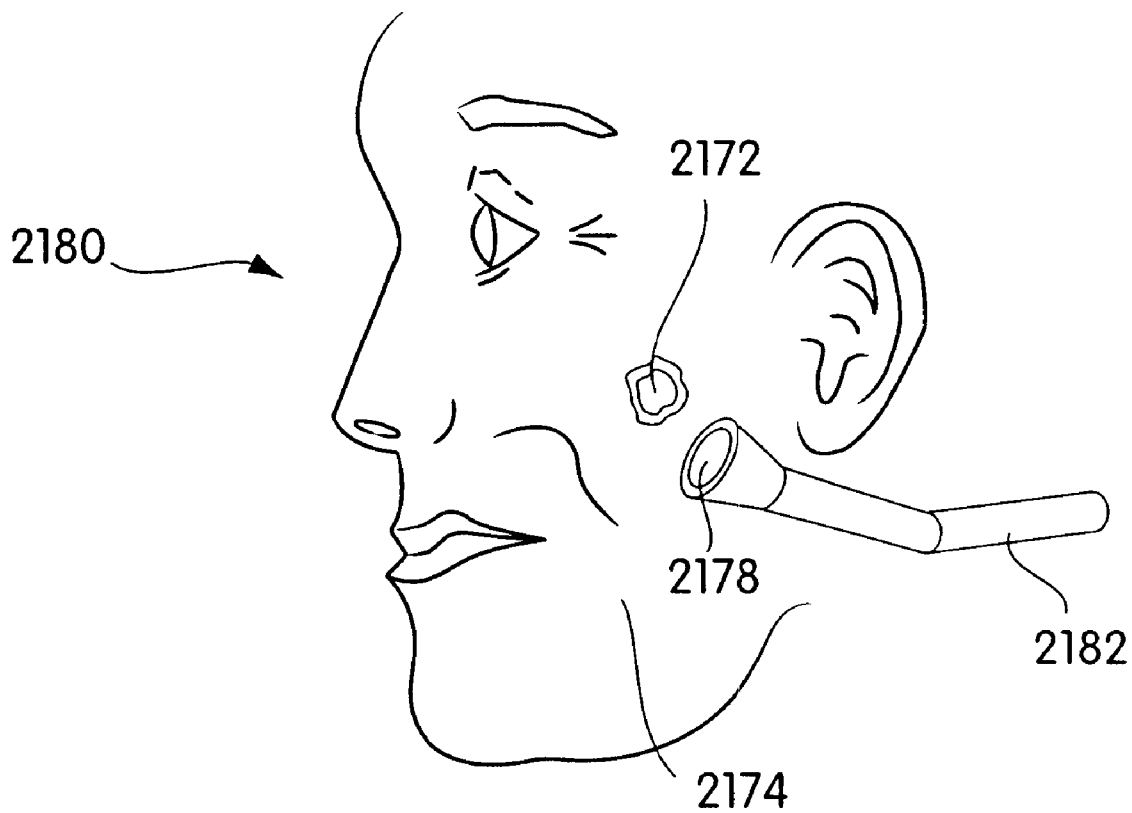
FIG. 94 depicts a method for treating a medical condition by illuminating with an embodiment of an LED system.

FIG. 94 shows a practice of these methods. This figure depicts a patient 2180 afflicted with a lesion 2172 on an external surface, here shown to be his cheek 2174. A LED system 2178 is directed to provide direct illumination to the lesion 2172. Here the LED system 2178 is shown affixed to the distal end of a positioning system 2182. Other arrangements for positioning the LED system can be envisioned by those of ordinary skill in these arts. It is understood that illumination of dermatological lesions with different spectra of light can have therapeutic effect. For example, acne, Bowen's disease of the penis and certain other skin cancers have responded to treatment with illumination. As another example, certain intranasal conditions are understood to respond to illumination therapies. In one practice of these methods, an agent can be administered to the patient that alters or increases the therapeutic effect of the set of colors of light directed towards the area being treated.

A variety of agents are familiar to practitioners in the arts relating to phototherapy and photodynamic therapy. Photodynamic therapy (PDT) is understood to comprise certain procedures that include the steps of administering an agent to a patient and illuminating the patient with a light source. Laser light is typically involved in PDT. Since the illumination provided by the LED system can provide full spectrum lighting, including infrared, visible and ultraviolet light spectra, the LED system is available for those therapeutic applications that rely on non-visible light wavelengths. A number of applications of topical illumination have been described in the relevant arts. LED technology has the additional advantage of avoiding heat generation, so prolonged illumination can be accomplished without tissue damage.

Although the practice depicted in FIG. 94 shows an LED system 2178 directed towards the skin of a patient 2180, various practices of this method can apply an LED system for illuminating body parts. Treatment can be directed towards internal or external body parts using modalities familiar to practitioners for accessing the particular body part. As described above, open surgical techniques or endoscopic techniques can be employed to access internal body parts. For example, an intraluminal tumor can be treated using these methods as applied through an endoscope such as a colonoscope or a cystoscope. Alternatively, illumination therapy can be provided following or during a surgical procedure. For example, following surgical extirpation of a tumor, an agent can be administered that is taken up by the residual microscopic tumor in the field and the surgical field can be illuminated by an LED system to sterilize any remaining tumor nodules. These methods can be employed palliatively for reducing tumor burden after gross excision. As another practice, these methods can be directed towards metastatic lesions that can be accessed directly or endoscopically.

These embodiments described herein are merely illustrative. A variety of embodiments pertaining to precision illumination can be envisioned by ordinary skilled practitioners in these arts without departing from the scope of the present invention.

In other embodiments of the present invention, LEDs are used to create attractive and useful ornamental or aesthetic effects. Such applications include disposition of the LEDs in various environments, such as those disclosed above, including multicolor, LED-based eyeglass rims, an LED-lit screwdriver, a multi color light source for artistic lamps or displays, such as a multicolor LED source for a Lava® lamp, and LED-based ornamental fire or fire log with a simulated fire flicker pattern and coloring, a light-up toothbrush or hairbrush using LEDs or other lighting devices. LEDs may also be disposed on ceiling fan blades for to create unusual lighting patterns for artistic effects or display. In particular, pattern generation may be possible with addition of LEDs to the blades of a fan. Also in accordance with the present invention are an LED-based ornamental simulated candle, a multicolor, LED-based light rope, an LED battery charge indicator and an LED color sensor feedback mechanism, through which an LED may respond to tension, temperature, pressure, cavitation, temperature, or moisture. Thus, an LED disposed near the body can serve as a skin temperature and skin moisture feedback color mechanism. Also provided is an LED-based multicolor hand held wand or indicator light. In particular, wands are provided that are similar to the popular glow sticks, which are widely used in the modern dance/night clubs and for dance expression. Multicolor electronic versions allow color control features as well as remote synchronization via a master lighting controller, provided that the LEDs are connected to a receiver and the master controller includes a transmitter. The LED-based personal devices are reusable, unlike chemically based current devices. The master controller may also control other LED items, such as drink coasters made of LEDs, in a controlled, synchronized manner. Such controllers can be used to control an LED disco ball, in which LEDs are disposed on the exterior or a sphere or other three-dimensional shape and may be controlled to simulate the flashing of a conventional disco ball. For example, effect simulated by the ball include ball strobe, spot movement, color changing, line lighting and plane lighting.

The present invention permits the user to control LEDs at the individual diode level. The effects that may be produced by generating light of a range of colors within the spectrum permit a number of useful applications in a wide range of technological fields. Among other effects, the controlled LEDs can produce color washes that can be instantly varied discretely or continuously over a wide range of colors and intensities, and that can flash or strobe with a wide range of frequencies. Applying a continuous range of color washes results in a number of unusual effects, some of which are aesthetically appealing, functionally valuable, or both. For example, affecting the same object with light of different colors may yield a very different appearance, as is readily apparent when, for example, a white object is shown under a so-called "black light." An observer viewing the object will perceive a change of color in the object being observed. Thus, a red object illuminated with a red light appears very different from a red object illuminated with a blue light. The former may be a vivid red, whereas the latter may appear purple or black. When objects having color contrast are viewed under colored lights, quite different effects may result. For example, a red and white checkerboard pattern may appear completely red under a red light, while the checkerboard pattern is evident under a white light. By strobing red and white light in an alternating time sequence over such a pattern, the white squares on the checkerboard will seem to appear and disappear. More complex patterns, such as those in multi-color paintings, can result in remarkable effects, such as disappearing and reappearing figures, or figures that undergo dramatic color changes to an observer. The appearance of movement, color change and appearance and disappearance can result in animation-like effects from a single still photograph, painting, design, or image, merely as a result of controlled lighting changes. Similarly, selecting appropriate light conditions can result in dramatic changes in the relative contrast of different-colored items. Items that have little contrast under certain lighting conditions may be perceived to have dramatic contrast under different color conditions. Furthermore, the spectrum of the light produced according to embodiments of the present invention extends to infrared and ultraviolet light, allowing the incorporation of effects such as fluorescence into the display. The lighting changes employed may be pre-programmed, or may be responsive to the environment of the lighting system, such as to the proximity of people, to the ambient lighting conditions, to the location of the display, or to the time of day.

Figure 95:
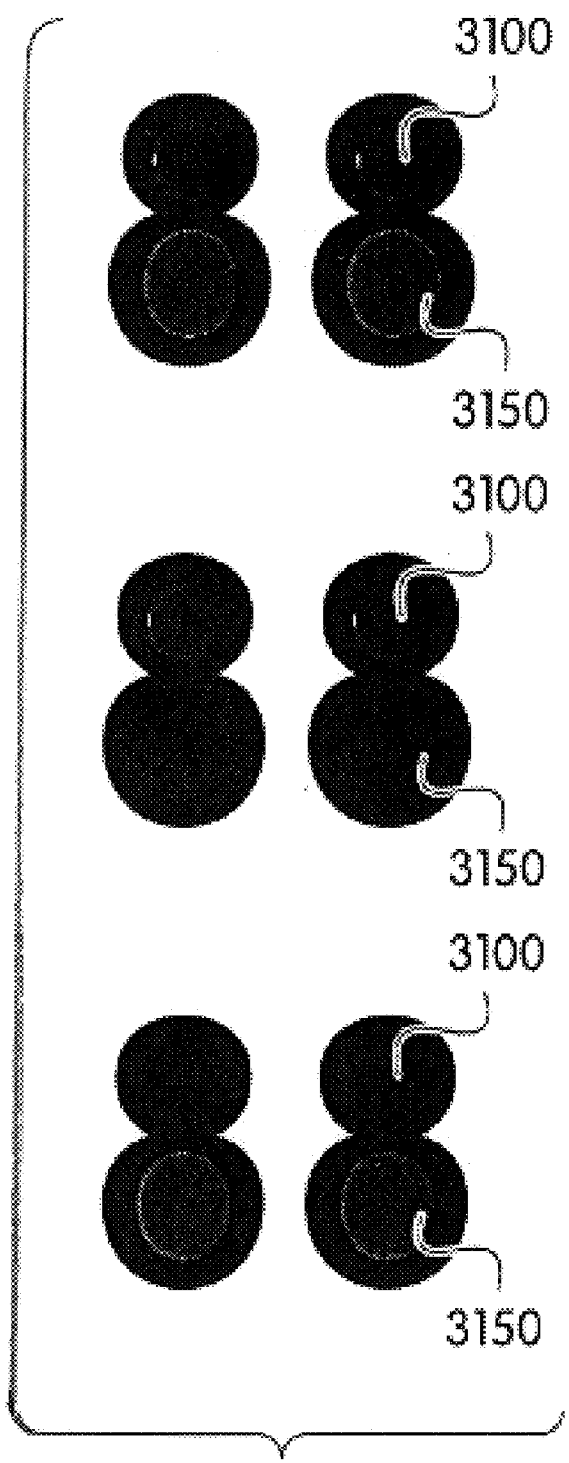
FIG. 95 depicts changing the perceived color of colored objects by chancing the color of the light projected thereon.

As an example, in FIG. 95 at the top, the numeral 88 is intended to represent such a numeral that is colored with green in the top half of the eights (3100) and red in the bottom half of the eights (3150). When lit with white light, the numeral 88 so colored will appear to have green in the top half (3100) and red in the bottom half (3150). When lit with green light, as shown in the middle of FIG. 95, the top half of the 88 (3100) still will appear green, but the bottom half (3150), originally red, will appear black. When lit with red light, as shown at the bottom of FIG. 95, the top half of the 88 (3100), originally green, will appear black, and the bottom half (3150) will appear red. Thus, by Gradually changing the color of the illumination, the different portions of the numeral will alternately stand out and fade to black. As will be apparent to a person of ordinary skill in the art, this technique can be used to create images designed to appear and disappear as the color of the illuminating light is altered. In addition, other color effects can be produced. For example, shining blue light on the two halves of the numeral would produce a blue-green color in the top half 3100 of the numeral and a purple color in the bottom half 3150.

Figure 96:
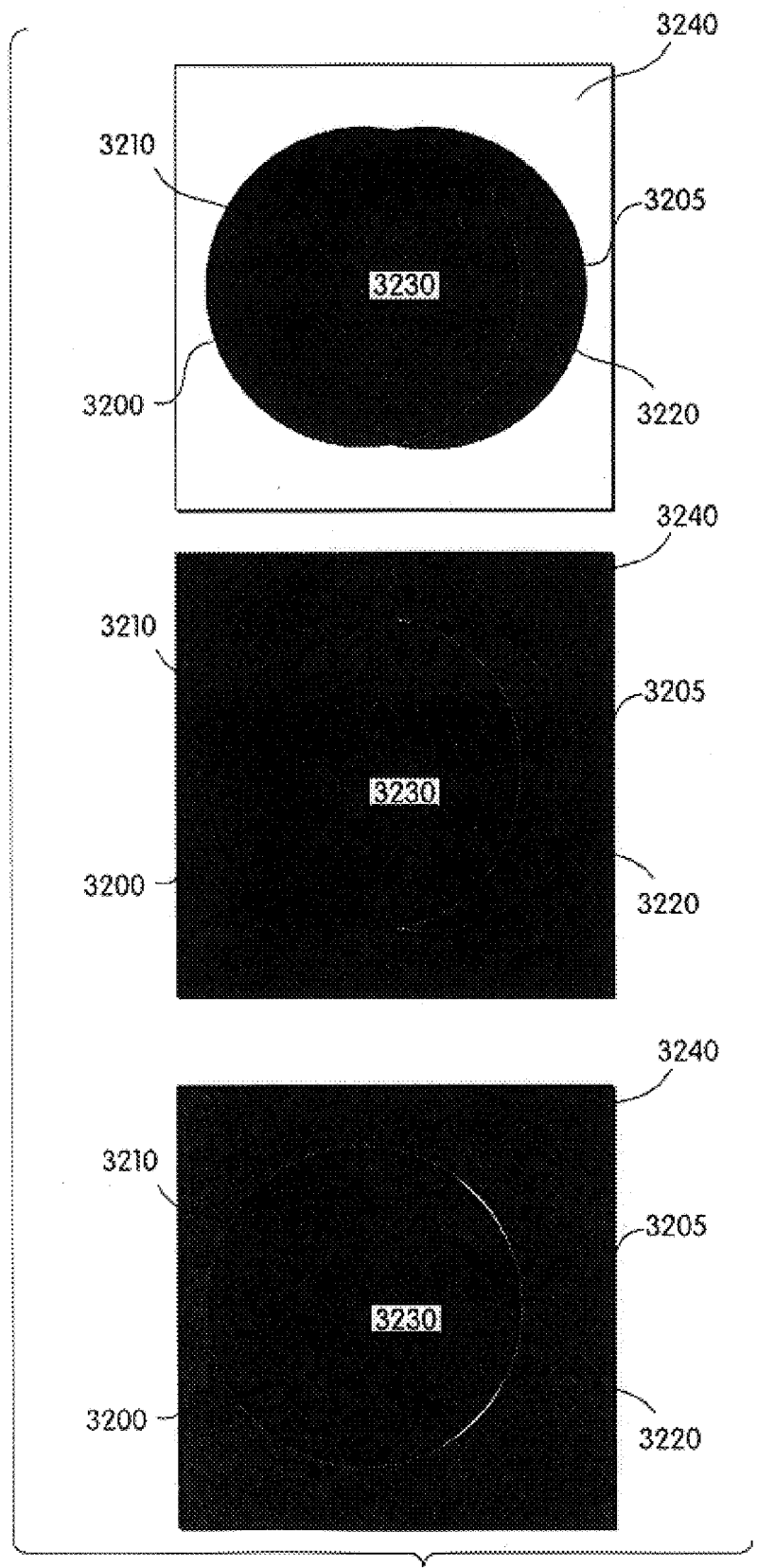
FIG. 96 depicts creating an illusion of motion in a colored design by changing the color of the light projected thereon.

As a second example, FIG. 96 at the top shows a pair of interlocking circles (left 3200, right 3205). When lit with white light, as shown at the. top, the drawing is intended to represent the following colors: the left crescent (3210) represents green, the right crescent (3220) represents red, the overlapping area (3230) is black, and the background (3240) is white. When lit with green light, as shown in the middle of FIG. 96, the left crescent (3210) appears green, the right crescent (3220), originally red, is now black, the overlapping area (3230) remains black, and the background (3240), originally white, appears green. Thus, the left crescent (3210) can no longer be distinguished from the background (3240), and the entire rightmost circle (3205) now appears black. When lit with red light, as shown at the bottom of FIG. 96, the left crescent (3210), originally green, now appears black, the right crescent (3220) appears red, the overlapping area (3230) appears black, and the background (3240), originally white, now appears red. Thus, the right crescent (3220) can no longer be distinguished from the background (3240) and the leftmost circle (3200) appears black. By changing the color of the illumination from green to red over time, the circle appears to move from right to left, imparting the illusion of motion to an observer. A skilled artisan will appreciate that variations upon this example will allow the creation of myriad displays that function in a like manner, permitting animation effects to be produced from a single image or object.

The nature of the lighting system of the present invention permits gradual chances of color from one side of a system to another. Furthermore, the color change can progress gradually along the system, effectively simulating motion of the color change. Additionally, the light can be delivered in a constant manner, or by flashing or strobing the lights. Flashing can also be programmed to occur with simultaneous change of color. These abilities, which can be directed by a microprocessor, can grant additional impetus and vitality to the effects described above.

It will also be apparent that similar effects can be obtained by passing colored light through a transparent or translucent colored screen, such as a stained glass window or a photographic slide, placed between the light source and an observer.

It will also be obvious to the skilled artisan that these effects can be used in more complex displays to create eye-catching illusions of motion and phantom objects that alternately emerge from and fade into the background. Such effects are particularly advantageous when used in applications such as museum exhibits, dioramas, display cases, retail displays, vending machines, display signs, information boards (including traffic information signs, silent radios, scoreboards, price boards, and advertisement boards), advertising displays, and other situations where the attracting the attention of observers is desired. Because the light generated according to embodiments of the present invention can include ultraviolet and infrared light, the objects can incorporate effects such as fluorescence that are particular to illumination with such light.

Figure 97:
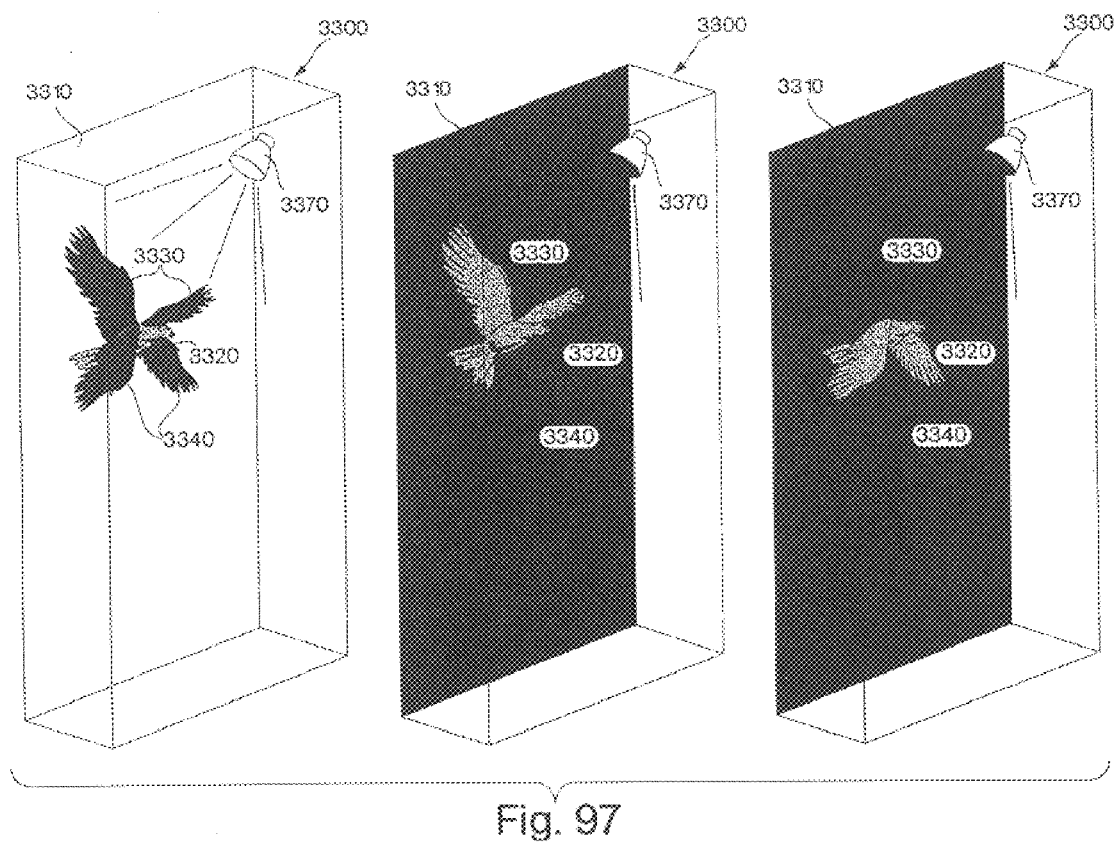
FIG. 97 depicts a vending machine in which an illusion of motion in a colored design is created by changing the color of the light projected thereon.

A vending machine, as contemplated by the present invention, is an apparatus which dispenses products contained therein, such as a soda machine, a snack machine, a gumball machine, a cigarette machine, a condom machine, or a novelty dispenser. Illumination provided according to the present invention can be used to attract the attention of an observer in a variety of ways. For example, a hypothetical olive-dispensing vending machine (3300) using a dove as a logo is depicted in FIG. 97. As seen in standard white light, depicted at the top of FIG. 97, the backing of the machine (3310) is white, the body of the dove (3320) is black, an upper set of wings (3330) are intended to be green, and a lower set of wings (3340) are intended to be red. When the color of the lighting in the machine is changed to red as in the middle of FIG. 97, the lower set of wings (3340), originally red, are invisible against the backing (3310) which now appears red. The upper set of wings (3330), originally green, appear black under red light, and so the image of the dove appears black with wings raised. When the color of the lighting in the machine is changed to green as shown in the bottom of FIG. 97, the upper set of wings (3330), originally green, now are invisible against the backing (3310), which now appears green. The lower set of wings (3340), originally red, now appear black in green light. Thus, the image of the dove appears black with wings raised. In this manner, the image of the dove appears to flap its wings, even though there is no actual motion. The illusion is created simply by changing the color of the light. It should be recognized that much more complicated effects can be produced by using of objects of many different colors and illuminating the objects with a wide variety of colors within the spectrum, ranging from infrared, to visible, to ultraviolet.

The vending machine of this and related embodiments may include an LED system (3370) illuminating the vending machine. The LED system may, in embodiments, include a light module 100, a smart light bulb 701, or another embodiment of an LED system, such as those disclosed herein. Accordingly, the LED system may have one or more of the characteristics and provide one or more of the functions of the various other embodiments disclosed elsewhere herein. It should be noted that the light source need not be disposed inside the vending machine, but may be placed outside the vending machine in any position that permits the light source to illuminate the vending machine. Those skilled in the art will recognize many opportunities for designing displays to take advantage of the color-changing attributes of the lighting systems of the present invention.

Figure 98:
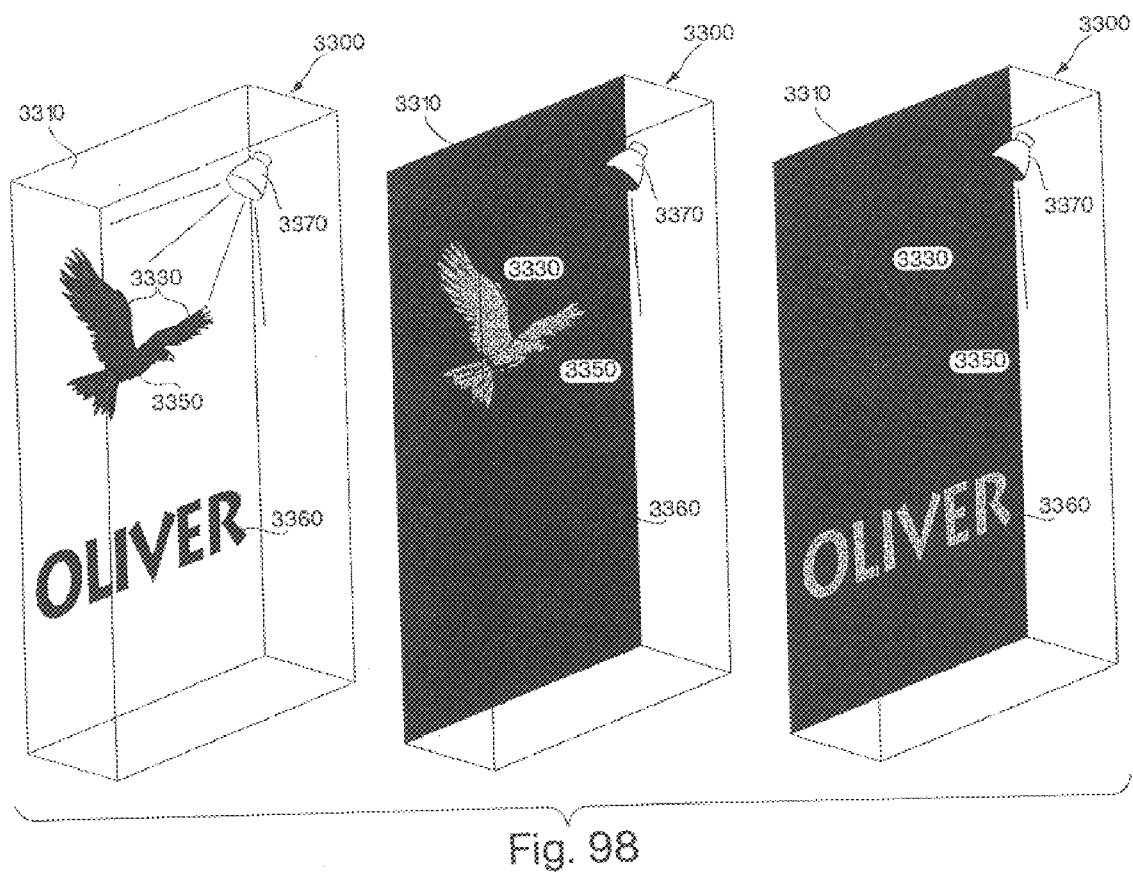
FIG. 98 depicts a vending machine in which objects appear and disappear in a colored design by changing the color of the light projected thereon.

As another technique available to the olive distributor of the above example, objects or designs may be made to appear and disappear as the color of light is changed. If the olive distributor should name its dove 'Oliver', this name might appear in the vending machine (3300) as shown in FIG. 98. The backing of the vending machine (3310) is white (FIG. 98, top), and displayed thereon are a dove (3350) colored red and the dove's name, 'Oliver', (3360) in green lettering. When the lighting in the vending machine is changed to green (FIG. 98, center), the lettering (3360) disappears against the green background (3310), while the dove (3350) appears black. When the lighting is changed to red (FIG. 98, bottom), the dove (3350) disappears against the background, which now also appears red, and the lettering (3360) appears black. Thus, by changing only the color of the light, the display in the vending machine varies between a dove, and the dove's name. This sort of a display is eye-catching, and therefore useful for advertising purposes.

Additionally, attention-grabbing effects can be achieved independent of a specific display tailored to take advantage of the color-changing properties of the lighting system of the present invention. The lights may be positioned within or about the display such that the color changes of the lights themselves serve to draw attention to the display. In one embodiment, the lights are positioned behind the display, such as behind a non-opaque backing of a vending machine, so that changing the color of the light is sufficient to attract attention from observers.

The above examples are intended for illustration only, and are not limiting with respect to the scope of the present invention. Those skilled in the art will readily devise other ways of using the lighting systems disclosed herein to achieve a variety of effects which attract the attention of observers, and these effects are encompassed by the present invention.

The present invention permits the user to change the lighting environment by strobing between different colors while taking feedback or spectrum sensor data from the surrounding environment. Such strobes may include a variable-cycle frequency color washing strobing effect using arrayed LEDs. The strobes may thus flash rapidly between colors, or may slowly change throughout the spectrum in a programmed order. The strobing effect can make otherwise unremarkable objects appear quite distinct and aesthetically appealing. Moreover, objects such as paintings may appear to become quite animated when periodically strobed with different colors of light. The attractive illumination effects of the variable frequency strobe permit improved, dynamic lighting environments in areas where lighting is attractive to customers, such as in retail stores, restaurants, museums and the like. The effect may be particularly useful in conjunction with the display of art, such as in art galleries, where known works of art may be radically changed by different lighting conditions. With works of art, for example, the lighting conditions may be controlled to reproduce the light intended by the creator, such as sunlight. Furthermore, the lighting system of the present invention can be used to project infrared and ultraviolet light, in addition to the more common visible wavelengths, and these uncommon frequencies can be used to induce fluorescence and other interesting effects.

Figure 99:
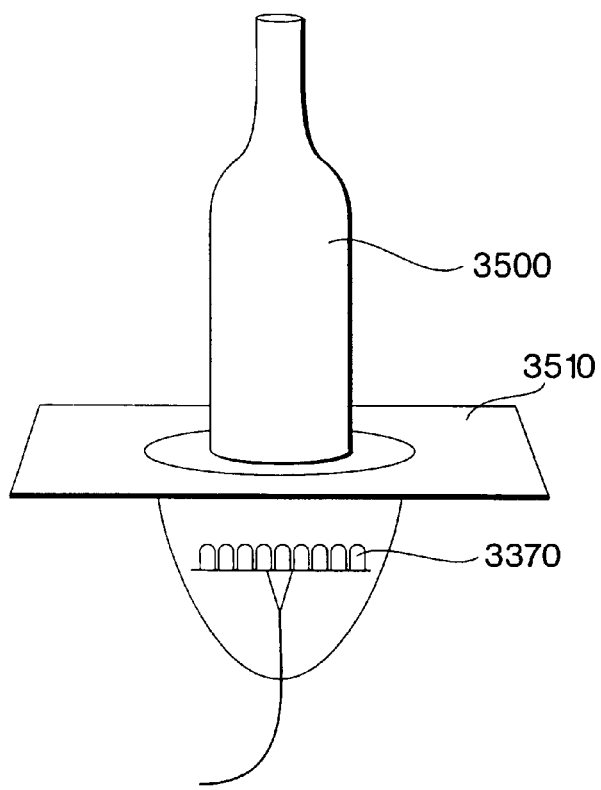
FIG. 99 depicts a system for illuminating a container.

In one embodiment of the invention, digitally-controlled, LED-based lights according to the present invention are used to illuminate a non-opaque object for display purposes. In one aspect of the invention, the object is a container containing a fluid, both of which may be substantially transparent. In one aspect, the container is a bottle of gin, vodka, rum, water, soda water, soft drink, or other beverage. An example of such a display is depicted in FIG. 99, wherein a beverage container (3500) is placed on a platform (3510) lit by an LED system (3370). Furthermore, the light source may be disposed on a coaster, to illuminate an individual drink from below. The LED system may, in embodiments, include a light module 100, a smart light bulb 701, or another embodiment of an LED system, such as those disclosed herein. Accordingly, the LED system may have one or more of the characteristics and provide one or more of the functions of the various other embodiments disclosed elsewhere herein. In another aspect, the object is a tank of substantially transparent liquid, such as a fish tank or aquarium. In yet another aspect, the object is a non-opaque solid object, such as an ice sculpture, glass figurine, crystal workpiece, or plastic statue. In another aspect, the light source is placed into a Lava® Lamp to provide illumination thereof The present invention also permits projection of attractive effects or works of art. In particular, in an embodiment of the present invention, a LED-based illumination source is used for projection images or patterns. This system may utilize an LED light source with a series of lenses and/or diffusers, an object containing distinct transparent and opaque areas such as a pattern, stencil, gobo, photographic slide, LCD display, micro-mirror device, or the like, and a final shaping lens. Only the light source, the patterned object, and a surface to receive the projection are necessary for this embodiment. This embodiment, for example, can be used to project a logo or sign onto a ceiling, floor, or wall, or onto a sidewalk outside of a business. In an alternate embodiment, the light may be projected on a cloud, a screen, or a fabric surface. The present invention is particularly advantageous in this regard, because it permits variation of the color of the projection coupled with a light source that does not generate heat.

The color strobe effect of the present invention may be used to create improved display case lighting, such as multicolor display case lighting. The lighting may be provided as part of a modular lighting system or in a standalone control panel. In general, the present lighting system may be used to alter lighting environment, such as work environments, museums, restaurants and the like. In certain applications, special lighting is required, such as in museums, where low UV lighting or heatless lighting may be needed. In other applications, such as cooled display cases, or illuminating edible objects such as food, the heatless light sources of the present invention offer advantages over standard incandescent lighting, which emits significant amounts of heat, while providing light of variable color. Standard fluorescent lighting, which also generates little heat, is often considered to look unappealing. The present invention projects attractive lighting of a controlled, variable spectrum without accompanying heat, while maintaining the flexibility to change the parameters of the generated light.

Figure 100:
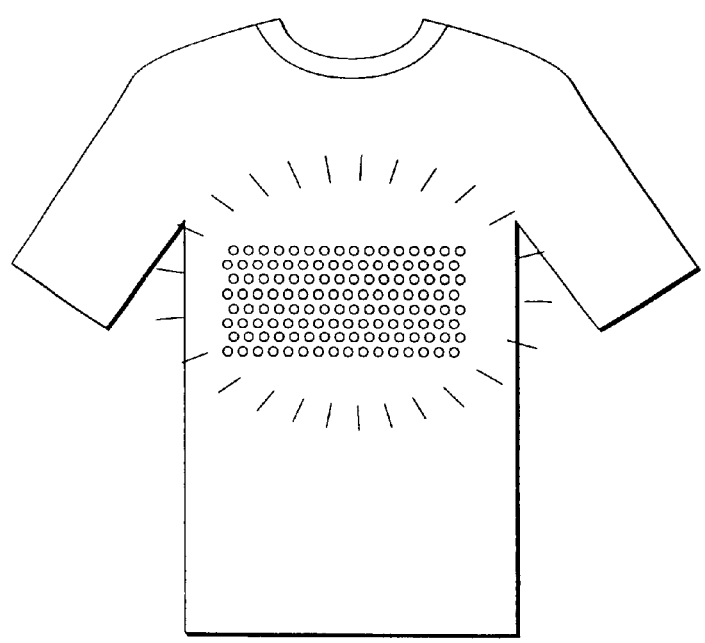
FIG. 100 depicts an article of clothing lit by an LED system.

LED systems of the present invention may be imbedded in articles of clothing to permit light to be projected from the clothing (FIG. 100). The LEDs may be mounted on a flexible circuit board and covered with latex, vinyl, plastic, cotton, etc. This embodiment includes a method for creating light weight flexible material suited for the construction of clothing. Sandwich of fabrics and silicone are provided, which then are lit by an LED. Conventional clothing using LEDs includes discrete LEDs in the form of words or patterns formed by the points of light. The LED-based clothing of the present invention may light clothing fabric without protruding. The LED-based clothing of the present invention may be controlled via a radio frequency or infrared signal by a remote control or a master controller having a transmitter element. The clothing can be made to fit the wearer in a manner that permits disposition of the LEDs in close proximity over the body, permitting the user's external appearance to be modified, for example to simulate an appearance, such as nudity or a particular type of clothing. The clothing can be paired with a sensor to allow the LED system to display a condition of the user, such as heart rate, or the like.

The utility of such clothing can be manifested in many ways. An LED display so disposed in the clothing can be used purely for effect, to generate dazzling patterns, visual effects, and the like. The LED displays can represent real-world images, such as the surrounding environment, or may simply reflect surrounding conditions by changing color in response to external data such as temperature, lighting conditions, or pressure. These displays might also be responsive to the proximity of a similar garment, or might receive data from transmitters in the environment. In one embodiment, the display on the clothing is responsive to pressure. Clothing of this embodiment might be worn in a sporting event to provide visual evidence of illegal contact. For example, in the game of baseball, a batter who is struck by the ball would have visible evidence thereof on the portion of clothing so struck. Furthermore, the clothing could include appropriate processors to enable recent data to be repeated on the clothing, effectively creating an 'instant replay' of the previous event. Clothing of these and related embodiments may include the sensors required for such responsive requirements.

In yet another embodiment, the display on the clothing could be a medical imaging display. Data from magnetic resonance imaging, for example, could be represented in three dimensions on the surface of clothing worn by the patient as an aid to physicians visualizing the information. Similarly, such clothing could serve as a wearable video screen for any application, such as television, video games, and related displays. The clothing could also be programmed to display a series of predetermined images. For example, pictures might be taken of a person wearing a series of outfits, the person might put on LED display clothing, the picture data might be adjusted for optimal correspondence with the LED clothing, and then the images might be serially displayed on the clothing to simulate instantaneous changes of clothing. Images may also be controlled remotely. Those skilled in the art will envision many related applications of this embodiment.

While the invention has been disclosed in connection with the preferred embodiments shown and described in detail, various modifications and improvements thereon will become readily apparent to those skilled in the art. Accordingly, the spirit and scope of the present invention is to be limited only by the following claims.

What is claimed is:

1. A system for illuminating a material, comprising:
    an LED system to generate a range of colors within a color spectrum;
    a processor to control an electrical current supplied to the LED system, the processor being configured to provide a particular amount of current to the LED system to generate a corresponding color within the color spectrum, the processor being further configured to respond to a signal relating to a feature of the material; and
    a positioning system capable of positioning the LED system in a spatial relationship with the material whereby the LED system illuminates the material.

2. The system of claim 1, further comprising a sensor to generate the signal relating to the feature.

3. The system of claim 2, wherein each of the sensor and the processor is configured to communicate the signal through wireless transmission.

4. The system of claim 2, wherein each of the sensor and the processor is configured to communicate the signal through wired transmission.

5. The system of claim 1, wherein the processor is configured to compare the signal to known light parameters.

6. The system of claim 5, wherein the known light parameters relate to an abnormal feature of the material.

7. The system of claim 5, wherein the material is a body part, and wherein the known light parameters relate to a pathological condition of the body part.

8. The system of claim 5, wherein the material comprises a biological entity, and wherein the known light parameters relate to a condition of the biological entity.

9. The system of claim 5, wherein the material is a living organism, and wherein the known light parameters relate to a condition of the living organism.

10. The system of claim 5, wherein the material is an inanimate entity, and wherein the known light parameters relate to a condition of the inanimate entity.

11. The system of claim 5, wherein the positioning system is configured such that the illumination of the material comprises trans-illumination of the material.

12. The system of claim 11, wherein the material is living tissue, and wherein the known light parameters relate to a condition of the living tissue.

13. The system of claim 1, wherein the positioning system is configured as a medical instrument.

14. The system of claim 13, wherein the positioning system comprises a handheld positioning system.

15. The system of claim 13, wherein the positioning system is configured for insertion within a body cavity.

16. The system of claim 1, further comprising an image capture system configured to capture an image of the material.

17. The system of claim 16, wherein the image capture system is configured to record the image of the material.

18. A system for illuminating a material, comprising:
   an LED system to generate a range of colors within a color spectrum;
   a processor to control an electrical current supplied to the LED system, the processor being configured to provide a particular amount of current to the LED system to generate a corresponding color within the color spectrum; and
   a positioning system capable of positioning the LED system in a spatial relationship with the material whereby the LED system illuminates the material, the positioning system comprising a remote control system.

19. The system of claim 18, wherein the remote control system is configured to be operated through wireless control.

20. The system of claim 18, wherein the remote control system is configured to operated through wired control.

21. The system of claim 18, further comprising an image capture system configured to capture an image of the material.

22. The system of claim 21, wherein the image capture system is configured to record an image of the material.

23. The system of claim 18, further comprising a sensor configured to communicate a signal to the processor.

24. The system of claim 23, wherein the sensor signal relates to a feature of the material.

25. A method using an apparatus including an LED system to illuminate a material, the method comprising acts of:
   a) controlling an electrical current supplied to the LED system, based on a feature of the material, to generate at least one color within a color spectrum; and
   b) positioning the LED system in a spatial relationship with the material whereby the LED system illuminates the material.

26. The method of claim 25; wherein the act a) includes acts of:
   a1) controlling the electrical current supplied to the LED system to generate a range of colors within a color spectrum; and
   a2) providing a particular amount of current to the LED system to generate the corresponding color within the color spectrum based on the feature of the material.

27. The method of claim 25, further comprising an act of: generating a signal relating to the feature of the material.

28. The method of claim 27, further comprising an act of: communicating the signal to the LED system through wireless transmission.

29. The method of claim 27, further comprising an act of: communicating the signal to the LED system through wired transmission.

30. The method of claim 27, further comprising an act of: comparing the signal to known light parameters.

31. The method of claim 30, wherein the known light parameters relate to an abnormal feature of the material, and wherein the act of comparing includes an act of comparing the signal to parameters that relate to the abnormal feature of the material.

32. The method of claim 31, wherein the material is a body part, wherein the known light parameters relate to an abnormal feature of the body part, and wherein the act of comparing includes an act of comparing the signal to parameters that relate to the abnormal feature of the body part.

33. The method of claim 31, wherein the known light parameters relate to a pathological condition of the body part, and wherein the act of comparing includes an act of comparing the signal to parameters that relate to the pathological condition of the body part.

34. The method of claim 31, wherein the material comprises a biological entity, wherein the known light parameters relate to an abnormal feature of the biological entity, and wherein the act of comparing includes an act of comparing the signal to parameters that relate to the abnormal feature of the biological entity.

35. The method of claim 31, wherein the material is a living organism, wherein the known light parameters relate to an abnormal feature of the living organism, and wherein the act of comparing includes an act of comparing the signal to parameters that relate to the abnormal feature of the living organism.

36. The method of claim 31, wherein the material is an inanimate entity, wherein the known light parameters relate to an abnormal feature of the inanimate entity, and wherein the act of comparing includes an act of comparing the signal to parameters that relate to the abnormal feature of the inanimate entity.

37. The method of claim 25, wherein the act b) includes an act of inserting the LED system within a body cavity.

38. The method of claim 25, wherein the act b) includes an act of positioning the LED system so as to trans-illuminate the material.

39. The method of claim 25, further comprising an act of capturing an image of the material.

40. The method of claim 39, wherein the act of capturing an image includes an act of recording the image of the material.

41. A method using an apparatus including an LED system to illuminate a material, the method comprising acts of:
   a) controlling an electrical current supplied to the LED system to generate at least one color within a color spectrum; and
   b) remotely controlling a position of the LED system in a spatial relationship with the material whereby the LED system illuminates the material.

42. The method of claim 41, wherein the act a) includes acts of:
   a1) controlling the electrical current supplied to the LED system to generate a range of colors within a color spectrum; and a2) providing a particular amount of current to the LED system to generate the corresponding color within the color spectrum based on a feature of the material.

43. The method of claim 42, wherein the act a2) comprises an act of communicating to the LED system a signal related to a feature of the material.

44. The method of claim 41, wherein the act b) includes an act of remotely controlling the position of the LED system through wireless control.

45. The method of claim 41, wherein the act b) includes an act of remotely controlling the position of the LED system through wired control.

46. The method of claim 41, further comprising an act of capturing an image of the material.

47. The method of claim 41, wherein the act of capturing includes an act of recording the image of the material.

* * * * *

UNITED STATES PATENT AND TRADEMARK OFFICE
CERTIFICATE OF CORRECTION

PATENT NO.     : 6,459,919 B1
DATED          : October 1, 2002
INVENTOR(S)    : Ihor Lys et al.

It is certified that error appears in the above-identified patent and that said Letters Patent is hereby corrected as shown below:

<u>Title page,</u>
Item [56], the following references should be appended to the list of
References Cited:

| | | | |
|---|---|---|---|
| -- 3,832,503 | 08/27/74 | Crane | 200/518 |
| 3,909,670 | 09/30/75 | Wakamatsu et al. | 315/276 |
| 3,958,885 | 05/25/76 | Stockinger et al. | 356/139 |
| 3,974,637 | 08/17/76 | Bergey et al. | 58/50 R |
| 4,082,395 | 04/04/78 | Donato et al. | 339/21 R |
| 4,388,589 | 06/14/83 | Molldrem, Jr. | 324/96 |
| 4,656,398 | 04/07/87 | Michael et al. | 315/293 |
| 4,688,154 | 08/18/87 | Nilssen | 362/147 |
| 4,818,072 | 04/04/89 | Mohebban | 350/336 |
| 5,083,063 | 01/21/92 | Brooks | 315/294 |
| 5,128,595 | 07/07/92 | Hara | 315/312 |
| 5,371,618 | 12/06/94 | Tai et al. | 359/53 |
| 5,912,653 | 06/15/99 | Fitch | 345/87 |
| 4,647,217 | 03/03/87 | Havel | 368/10 |
| 4,687,340 | 08/18/87 | Havel | 368/10 |
| 4,705,406 | 11/10/87 | Havel | 368/10 |
| 4,707,141 | 11/17/87 | Havel | 368/11 |
| 4,771,274 | 09/13/88 | Havel | 340/703 |
| 4,845,745 | 07/04/89 | Havel | 379/354 |
| 4,965,561 | 10/23/90 | Havel | 340/762 |
| 5,752,766 | 05/19/98 | Bailey et al. | 362/250 |
| 5,803,579 | 09/08/98 | Turnbull et al. | 362/83.1 |
| 6,132,072 | 10/17/00 | Turnbull et al. | 362/494 |
| 6,135,604 | 10/24/00 | Lin | 362/101 |
| 6,183,086 | 02/06/01 | Neubert | 351/221 |
| 6,184,628 | 02/06/01 | Ruthemberg | 315/185 R |
| 6,196,471 | 03/06/01 | Ruthenberg | 238/18 |

UNITED STATES PATENT AND TRADEMARK OFFICE
CERTIFICATE OF CORRECTION

PATENT NO. : 6,459,919 B1
DATED : October 1, 2002
INVENTOR(S) : Ihor Lys et al.

It is certified that error appears in the above-identified patent and that said Letters Patent is hereby corrected as shown below:

Item [56], References Cited, cont'd,

High End Systems, Inc. Trackspot User Manual, August 1997, Excerpts (cover, Title page, pp. ii through iii and 2-13 through 2-14)

Artistic License, AL4000 DMX512 Processors, Revision 3.4, June 2000, Excerpts (Cover, pgs. 7,92 through 102)

Artistic License, Miscellaneous Drawings (3 sheets), January 12, 1995

Artistic License, Miscellaneous Documents (2 sheets), February 1995 and April 1996 --

Signed and Sealed this

Eighteenth Day of March, 2003

JAMES E. ROGAN
*Director of the United States Patent and Trademark Office*